(12) United States Patent
Geierstanger et al.

(10) Patent No.: US 11,596,695 B2
(45) Date of Patent: *Mar. 7, 2023

(54) SPECIFIC SITES FOR MODIFYING ANTIBODIES TO MAKE IMMUNOCONJUGATES

(71) Applicant: Novartis AG, Basel (CH)

(72) Inventors: Bernhard Hubert Geierstanger, San Diego, CA (US); Weijia Ou, San Diego, CA (US); Tetsuo Uno, San Diego, CA (US)

(73) Assignee: Novartis AG, Basel (CH)

( * ) Notice: Subject to any disclaimer, the term of this patent is extended or adjusted under 35 U.S.C. 154(b) by 369 days.

This patent is subject to a terminal disclaimer.

(21) Appl. No.: 16/701,576

(22) Filed: Dec. 3, 2019

(65) Prior Publication Data

US 2020/0338207 A1 Oct. 29, 2020

Related U.S. Application Data

(63) Continuation of application No. 14/764,026, filed as application No. PCT/US2014/015393 on Feb. 7, 2014, now abandoned.

(60) Provisional application No. 61/762,563, filed on Feb. 8, 2013.

(51) Int. Cl.
| | | |
|---|---|---|
| *A61K 47/68* | (2017.01) | |
| *C07K 16/32* | (2006.01) | |
| *C07K 16/28* | (2006.01) | |

(52) U.S. Cl.
CPC ...... *A61K 47/6817* (2017.08); *A61K 47/6803* (2017.08); *A61K 47/6855* (2017.08); *A61K 47/6871* (2017.08); *C07K 16/32* (2013.01); *C07K 16/2863* (2013.01); *C07K 2317/24* (2013.01); *C07K 2317/73* (2013.01); *C07K 2317/94* (2013.01)

(58) Field of Classification Search
None
See application file for complete search history.

(56) References Cited

U.S. PATENT DOCUMENTS

| | | |
|---|---|---|
| 5,219,996 A | 6/1993 | Bodmer et al. |
| 6,737,056 B1 | 5/2004 | Presta |
| 7,442,778 B2 | 10/2008 | Gegg et al. |
| 7,521,541 B2 | 4/2009 | Eigenbrot et al. |
| 7,645,861 B2 | 1/2010 | Gegg et al. |
| 7,655,764 B2 | 2/2010 | Gegg et al. |
| 7,655,765 B2 | 2/2010 | Gegg et al. |
| 7,662,931 B2 | 2/2010 | Gegg et al. |
| 7,750,127 B2 | 7/2010 | Gegg et al. |
| 7,750,128 B2 | 7/2010 | Gegg et al. |
| 7,855,275 B2 | 12/2010 | Eigenbrot et al. |
| 8,008,453 B2 | 8/2011 | Gegg et al. |
| 8,309,300 B2 | 11/2012 | Junutula et al. |
| 8,455,622 B2 | 6/2013 | Carter et al. |
| 9,884,817 B2 * | 2/2018 | Geierstanger ...... A61K 47/6803 |
| 9,938,323 B2 * | 4/2018 | Grunewald ............ A61P 35/00 |
| 9,988,420 B2 * | 6/2018 | Geierstanger ...... A61K 47/6817 |
| 10,392,421 B2 * | 8/2019 | Geierstanger .......... A61P 43/00 |
| 10,787,480 B2 * | 9/2020 | Geierstanger .......... C07K 16/32 |
| 10,973,826 B2 * | 4/2021 | Cortez .................. C07H 15/26 |
| 2005/0271663 A1 | 12/2005 | Ignatovich et al. |
| 2006/0166319 A1 | 7/2006 | Chan et al. |
| 2006/0183888 A1 | 8/2006 | Chan et al. |
| 2009/0117100 A1 | 5/2009 | Mao et al. |
| 2009/0258420 A1 | 10/2009 | van Vlijmen et al. |
| 2010/0111856 A1 | 5/2010 | Gill et al. |
| 2010/0184959 A1 | 7/2010 | Guler-Gane et al. |
| 2010/0196362 A1 | 8/2010 | Stavenhagen et al. |
| 2011/0301334 A1 | 6/2011 | Bhakta et al. |
| 2011/0206658 A1 | 8/2011 | Crowley et al. |
| 2012/0009205 A1 | 1/2012 | Gegg et al. |
| 2012/0009621 A1 | 1/2012 | Yamasaki et al. |

FOREIGN PATENT DOCUMENTS

| | | |
|---|---|---|
| CN | 101709047 | 5/2010 |
| EP | 1020179 | 2/2011 |
| EP | 2501721 | 9/2012 |
| WO | 8901782 | 3/1989 |
| WO | 9306217 | 4/1993 |
| WO | 9614339 | 5/1996 |
| WO | 2000044788 | 8/2000 |
| WO | 2005003294 A2 | 1/2005 |
| WO | 2005027966 A2 | 3/2005 |
| WO | 2006034488 A2 | 3/2006 |
| WO | 2008020827 A2 | 2/2008 |
| WO | 2008032833 A1 | 3/2008 |

(Continued)

OTHER PUBLICATIONS

Alley, Stephen C. et al. "Contribution of Linker Stability to the Activities of Anticancer Immunoconjugates." Bioconjugate Chemistry. vol. 19, No. 3. Mar. 1, 2008. pp. 759-765. XP055037546.

Anonymous. "www.bioinf.org.uk: Dr. Andrew C.R. Martin's Group at UCL." http://www.bioinf.org.uk/abs. Retrieved on Jun. 6, 2004. Feb. 25, 2014. XP055122195.

Axup, J.Y et al. "Synthesis of Site-Specific Antibody-drug Conjugates Using Unnatural Amino Acids." Proceedings of the National Academy of Sciences. vol. 109, No. 40. Oct. 2, 2012. pp. 16101-16106. XP055076259.

(Continued)

*Primary Examiner* — Phuong Huynh

(74) *Attorney, Agent, or Firm* — K&L Gates LLP

(57) ABSTRACT

The present invention provides specific sites for modifying antibodies or antibody fragments by replacing at least one native amino acid in the constant region of a parental antibody or antibody fragment with cysteine, which can be used as a site of attachment for a payload or linker-payload combination.

18 Claims, 44 Drawing Sheets

Specification includes a Sequence Listing.

(56) References Cited

FOREIGN PATENT DOCUMENTS

| | | | |
|---|---|---|---|
| WO | 2008052187 | A2 | 5/2008 |
| WO | 2009092011 | A1 | 7/2009 |
| WO | 2010048582 | A1 | 4/2010 |
| WO | 2010141902 | A2 | 12/2010 |
| WO | 2011003811 | A1 | 1/2011 |
| WO | 2011005481 | A1 | 1/2011 |
| WO | 2011056983 | A1 | 5/2011 |
| WO | 2011061246 | A2 | 5/2011 |
| WO | 2011061492 | A2 | 5/2011 |
| WO | 2011118739 | A1 | 9/2011 |
| WO | 2011/156328 | A1 | 12/2011 |
| WO | 2012022982 | A2 | 2/2012 |
| WO | 2013185115 | A1 | 12/2012 |
| WO | 2013093809 | A1 | 6/2013 |
| WO | 2013096291 | A2 | 6/2013 |
| WO | 2013184514 | A1 | 12/2013 |
| WO | 2014124258 | A2 | 8/2014 |
| WO | 2014124316 | A2 | 8/2014 |
| WO | 2014151030 | A1 | 9/2014 |
| WO | 2014165277 | A2 | 10/2014 |
| WO | 2015138615 | A2 | 9/2015 |

OTHER PUBLICATIONS

Chiu, Hsein-Po et al. "Simultaneous Purification and Site-Specific Modification of Pyrroline-Carboxy-Lysine Proteins." Chembiochem. Vol. 13, No. 3. Jan. 5, 2012. pp. 364-366. XP055122231.

Edelman, Gerald M. et al. I0Chemistry. Jun. 1, 1969. pp. 78-85. XP055122293.

Gaston, Marsha A. et al. "The Complete Biosynthesis of the Genetically Encoded Amino Acid Pyrrolysine from Lysine." Nature. vol. 471, No. 7340. Mar. 31, 2011. pp. 647-650. XP055081693.

Jackson, Dowdy et al. "In Vitro and In Vivo Evaluation of Cysteine and Site Specific Conjugated Herceptin Antibody-Drug Conjugates." PLOS ONE. vol. 9, No. 1. Jan. 14, 2014. XP055101735.

Junutula, Jagath R. et al. "Site-Specific Conjugation of a Cytotoxic Drug to an Antibody Improves the Therapeutic Index." Retrieved Jul. 24, 2008. http://dx.doi.org/10.1038/nbt.1480. pp. 1-8. XP007905289.

Lyons, A. et al. "Site-Specific Attachment to Recombinant Antibodies via Introduced Surface Cysteine Residues." Protein Engineering, Oxford University Press, Surry, GB. vol. 3, No. 8, Jan. 1, 1990. pp. 703-708. XP001000052.

Ou, W. et al. "Site-Specific Protein Modifications Through Pyrroline-Carboxy-Lysine Residues." Proceedings of the National Academy of Sciences. vol. 108, No. 26. Jun. 28, 2011. pp. 10437-10442. XP055122289.

PCT Search Report for International Application No. PCT/US2014/015302 dated Sep. 29, 2014. 8 pages.

PCT Search Report for International Application No. PCT/US2015/019984 dated Oct. 21, 2015. 7 pages.

PCT Search Report from International Application No. PCT/US2014/015393 dated Sep. 29, 2014. 10 pages.

Tian, F. et al. "A General Approach to Site-Specific Antibody Drug Conjugates." Proceedings of the National Academy of Sciences. vol. 111, No. 5. Jan. 17, 2014. pp. 1766-1771. XP055101730.

Voynov, Vladimir et al. "Design and Application of Antibody Cysteine Variants." Bioconjugate Chemistry, ACS, Washington, DC. vol. 21, No. 2. Feb. 17, 2010. pp. 385-392. XP002598497.

* cited by examiner

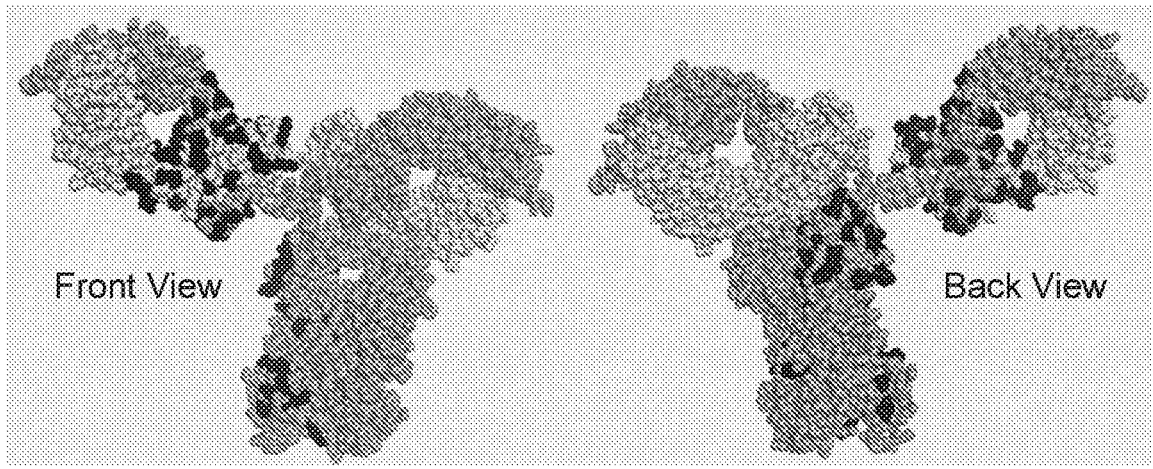

FIG.2

```
Tras   SASTKGPSVFPLAPSSKSTSGGTAALGCLVKDYFPEPVTVSWNSGALTSGVHTFPAVLQS 176
14090  SASTKGPSVFPLAPSSKSTSGGTAALGCLVKDYFPEPVTVSWNSGALTSGVHTFPAVLQS 176
Tras   SGLYSLSSVVTVPSSSLGTQTYICNVNHKPSNTKVDKKVEPKSCDKTHTCPPCPAPELLG 236
14090  SGLYSLSSVVTVPSSSLGTQTYICNVNHKPSNTKVDKKVEPKSCDKTHTCPPCPAPELLG 236
Tras   GPSVFLFPPKPKDTLMISRTPEVTCVVVDVSHEDPEVKFNWYVDGVEVHNAKTKPREEQY 296
14090  GPSVFLFPPKPKDTLMISRTPEVTCVVVDVSHEDPEVKFNWYVDGVEVHNAKTKPREEQY 296
Tras   NSTYRVVSVLTVLHQDWLNGKEYKCKVSNKALPAPIEKTISKAKGQPREPQVYTLPPSRE 356
14090  NSTYRVVSVLTVLHQDWLNGKEYKCKVSNKALPAPIEKTISKAKGQPREPQVYTLPPSRE 356
Tras   EMTKNQVSLTCLVKGFYPSDIAVEWESNGQPENNYKTTPPVLDSDGSFFLYSKLTVDKSR 416
14090  EMTKNQVSLTCLVKGFYPSDIAVEWESNGQPENNYKTTPPVLDSDGSFFLYSKLTVDKSR 416
Tras   WQQGNVFSCSVMHEALHNHYTQKSLSLSPGK 447
14090  WQQGNVFSCSVMHEALHNHYTQKSLSLSPGK 447
```

| | | |
|---|---|---|
| trastuzumab, Ig gamma-1 chain C region | 119 STKGPSVFPLAPSSKSTSGGTAALGCLVKDYFPEPVTVSWNSGALTSGVHTFPAVLQSSGLYSLSSVVTVPSSSLGTQT 197 | |
| P01857[1-330], Ig gamma-1 chain C region, | Homo sapiens | 119 STKGPSVFPLAPSSKSTSGGTAALGCLVKDYFPEPVTVSWNSGALTSGVHTFPAVLQSSGLYSLSSVVTVPSSSLGTQT 197 |
| P01859[f-326], Ig gamma-2 chain C region, | Homo sapiens | 119 STKGPSVFPLAPCSRSTSESTAALGCLVKDYFPEPVTVSWNSGALTSGVHTFPAVLQSSGLYSLSSVVTVPSSNFGTQT 197 |
| P01860[1-377], Ig gamma-3 chain C region, | Homo sapiens | 119 STKGPSVFPLAPCSRSTSESTAALGCLVKDYFPEPVTVSWNSGALTSGVHTFPAVLQSSGLYSLSSVVTVPSSSLGTQT 197 |
| P01861[1-327], Ig gamma-4 chain C region, | Homo sapiens | 119 STKGPSVFPLAPCSRSTSESTAALGCLVKDYFPEPVTVSWNSGALTSGVHTFPAVLQSSGLYSLSSVVTVPSSSLGTKT 197 |

| | | |
|---|---|---|
| trastuzumab, Ig gamma-1 chain C region | 198 YICNVNHKPSNTKVDKKVE----------PKSCDKTHTCPPCP 230 | |
| P01857[1-330] | Homo sapiens | 198 YICNVNHKPSNTKVDKKVE----------PKSCDKTHTCPPCP 230 |
| P01859[f-326] | Homo sapiens | 198 YICNVDHKPSNTKVDKTVER---------------KCCVECPPCP 227 |
| P01860[1-377] | Homo sapiens | 198 YTCNVNHKPSNTKVDKRVELKTPLGDTTHTCPRCPEPKSCDTPPPCPRCPEPKSCDTPPPCPRCP 277 |
| P01861[1-327] | Homo sapiens | 198 YTCNVDHKPSNTKVDKRVES----------------KYGPPCPSCP 227 |

| | | |
|---|---|---|
| trastuzumab, Ig gamma-1 chain C region | 231 APELLGGPSVFLFPPKPKDTLMISRTPEVTCVVVDVSHEDPEVKFNWYVDGVEVHNAKTKPREEQYNSTYRVVSVLTVLH 310 | |
| P01857[1-330] | Homo sapiens | 231 APELLGGPSVFLFPPKPKDTLMISRTPEVTCVVVDVSHEDPEVKFNWYVDGVEVHNAKTKPREEQYNSTYRVVSVLTVLH 310 |
| P01859[f-326] | Homo sapiens | 228 APPVAG-PSVFLFPPKPKDTLMISRTPEVTCVVVDVSHEDPEVQFNWYVDGVEVHNAKTKPREEQFNSTYRVVSVLTVVH 306 |
| P01860[1-377] | Homo sapiens | 278 APELLGGPSVFLFPPKPKDTLMISRTPEVTCVVVDVSHEDPEVQFKWYVDGVEVHNAKTKPREEQYNSTYRVVSVLTVLH 357 |
| P01861[1-327] | Homo sapiens | 228 APEFLGGPSVFLFPPKPKDTLMISRTPEVTCVVVDVSQEDPEVQFNWYVDGVEVHNAKTKPREEQFNSTYRVVSVLTVLH 307 |

| | | |
|---|---|---|
| trastuzumab, Ig gamma-1 chain C region | 311 QDWLNGKEYKCKVSNKALPAPIEKTISKAKGQPREPQVYTLPPSREEMTKNQVSLTCLVKGFYPSDIAVEWESNGQPENN 390 | |
| P01857[1-330] | Homo sapiens | 311 QDWLNGKEYKCKVSNKALPAPIEKTISKAKGQPREPQVYTLPPSREEMTKNQVSLTCLVKGFYPSDIAVEWESNGQPENN 390 |
| P01859[f-326] | Homo sapiens | 307 QDWLNGKEYKCKVSNKGLPAPIEKTISKTKGQPREPQVYTLPPSREEMTKNQVSLTCLVKGFYPSDISVEWESNGQPENN 386 |
| P01860[1-377] | Homo sapiens | 358 QDWLNGKEYKCKVSNKALPAPIEKTISKTKGQPREPQVYTLPPSREEMTKNQVSLTCLVKGFYPSDIAVEWESSGQPENN 437 |
| P01861[1-327] | Homo sapiens | 308 QDWLNGKEYKCKVSNKGLPSSIEKTISKAKGQPREPQVYTLPPSQEEMTKNQVSLTCLVKGFYPSDIAVEWESNGQPENN 387 |

| | | |
|---|---|---|
| trastuzumab, Ig gamma-1 chain C region | 391 YKTTPPVLDSDGSFFLYSKLTVDKSRWQQGNVFSCSVMHEALHNHYTQKSLSLSPG 446 | |
| P01857[1-330] | Homo sapiens | 391 YKTTPPVLDSDGSFFLYSKLTVDKSRWQQGNVFSCSVMHEALHNHYTQKSLSLSPG 446 |
| P01859[f-326] | Homo sapiens | 387 YKTTPPMLDSDGSFFLYSKLTVDKSRWQQGNVFSCSVMHEALHNHYTQKSLSLSPG 442 |
| P01860[1-377] | Homo sapiens | 438 YKTTPPMLDSDGSFFLYSKLTVDKSRWQQGNIFSCSVMHEALHNRYTQKSLSLSPG 493 |
| P01861[1-327] | Homo sapiens | 388 YKTTPPVLDSDGSFFLYSRLTVDKSRWQEGNVFSCSVMHEALHNHYTQKSLSLSLG 443 |

```
Kappa   RTVAAPSVFIFPPSDEQLKSGTASVVCLLNNFYPREAKVQWKVDNA-LQSGNSQESVTEQDSK
         AAPSV +FPPS E+L++ A++VCL+++FYP    V WK D++ +++G   E+ T
Lambda  QPKAAPSVTLFPPSSEELQANKATLVCLISDFYPGAVTVAWKADSSPVKAG--VETTTPSKQS
Kappa   DSTYSLSSTLTLSKADYEKHKVYACEVTHQGLSSPVTKSFNRGEC
         ++ Y+ SS L+L+    ++ H+ Y+C+VTH+G   S V K+    EC
Lambda  NNKYAASSYLSLTPEQWKSHRSYSCQVTHEG--STVEKTVAPTECS
```

FIG.5A

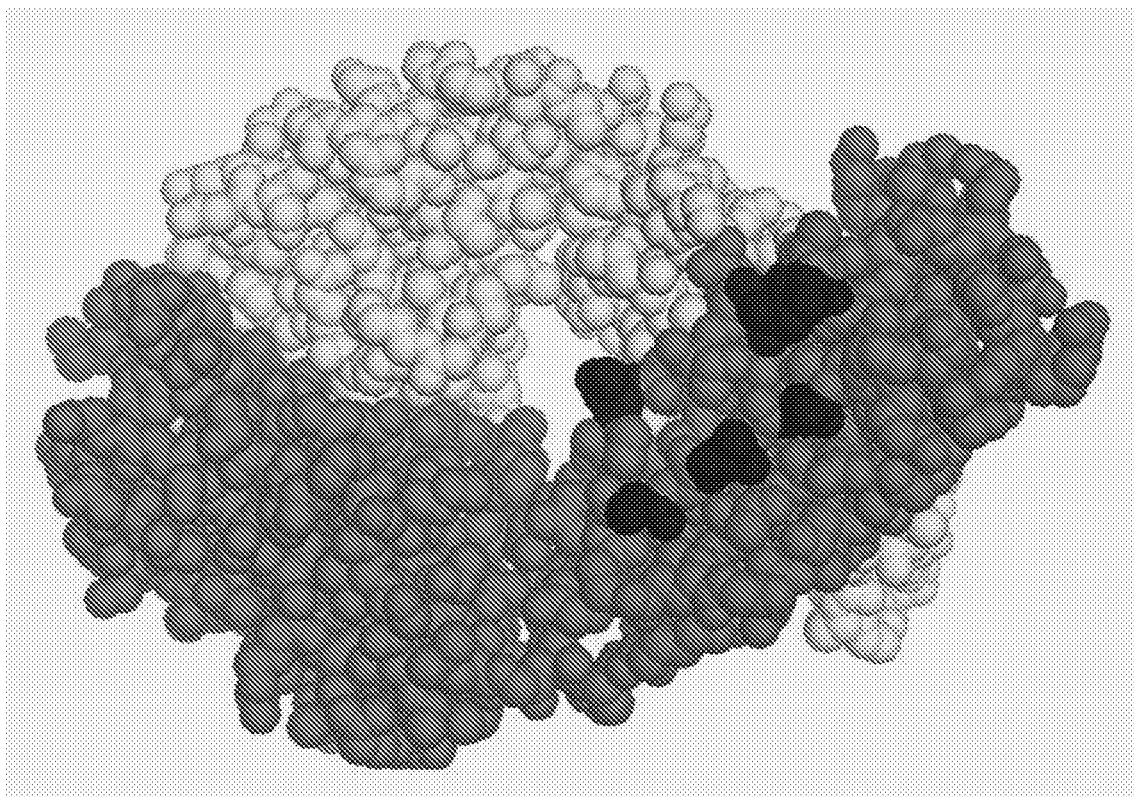

FIG.5B

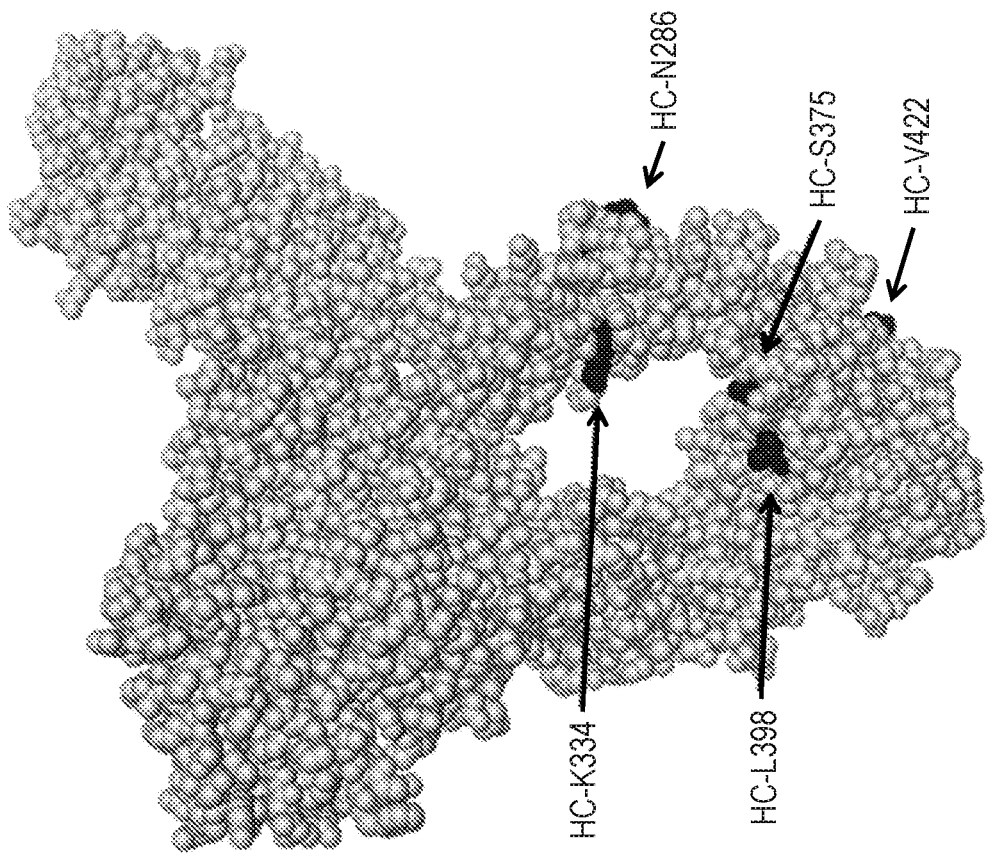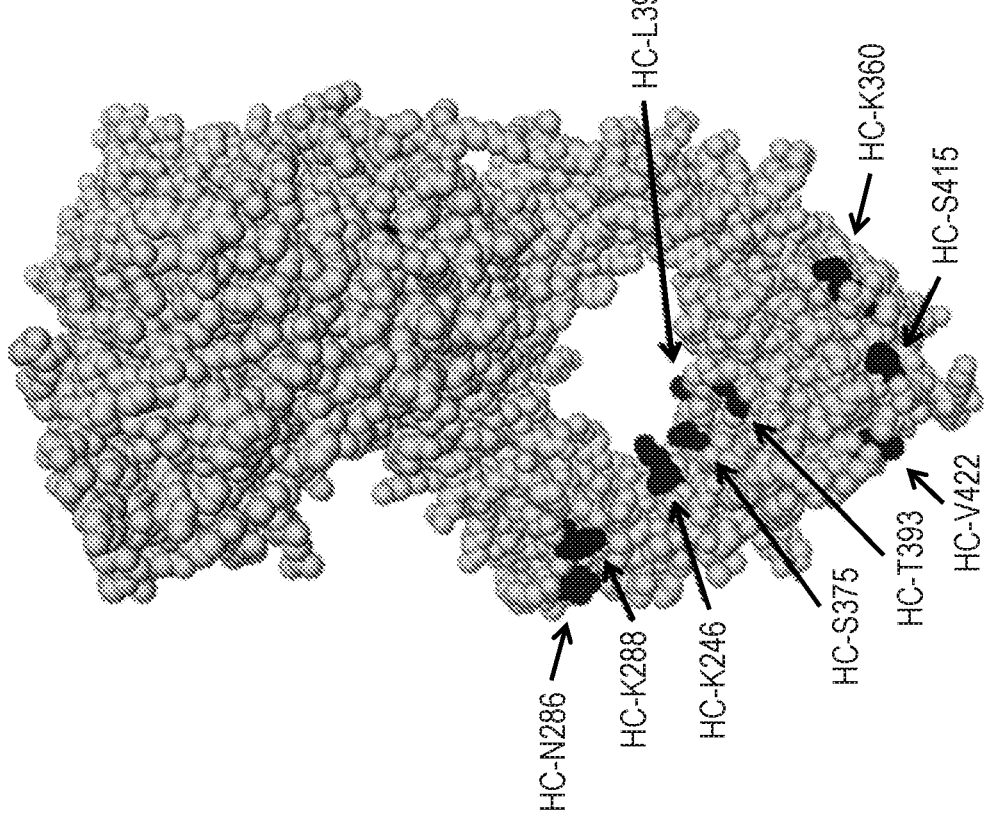
FIG. 24C

SEQUENCE LISTING

```
<160> NUMBER OF SEQ ID NOS: 309

<210> SEQ ID NO 1
<211> LENGTH: 450
<212> TYPE: PRT
<213> ORGANISM: Homo sapiens

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
```

```
                290                 295                 300
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 2
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Cys Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
                20                  25                  30

Tyr Phe Pro Glu Pro Val Thr Val Ser Trp Asn Ser Gly Ala Leu Thr
                35                  40                  45

Ser Gly Val His Thr Phe Pro Ala Val Leu Gln Ser Ser Gly Leu Tyr
            50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
                100                 105                 110

Cys Pro Ala Pro Glu Leu Leu Gly Gly Pro Ser Val Phe Leu Phe Pro
                115                 120                 125

Pro Lys Pro Lys Asp Thr Leu Met Ile Ser Arg Thr Pro Glu Val Thr
            130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
                180                 185                 190
```

```
Leu His Gln Asp Trp Leu Asn Gly Lys Glu Tyr Lys Cys Lys Val Ser
            195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
                260                 265                 270

Asn Asn Tyr Lys Thr Thr Pro Pro Val Leu Asp Ser Asp Gly Ser Phe
            275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330
```

<210> SEQ ID NO 3
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

```
Ser Ala Cys Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
                20                  25                  30

Tyr Phe Pro Glu Pro Val Thr Val Ser Trp Asn Ser Gly Ala Leu Thr
            35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
                100                 105                 110

Cys Pro Ala Pro Glu Leu Leu Gly Gly Pro Ser Val Phe Leu Phe Pro
            115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
    195                 200                 205
```

```
Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
                260                 265                 270

Asn Asn Tyr Lys Thr Thr Pro Pro Val Leu Asp Ser Asp Gly Ser Phe
            275                 280                 285

Phe Leu Tyr Ser Lys Leu Thr Val Asp Lys Ser Arg Trp Gln Gln Gly
290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330
```

<210> SEQ ID NO 4
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 4

```
Ser Ala Ser Thr Cys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
                20                  25                  30

Tyr Phe Pro Glu Pro Val Thr Val Ser Trp Asn Ser Gly Ala Leu Thr
            35                  40                  45

Ser Gly Val His Thr Phe Pro Ala Val Leu Gln Ser Ser Gly Leu Tyr
        50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
                100                 105                 110

Cys Pro Ala Pro Glu Leu Leu Gly Gly Pro Ser Val Phe Leu Phe Pro
            115                 120                 125

Pro Lys Pro Lys Asp Thr Leu Met Ile Ser Arg Thr Pro Glu Val Thr
        130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
                180                 185                 190

Leu His Gln Asp Trp Leu Asn Gly Lys Glu Tyr Lys Cys Lys Val Ser
            195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
```

```
                        225                 230                 235                 240

Glu Met Thr Lys Asn Gln Val Ser Leu Thr Cys Leu Val Lys Gly Phe
                        245                 250                 255

Tyr Pro Ser Asp Ile Ala Val Glu Trp Glu Ser Asn Gly Gln Pro Glu
                260                 265                 270

Asn Asn Tyr Lys Thr Thr Pro Pro Val Leu Asp Ser Asp Gly Ser Phe
            275                 280                 285

Phe Leu Tyr Ser Lys Leu Thr Val Asp Lys Ser Arg Trp Gln Gln Gly
290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 5
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Ser Ala Ser Thr Lys Gly Pro Cys Val Phe Pro Leu Ala Pro Ser Ser
1               5                   10                  15

Lys Ser Thr Ser Gly Gly Thr Ala Ala Leu Gly Cys Leu Val Lys Asp
                20                  25                  30

Tyr Phe Pro Glu Pro Val Thr Val Ser Trp Asn Ser Gly Ala Leu Thr
            35                  40                  45

Ser Gly Val His Thr Phe Pro Ala Val Leu Gln Ser Ser Gly Leu Tyr
        50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255
```

```
Tyr Pro Ser Asp Ile Ala Val Glu Trp Glu Ser Asn Gly Gln Pro Glu
            260                 265                 270

Asn Asn Tyr Lys Thr Thr Pro Val Leu Asp Ser Asp Gly Ser Phe
        275                 280                 285

Phe Leu Tyr Ser Lys Leu Thr Val Asp Lys Ser Arg Trp Gln Gln Gly
290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 6
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Ser Ala Ser Thr Lys Gly Pro Ser Val Phe Pro Leu Ala Pro Ser Cys
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270
```

```
Asn Asn Tyr Lys Thr Thr Pro Pro Val Leu Asp Ser Asp Gly Ser Phe
                275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 7
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Ser Ala Ser Thr Lys Gly Pro Ser Val Phe Pro Leu Ala Pro Ser Ser
1               5                   10                  15

Lys Cys Thr Ser Gly Gly Thr Ala Ala Leu Gly Cys Leu Val Lys Asp
                20                  25                  30

Tyr Phe Pro Glu Pro Val Thr Val Ser Trp Asn Ser Gly Ala Leu Thr
            35                  40                  45

Ser Gly Val His Thr Phe Pro Ala Val Leu Gln Ser Ser Gly Leu Tyr
        50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
                100                 105                 110

Cys Pro Ala Pro Glu Leu Leu Gly Gly Pro Ser Val Phe Leu Phe Pro
            115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
```

```
                290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 8
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Ser Ala Ser Thr Lys Gly Pro Ser Val Phe Pro Leu Ala Pro Ser Ser
1               5                   10                  15

Lys Ser Thr Cys Gly Gly Thr Ala Ala Leu Gly Cys Leu Val Lys Asp
                20                  25                  30

Tyr Phe Pro Glu Pro Val Thr Val Ser Trp Asn Ser Gly Ala Leu Thr
            35                  40                  45

Ser Gly Val His Thr Phe Pro Ala Val Leu Gln Ser Ser Gly Leu Tyr
        50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
                100                 105                 110

Cys Pro Ala Pro Glu Leu Leu Gly Gly Pro Ser Val Phe Leu Phe Pro
            115                 120                 125

Pro Lys Pro Lys Asp Thr Leu Met Ile Ser Arg Thr Pro Glu Val Thr
        130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
                180                 185                 190

Leu His Gln Asp Trp Leu Asn Gly Lys Glu Tyr Lys Cys Lys Val Ser
            195                 200                 205

Asn Lys Ala Leu Pro Ala Pro Ile Glu Lys Thr Ile Ser Lys Ala Lys
        210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
                260                 265                 270

Asn Asn Tyr Lys Thr Thr Pro Pro Val Leu Asp Ser Asp Gly Ser Phe
            275                 280                 285

Phe Leu Tyr Ser Lys Leu Thr Val Asp Lys Ser Arg Trp Gln Gln Gly
        290                 295                 300

Asn Val Phe Ser Cys Ser Val Met His Glu Ala Leu His Asn His Tyr
305                 310                 315                 320
```

Thr Gln Lys Ser Leu Ser Leu Ser Pro Gly Lys
            325                 330

<210> SEQ ID NO 9
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Ser Ala Ser Thr Lys Gly Pro Ser Val Phe Pro Leu Ala Pro Ser Ser
1               5                   10                  15

Lys Ser Thr Ser Gly Gly Cys Ala Ala Leu Gly Cys Leu Val Lys Asp
                20                  25                  30

Tyr Phe Pro Glu Pro Val Thr Val Ser Trp Asn Ser Gly Ala Leu Thr
            35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

```
<210> SEQ ID NO 10
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Cys Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 11
<211> LENGTH: 331
<212> TYPE: PRT
```

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 11

```
Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Cys Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330
```

<210> SEQ ID NO 12
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 12

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Cys Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 13
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

```
Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Cys Trp Asn Ser Gly Ala Leu Thr
            35                  40                  45

Ser Gly Val His Thr Phe Pro Ala Val Leu Gln Ser Ser Gly Leu Tyr
50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
                100                 105                 110

Cys Pro Ala Pro Glu Leu Leu Gly Gly Pro Ser Val Phe Leu Phe Pro
145             115                 120                 125

Pro Lys Pro Lys Asp Thr Leu Met Ile Ser Arg Thr Pro Glu Val Thr
            130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
                180                 185                 190

Leu His Gln Asp Trp Leu Asn Gly Lys Glu Tyr Lys Cys Lys Val Ser
            195                 200                 205

Asn Lys Ala Leu Pro Ala Pro Ile Glu Lys Thr Ile Ser Lys Ala Lys
            210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
                260                 265                 270

Asn Asn Tyr Lys Thr Thr Pro Pro Val Leu Asp Ser Asp Gly Ser Phe
                275                 280                 285

Phe Leu Tyr Ser Lys Leu Thr Val Asp Lys Ser Arg Trp Gln Gln Gly
            290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 14
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
```

```
            20                  25                  30
Tyr Phe Pro Glu Pro Val Thr Val Ser Trp Asn Ser Gly Ala Leu Cys
         35                  40                  45

Ser Gly Val His Thr Phe Pro Ala Val Leu Gln Ser Ser Gly Leu Tyr
 50                  55                  60

Ser Leu Ser Ser Val Val Thr Val Pro Ser Ser Leu Gly Thr Gln
 65                  70                  75                  80

Thr Tyr Ile Cys Asn Val Asn His Lys Pro Ser Asn Thr Lys Val Asp
                 85                  90                  95

Lys Lys Val Glu Pro Lys Ser Cys Asp Lys Thr His Thr Cys Pro Pro
             100                 105                 110

Cys Pro Ala Pro Glu Leu Leu Gly Gly Pro Ser Val Phe Leu Phe Pro
             115                 120                 125

Pro Lys Pro Lys Asp Thr Leu Met Ile Ser Arg Thr Pro Glu Val Thr
             130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                 165                 170                 175

Glu Glu Gln Tyr Asn Ser Thr Tyr Arg Val Val Ser Val Leu Thr Val
             180                 185                 190

Leu His Gln Asp Trp Leu Asn Gly Lys Glu Tyr Lys Cys Lys Val Ser
             195                 200                 205

Asn Lys Ala Leu Pro Ala Pro Ile Glu Lys Thr Ile Ser Lys Ala Lys
         210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                 245                 250                 255

Tyr Pro Ser Asp Ile Ala Val Glu Trp Glu Ser Asn Gly Gln Pro Glu
             260                 265                 270

Asn Asn Tyr Lys Thr Thr Pro Pro Val Leu Asp Ser Asp Gly Ser Phe
             275                 280                 285

Phe Leu Tyr Ser Lys Leu Thr Val Asp Lys Ser Arg Trp Gln Gln Gly
         290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                 325                 330

<210> SEQ ID NO 15
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
             20                  25                  30

Tyr Phe Pro Glu Pro Val Thr Val Ser Trp Asn Ser Gly Ala Leu Thr
         35                  40                  45
```

```
Cys Gly Val His Thr Phe Pro Ala Val Leu Gln Ser Gly Leu Tyr
         50                  55                  60

Ser Leu Ser Ser Val Val Thr Val Pro Ser Ser Leu Gly Thr Gln
 65                  70                  75                  80

Thr Tyr Ile Cys Asn Val Asn His Lys Pro Ser Asn Thr Lys Val Asp
             85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
            115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
                180                 185                 190

Leu His Gln Asp Trp Leu Asn Gly Lys Glu Tyr Lys Cys Lys Val Ser
                195                 200                 205

Asn Lys Ala Leu Pro Ala Pro Ile Glu Lys Thr Ile Ser Lys Ala Lys
210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
                260                 265                 270

Asn Asn Tyr Lys Thr Thr Pro Pro Val Leu Asp Ser Asp Gly Ser Phe
                275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 16
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Ser Ala Ser Thr Lys Gly Pro Ser Val Phe Pro Leu Ala Pro Ser Ser
 1               5                  10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Cys Phe Pro Ala Val Leu Gln Ser Ser Gly Leu Tyr
    50                  55                  60
```

```
Ser Leu Ser Ser Val Val Thr Val Pro Ser Ser Leu Gly Thr Gln
 65                  70                  75                  80

Thr Tyr Ile Cys Asn Val Asn His Lys Pro Ser Asn Thr Lys Val Asp
                 85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 17
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Ser Ala Ser Thr Lys Gly Pro Ser Val Phe Pro Leu Ala Pro Ser Ser
  1               5                  10                  15

Lys Ser Thr Ser Gly Gly Thr Ala Ala Leu Gly Cys Leu Val Lys Asp
                 20                  25                  30

Tyr Phe Pro Glu Pro Val Thr Val Ser Trp Asn Ser Gly Ala Leu Thr
            35                  40                  45

Ser Gly Val His Thr Phe Cys Ala Val Leu Gln Ser Ser Gly Leu Tyr
        50                  55                  60

Ser Leu Ser Ser Val Val Thr Val Pro Ser Ser Leu Gly Thr Gln
 65                  70                  75                  80

Thr Tyr Ile Cys Asn Val Asn His Lys Pro Ser Asn Thr Lys Val Asp
```

```
                85                  90                  95
Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 18
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Cys Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110
```

-continued

Cys Pro Ala Pro Glu Leu Leu Gly Gly Pro Ser Val Phe Leu Phe Pro
            115                 120                 125

Pro Lys Pro Lys Asp Thr Leu Met Ile Ser Arg Thr Pro Glu Val Thr
        130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 19
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Cys Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

```
Pro Lys Pro Lys Asp Thr Leu Met Ile Ser Arg Thr Pro Glu Val Thr
130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 20
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
                20                  25                  30

Tyr Phe Pro Glu Pro Val Thr Val Ser Trp Asn Ser Gly Ala Leu Thr
            35                  40                  45

Ser Gly Val His Thr Phe Pro Ala Val Leu Gln Ser Cys Gly Leu Tyr
        50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
130                 135                 140

Cys Val Val Val Asp Val Ser His Glu Asp Pro Glu Val Lys Phe Asn
```

```
                145                 150                 155                 160
Trp Tyr Val Asp Gly Val Glu Val His Asn Ala Lys Thr Lys Pro Arg
                165                 170                 175
Glu Glu Gln Tyr Asn Ser Thr Tyr Arg Val Val Ser Val Leu Thr Val
                180                 185                 190
Leu His Gln Asp Trp Leu Asn Gly Lys Glu Tyr Lys Cys Lys Val Ser
                195                 200                 205
Asn Lys Ala Leu Pro Ala Pro Ile Glu Lys Thr Ile Ser Lys Ala Lys
                210                 215                 220
Gly Gln Pro Arg Glu Pro Gln Val Tyr Thr Leu Pro Pro Ser Arg Glu
225                 230                 235                 240
Glu Met Thr Lys Asn Gln Val Ser Leu Thr Cys Leu Val Lys Gly Phe
                245                 250                 255
Tyr Pro Ser Asp Ile Ala Val Glu Trp Glu Ser Asn Gly Gln Pro Glu
                260                 265                 270
Asn Asn Tyr Lys Thr Thr Pro Pro Val Leu Asp Ser Asp Gly Ser Phe
                275                 280                 285
Phe Leu Tyr Ser Lys Leu Thr Val Asp Lys Ser Arg Trp Gln Gln Gly
                290                 295                 300
Asn Val Phe Ser Cys Ser Val Met His Glu Ala Leu His Asn His Tyr
305                 310                 315                 320
Thr Gln Lys Ser Leu Ser Leu Ser Pro Gly Lys
                325                 330

<210> SEQ ID NO 21
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Ser Ala Ser Thr Lys Gly Pro Ser Val Phe Pro Leu Ala Pro Ser Ser
1               5                   10                  15
Lys Ser Thr Ser Gly Gly Thr Ala Ala Leu Gly Cys Leu Val Lys Asp
                20                  25                  30
Tyr Phe Pro Glu Pro Val Thr Val Ser Trp Asn Ser Gly Ala Leu Thr
                35                  40                  45
Ser Gly Val His Thr Phe Pro Ala Val Leu Gln Ser Ser Gly Leu Tyr
                50                  55                  60
Ser Leu Ser Ser Val Val Thr Val Cys Ser Ser Ser Leu Gly Thr Gln
65                  70                  75                  80
Thr Tyr Ile Cys Asn Val Asn His Lys Pro Ser Asn Thr Lys Val Asp
                85                  90                  95
Lys Lys Val Glu Pro Lys Ser Cys Asp Lys Thr His Thr Cys Pro Pro
                100                 105                 110
Cys Pro Ala Pro Glu Leu Leu Gly Gly Pro Ser Val Phe Leu Phe Pro
                115                 120                 125
Pro Lys Pro Lys Asp Thr Leu Met Ile Ser Arg Thr Pro Glu Val Thr
                130                 135                 140
Cys Val Val Val Asp Val Ser His Glu Asp Pro Glu Val Lys Phe Asn
145                 150                 155                 160
Trp Tyr Val Asp Gly Val Glu Val His Asn Ala Lys Thr Lys Pro Arg
                165                 170                 175
```

```
Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
            195                 200                 205

Asn Lys Ala Leu Pro Ala Pro Ile Glu Lys Thr Ile Ser Lys Ala Lys
210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
            275                 280                 285

Phe Leu Tyr Ser Lys Leu Thr Val Asp Lys Ser Arg Trp Gln Gln Gly
            290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 22
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Cys Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190
```

Leu His Gln Asp Trp Leu Asn Gly Lys Glu Tyr Lys Cys Lys Val Ser
            195                 200                 205

Asn Lys Ala Leu Pro Ala Pro Ile Glu Lys Thr Ile Ser Lys Ala Lys
210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
                260                 265                 270

Asn Asn Tyr Lys Thr Thr Pro Pro Val Leu Asp Ser Asp Gly Ser Phe
            275                 280                 285

Phe Leu Tyr Ser Lys Leu Thr Val Asp Lys Ser Arg Trp Gln Gln Gly
290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 23
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
                20                  25                  30

Tyr Phe Pro Glu Pro Val Thr Val Ser Trp Asn Ser Gly Ala Leu Thr
            35                  40                  45

Ser Gly Val His Thr Phe Pro Ala Val Leu Gln Ser Ser Gly Leu Tyr
50                  55                  60

Ser Leu Ser Ser Val Val Thr Val Pro Ser Ser Ser Leu Gly Cys Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
210                 215                 220

```
            210                 215                 220
Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
                260                 265                 270

Asn Asn Tyr Lys Thr Thr Pro Pro Val Leu Asp Ser Asp Gly Ser Phe
            275                 280                 285

Phe Leu Tyr Ser Lys Leu Thr Val Asp Lys Ser Arg Trp Gln Gln Gly
        290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 24
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
                20                  25                  30

Tyr Phe Pro Glu Pro Val Thr Val Ser Trp Asn Ser Gly Ala Leu Thr
            35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Cys Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
                100                 105                 110

Cys Pro Ala Pro Glu Leu Leu Gly Gly Pro Ser Val Phe Leu Phe Pro
            115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
                180                 185                 190

Leu His Gln Asp Trp Leu Asn Gly Lys Glu Tyr Lys Cys Lys Val Ser
            195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240
```

```
Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330
```

<210> SEQ ID NO 25
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 25

```
Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Cys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255
```

```
Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 26
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Cys Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
```

```
                    275                 280                 285
Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 27
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Cys
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300
```

-continued

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 28
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
                20                  25                  30

Tyr Phe Pro Glu Pro Val Thr Val Ser Trp Asn Ser Gly Ala Leu Thr
            35                  40                  45

Ser Gly Val His Thr Phe Pro Ala Val Leu Gln Ser Ser Gly Leu Tyr
        50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Cys Pro Lys Asp Thr Leu Met Ile Ser Arg Thr Pro Glu Val Thr
130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

```
<210> SEQ ID NO 29
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Cys Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330
```

-continued

```
<210> SEQ ID NO 30
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30
```

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Cys Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

```
<210> SEQ ID NO 31
<211> LENGTH: 331
<212> TYPE: PRT
<213> ORGANISM: Artificial Sequence
```

<220> FEATURE:
<221> NAME/KEY: source
<223> OTHER INFORMATION: /note="Description of Artificial Sequence: Synthetic polypeptide"

<400> SEQUENCE: 31

```
Ser Ala Ser Thr Lys Gly Pro Ser Val Phe Pro Leu Ala Pro Ser Ser
1               5                   10                  15
Lys Ser Thr Ser Gly Gly Thr Ala Ala Leu Gly Cys Leu Val Lys Asp
            20                  25                  30
Tyr Phe Pro Glu Pro Val Thr Val Ser Trp Asn Ser Gly Ala Leu Thr
        35                  40                  45
Ser Gly Val His Thr Phe Pro Ala Val Leu Gln Ser Ser Gly Leu Tyr
    50                  55                  60
Ser Leu Ser Ser Val Val Thr Val Pro Ser Ser Ser Leu Gly Thr Gln
65                  70                  75                  80
Thr Tyr Ile Cys Asn Val Asn His Lys Pro Ser Asn Thr Lys Val Asp
                85                  90                  95
Lys Lys Val Glu Pro Lys Ser Cys Asp Lys Thr His Thr Cys Pro Pro
            100                 105                 110
Cys Pro Ala Pro Glu Leu Leu Gly Gly Pro Ser Val Phe Leu Phe Pro
        115                 120                 125
Pro Lys Pro Lys Asp Thr Leu Met Ile Ser Arg Thr Pro Glu Val Thr
130                 135                 140
Cys Val Val Val Asp Val Ser His Glu Asp Pro Glu Val Cys Phe Asn
145                 150                 155                 160
Trp Tyr Val Asp Gly Val Glu Val His Asn Ala Lys Thr Lys Pro Arg
                165                 170                 175
Glu Glu Gln Tyr Asn Ser Thr Tyr Arg Val Val Ser Val Leu Thr Val
            180                 185                 190
Leu His Gln Asp Trp Leu Asn Gly Lys Glu Tyr Lys Cys Lys Val Ser
        195                 200                 205
Asn Lys Ala Leu Pro Ala Pro Ile Glu Lys Thr Ile Ser Lys Ala Lys
    210                 215                 220
Gly Gln Pro Arg Glu Pro Gln Val Tyr Thr Leu Pro Pro Ser Arg Glu
225                 230                 235                 240
Glu Met Thr Lys Asn Gln Val Ser Leu Thr Cys Leu Val Lys Gly Phe
                245                 250                 255
Tyr Pro Ser Asp Ile Ala Val Glu Trp Glu Ser Asn Gly Gln Pro Glu
            260                 265                 270
Asn Asn Tyr Lys Thr Thr Pro Pro Val Leu Asp Ser Asp Gly Ser Phe
        275                 280                 285
Phe Leu Tyr Ser Lys Leu Thr Val Asp Lys Ser Arg Trp Gln Gln Gly
    290                 295                 300
Asn Val Phe Ser Cys Ser Val Met His Glu Ala Leu His Asn His Tyr
305                 310                 315                 320
Thr Gln Lys Ser Leu Ser Leu Ser Pro Gly Lys
                325                 330
```

<210> SEQ ID NO 32
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

-continued

<400> SEQUENCE: 32

```
Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Cys Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330
```

<210> SEQ ID NO 33
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 33

Ser Ala Ser Thr Lys Gly Pro Ser Val Phe Pro Leu Ala Pro Ser Ser

```
            1               5                  10                 15
Lys Ser Thr Ser Gly Gly Thr Ala Ala Leu Gly Cys Leu Val Lys Asp
            20                 25                 30

Tyr Phe Pro Glu Pro Val Thr Val Ser Trp Asn Ser Gly Ala Leu Thr
            35                 40                 45

Ser Gly Val His Thr Phe Pro Ala Val Leu Gln Ser Ser Gly Leu Tyr
            50                 55                 60

Ser Leu Ser Ser Val Val Thr Val Pro Ser Ser Ser Leu Gly Thr Gln
 65                 70                 75                 80

Thr Tyr Ile Cys Asn Val Asn His Lys Pro Ser Asn Thr Lys Val Asp
                    85                 90                 95

Lys Lys Val Glu Pro Lys Ser Cys Asp Lys Thr His Thr Cys Pro Pro
                100                105                110

Cys Pro Ala Pro Glu Leu Leu Gly Gly Pro Ser Val Phe Leu Phe Pro
                115                120                125

Pro Lys Pro Lys Asp Thr Leu Met Ile Ser Arg Thr Pro Glu Val Thr
            130                135                140

Cys Val Val Val Asp Val Ser His Glu Asp Pro Glu Val Lys Phe Asn
145                150                155                160

Trp Tyr Val Asp Gly Val Glu Val His Asn Ala Cys Thr Lys Pro Arg
                165                170                175

Glu Glu Gln Tyr Asn Ser Thr Tyr Arg Val Val Ser Val Leu Thr Val
                180                185                190

Leu His Gln Asp Trp Leu Asn Gly Lys Glu Tyr Lys Cys Lys Val Ser
            195                200                205

Asn Lys Ala Leu Pro Ala Pro Ile Glu Lys Thr Ile Ser Lys Ala Lys
            210                215                220

Gly Gln Pro Arg Glu Pro Gln Val Tyr Thr Leu Pro Pro Ser Arg Glu
225                230                235                240

Glu Met Thr Lys Asn Gln Val Ser Leu Thr Cys Leu Val Lys Gly Phe
                245                250                255

Tyr Pro Ser Asp Ile Ala Val Glu Trp Glu Ser Asn Gly Gln Pro Glu
                260                265                270

Asn Asn Tyr Lys Thr Thr Pro Pro Val Leu Asp Ser Asp Gly Ser Phe
            275                280                285

Phe Leu Tyr Ser Lys Leu Thr Val Asp Lys Ser Arg Trp Gln Gln Gly
            290                295                300

Asn Val Phe Ser Cys Ser Val Met His Glu Ala Leu His Asn His Tyr
305                310                315                320

Thr Gln Lys Ser Leu Ser Leu Ser Pro Gly Lys
                325                330

<210> SEQ ID NO 34
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Ser Ala Ser Thr Lys Gly Pro Ser Val Phe Pro Leu Ala Pro Ser Ser
 1               5                 10                 15

Lys Ser Thr Ser Gly Gly Thr Ala Ala Leu Gly Cys Leu Val Lys Asp
            20                 25                 30
```

Tyr Phe Pro Glu Pro Val Thr Val Ser Trp Asn Ser Gly Ala Leu Thr
            35                  40                  45

Ser Gly Val His Thr Phe Pro Ala Val Leu Gln Ser Ser Gly Leu Tyr
        50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Cys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 35
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

```
Ser Gly Val His Thr Phe Pro Ala Val Leu Gln Ser Ser Gly Leu Tyr
 50                  55                  60

Ser Leu Ser Ser Val Val Thr Val Pro Ser Ser Ser Leu Gly Thr Gln
 65                  70                  75                  80

Thr Tyr Ile Cys Asn Val Asn His Lys Pro Ser Asn Thr Lys Val Asp
                 85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
            115                 120                 125

Pro Lys Pro Lys Asp Thr Leu Met Ile Ser Arg Thr Pro Glu Val Thr
            130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Cys
                165                 170                 175

Glu Glu Gln Tyr Asn Ser Thr Tyr Arg Val Val Ser Val Leu Thr Val
                180                 185                 190

Leu His Gln Asp Trp Leu Asn Gly Lys Glu Tyr Lys Cys Lys Val Ser
                195                 200                 205

Asn Lys Ala Leu Pro Ala Pro Ile Glu Lys Thr Ile Ser Lys Ala Lys
210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
                260                 265                 270

Asn Asn Tyr Lys Thr Thr Pro Pro Val Leu Asp Ser Asp Gly Ser Phe
            275                 280                 285

Phe Leu Tyr Ser Lys Leu Thr Val Asp Lys Ser Arg Trp Gln Gln Gly
            290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 36
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Ser Ala Ser Thr Lys Gly Pro Ser Val Phe Pro Leu Ala Pro Ser Ser
 1               5                  10                  15

Lys Ser Thr Ser Gly Gly Thr Ala Ala Leu Gly Cys Leu Val Lys Asp
             20                  25                  30

Tyr Phe Pro Glu Pro Val Thr Val Ser Trp Asn Ser Gly Ala Leu Thr
             35                  40                  45

Ser Gly Val His Thr Phe Pro Ala Val Leu Gln Ser Ser Gly Leu Tyr
 50                  55                  60

Ser Leu Ser Ser Val Val Thr Val Pro Ser Ser Ser Leu Gly Thr Gln
```

```
                65                  70                  75                  80
        Thr Tyr Ile Cys Asn Val Asn His Lys Pro Ser Asn Thr Lys Val Asp
                        85                  90                  95
        Lys Lys Val Glu Pro Lys Ser Cys Asp Lys Thr His Thr Cys Pro Pro
                        100                 105                 110
        Cys Pro Ala Pro Glu Leu Leu Gly Gly Pro Ser Val Phe Leu Phe Pro
                        115                 120                 125
        Pro Lys Pro Lys Asp Thr Leu Met Ile Ser Arg Thr Pro Glu Val Thr
                130                 135                 140
        Cys Val Val Val Asp Val Ser His Glu Asp Pro Glu Val Lys Phe Asn
        145                 150                 155                 160
        Trp Tyr Val Asp Gly Val Glu Val His Asn Ala Lys Thr Lys Pro Arg
                        165                 170                 175
        Cys Glu Gln Tyr Asn Ser Thr Tyr Arg Val Val Ser Val Leu Thr Val
                        180                 185                 190
        Leu His Gln Asp Trp Leu Asn Gly Lys Glu Tyr Lys Cys Lys Val Ser
                        195                 200                 205
        Asn Lys Ala Leu Pro Ala Pro Ile Glu Lys Thr Ile Ser Lys Ala Lys
                210                 215                 220
        Gly Gln Pro Arg Glu Pro Gln Val Tyr Thr Leu Pro Pro Ser Arg Glu
        225                 230                 235                 240
        Glu Met Thr Lys Asn Gln Val Ser Leu Thr Cys Leu Val Lys Gly Phe
                        245                 250                 255
        Tyr Pro Ser Asp Ile Ala Val Glu Trp Glu Ser Asn Gly Gln Pro Glu
                        260                 265                 270
        Asn Asn Tyr Lys Thr Thr Pro Pro Val Leu Asp Ser Asp Gly Ser Phe
                        275                 280                 285
        Phe Leu Tyr Ser Lys Leu Thr Val Asp Lys Ser Arg Trp Gln Gln Gly
                290                 295                 300
        Asn Val Phe Ser Cys Ser Val Met His Glu Ala Leu His Asn His Tyr
        305                 310                 315                 320
        Thr Gln Lys Ser Leu Ser Leu Ser Pro Gly Lys
                        325                 330

<210> SEQ ID NO 37
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Ser Ala Ser Thr Lys Gly Pro Ser Val Phe Pro Leu Ala Pro Ser Ser
        1               5                   10                  15
        Lys Ser Thr Ser Gly Gly Thr Ala Ala Leu Gly Cys Leu Val Lys Asp
                        20                  25                  30
        Tyr Phe Pro Glu Pro Val Thr Val Ser Trp Asn Ser Gly Ala Leu Thr
                        35                  40                  45
        Ser Gly Val His Thr Phe Pro Ala Val Leu Gln Ser Ser Gly Leu Tyr
                        50                  55                  60
        Ser Leu Ser Ser Val Val Thr Val Pro Ser Ser Ser Leu Gly Thr Gln
        65                  70                  75                  80
        Thr Tyr Ile Cys Asn Val Asn His Lys Pro Ser Asn Thr Lys Val Asp
                        85                  90                  95
```

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Cys Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 38
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

```
Cys Pro Ala Pro Glu Leu Leu Gly Gly Pro Ser Val Phe Leu Phe Pro
            115                 120                 125

Pro Lys Pro Lys Asp Thr Leu Met Ile Ser Arg Thr Pro Glu Val Thr
        130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Cys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 39
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
```

```
            130                 135                 140
Cys Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
                180                 185                 190

Leu His Gln Asp Trp Leu Asn Gly Lys Glu Tyr Lys Cys Cys Val Ser
                195                 200                 205

Asn Lys Ala Leu Pro Ala Pro Ile Glu Lys Thr Ile Ser Lys Ala Lys
                210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
                260                 265                 270

Asn Asn Tyr Lys Thr Thr Pro Pro Val Leu Asp Ser Asp Gly Ser Phe
                275                 280                 285

Phe Leu Tyr Ser Lys Leu Thr Val Asp Lys Ser Arg Trp Gln Gln Gly
                290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 40
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
                20                  25                  30

Tyr Phe Pro Glu Pro Val Thr Val Ser Trp Asn Ser Gly Ala Leu Thr
            35                  40                  45

Ser Gly Val His Thr Phe Pro Ala Val Leu Gln Ser Ser Gly Leu Tyr
        50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160
```

```
Trp Tyr Val Asp Gly Val Glu Val His Asn Ala Lys Thr Lys Pro Arg
            165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
            195                 200                 205

Asn Cys Ala Leu Pro Ala Pro Ile Glu Lys Thr Ile Ser Lys Ala Lys
        210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
            245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
            275                 280                 285

Phe Leu Tyr Ser Lys Leu Thr Val Asp Lys Ser Arg Trp Gln Gln Gly
        290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
            325                 330

<210> SEQ ID NO 41
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
            85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
            165                 170                 175
```

```
Glu Glu Gln Tyr Asn Ser Thr Tyr Arg Val Val Ser Val Leu Thr Val
                180                 185                 190

Leu His Gln Asp Trp Leu Asn Gly Lys Glu Tyr Lys Cys Lys Val Ser
            195                 200                 205

Asn Lys Ala Leu Pro Cys Pro Ile Glu Lys Thr Ile Ser Lys Ala Lys
        210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 42
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
```

```
            195                 200                 205

Asn Lys Ala Leu Pro Ala Pro Ile Cys Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 43
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
                20                  25                  30

Tyr Phe Pro Glu Pro Val Thr Val Ser Trp Asn Ser Gly Ala Leu Thr
            35                  40                  45

Ser Gly Val His Thr Phe Pro Ala Val Leu Gln Ser Ser Gly Leu Tyr
        50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Cys Thr Ile Ser Lys Ala Lys
    210                 215                 220
```

```
Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
            245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
            275                 280                 285

Phe Leu Tyr Ser Lys Leu Thr Val Asp Lys Ser Arg Trp Gln Gln Gly
290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
            325                 330
```

<210> SEQ ID NO 44
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 44

```
Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
            35                  40                  45

Ser Gly Val His Thr Phe Pro Ala Val Leu Gln Ser Ser Gly Leu Tyr
50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
            85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
            115                 120                 125

Pro Lys Pro Lys Asp Thr Leu Met Ile Ser Arg Thr Pro Glu Val Thr
130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
            165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
            195                 200                 205

Asn Lys Ala Leu Pro Ala Pro Ile Glu Lys Cys Ile Ser Lys Ala Lys
            210                 215                 220

Gly Gln Pro Arg Glu Pro Gln Val Tyr Thr Leu Pro Pro Ser Arg Glu
225                 230                 235                 240
```

```
Glu Met Thr Lys Asn Gln Val Ser Leu Thr Cys Leu Val Lys Gly Phe
                    245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
                275                 280                 285

Phe Leu Tyr Ser Lys Leu Thr Val Asp Lys Ser Arg Trp Gln Gln Gly
            290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 45
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
                20                  25                  30

Tyr Phe Pro Glu Pro Val Thr Val Ser Trp Asn Ser Gly Ala Leu Thr
            35                  40                  45

Ser Gly Val His Thr Phe Pro Ala Val Leu Gln Ser Ser Gly Leu Tyr
        50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Cys Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
```

```
                    260                 265                 270
Asn Asn Tyr Lys Thr Thr Pro Pro Val Leu Asp Ser Asp Gly Ser Phe
                275                 280                 285
Phe Leu Tyr Ser Lys Leu Thr Val Asp Lys Ser Arg Trp Gln Gln Gly
                290                 295                 300
Asn Val Phe Ser Cys Ser Val Met His Glu Ala Leu His Asn His Tyr
305                 310                 315                 320
Thr Gln Lys Ser Leu Ser Leu Ser Pro Gly Lys
                325                 330

<210> SEQ ID NO 46
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Ser Ala Ser Thr Lys Gly Pro Ser Val Phe Pro Leu Ala Pro Ser Ser
1               5                   10                  15
Lys Ser Thr Ser Gly Gly Thr Ala Ala Leu Gly Cys Leu Val Lys Asp
                20                  25                  30
Tyr Phe Pro Glu Pro Val Thr Val Ser Trp Asn Ser Gly Ala Leu Thr
            35                  40                  45
Ser Gly Val His Thr Phe Pro Ala Val Leu Gln Ser Ser Gly Leu Tyr
        50                  55                  60
Ser Leu Ser Ser Val Val Thr Val Pro Ser Ser Ser Leu Gly Thr Gln
65                  70                  75                  80
Thr Tyr Ile Cys Asn Val Asn His Lys Pro Ser Asn Thr Lys Val Asp
                85                  90                  95
Lys Lys Val Glu Pro Lys Ser Cys Asp Lys Thr His Thr Cys Pro Pro
            100                 105                 110
Cys Pro Ala Pro Glu Leu Leu Gly Gly Pro Ser Val Phe Leu Phe Pro
        115                 120                 125
Pro Lys Pro Lys Asp Thr Leu Met Ile Ser Arg Thr Pro Glu Val Thr
130                 135                 140
Cys Val Val Val Asp Val Ser His Glu Asp Pro Glu Val Lys Phe Asn
145                 150                 155                 160
Trp Tyr Val Asp Gly Val Glu Val His Asn Ala Lys Thr Lys Pro Arg
                165                 170                 175
Glu Glu Gln Tyr Asn Ser Thr Tyr Arg Val Val Ser Val Leu Thr Val
            180                 185                 190
Leu His Gln Asp Trp Leu Asn Gly Lys Glu Tyr Lys Cys Lys Val Ser
        195                 200                 205
Asn Lys Ala Leu Pro Ala Pro Ile Glu Lys Thr Ile Ser Lys Ala Lys
    210                 215                 220
Gly Gln Pro Cys Glu Pro Gln Val Tyr Thr Leu Pro Pro Ser Arg Glu
225                 230                 235                 240
Glu Met Thr Lys Asn Gln Val Ser Leu Thr Cys Leu Val Lys Gly Phe
                245                 250                 255
Tyr Pro Ser Asp Ile Ala Val Glu Trp Glu Ser Asn Gly Gln Pro Glu
            260                 265                 270
Asn Asn Tyr Lys Thr Thr Pro Pro Val Leu Asp Ser Asp Gly Ser Phe
        275                 280                 285
```

Phe Leu Tyr Ser Lys Leu Thr Val Asp Lys Ser Arg Trp Gln Gln Gly
                290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 47
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
                20                  25                  30

Tyr Phe Pro Glu Pro Val Thr Val Ser Trp Asn Ser Gly Ala Leu Thr
            35                  40                  45

Ser Gly Val His Thr Phe Pro Ala Val Leu Gln Ser Ser Gly Leu Tyr
        50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
210                 215                 220

Gly Gln Pro Arg Glu Pro Gln Val Tyr Thr Leu Pro Pro Ser Cys Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
290                 295                 300

```
Asn Val Phe Ser Cys Ser Val Met His Glu Ala Leu His Asn His Tyr
305                 310                 315                 320

Thr Gln Lys Ser Leu Ser Leu Ser Pro Gly Lys
            325                 330
```

<210> SEQ ID NO 48
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

```
Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
210                 215                 220

Gly Gln Pro Arg Glu Pro Gln Val Tyr Thr Leu Pro Pro Ser Arg Glu
225                 230                 235                 240

Glu Met Thr Cys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
            325                 330
```

325           330

<210> SEQ ID NO 49
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Cys Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 50

<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 50

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Cys Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 51
<211> LENGTH: 331
<212> TYPE: PRT
<213> ORGANISM: Artificial Sequence
<220> FEATURE:

<221> NAME/KEY: source
<223> OTHER INFORMATION: /note="Description of Artificial Sequence: Synthetic polypeptide"

<400> SEQUENCE: 51

```
Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Cys Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330
```

<210> SEQ ID NO 52
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 52

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Cys Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 53
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Cys Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 54
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 54

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
            35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
            115                 120                 125

Pro Lys Pro Lys Asp Thr Leu Met Ile Ser Arg Thr Pro Glu Val Thr
        130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Cys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 55
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 55

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
            35                  40                  45

Ser Gly Val His Thr Phe Pro Ala Val Leu Gln Ser Ser Gly Leu Tyr

```
                 50                  55                  60
Ser Leu Ser Ser Val Val Thr Val Pro Ser Ser Leu Gly Thr Gln
 65                  70                  75                  80

Thr Tyr Ile Cys Asn Val Asn His Lys Pro Ser Asn Thr Lys Val Asp
                 85                  90                  95

Lys Lys Val Glu Pro Lys Ser Cys Asp Lys Thr His Thr Cys Pro Pro
                100                 105                 110

Cys Pro Ala Pro Glu Leu Leu Gly Gly Pro Ser Val Phe Leu Phe Pro
                115                 120                 125

Pro Lys Pro Lys Asp Thr Leu Met Ile Ser Arg Thr Pro Glu Val Thr
                130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
                180                 185                 190

Leu His Gln Asp Trp Leu Asn Gly Lys Glu Tyr Lys Cys Lys Val Ser
                195                 200                 205

Asn Lys Ala Leu Pro Ala Pro Ile Glu Lys Thr Ile Ser Lys Ala Lys
                210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
                260                 265                 270

Asn Asn Tyr Lys Cys Thr Pro Pro Val Leu Asp Ser Asp Gly Ser Phe
                275                 280                 285

Phe Leu Tyr Ser Lys Leu Thr Val Asp Lys Ser Arg Trp Gln Gln Gly
                290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 56
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56

Ser Ala Ser Thr Lys Gly Pro Ser Val Phe Pro Leu Ala Pro Ser Ser
 1                   5                  10                  15

Lys Ser Thr Ser Gly Gly Thr Ala Ala Leu Gly Cys Leu Val Lys Asp
                 20                  25                  30

Tyr Phe Pro Glu Pro Val Thr Val Ser Trp Asn Ser Gly Ala Leu Thr
                 35                  40                  45

Ser Gly Val His Thr Phe Pro Ala Val Leu Gln Ser Ser Gly Leu Tyr
     50                  55                  60

Ser Leu Ser Ser Val Val Thr Val Pro Ser Ser Ser Leu Gly Thr Gln
 65                  70                  75                  80
```

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Cys Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 57
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 57

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

```
Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Cys Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 58
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
```

```
            115                 120                 125
Pro Lys Pro Lys Asp Thr Leu Met Ile Ser Arg Thr Pro Glu Val Thr
            130                 135                 140

Cys Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                    165                 170                 175

Glu Glu Gln Tyr Asn Ser Thr Tyr Arg Val Val Ser Val Leu Thr Val
                180                 185                 190

Leu His Gln Asp Trp Leu Asn Gly Lys Glu Tyr Lys Cys Lys Val Ser
            195                 200                 205

Asn Lys Ala Leu Pro Ala Pro Ile Glu Lys Thr Ile Ser Lys Ala Lys
            210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
                260                 265                 270

Asn Asn Tyr Lys Thr Thr Pro Pro Val Leu Asp Ser Asp Gly Ser Phe
            275                 280                 285

Phe Leu Tyr Ser Lys Leu Thr Val Cys Lys Ser Arg Trp Gln Gln Gly
            290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 59
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 59

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
                20                  25                  30

Tyr Phe Pro Glu Pro Val Thr Val Ser Trp Asn Ser Gly Ala Leu Thr
            35                  40                  45

Ser Gly Val His Thr Phe Pro Ala Val Leu Gln Ser Ser Gly Leu Tyr
        50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140
```

```
Cys Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
                260                 265                 270

Asn Asn Tyr Lys Thr Thr Pro Pro Val Leu Asp Ser Asp Gly Ser Phe
            275                 280                 285

Phe Leu Tyr Ser Lys Leu Thr Val Asp Lys Cys Arg Trp Gln Gln Gly
        290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 60
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 60

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160
```

```
Trp Tyr Val Asp Gly Val Glu Val His Asn Ala Lys Thr Lys Pro Arg
                165                 170                 175
Glu Glu Gln Tyr Asn Ser Thr Tyr Arg Val Val Ser Val Leu Thr Val
            180                 185                 190
Leu His Gln Asp Trp Leu Asn Gly Lys Glu Tyr Lys Cys Lys Val Ser
        195                 200                 205
Asn Lys Ala Leu Pro Ala Pro Ile Glu Lys Thr Ile Ser Lys Ala Lys
    210                 215                 220
Gly Gln Pro Arg Glu Pro Gln Val Tyr Thr Leu Pro Pro Ser Arg Glu
225                 230                 235                 240
Glu Met Thr Lys Asn Gln Val Ser Leu Thr Cys Leu Val Lys Gly Phe
                245                 250                 255
Tyr Pro Ser Asp Ile Ala Val Glu Trp Glu Ser Asn Gly Gln Pro Glu
            260                 265                 270
Asn Asn Tyr Lys Thr Thr Pro Pro Val Leu Asp Ser Asp Gly Ser Phe
        275                 280                 285
Phe Leu Tyr Ser Lys Leu Thr Val Asp Lys Ser Arg Trp Gln Gln Gly
    290                 295                 300
Asn Cys Phe Ser Cys Ser Val Met His Glu Ala Leu His Asn His Tyr
305                 310                 315                 320
Thr Gln Lys Ser Leu Ser Leu Ser Pro Gly Lys
                325                 330

<210> SEQ ID NO 61
<211> LENGTH: 108
<212> TYPE: PRT
<213> ORGANISM: Homo sapiens

<400> SEQUENCE: 61

Cys Arg Thr Val Ala Ala Pro Ser Val Phe Ile Phe Pro Pro Ser Asp
1               5                   10                  15
Glu Gln Leu Lys Ser Gly Thr Ala Ser Val Val Cys Leu Leu Asn Asn
            20                  25                  30
Phe Tyr Pro Arg Glu Ala Lys Val Gln Trp Lys Val Asp Asn Ala Leu
        35                  40                  45
Gln Ser Gly Asn Ser Gln Glu Ser Val Thr Glu Gln Asp Ser Lys Asp
    50                  55                  60
Ser Thr Tyr Ser Leu Ser Ser Thr Leu Thr Leu Ser Lys Ala Asp Tyr
65                  70                  75                  80
Glu Lys His Lys Val Tyr Ala Cys Glu Val Thr His Gln Gly Leu Ser
                85                  90                  95
Ser Pro Val Thr Lys Ser Phe Asn Arg Gly Glu Cys
            100                 105

<210> SEQ ID NO 62
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 62

Lys Cys Thr Val Ala Ala Pro Ser Val Phe Ile Phe Pro Pro Ser Asp
1               5                   10                  15
Glu Gln Leu Lys Ser Gly Thr Ala Ser Val Val Cys Leu Leu Asn Asn
            20                  25                  30
```

```
Phe Tyr Pro Arg Glu Ala Lys Val Gln Trp Lys Val Asp Asn Ala Leu
            35                  40                  45

Gln Ser Gly Asn Ser Gln Glu Ser Val Thr Glu Gln Asp Ser Lys Asp
        50                  55                  60

Ser Thr Tyr Ser Leu Ser Ser Thr Leu Thr Leu Ser Lys Ala Asp Tyr
 65                  70                  75                  80

Glu Lys His Lys Val Tyr Ala Cys Glu Val Thr His Gln Gly Leu Ser
                85                  90                  95

Ser Pro Val Thr Lys Ser Phe Asn Arg Gly Glu Cys
               100                 105

<210> SEQ ID NO 63
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 63

Lys Arg Cys Val Ala Ala Pro Ser Val Phe Ile Phe Pro Pro Ser Asp
 1               5                  10                  15

Glu Gln Leu Lys Ser Gly Thr Ala Ser Val Val Cys Leu Leu Asn Asn
            20                  25                  30

Phe Tyr Pro Arg Glu Ala Lys Val Gln Trp Lys Val Asp Asn Ala Leu
            35                  40                  45

Gln Ser Gly Asn Ser Gln Glu Ser Val Thr Glu Gln Asp Ser Lys Asp
        50                  55                  60

Ser Thr Tyr Ser Leu Ser Ser Thr Leu Thr Leu Ser Lys Ala Asp Tyr
 65                  70                  75                  80

Glu Lys His Lys Val Tyr Ala Cys Glu Val Thr His Gln Gly Leu Ser
                85                  90                  95

Ser Pro Val Thr Lys Ser Phe Asn Arg Gly Glu Cys
               100                 105

<210> SEQ ID NO 64
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 64

Lys Arg Thr Val Ala Cys Pro Ser Val Phe Ile Phe Pro Pro Ser Asp
 1               5                  10                  15

Glu Gln Leu Lys Ser Gly Thr Ala Ser Val Val Cys Leu Leu Asn Asn
            20                  25                  30

Phe Tyr Pro Arg Glu Ala Lys Val Gln Trp Lys Val Asp Asn Ala Leu
            35                  40                  45

Gln Ser Gly Asn Ser Gln Glu Ser Val Thr Glu Gln Asp Ser Lys Asp
        50                  55                  60

Ser Thr Tyr Ser Leu Ser Ser Thr Leu Thr Leu Ser Lys Ala Asp Tyr
 65                  70                  75                  80

Glu Lys His Lys Val Tyr Ala Cys Glu Val Thr His Gln Gly Leu Ser
                85                  90                  95
```

Ser Pro Val Thr Lys Ser Phe Asn Arg Gly Glu Cys
            100                 105

<210> SEQ ID NO 65
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 65

Lys Arg Thr Val Ala Ala Pro Cys Val Phe Ile Phe Pro Pro Ser Asp
1               5                   10                  15

Glu Gln Leu Lys Ser Gly Thr Ala Ser Val Val Cys Leu Leu Asn Asn
            20                  25                  30

Phe Tyr Pro Arg Glu Ala Lys Val Gln Trp Lys Val Asp Asn Ala Leu
        35                  40                  45

Gln Ser Gly Asn Ser Gln Glu Ser Val Thr Glu Gln Asp Ser Lys Asp
    50                  55                  60

Ser Thr Tyr Ser Leu Ser Ser Thr Leu Thr Leu Ser Lys Ala Asp Tyr
65                  70                  75                  80

Glu Lys His Lys Val Tyr Ala Cys Glu Val Thr His Gln Gly Leu Ser
                85                  90                  95

Ser Pro Val Thr Lys Ser Phe Asn Arg Gly Glu Cys
            100                 105

<210> SEQ ID NO 66
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 66

Lys Arg Thr Val Ala Ala Pro Ser Val Phe Ile Phe Pro Pro Ser Cys
1               5                   10                  15

Glu Gln Leu Lys Ser Gly Thr Ala Ser Val Val Cys Leu Leu Asn Asn
            20                  25                  30

Phe Tyr Pro Arg Glu Ala Lys Val Gln Trp Lys Val Asp Asn Ala Leu
        35                  40                  45

Gln Ser Gly Asn Ser Gln Glu Ser Val Thr Glu Gln Asp Ser Lys Asp
    50                  55                  60

Ser Thr Tyr Ser Leu Ser Ser Thr Leu Thr Leu Ser Lys Ala Asp Tyr
65                  70                  75                  80

Glu Lys His Lys Val Tyr Ala Cys Glu Val Thr His Gln Gly Leu Ser
                85                  90                  95

Ser Pro Val Thr Lys Ser Phe Asn Arg Gly Glu Cys
            100                 105

<210> SEQ ID NO 67
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 67

Lys Arg Thr Val Ala Ala Pro Ser Val Phe Ile Phe Pro Pro Ser Asp
1               5                   10                  15

Cys Gln Leu Lys Ser Gly Thr Ala Ser Val Val Cys Leu Leu Asn Asn
            20                  25                  30

Phe Tyr Pro Arg Glu Ala Lys Val Gln Trp Lys Val Asp Asn Ala Leu
        35                  40                  45

Gln Ser Gly Asn Ser Gln Glu Ser Val Thr Gln Asp Ser Lys Asp
    50                  55                  60

Ser Thr Tyr Ser Leu Ser Ser Thr Leu Thr Leu Ser Lys Ala Asp Tyr
65                  70                  75                  80

Glu Lys His Lys Val Tyr Ala Cys Glu Val Thr His Gln Gly Leu Ser
                85                  90                  95

Ser Pro Val Thr Lys Ser Phe Asn Arg Gly Glu Cys
                100                 105

<210> SEQ ID NO 68
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 68

Lys Arg Thr Val Ala Ala Pro Ser Val Phe Ile Phe Pro Pro Ser Asp
1               5                   10                  15

Glu Gln Leu Lys Ser Gly Cys Ala Ser Val Val Cys Leu Leu Asn Asn
            20                  25                  30

Phe Tyr Pro Arg Glu Ala Lys Val Gln Trp Lys Val Asp Asn Ala Leu
        35                  40                  45

Gln Ser Gly Asn Ser Gln Glu Ser Val Thr Gln Asp Ser Lys Asp
    50                  55                  60

Ser Thr Tyr Ser Leu Ser Ser Thr Leu Thr Leu Ser Lys Ala Asp Tyr
65                  70                  75                  80

Glu Lys His Lys Val Tyr Ala Cys Glu Val Thr His Gln Gly Leu Ser
                85                  90                  95

Ser Pro Val Thr Lys Ser Phe Asn Arg Gly Glu Cys
                100                 105

<210> SEQ ID NO 69
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 69

Lys Arg Thr Val Ala Ala Pro Ser Val Phe Ile Phe Pro Pro Ser Asp
1               5                   10                  15

Glu Gln Leu Lys Ser Gly Thr Ala Ser Val Val Cys Leu Leu Asn Asn
            20                  25                  30

Phe Tyr Pro Cys Glu Ala Lys Val Gln Trp Lys Val Asp Asn Ala Leu
        35                  40                  45

Gln Ser Gly Asn Ser Gln Glu Ser Val Thr Glu Gln Asp Ser Lys Asp
    50                  55                  60

Ser Thr Tyr Ser Leu Ser Ser Thr Leu Thr Leu Ser Lys Ala Asp Tyr
65                  70                  75                  80

Glu Lys His Lys Val Tyr Ala Cys Glu Val Thr His Gln Gly Leu Ser
                85                  90                  95

Ser Pro Val Thr Lys Ser Phe Asn Arg Gly Glu Cys
            100                 105

<210> SEQ ID NO 70
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 70

Lys Arg Thr Val Ala Ala Pro Ser Val Phe Ile Phe Pro Pro Ser Asp
1               5                   10                  15

Glu Gln Leu Lys Ser Gly Thr Ala Ser Val Val Cys Leu Leu Asn Asn
            20                  25                  30

Phe Tyr Pro Arg Cys Ala Lys Val Gln Trp Lys Val Asp Asn Ala Leu
        35                  40                  45

Gln Ser Gly Asn Ser Gln Glu Ser Val Thr Glu Gln Asp Ser Lys Asp
    50                  55                  60

Ser Thr Tyr Ser Leu Ser Ser Thr Leu Thr Leu Ser Lys Ala Asp Tyr
65                  70                  75                  80

Glu Lys His Lys Val Tyr Ala Cys Glu Val Thr His Gln Gly Leu Ser
                85                  90                  95

Ser Pro Val Thr Lys Ser Phe Asn Arg Gly Glu Cys
            100                 105

<210> SEQ ID NO 71
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 71

Lys Arg Thr Val Ala Ala Pro Ser Val Phe Ile Phe Pro Pro Ser Asp
1               5                   10                  15

Glu Gln Leu Lys Ser Gly Thr Ala Ser Val Val Cys Leu Leu Asn Asn
            20                  25                  30

Phe Tyr Pro Arg Glu Ala Cys Val Gln Trp Lys Val Asp Asn Ala Leu
        35                  40                  45

Gln Ser Gly Asn Ser Gln Glu Ser Val Thr Glu Gln Asp Ser Lys Asp
    50                  55                  60

Ser Thr Tyr Ser Leu Ser Ser Thr Leu Thr Leu Ser Lys Ala Asp Tyr
65                  70                  75                  80

Glu Lys His Lys Val Tyr Ala Cys Glu Val Thr His Gln Gly Leu Ser
                85                  90                  95

Ser Pro Val Thr Lys Ser Phe Asn Arg Gly Glu Cys
            100                 105

<210> SEQ ID NO 72
<211> LENGTH: 108

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 72

Lys Arg Thr Val Ala Ala Pro Ser Val Phe Ile Phe Pro Pro Ser Asp
1               5                   10                  15

Glu Gln Leu Lys Ser Gly Thr Ala Ser Val Val Cys Leu Leu Asn Asn
            20                  25                  30

Phe Tyr Pro Arg Glu Ala Lys Val Gln Trp Lys Val Asp Cys Ala Leu
        35                  40                  45

Gln Ser Gly Asn Ser Gln Glu Ser Val Thr Glu Gln Asp Ser Lys Asp
    50                  55                  60

Ser Thr Tyr Ser Leu Ser Ser Thr Leu Thr Leu Ser Lys Ala Asp Tyr
65                  70                  75                  80

Glu Lys His Lys Val Tyr Ala Cys Glu Val Thr His Gln Gly Leu Ser
                85                  90                  95

Ser Pro Val Thr Lys Ser Phe Asn Arg Gly Glu Cys
            100                 105

<210> SEQ ID NO 73
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 73

Lys Arg Thr Val Ala Ala Pro Ser Val Phe Ile Phe Pro Pro Ser Asp
1               5                   10                  15

Glu Gln Leu Lys Ser Gly Thr Ala Ser Val Val Cys Leu Leu Asn Asn
            20                  25                  30

Phe Tyr Pro Arg Glu Ala Lys Val Gln Trp Lys Val Asp Asn Ala Cys
        35                  40                  45

Gln Ser Gly Asn Ser Gln Glu Ser Val Thr Glu Gln Asp Ser Lys Asp
    50                  55                  60

Ser Thr Tyr Ser Leu Ser Ser Thr Leu Thr Leu Ser Lys Ala Asp Tyr
65                  70                  75                  80

Glu Lys His Lys Val Tyr Ala Cys Glu Val Thr His Gln Gly Leu Ser
                85                  90                  95

Ser Pro Val Thr Lys Ser Phe Asn Arg Gly Glu Cys
            100                 105

<210> SEQ ID NO 74
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 74

Lys Arg Thr Val Ala Ala Pro Ser Val Phe Ile Phe Pro Pro Ser Asp
1               5                   10                  15

Glu Gln Leu Lys Ser Gly Thr Ala Ser Val Val Cys Leu Leu Asn Asn
```

```
            20                  25                  30

Phe Tyr Pro Arg Glu Ala Lys Val Gln Trp Lys Val Asp Asn Ala Leu
            35                  40                  45

Gln Cys Gly Asn Ser Gln Glu Ser Val Thr Glu Gln Asp Ser Lys Asp
        50                  55                  60

Ser Thr Tyr Ser Leu Ser Ser Thr Leu Thr Leu Ser Lys Ala Asp Tyr
65                  70                  75                  80

Glu Lys His Lys Val Tyr Ala Cys Glu Val Thr His Gln Gly Leu Ser
                85                  90                  95

Ser Pro Val Thr Lys Ser Phe Asn Arg Gly Glu Cys
            100                 105

<210> SEQ ID NO 75
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 75

Lys Arg Thr Val Ala Ala Pro Ser Val Phe Ile Phe Pro Pro Ser Asp
1               5                   10                  15

Glu Gln Leu Lys Ser Gly Thr Ala Ser Val Val Cys Leu Leu Asn Asn
            20                  25                  30

Phe Tyr Pro Arg Glu Ala Lys Val Gln Trp Lys Val Asp Asn Ala Leu
            35                  40                  45

Gln Ser Gly Asn Cys Gln Glu Ser Val Thr Glu Gln Asp Ser Lys Asp
        50                  55                  60

Ser Thr Tyr Ser Leu Ser Ser Thr Leu Thr Leu Ser Lys Ala Asp Tyr
65                  70                  75                  80

Glu Lys His Lys Val Tyr Ala Cys Glu Val Thr His Gln Gly Leu Ser
                85                  90                  95

Ser Pro Val Thr Lys Ser Phe Asn Arg Gly Glu Cys
            100                 105

<210> SEQ ID NO 76
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 76

Lys Arg Thr Val Ala Ala Pro Ser Val Phe Ile Phe Pro Pro Ser Asp
1               5                   10                  15

Glu Gln Leu Lys Ser Gly Thr Ala Ser Val Val Cys Leu Leu Asn Asn
            20                  25                  30

Phe Tyr Pro Arg Glu Ala Lys Val Gln Trp Lys Val Asp Asn Ala Leu
            35                  40                  45

Gln Ser Gly Asn Ser Gln Cys Ser Val Thr Glu Gln Asp Ser Lys Asp
        50                  55                  60

Ser Thr Tyr Ser Leu Ser Ser Thr Leu Thr Leu Ser Lys Ala Asp Tyr
65                  70                  75                  80

Glu Lys His Lys Val Tyr Ala Cys Glu Val Thr His Gln Gly Leu Ser
                85                  90                  95
```

Ser Pro Val Thr Lys Ser Phe Asn Arg Gly Glu Cys
            100                 105

<210> SEQ ID NO 77
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 77

Lys Arg Thr Val Ala Ala Pro Ser Val Phe Ile Phe Pro Pro Ser Asp
1               5                   10                  15

Glu Gln Leu Lys Ser Gly Thr Ala Ser Val Val Cys Leu Leu Asn Asn
            20                  25                  30

Phe Tyr Pro Arg Glu Ala Lys Val Gln Trp Lys Val Asp Asn Ala Leu
        35                  40                  45

Gln Ser Gly Asn Ser Gln Glu Ser Val Thr Cys Gln Asp Ser Lys Asp
    50                  55                  60

Ser Thr Tyr Ser Leu Ser Ser Thr Leu Thr Leu Ser Lys Ala Asp Tyr
65                  70                  75                  80

Glu Lys His Lys Val Tyr Ala Cys Glu Val Thr His Gln Gly Leu Ser
                85                  90                  95

Ser Pro Val Thr Lys Ser Phe Asn Arg Gly Glu Cys
            100                 105

<210> SEQ ID NO 78
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 78

Lys Arg Thr Val Ala Ala Pro Ser Val Phe Ile Phe Pro Pro Ser Asp
1               5                   10                  15

Glu Gln Leu Lys Ser Gly Thr Ala Ser Val Val Cys Leu Leu Asn Asn
            20                  25                  30

Phe Tyr Pro Arg Glu Ala Lys Val Gln Trp Lys Val Asp Asn Ala Leu
        35                  40                  45

Gln Ser Gly Asn Ser Gln Glu Ser Val Thr Glu Gln Asp Cys Lys Asp
    50                  55                  60

Ser Thr Tyr Ser Leu Ser Ser Thr Leu Thr Leu Ser Lys Ala Asp Tyr
65                  70                  75                  80

Glu Lys His Lys Val Tyr Ala Cys Glu Val Thr His Gln Gly Leu Ser
                85                  90                  95

Ser Pro Val Thr Lys Ser Phe Asn Arg Gly Glu Cys
            100                 105

<210> SEQ ID NO 79
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 79

Lys Arg Thr Val Ala Ala Pro Ser Val Phe Ile Phe Pro Pro Ser Asp
1               5                   10                  15

Glu Gln Leu Lys Ser Gly Thr Ala Ser Val Val Cys Leu Leu Asn Asn
            20                  25                  30

Phe Tyr Pro Arg Glu Ala Lys Val Gln Trp Lys Val Asp Asn Ala Leu
        35                  40                  45

Gln Ser Gly Asn Ser Gln Glu Ser Val Thr Glu Gln Asp Ser Cys Asp
    50                  55                  60

Ser Thr Tyr Ser Leu Ser Ser Thr Leu Thr Leu Ser Lys Ala Asp Tyr
65                  70                  75                  80

Glu Lys His Lys Val Tyr Ala Cys Glu Val Thr His Gln Gly Leu Ser
                85                  90                  95

Ser Pro Val Thr Lys Ser Phe Asn Arg Gly Glu Cys
            100                 105

<210> SEQ ID NO 80
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 80

Lys Arg Thr Val Ala Ala Pro Ser Val Phe Ile Phe Pro Pro Ser Asp
1               5                   10                  15

Glu Gln Leu Lys Ser Gly Thr Ala Ser Val Val Cys Leu Leu Asn Asn
            20                  25                  30

Phe Tyr Pro Arg Glu Ala Lys Val Gln Trp Lys Val Asp Asn Ala Leu
        35                  40                  45

Gln Ser Gly Asn Ser Gln Glu Ser Val Thr Glu Gln Asp Ser Lys Cys
    50                  55                  60

Ser Thr Tyr Ser Leu Ser Ser Thr Leu Thr Leu Ser Lys Ala Asp Tyr
65                  70                  75                  80

Glu Lys His Lys Val Tyr Ala Cys Glu Val Thr His Gln Gly Leu Ser
                85                  90                  95

Ser Pro Val Thr Lys Ser Phe Asn Arg Gly Glu Cys
            100                 105

<210> SEQ ID NO 81
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 81

Lys Arg Thr Val Ala Ala Pro Ser Val Phe Ile Phe Pro Pro Ser Asp
1               5                   10                  15

Glu Gln Leu Lys Ser Gly Thr Ala Ser Val Val Cys Leu Leu Asn Asn
            20                  25                  30

Phe Tyr Pro Arg Glu Ala Lys Val Gln Trp Lys Val Asp Asn Ala Leu
        35                  40                  45

Gln Ser Gly Asn Ser Gln Glu Ser Val Thr Glu Gln Asp Ser Lys Asp

```
                50                  55                  60
Ser Thr Tyr Ser Leu Ser Ser Thr Leu Thr Leu Cys Lys Ala Asp Tyr
 65                  70                  75                  80

Glu Lys His Lys Val Tyr Ala Cys Glu Val Thr His Gln Gly Leu Ser
                 85                  90                  95

Ser Pro Val Thr Lys Ser Phe Asn Arg Gly Glu Cys
                100                 105
```

<210> SEQ ID NO 82
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 82

```
Lys Arg Thr Val Ala Ala Pro Ser Val Phe Ile Phe Pro Pro Ser Asp
  1               5                  10                  15

Glu Gln Leu Lys Ser Gly Thr Ala Ser Val Val Cys Leu Leu Asn Asn
                 20                  25                  30

Phe Tyr Pro Arg Glu Ala Lys Val Gln Trp Lys Val Asp Asn Ala Leu
                 35                  40                  45

Gln Ser Gly Asn Ser Gln Glu Ser Val Thr Gln Asp Ser Lys Asp
 50                  55                  60

Ser Thr Tyr Ser Leu Ser Ser Thr Leu Thr Leu Ser Cys Ala Asp Tyr
 65                  70                  75                  80

Glu Lys His Lys Val Tyr Ala Cys Glu Val Thr His Gln Gly Leu Ser
                 85                  90                  95

Ser Pro Val Thr Lys Ser Phe Asn Arg Gly Glu Cys
                100                 105
```

<210> SEQ ID NO 83
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 83

```
Lys Arg Thr Val Ala Ala Pro Ser Val Phe Ile Phe Pro Pro Ser Asp
  1               5                  10                  15

Glu Gln Leu Lys Ser Gly Thr Ala Ser Val Val Cys Leu Leu Asn Asn
                 20                  25                  30

Phe Tyr Pro Arg Glu Ala Lys Val Gln Trp Lys Val Asp Asn Ala Leu
                 35                  40                  45

Gln Ser Gly Asn Ser Gln Glu Ser Val Thr Gln Asp Ser Lys Asp
 50                  55                  60

Ser Thr Tyr Ser Leu Ser Ser Thr Leu Thr Leu Ser Lys Ala Asp Tyr
 65                  70                  75                  80

Glu Cys His Lys Val Tyr Ala Cys Glu Val Thr His Gln Gly Leu Ser
                 85                  90                  95

Ser Pro Val Thr Lys Ser Phe Asn Arg Gly Glu Cys
                100                 105
```

<210> SEQ ID NO 84

```
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 84
```

Lys Arg Thr Val Ala Ala Pro Ser Val Phe Ile Phe Pro Pro Ser Asp
1               5                   10                  15

Glu Gln Leu Lys Ser Gly Thr Ala Ser Val Val Cys Leu Leu Asn Asn
            20                  25                  30

Phe Tyr Pro Arg Glu Ala Lys Val Gln Trp Lys Val Asp Asn Ala Leu
        35                  40                  45

Gln Ser Gly Asn Ser Gln Glu Ser Val Thr Glu Gln Asp Ser Lys Asp
    50                  55                  60

Ser Thr Tyr Ser Leu Ser Ser Thr Leu Thr Leu Ser Lys Ala Asp Tyr
65                  70                  75                  80

Glu Lys His Cys Val Tyr Ala Cys Glu Val Thr His Gln Gly Leu Ser
                85                  90                  95

Ser Pro Val Thr Lys Ser Phe Asn Arg Gly Glu Cys
            100                 105

```
<210> SEQ ID NO 85
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 85
```

Lys Arg Thr Val Ala Ala Pro Ser Val Phe Ile Phe Pro Pro Ser Asp
1               5                   10                  15

Glu Gln Leu Lys Ser Gly Thr Ala Ser Val Val Cys Leu Leu Asn Asn
            20                  25                  30

Phe Tyr Pro Arg Glu Ala Lys Val Gln Trp Lys Val Asp Asn Ala Leu
        35                  40                  45

Gln Ser Gly Asn Ser Gln Glu Ser Val Thr Glu Gln Asp Ser Lys Asp
    50                  55                  60

Ser Thr Tyr Ser Leu Ser Ser Thr Leu Thr Leu Ser Lys Ala Asp Tyr
65                  70                  75                  80

Glu Lys His Lys Cys Tyr Ala Cys Glu Val Thr His Gln Gly Leu Ser
                85                  90                  95

Ser Pro Val Thr Lys Ser Phe Asn Arg Gly Glu Cys
            100                 105

```
<210> SEQ ID NO 86
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 86
```

Lys Arg Thr Val Ala Ala Pro Ser Val Phe Ile Phe Pro Pro Ser Asp
1               5                   10                  15

```
Glu Gln Leu Lys Ser Gly Thr Ala Ser Val Val Cys Leu Leu Asn Asn
                20                  25                  30

Phe Tyr Pro Arg Glu Ala Lys Val Gln Trp Lys Val Asp Asn Ala Leu
            35                  40                  45

Gln Ser Gly Asn Ser Gln Glu Ser Val Thr Glu Gln Asp Ser Lys Asp
 50                  55                  60

Ser Thr Tyr Ser Leu Ser Ser Thr Leu Thr Leu Ser Lys Ala Asp Tyr
 65                  70                  75                  80

Glu Lys His Lys Val Tyr Ala Cys Glu Val Cys His Gln Gly Leu Ser
                85                  90                  95

Ser Pro Val Thr Lys Ser Phe Asn Arg Gly Glu Cys
            100                 105
```

<210> SEQ ID NO 87
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 87

```
Lys Arg Thr Val Ala Ala Pro Ser Val Phe Ile Phe Pro Pro Ser Asp
1               5                   10                  15

Glu Gln Leu Lys Ser Gly Thr Ala Ser Val Val Cys Leu Leu Asn Asn
                20                  25                  30

Phe Tyr Pro Arg Glu Ala Lys Val Gln Trp Lys Val Asp Asn Ala Leu
            35                  40                  45

Gln Ser Gly Asn Ser Gln Glu Ser Val Thr Glu Gln Asp Ser Lys Asp
 50                  55                  60

Ser Thr Tyr Ser Leu Ser Ser Thr Leu Thr Leu Ser Lys Ala Asp Tyr
 65                  70                  75                  80

Glu Lys His Lys Val Tyr Ala Cys Glu Val Thr His Cys Gly Leu Ser
                85                  90                  95

Ser Pro Val Thr Lys Ser Phe Asn Arg Gly Glu Cys
            100                 105
```

<210> SEQ ID NO 88
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 88

```
Lys Arg Thr Val Ala Ala Pro Ser Val Phe Ile Phe Pro Pro Ser Asp
1               5                   10                  15

Glu Gln Leu Lys Ser Gly Thr Ala Ser Val Val Cys Leu Leu Asn Asn
                20                  25                  30

Phe Tyr Pro Arg Glu Ala Lys Val Gln Trp Lys Val Asp Asn Ala Leu
            35                  40                  45

Gln Ser Gly Asn Ser Gln Glu Ser Val Thr Glu Gln Asp Ser Lys Asp
 50                  55                  60

Ser Thr Tyr Ser Leu Ser Ser Thr Leu Thr Leu Ser Lys Ala Asp Tyr
 65                  70                  75                  80

Glu Lys His Lys Val Tyr Ala Cys Glu Val Thr His Gln Gly Leu Ser
```

```
                        85                  90                  95

Cys Pro Val Thr Lys Ser Phe Asn Arg Gly Glu Cys
                100                 105

<210> SEQ ID NO 89
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 89

Lys Arg Thr Val Ala Ala Pro Ser Val Phe Ile Phe Pro Pro Ser Asp
1               5                   10                  15

Glu Gln Leu Lys Ser Gly Thr Ala Ser Val Val Cys Leu Leu Asn Asn
            20                  25                  30

Phe Tyr Pro Arg Glu Ala Lys Val Gln Trp Lys Val Asp Asn Ala Leu
        35                  40                  45

Gln Ser Gly Asn Ser Gln Glu Ser Val Thr Glu Gln Asp Ser Lys Asp
    50                  55                  60

Ser Thr Tyr Ser Leu Ser Ser Thr Leu Thr Leu Ser Lys Ala Asp Tyr
65                  70                  75                  80

Glu Lys His Lys Val Tyr Ala Cys Glu Val Thr His Gln Gly Leu Ser
                85                  90                  95

Ser Pro Val Cys Lys Ser Phe Asn Arg Gly Glu Cys
                100                 105

<210> SEQ ID NO 90
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160
```

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 91
<211> LENGTH: 105
<212> TYPE: PRT
<213> ORGANISM: Homo sapiens

<400> SEQUENCE: 91

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 92
<211> LENGTH: 105
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 92

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Cys Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 93
<211> LENGTH: 105
<212> TYPE: PRT

<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 93

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Cys Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 94
<211> LENGTH: 105
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 94

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Cys Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 95
<211> LENGTH: 105
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 95

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
            35                  40                  45

Cys Ala Gly Val Glu Thr Thr Thr Pro Ser Lys Gln Ser Asn Asn Lys
 50                  55                  60

Tyr Ala Ala Ser Ser Tyr Leu Ser Leu Thr Pro Glu Gln Trp Lys Ser
 65                  70                  75                  80

His Arg Ser Tyr Ser Cys Gln Val Thr His Glu Gly Ser Thr Val Glu
                 85                  90                  95

Lys Thr Val Ala Pro Thr Glu Cys Ser
            100                 105

<210> SEQ ID NO 96
<211> LENGTH: 105
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 96

Gln Pro Lys Ala Ala Pro Ser Val Thr Leu Phe Pro Pro Ser Ser Glu
 1               5                  10                  15

Glu Leu Gln Ala Asn Lys Ala Thr Leu Val Cys Leu Ile Ser Asp Phe
                20                  25                  30

Tyr Pro Gly Ala Val Thr Val Ala Trp Lys Ala Asp Ser Ser Pro Val
            35                  40                  45

Lys Ala Gly Cys Glu Thr Thr Thr Pro Ser Lys Gln Ser Asn Asn Lys
 50                  55                  60

Tyr Ala Ala Ser Ser Tyr Leu Ser Leu Thr Pro Glu Gln Trp Lys Ser
 65                  70                  75                  80

His Arg Ser Tyr Ser Cys Gln Val Thr His Glu Gly Ser Thr Val Glu
                 85                  90                  95

Lys Thr Val Ala Pro Thr Glu Cys Ser
            100                 105

<210> SEQ ID NO 97
<211> LENGTH: 105
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 97

Gln Pro Lys Ala Ala Pro Ser Val Thr Leu Phe Pro Pro Ser Ser Glu
 1               5                  10                  15

Glu Leu Gln Ala Asn Lys Ala Thr Leu Val Cys Leu Ile Ser Asp Phe
                20                  25                  30

Tyr Pro Gly Ala Val Thr Val Ala Trp Lys Ala Asp Ser Ser Pro Val
            35                  40                  45

Lys Ala Gly Val Glu Thr Thr Cys Pro Ser Lys Gln Ser Asn Asn Lys
 50                  55                  60

Tyr Ala Ala Ser Ser Tyr Leu Ser Leu Thr Pro Glu Gln Trp Lys Ser
 65                  70                  75                  80

His Arg Ser Tyr Ser Cys Gln Val Thr His Glu Gly Ser Thr Val Glu
                 85                  90                  95

```
Lys Thr Val Ala Pro Thr Glu Cys Ser
            100                 105
```

<210> SEQ ID NO 98
<211> LENGTH: 105
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 98

```
Gln Pro Lys Ala Ala Pro Ser Val Thr Leu Phe Pro Pro Ser Ser Glu
 1               5                  10                  15

Glu Leu Gln Ala Asn Lys Ala Thr Leu Val Cys Leu Ile Ser Asp Phe
                20                  25                  30

Tyr Pro Gly Ala Val Thr Val Ala Trp Lys Ala Asp Ser Ser Pro Val
            35                  40                  45

Lys Ala Gly Val Glu Thr Thr Thr Pro Ser Lys Gln Cys Asn Asn Lys
        50                  55                  60

Tyr Ala Ala Ser Ser Tyr Leu Ser Leu Thr Pro Glu Gln Trp Lys Ser
 65                 70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105
```

<210> SEQ ID NO 99
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 99

```
Met Lys Thr Phe Ile Leu Leu Leu Trp Val Leu Leu Leu Trp Val Ile
 1               5                  10                  15

Phe Leu Leu Pro Gly Ala Thr Ala
                20
```

<210> SEQ ID NO 100
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 100
gtggagatct gtcgaacggt ggccgctccc agcgtgttca                40

<210> SEQ ID NO 101
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 101

```
accgttcgac agatctccac cttggtaccc tgtccgaac                                    39
```

<210> SEQ ID NO 102
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 102

```
ggagatcaaa tgcacggtgg ccgctcccag cgtgttcatc t                                 41
```

<210> SEQ ID NO 103
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 103

```
gccaccgtgc atttgatctc caccttggta ccctgtccga                                   40
```

<210> SEQ ID NO 104
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 104

```
gatcaaacga tgtgtggccg ctcccagcgt gttcatcttc c                                 41
```

<210> SEQ ID NO 105
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 105

```
gcggccacac atcgtttgat ctccaccttg gtaccctgtc                                   40
```

<210> SEQ ID NO 106
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 106

```
acggtggcct gtcccagcgt gttcatcttc cccccagcg a                                  41
```

<210> SEQ ID NO 107
<211> LENGTH: 40
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic primer"

<400> SEQUENCE: 107
cacgctggga caggccaccg ttcgtttgat ctccaccttg                        40

<210> SEQ ID NO 108
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 108
gccgctccct gcgtgttcat cttccccccc agcgacgagc a                     41

<210> SEQ ID NO 109
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 109
atgaacacgc agggagcggc caccgttcgt tgatctcca                        40

<210> SEQ ID NO 110
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 110
cccccagctg tgagcagctg aagagcggca ccgccagcgt                       40

<210> SEQ ID NO 111
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 111
cagctgctca cagctggggg ggaagatgaa cacgctggga                       40

<210> SEQ ID NO 112
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 112
cccagcgact gtcagctgaa gagcggcacc gccagcgtg                        39
```

<210> SEQ ID NO 113
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 113
ttcagctgac agtcgctggg ggggaagatg aacacgctg                    39

<210> SEQ ID NO 114
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 114
agagcggctg tgccagcgtg gtgtgcctgc tgaacaactt                   40

<210> SEQ ID NO 115
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 115
cacgctggca cagccgctct tcagctgctc gtcgctgggg                   40

<210> SEQ ID NO 116
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 116
tctacccctg tgaggccaag gtgcagtgga aggtggacaa                   40

<210> SEQ ID NO 117
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 117
ttggcctcac aggggtagaa gttgttcagc aggcacacca                   40

<210> SEQ ID NO 118
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 118 taccccggt gtgccaaggt gcagtggaag gtggacaac                    39

<210> SEQ ID NO 119
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 119
accttggcac accgggggta gaagttgttc agcaggcaca                  40

<210> SEQ ID NO 120
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 120
cgggaggcct gcgtgcagtg gaaggtggac aacgccctgc                  40

<210> SEQ ID NO 121
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 121
cactgcacgc aggcctcccg ggggtagaag ttgttcagca                  40

<210> SEQ ID NO 122
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 122
aaggtggact gtgccctgca gagcggcaac agccaggaga                  40

<210> SEQ ID NO 123
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 123
tgcagggcac agtccacctt ccactgcacc ttggcctccc                  40

<210> SEQ ID NO 124
<211> LENGTH: 40
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic primer"

<400> SEQUENCE: 124
gacaacgcct gtcagagcgg caacagccag gagagcgtca                            40

<210> SEQ ID NO 125
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 125
tgccgctctg acaggcgttg tccaccttcc actgcacctt g                          41

<210> SEQ ID NO 126
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 126
gccctgcagt gtggcaacag ccaggagagc gtcaccgagc a                          41

<210> SEQ ID NO 127
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 127
gctgttgcca cactgcaggg cgttgtccac cttccactgc a                          41

<210> SEQ ID NO 128
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 128
agcggcaact gtcaggagag cgtcaccgag caggacagca a                          41

<210> SEQ ID NO 129
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 129
ctctcctgac agttgccgct ctgcagggcg ttgtccacct                            40
```

<210> SEQ ID NO 130
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 130
aacagccagt gcagcgtcac cgagcaggac agcaaggact                                    40

<210> SEQ ID NO 131
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 131
gtgacgctgc actggctgtt gccgctctgc agggcgttgt                                    40

<210> SEQ ID NO 132
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 132
gagcgtcacc tgtcaggaca gcaaggactc cacctacagc                                    40

<210> SEQ ID NO 133
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 133
ctgtcctgac aggtgacgct ctcctggctg ttgccgctct                                    40

<210> SEQ ID NO 134
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 134
gagcaggact gcaaggactc cacctacagc ctgagcagca                                    40

<210> SEQ ID NO 135
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 135
gagtccttgc agtcctgctc ggtgacgctc tcctggctgt                    40

<210> SEQ ID NO 136
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 136
caggacagct gtgactccac ctacagcctg agcagcacc                     39

<210> SEQ ID NO 137
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 137
gtggagtcac agctgtcctg ctcggtgacg ctctcctgg                     39

<210> SEQ ID NO 138
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 138
acagcaagta gtccacctac agcctgagca gcaccctgac                    40

<210> SEQ ID NO 139
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 139
taggtggact acttgctgtc ctgctcggtg acgctctcct                    40

<210> SEQ ID NO 140
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 140
tgaccctgtg caaggccgac tacgagaagc ataaggtgta                    40

<210> SEQ ID NO 141
<211> LENGTH: 40
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 141
gtcggccttg cacagggtca gggtgctgct caggctgtag                     40

<210> SEQ ID NO 142
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 142
gaccctgagc tgtgccgact acgagaagca taaggtgtac                     40

<210> SEQ ID NO 143
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 143
tagtcggcac agctcagggt cagggtgctg ctcaggctgt                     40

<210> SEQ ID NO 144
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 144
gactacgagt gccataaggt gtacgcctgc gaggtgac                       38

<210> SEQ ID NO 145
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 145
accttatggc actcgtagtc ggccttgctc agggtcagg                      39

<210> SEQ ID NO 146
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 146
gagaagcatt gcgtgtacgc ctgcgaggtg acccaccag                      39
```

<210> SEQ ID NO 147
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 147
ggcgtacacg caatgcttct cgtagtcggc cttgctcagg                                40

<210> SEQ ID NO 148
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 148
agcataagta gtacgcctgc gaggtgaccc accagggcct                                40

<210> SEQ ID NO 149
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 149
caggcgtact acttatgctt ctcgtagtcg gccttgctca                                40

<210> SEQ ID NO 150
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 150
gcgaggtgtg tcaccagggc ctgtccagcc ccgtgaccaa                                40

<210> SEQ ID NO 151
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 151
ccctggtgac acacctcgca ggcgtacacc ttatgcttct                                40

<210> SEQ ID NO 152
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic primer"

<400> SEQUENCE: 152
gtgacccact gtggcctgtc cagccccgtg accaagagct           40

<210> SEQ ID NO 153
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 153
gacaggccac agtgggtcac ctcgcaggcg tacaccttat           40

<210> SEQ ID NO 154
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 154
ggcctgtcct gtcccgtgac caagagcttc aacaggggcg a         41

<210> SEQ ID NO 155
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 155
gtcacgggac aggacaggcc ctggtgggtc acctcgcagg           40

<210> SEQ ID NO 156
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 156
cagccccgtg tgcaagagct tcaacagggg cgagtgctaa           40

<210> SEQ ID NO 157
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 157
aagctcttgc acacggggct ggacaggccc tggtgggtc            39

<210> SEQ ID NO 158
<211> LENGTH: 38

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 158
ccgtctcctg cgctagcacc aagggcccca gcgtgttc                              38

<210> SEQ ID NO 159
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 159
ggtgctagcg caggagacgg tgaccagggt tccttgac                              38

<210> SEQ ID NO 160
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 160
tcctcggctt gtaccaaggg ccccagcgtg ttccccctgg                            40

<210> SEQ ID NO 161
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 161
cccttggtac aagccgagga gacggtgacc agggttcctt                            40

<210> SEQ ID NO 162
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 162
ctagcacctg tggccccagc gtgttccccc tggccccca                             39

<210> SEQ ID NO 163
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 163
```
gctggggcca caggtgctag ccgaggagac ggtgaccag                                39

<210> SEQ ID NO 164
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 164
agggcccctg tgtgttcccc ctggccccca gcagcaaga                                39

<210> SEQ ID NO 165
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 165
ggggaacaca caggggccct tggtgctagc cgaggagacg                               40

<210> SEQ ID NO 166
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 166
cccccagctg caagagcacc agcggcggca cagccgccct                               40

<210> SEQ ID NO 167
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 167
ggtgctcttg cagctggggg ccaggggaa cacgctgggg                                40

<210> SEQ ID NO 168
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 168
agcagcaagt gtaccagcgg cggcacagcc gccctgggct                               40

<210> SEQ ID NO 169
<211> LENGTH: 39
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic primer"

<400> SEQUENCE: 169
ccgctggtac acttgctgct gggggccagg gggaacacg                              39

<210> SEQ ID NO 170
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 170
agagcacctg tggcggcaca gccgccctgg gctgcctggt                             40

<210> SEQ ID NO 171
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 171
gtgccgccac aggtgctctt gctgctgggg gccaggggga                             40

<210> SEQ ID NO 172
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 172
agcggcggct gtgccgccct gggctgcctg gtgaaggact                             40

<210> SEQ ID NO 173
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 173
cagggcggca cagccgccgc tggtgctctt gctgctgggg                             40

<210> SEQ ID NO 174
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 174
tacttcccct gtcccgtgac cgtgtcctgg aacagcgga                              39

<210> SEQ ID NO 175
```

```
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 175
ggtcacggga caggggaagt agtccttcac caggcagc                              38

<210> SEQ ID NO 176
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 176
tccccgagtg cgtgaccgtg tcctggaaca gcggagccct                            40

<210> SEQ ID NO 177
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 177
cacggtcacg cactcgggga agtagtcctt caccaggcag                            40

<210> SEQ ID NO 178
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 178
gagcccgtgt gcgtgtcctg gaacagcgga gccctgacct                            40

<210> SEQ ID NO 179
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 179
caggacacgc acacgggctc ggggaagtag tccttcacca                            40

<210> SEQ ID NO 180
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 180
```
tgaccgtgtg ctggaacagc ggagccctga cctccggcgt                                40

<210> SEQ ID NO 181
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 181
ctgttccagc acacggtcac gggctcgggg aagtagtcct                                40

<210> SEQ ID NO 182
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 182
ggagccctgt gctccggcgt gcacaccttc cccgccgtgc t                              41

<210> SEQ ID NO 183
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 183
acgccggagc acagggctcc gctgttccag gacacggtca                                40

<210> SEQ ID NO 184
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 184
ccctgacctg tggcgtgcac accttccccg ccgtgctgca                                40

<210> SEQ ID NO 185
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 185
tgtgcacgcc acaggtcagg gctccgctgt tccaggacac                                40

<210> SEQ ID NO 186
<211> LENGTH: 40
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic primer"

<400> SEQUENCE: 186
gcgtgcactg cttccccgcc gtgctgcaga gcagcggcct                              40

<210> SEQ ID NO 187
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 187
ggcggggaag cagtgcacgc cggaggtcag ggctccgctg                              40

<210> SEQ ID NO 188
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 188
cacaccttct gtgccgtgct gcagagcagc ggcctgtaca                              40

<210> SEQ ID NO 189
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 189
cagcacggca cagaaggtgt gcacgccgga ggtcagggct                              40

<210> SEQ ID NO 190
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 190
ccgccgtgtg tcagagcagc ggcctgtaca gcctgtcca                               39

<210> SEQ ID NO 191
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 191
gctgctctga cacacggcgg ggaaggtgtg cacgccggag                              40
```

<210> SEQ ID NO 192
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 192
tgctgcagtg cagcggcctg tacagcctgt ccagcgtggt                40

<210> SEQ ID NO 193
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 193
acaggccgct gcactgcagc acggcgggga aggtgtgcac g              41

<210> SEQ ID NO 194
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 194
ctgcagagct gtggcctgta cagcctgtcc agcgtggtga                40

<210> SEQ ID NO 195
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 195
tacaggccac agctctgcag cacggcgggg aaggtgtgca                40

<210> SEQ ID NO 196
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 196
tgacagtgtg cagcagcagc ctgggcaccc agacctacat                40

<210> SEQ ID NO 197
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 197
ctgctgctgc acactgtcac cacgctggac aggctgtaca                                40

<210> SEQ ID NO 198
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 198
tgcccagctg cagcctgggc acccagacct acatctgcaa                                40

<210> SEQ ID NO 199
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 199
cccaggctgc agctgggcac tgtcaccacg ctggacaggc t                              41

<210> SEQ ID NO 200
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 200
gcctgggctg tcagacctac atctgcaacg tgaaccacaa                                40

<210> SEQ ID NO 201
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 201
gtaggtctga cagcccaggc tgctgctggg cactgtcacc a                              41

<210> SEQ ID NO 202
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 202
gcacccagtg ctacatctgc aacgtgaacc acaagccca                                 39

<210> SEQ ID NO 203
<211> LENGTH: 40
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic primer"

<400> SEQUENCE: 203
gcagatgtag cactgggtgc ccaggctgct gctgggcact                           40

<210> SEQ ID NO 204
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 204
tgaaccactg tcccagcaac accaaggtgg acaagagagt                           40

<210> SEQ ID NO 205
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 205
tgttgctggg acagtggttc acgttgcaga tgtaggtctg g                         41

<210> SEQ ID NO 206
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 206
acaagccctg caacaccaag gtggacaaga gagtggagc                            39

<210> SEQ ID NO 207
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 207
cttggtgttg cagggcttgt ggttcacgtt gcagatgtag                           40

<210> SEQ ID NO 208
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 208
accaaggtgt gcaagagagt ggagcccaag agctgcgaca                           40
```

<210> SEQ ID NO 209
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 209
cactctcttg cacaccttgg tgttgctggg cttgtggttc a            41

<210> SEQ ID NO 210
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 210
tccccccctg tcccaaggac accctgatga tcagcagga             39

<210> SEQ ID NO 211
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 211
gtccttggga caggggggga acaggaacac ggagggtccg            40

<210> SEQ ID NO 212
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 212
aggaccccct gcgtgacctg cgtggtggtg gacgtgag              38

<210> SEQ ID NO 213
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 213
caggtcacgc aggggggtcct gctgatcatc agggtgtcct           40

<210> SEQ ID NO 214
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 214
tgagccactg tgacccagag gtgaagttca actggtacg                    39

<210> SEQ ID NO 215
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 215
ctctgggtca cagtggctca cgtccaccac cacgcaggtc                   40

<210> SEQ ID NO 216
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 216
ccagaggtgt gcttcaactg gtacgtggac ggcgtggagg                   40

<210> SEQ ID NO 217
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 217
ccagttgaag cacacctctg ggtcctcgtg gctcacgtcc a                 41

<210> SEQ ID NO 218
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 218
gaggtgcact gtgccaagac caagcccaga gaggagcagt                   40

<210> SEQ ID NO 219
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 219
ggtcttggca cagtgcacct ccacgccgtc cacgtaccag t                 41

<210> SEQ ID NO 220
<211> LENGTH: 40
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 220
cacaacgcct gtaccaagcc cagagaggag cagtacaaca                              40

<210> SEQ ID NO 221
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 221
ggcttggtac aggcgttgtg cacctccacg ccgtccacgt                              40

<210> SEQ ID NO 222
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 222
gccaagacct gtcccagaga ggagcagtac aacagcacct                              40

<210> SEQ ID NO 223
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 223
ctctctggga caggtcttgg cgttgtgcac ctccacgccg t                            41

<210> SEQ ID NO 224
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 224
accaagccct gtgaggagca gtacaacagc acctacaggg t                            41

<210> SEQ ID NO 225
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 225
ctgctcctca cagggcttgg tcttggcgtt gtgcacctcc a                            41
```

<210> SEQ ID NO 226
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 226
caagcccaga tgcgagcagt acaacagcac ctacagggtg                 40

<210> SEQ ID NO 227
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 227
gtactgctcg catctgggct tggtcttggc gttgtgcacc t               41

<210> SEQ ID NO 228
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 228
gcccagagag tgtcagtaca acagcaccta cagggtggt                  39

<210> SEQ ID NO 229
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 229
ttgtactgac actctctggg cttggtcttg gcgttgtgca                 40

<210> SEQ ID NO 230
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 230
caaggaatac tgctgcaagg tctccaacaa ggccctgcca                 40

<210> SEQ ID NO 231
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:

-continued

Synthetic primer"

<400> SEQUENCE: 231
gaccttgcag cagtattcct tgccgttcag ccagtcctgg t             41

<210> SEQ ID NO 232
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 232
tacaagtgct gcgtctccaa caaggccctg ccagccccca             40

<210> SEQ ID NO 233
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 233
gttggagacg cagcacttgt attccttgcc gttcagccag t             41

<210> SEQ ID NO 234
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 234
ggtctccaac tgtgccctgc cagcccccat cgaaaagacc             40

<210> SEQ ID NO 235
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 235
ggcagggcac agttggagac cttgcacttg tattccttgc             40

<210> SEQ ID NO 236
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 236
gccctgccat gtcccatcga aaagaccatc agcaaggcca             40

<210> SEQ ID NO 237
<211> LENGTH: 41

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 237
ttcgatggga catggcaggg ccttgttgga gaccttgcac t                 41

<210> SEQ ID NO 238
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 238
gcccccatct gcaagaccat cagcaaggcc aagggccagc                   40

<210> SEQ ID NO 239
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 239
gatggtcttg cagatggggg ctggcagggc cttgttggag a                 41

<210> SEQ ID NO 240
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 240
cccatcgaat gcaccatcag caaggccaag ggccagcca                    39

<210> SEQ ID NO 241
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 241
gctgatggtg cattcgatgg gggctggcag ggccttgttg                   40

<210> SEQ ID NO 242
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 242
```
tcgaaaagtg catcagcaag gccaagggcc agccacggga                    40

<210> SEQ ID NO 243
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 243
cttgctgatg cacttttcga tgggggctgg cagggccttg t                  41

<210> SEQ ID NO 244
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 244
agaccatctg caaggccaag ggccagccac gggagcccca                    40

<210> SEQ ID NO 245
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 245
ccttggcctt gcagatggtc ttttcgatgg gggctggcag g                  41

<210> SEQ ID NO 246
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 246
ggccagccat gcgagcccca ggtgtacacc ctgcctccat                    40

<210> SEQ ID NO 247
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 247
ctggggctcg catggctggc ccttggcctt gctgatggtc t                  41

<210> SEQ ID NO 248
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 248
ctccatcctg cgacgagctg accaagaacc aggtgtccct            40

<210> SEQ ID NO 249
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 249
cagctcgtcg caggatggag gcagggtgta cacctggggc t            41

<210> SEQ ID NO 250
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 250
agctgacctg caaccaggtg tccctgacct gtctggtga            39

<210> SEQ ID NO 251
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 251
cacctggttg caggtcagct cgtcccggga tggaggcagg            40

<210> SEQ ID NO 252
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 252
ccaagaactg cgtgtccctg acctgtctgg tgaagggctt            40

<210> SEQ ID NO 253
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 253
tcagggacac gcagttcttg gtcagctcgt cccgggatgg a            41

<210> SEQ ID NO 254

```
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 254
ttctacccct gcgacatcgc cgtggagtgg gagagcaacg                          40

<210> SEQ ID NO 255
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 255
ggcgatgtcg cagggqtaga agcccttcac cagacaggtc a                       41

<210> SEQ ID NO 256
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 256
tggagtggtg cagcaacggc cagcccgaga acaactaca                          39

<210> SEQ ID NO 257
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 257
ggccgttgct gcaccactcc acggcgatgt cgctggggta g                       41

<210> SEQ ID NO 258
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 258
agcccgagtg caactacaag accacccccc cagtgctgga                         40

<210> SEQ ID NO 259
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 259
```
cttgtagttg cactcgggct ggccgttgct ctcccactcc a         41

<210> SEQ ID NO 260
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 260
cccgagaact gctacaagac cacccccca gtgctggaca             40

<210> SEQ ID NO 261
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 261
ggtcttgtag cagttctcgg gctggccgtt gctctcccac t          41

<210> SEQ ID NO 262
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 262
gaacaactac tgcaccaccc ccccagtgct ggacagcgac             40

<210> SEQ ID NO 263
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 263
ggggtggtgc agtagttgtt ctcgggctgg ccgttgctct             40

<210> SEQ ID NO 264
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 264
aactacaagt gtaccccccc agtgctggac agcgacggca             40

<210> SEQ ID NO 265
<211> LENGTH: 40
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic primer"

<400> SEQUENCE: 265
tgggggggta cacttgtagt tgttctcggg ctggccgttg            40

<210> SEQ ID NO 266
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 266
ccccagtgtg tgacagcgac ggcagcttct tcctgtaca             39

<210> SEQ ID NO 267
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 267
gtcgctgtca cacactgggg gggtggtctt gtagttgttc t          41

<210> SEQ ID NO 268
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 268
tgctggactg cgacggcagc ttcttcctgt acagcaagct            40

<210> SEQ ID NO 269
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 269
gctgccgtcg cagtccagca ctgggggggt ggtcttgtag t          41

<210> SEQ ID NO 270
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 270
tgaccgtgtg caagtccagg tggcagcagg gcaacgtgtt            40

```
<210> SEQ ID NO 271
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 271
acctggactt gcacacggtc agcttgctgt acaggaagaa g                      41

<210> SEQ ID NO 272
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 272
tggacaagtg caggtggcag cagggcaacg tgttcagct                         39

<210> SEQ ID NO 273
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 273
ctgccacctg cacttgtcca cggtcagctt gctgtacagg                        40

<210> SEQ ID NO 274
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 274
agggcaactg cttcagctgc agcgtgatgc acgaggccct                        40

<210> SEQ ID NO 275
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 275
gcagctgaag cagttgccct gctgccacct ggacttgtcc a                      41

<210> SEQ ID NO 276
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

<400> SEQUENCE: 276
ccgggatgcg tgacagtggc ctggaaggca gatagc                                36

<210> SEQ ID NO 277
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 277
tgtcacgcat cccgggtaga agtcacttat gagaca                                36

<210> SEQ ID NO 278
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 278
gccgtgtgtg tggcctggaa ggcagatagc agcccc                                36

<210> SEQ ID NO 279
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 279
ggccacacac acggctcccg ggtagaagtc acttat                                36

<210> SEQ ID NO 280
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 280
acagtgtgtt ggaaggcaga tagcagcccc gtcaag                                36

<210> SEQ ID NO 281
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 281
cttccaacac actgtcacgg ctcccgggta gaagtc                                36

<210> SEQ ID NO 282
<211> LENGTH: 36
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic primer"

<400> SEQUENCE: 282
cccgtctgtg cgggagtgga gaccaccaca ccctcc                         36

<210> SEQ ID NO 283
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 283
tcccgcacag acggggctgc tatctgcctt ccaggc                         36

<210> SEQ ID NO 284
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 284
gcgggatgtg agaccaccac accctccaaa caaagc                         36

<210> SEQ ID NO 285
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 285
ggtctcacat cccgccttga cggggctgct atctgc                         36

<210> SEQ ID NO 286
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 286
accacctgtc cctccaaaca aagcaacaac aagtac                         36

<210> SEQ ID NO 287
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 287
ggagggacag gtggtctcca ctcccgcctt gacggg                         36
```

<210> SEQ ID NO 288
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 288
aaacaatgca acaacaagta cgcggccagc agctat                                36

<210> SEQ ID NO 289
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 289
gttgttgcat tgtttggagg gtgtggtggt ctccac                                36

<210> SEQ ID NO 290
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 290

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

-continued

```
Asn Lys Ala Leu Pro Ala Pro Ile Glu Cys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Cys Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330
```

<210> SEQ ID NO 291
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 291

```
Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
                20                  25                  30

Tyr Phe Pro Glu Pro Val Thr Val Ser Trp Asn Ser Gly Ala Leu Thr
            35                  40                  45

Ser Gly Val His Thr Phe Pro Ala Val Leu Gln Ser Ser Gly Leu Tyr
        50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
                100                 105                 110

Cys Pro Ala Pro Glu Leu Leu Gly Gly Pro Ser Val Phe Leu Phe Pro
            115                 120                 125

Pro Lys Pro Lys Asp Thr Leu Met Ile Ser Arg Thr Pro Glu Val Thr
130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Cys Thr Ile Ser Lys Ala Lys
    210                 215                 220

Gly Gln Pro Arg Glu Pro Gln Val Tyr Thr Leu Pro Pro Ser Arg Glu
```

```
            225                 230                 235                 240

Glu Met Thr Lys Asn Gln Val Ser Leu Thr Cys Leu Val Lys Gly Phe
                        245                 250                 255

Tyr Pro Ser Asp Ile Ala Val Glu Trp Glu Ser Asn Gly Gln Pro Glu
                        260                 265                 270

Asn Asn Tyr Cys Thr Thr Pro Pro Val Leu Asp Ser Asp Gly Ser Phe
                        275                 280                 285

Phe Leu Tyr Ser Lys Leu Thr Val Asp Lys Ser Arg Trp Gln Gln Gly
        290                 295                 300

Asn Val Phe Ser Cys Ser Val Met His Glu Ala Leu His Asn His Tyr
        305                 310                 315                 320

Thr Gln Lys Ser Leu Ser Leu Ser Pro Gly Lys
                        325                 330

<210> SEQ ID NO 292
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 292

Ser Ala Ser Thr Lys Gly Pro Ser Val Phe Pro Leu Ala Pro Ser Ser
        1               5                   10                  15

Lys Ser Thr Ser Gly Gly Thr Ala Ala Leu Gly Cys Leu Val Lys Asp
                        20                  25                  30

Tyr Phe Pro Glu Pro Val Thr Val Ser Trp Asn Ser Gly Ala Leu Thr
                        35                  40                  45

Ser Gly Val His Thr Phe Pro Ala Val Leu Gln Ser Ser Gly Leu Tyr
                50                  55                  60

Ser Leu Ser Ser Val Val Thr Val Pro Ser Ser Ser Leu Gly Thr Gln
        65                  70                  75                  80

Thr Tyr Ile Cys Asn Val Asn His Lys Pro Ser Asn Thr Lys Val Asp
                        85                  90                  95

Lys Lys Val Glu Pro Lys Ser Cys Asp Lys Thr His Thr Cys Pro Pro
                        100                 105                 110

Cys Pro Ala Pro Glu Leu Leu Gly Gly Pro Ser Val Phe Leu Phe Pro
                        115                 120                 125

Pro Lys Pro Lys Asp Thr Leu Met Ile Ser Arg Thr Pro Glu Val Thr
                        130                 135                 140

Cys Val Val Val Asp Val Ser His Glu Asp Pro Glu Val Lys Phe Asn
        145                 150                 155                 160

Trp Tyr Val Asp Gly Val Glu Val His Asn Ala Lys Thr Lys Pro Arg
                        165                 170                 175

Glu Glu Gln Tyr Asn Ser Thr Tyr Arg Val Val Ser Val Leu Thr Val
                        180                 185                 190

Leu His Gln Asp Trp Leu Asn Gly Lys Glu Tyr Lys Cys Lys Val Ser
                        195                 200                 205

Asn Lys Ala Leu Pro Ala Pro Ile Glu Cys Thr Ile Ser Lys Ala Lys
                        210                 215                 220

Gly Gln Pro Arg Glu Pro Gln Val Tyr Thr Leu Pro Pro Ser Arg Glu
        225                 230                 235                 240

Glu Met Thr Cys Asn Gln Val Ser Leu Thr Cys Leu Val Lys Gly Phe
                        245                 250                 255
```

Tyr Pro Cys Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
            275                 280                 285

Phe Leu Tyr Ser Lys Leu Thr Val Asp Lys Ser Arg Trp Gln Gln Gly
290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
            325                 330

<210> SEQ ID NO 293
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 293

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Cys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Cys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

```
Asn Asn Tyr Cys Thr Thr Pro Pro Val Leu Asp Ser Asp Gly Ser Phe
            275                 280                 285

Phe Leu Tyr Ser Lys Leu Thr Val Asp Lys Ser Arg Trp Gln Gln Gly
            290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
            325                 330

<210> SEQ ID NO 294
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 294

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Cys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Cys Asp Ile Ala Val Glu Trp Glu Ser Asn Gly Gln Pro Glu
            260                 265                 270

Asn Asn Tyr Cys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
```

```
            290                 295                 300
Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 295
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 295

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Cys Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Cys Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320
```

```
Thr Gln Lys Ser Leu Ser Leu Ser Pro Gly Lys
                325                 330

<210> SEQ ID NO 296
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 296

His His His His His His
1               5

<210> SEQ ID NO 297
<211> LENGTH: 328
<212> TYPE: PRT
<213> ORGANISM: Homo sapiens

<400> SEQUENCE: 297

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Ala Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Asp
225                 230                 235                 240

Glu Leu Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
```

```
            275                 280                 285
Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser
                325

<210> SEQ ID NO 298
<211> LENGTH: 108
<212> TYPE: PRT
<213> ORGANISM: Homo sapiens

<400> SEQUENCE: 298

Lys Arg Thr Val Ala Ala Pro Ser Val Phe Ile Phe Pro Pro Ser Asp
1               5                   10                  15

Glu Gln Leu Lys Ser Gly Thr Ala Ser Val Val Cys Leu Leu Asn Asn
            20                  25                  30

Phe Tyr Pro Arg Glu Ala Lys Val Gln Trp Lys Val Asp Asn Ala Leu
        35                  40                  45

Gln Ser Gly Asn Ser Gln Glu Ser Val Thr Glu Gln Asp Ser Lys Asp
    50                  55                  60

Ser Thr Tyr Ser Leu Ser Ser Thr Leu Thr Leu Ser Lys Ala Asp Tyr
65                  70                  75                  80

Glu Lys His Lys Val Tyr Ala Cys Glu Val Thr His Gln Gly Leu Arg
                85                  90                  95

Ser Pro Val Thr Lys Ser Phe Asn Arg Gly Glu Cys
            100                 105

<210> SEQ ID NO 299
<211> LENGTH: 331
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 299

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140
```

```
Cys Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
                180                 185                 190

Leu His Gln Asp Trp Leu Asn Gly Lys Glu Tyr Lys Cys Lys Val Ser
            195                 200                 205

Asn Lys Ala Leu Pro Ala Pro Ile Glu Lys Thr Ile Ser Lys Ala Lys
        210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
                260                 265                 270

Asn Asn Tyr Lys Thr Thr Pro Pro Val Leu Asp Ser Asp Gly Ser Phe
                275                 280                 285

Phe Leu Tyr Ser Lys Leu Thr Val Asp Lys Ser Arg Trp Gln Gln Gly
290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 300
<211> LENGTH: 328
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 300

Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
                20                  25                  30

Pro Glu Pro Val Thr Val Ser Trp Asn Ser Gly Ala Leu Thr Ser Gly
            35                  40                  45

Val His Thr Phe Pro Ala Val Leu Gln Ser Ser Gly Leu Tyr Ser Leu
        50                  55                  60

Ser Ser Val Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Lys
                85                  90                  95

Val Glu Pro Lys Ser Cys Asp Lys Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
```

```
                    165                 170                 175
Gln Tyr Asn Ser Thr Tyr Arg Val Val Ser Val Leu Thr Val Leu His
                180                 185                 190

Gln Asp Trp Leu Asn Gly Lys Glu Tyr Lys Cys Lys Val Ser Asn Lys
            195                 200                 205

Ala Leu Pro Ala Pro Ile Glu Lys Thr Ile Ser Lys Ala Lys Gly Gln
        210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
290                 295                 300

Phe Ser Cys Ser Val Met His Glu Ala Leu His Asn His Tyr Thr Gln
305                 310                 315                 320

Lys Ser Leu Ser Leu Ser Pro Gly
                325

<210> SEQ ID NO 301
<211> LENGTH: 328
<212> TYPE: PRT
<213> ORGANISM: Homo sapiens

<400> SEQUENCE: 301

Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Lys
                85                  90                  95

Val Glu Pro Lys Ser Cys Asp Lys Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205
```

```
Ala Leu Pro Ala Pro Ile Glu Lys Thr Ile Ser Lys Ala Lys Gly Gln
    210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly
                325

<210> SEQ ID NO 302
<211> LENGTH: 324
<212> TYPE: PRT
<213> ORGANISM: Homo sapiens

<400> SEQUENCE: 302

Ser Thr Lys Gly Pro Ser Val Phe Pro Leu Ala Pro Cys Ser Arg Ser
1               5                   10                  15

Thr Ser Glu Ser Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Asn Phe Gly Thr Gln Thr Tyr
65                  70                  75                  80

Thr Cys Asn Val Asp His Lys Pro Ser Asn Thr Lys Val Asp Lys Thr
                85                  90                  95

Val Glu Arg Lys Cys Cys Val Glu Cys Pro Pro Cys Pro Ala Pro Pro
            100                 105                 110

Val Ala Gly Pro Ser Val Phe Leu Phe Pro Pro Lys Pro Lys Asp Thr
        115                 120                 125

Leu Met Ile Ser Arg Thr Pro Glu Val Thr Cys Val Val Val Asp Val
    130                 135                 140

Ser His Glu Asp Pro Glu Val Gln Phe Asn Trp Tyr Val Asp Gly Val
145                 150                 155                 160

Glu Val His Asn Ala Lys Thr Lys Pro Arg Glu Glu Gln Phe Asn Ser
                165                 170                 175

Thr Phe Arg Val Val Ser Val Leu Thr Val Val His Gln Asp Trp Leu
            180                 185                 190

Asn Gly Lys Glu Tyr Lys Cys Lys Val Ser Asn Lys Gly Leu Pro Ala
        195                 200                 205

Pro Ile Glu Lys Thr Ile Ser Lys Thr Lys Gly Gln Pro Arg Glu Pro
    210                 215                 220

Gln Val Tyr Thr Leu Pro Pro Ser Arg Glu Glu Met Thr Lys Asn Gln
225                 230                 235                 240

Val Ser Leu Thr Cys Leu Val Lys Gly Phe Tyr Pro Ser Asp Ile Ser
                245                 250                 255
```

```
Val Glu Trp Glu Ser Asn Gly Gln Pro Glu Asn Asn Tyr Lys Thr Thr
            260                 265                 270

Pro Pro Met Leu Asp Ser Asp Gly Ser Phe Phe Leu Tyr Ser Lys Leu
            275                 280                 285

Thr Val Asp Lys Ser Arg Trp Gln Gln Gly Asn Val Phe Ser Cys Ser
        290                 295                 300

Val Met His Glu Ala Leu His Asn His Tyr Thr Gln Lys Ser Leu Ser
305                 310                 315                 320

Leu Ser Pro Gly

<210> SEQ ID NO 303
<211> LENGTH: 375
<212> TYPE: PRT
<213> ORGANISM: Homo sapiens

<400> SEQUENCE: 303

Ser Thr Lys Gly Pro Ser Val Phe Pro Leu Ala Pro Cys Ser Arg Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Thr Cys Asn Val Asn His Lys Pro Ser Asn Thr Lys Val Asp Lys Arg
                85                  90                  95

Val Glu Leu Lys Thr Pro Leu Gly Asp Thr Thr His Thr Cys Pro Arg
            100                 105                 110

Cys Pro Glu Pro Lys Ser Cys Asp Thr Pro Pro Pro Cys Pro Arg Cys
        115                 120                 125

Pro Glu Pro Lys Ser Cys Asp Thr Pro Pro Pro Cys Pro Arg Cys Pro
    130                 135                 140

Glu Pro Lys Ser Cys Asp Thr Pro Pro Pro Cys Pro Arg Cys Pro Ala
145                 150                 155                 160

Pro Glu Leu Leu Gly Gly Pro Ser Val Phe Leu Phe Pro Pro Lys Pro
                165                 170                 175

Lys Asp Thr Leu Met Ile Ser Arg Thr Pro Glu Val Thr Cys Val Val
            180                 185                 190

Val Asp Val Ser His Glu Asp Pro Glu Val Gln Phe Lys Trp Tyr Val
        195                 200                 205

Asp Gly Val Glu Val His Asn Ala Lys Thr Lys Pro Arg Glu Glu Gln
    210                 215                 220

Tyr Asn Ser Thr Phe Arg Val Val Ser Val Leu Thr Val Leu His Gln
225                 230                 235                 240

Asp Trp Leu Asn Gly Lys Glu Tyr Lys Cys Lys Val Ser Asn Lys Ala
                245                 250                 255

Leu Pro Ala Pro Ile Glu Lys Thr Ile Ser Lys Thr Lys Gly Gln Pro
            260                 265                 270

Arg Glu Pro Gln Val Tyr Thr Leu Pro Pro Ser Arg Glu Glu Met Thr
        275                 280                 285

Lys Asn Gln Val Ser Leu Thr Cys Leu Val Lys Gly Phe Tyr Pro Ser
    290                 295                 300
```

Asp Ile Ala Val Glu Trp Glu Ser Ser Gly Gln Pro Glu Asn Asn Tyr
305                 310                 315                 320

Asn Thr Thr Pro Pro Met Leu Asp Ser Asp Gly Ser Phe Phe Leu Tyr
                325                 330                 335

Ser Lys Leu Thr Val Asp Lys Ser Arg Trp Gln Gln Gly Asn Ile Phe
            340                 345                 350

Ser Cys Ser Val Met His Glu Ala Leu His Asn Arg Phe Thr Gln Lys
        355                 360                 365

Ser Leu Ser Leu Ser Pro Gly
    370                 375

<210> SEQ ID NO 304
<211> LENGTH: 325
<212> TYPE: PRT
<213> ORGANISM: Homo sapiens

<400> SEQUENCE: 304

Ser Thr Lys Gly Pro Ser Val Phe Pro Leu Ala Pro Cys Ser Arg Ser
1               5                   10                  15

Thr Ser Glu Ser Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Lys Thr Tyr
65                  70                  75                  80

Thr Cys Asn Val Asp His Lys Pro Ser Asn Thr Lys Val Asp Lys Arg
                85                  90                  95

Val Glu Ser Lys Tyr Gly Pro Pro Cys Pro Ser Cys Pro Ala Pro Glu
            100                 105                 110

Phe Leu Gly Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
        275                 280                 285

Leu Thr Val Asp Lys Ser Arg Trp Gln Glu Gly Asn Val Phe Ser Cys

```
                 290                 295                 300
Ser Val Met His Glu Ala Leu His Asn His Tyr Thr Gln Lys Ser Leu
305                 310                 315                 320

Ser Leu Ser Leu Gly
                325

<210> SEQ ID NO 305
<211> LENGTH: 107
<212> TYPE: PRT
<213> ORGANISM: Homo sapiens

<400> SEQUENCE: 305

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 306
<211> LENGTH: 332
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 306

Ser Ser Ala Ser Thr Lys Gly Pro Ser Val Phe Pro Leu Ala Pro Ser
1               5                   10                  15

Ser Lys Ser Thr Ser Gly Gly Thr Ala Ala Leu Gly Cys Leu Val Lys
            20                  25                  30

Asp Tyr Phe Pro Glu Pro Val Thr Val Ser Trp Asn Ser Gly Ala Leu
        35                  40                  45

Thr Ser Gly Val His Thr Phe Pro Ala Val Leu Gln Ser Ser Gly Leu
    50                  55                  60

Tyr Ser Leu Ser Ser Val Val Thr Val Pro Ser Ser Ser Leu Gly Thr
65                  70                  75                  80

Gln Thr Tyr Ile Cys Asn Val Asn His Lys Pro Ser Asn Thr Lys Val
                85                  90                  95

Asp Lys Lys Val Glu Pro Lys Ser Cys Asp Lys Thr His Thr Cys Pro
            100                 105                 110

Pro Cys Pro Ala Pro Glu Leu Leu Gly Gly Pro Ser Val Phe Leu Phe
        115                 120                 125

Pro Pro Lys Pro Lys Asp Thr Leu Met Ile Ser Arg Thr Pro Glu Val
    130                 135                 140

Thr Cys Val Val Val Asp Val Ser His Glu Asp Pro Glu Val Lys Phe
145                 150                 155                 160
```

-continued

```
Asn Trp Tyr Val Asp Gly Val Glu Val His Asn Ala Lys Thr Lys Pro
                165                 170                 175
Arg Glu Glu Gln Tyr Asn Ser Thr Tyr Arg Val Val Ser Val Leu Thr
            180                 185                 190
Val Leu His Gln Asp Trp Leu Asn Gly Lys Glu Tyr Lys Cys Lys Val
        195                 200                 205
Ser Asn Lys Ala Leu Pro Ala Pro Ile Glu Lys Thr Ile Ser Lys Ala
    210                 215                 220
Lys Gly Gln Pro Arg Glu Pro Gln Val Tyr Thr Leu Pro Pro Ser Arg
225                 230                 235                 240
Glu Glu Met Thr Cys Asn Gln Val Ser Leu Thr Cys Leu Val Lys Gly
                245                 250                 255
Phe Tyr Pro Ser Asp Ile Ala Val Glu Trp Glu Ser Asn Gly Gln Pro
            260                 265                 270
Glu Asn Asn Tyr Lys Thr Thr Pro Pro Val Leu Asp Ser Asp Gly Ser
        275                 280                 285
Phe Phe Leu Tyr Ser Lys Leu Thr Val Asp Lys Ser Arg Trp Gln Gln
    290                 295                 300
Gly Asn Val Phe Ser Cys Ser Val Met His Glu Ala Leu His Asn His
305                 310                 315                 320
Tyr Thr Gln Lys Ser Leu Ser Leu Ser Pro Gly Lys
                325                 330

<210> SEQ ID NO 307
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 307

Cys Arg Thr Val Ala Ala Pro Ser Val Phe Ile Phe Pro Pro Ser Asp
1               5                   10                  15
Glu Gln Leu Lys Ser Gly Thr Ala Ser Val Val Cys Leu Leu Asn Asn
            20                  25                  30
Phe Tyr Pro Arg Glu Ala Lys Val Gln Trp Lys Val Asp Asn Ala Leu
        35                  40                  45
Gln Ser Gly Asn Ser Gln Glu Ser Val Thr Glu Gln Asp Ser Lys Asp
    50                  55                  60
Ser Thr Tyr Ser Leu Ser Ser Thr Leu Thr Leu Ser Lys Ala Asp Tyr
65                  70                  75                  80
Glu Lys His Lys Val Tyr Ala Cys Glu Val Thr His Gln Gly Leu Ser
                85                  90                  95
Ser Pro Val Thr Lys Ser Phe Asn Arg Gly Glu Cys
            100                 105

<210> SEQ ID NO 308
<211> LENGTH: 332
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 308

Ser Ser Ala Ser Thr Lys Gly Pro Ser Val Phe Pro Leu Ala Pro Ser
```

```
              1               5                  10                 15
            Ser Lys Ser Thr Ser Gly Gly Thr Ala Ala Leu Gly Cys Leu Val Lys
                         20                 25                 30

Asp Tyr Phe Pro Cys Pro Val Thr Val Ser Trp Asn Ser Gly Ala Leu
                         35                 40                 45

Thr Ser Gly Val His Thr Phe Pro Ala Val Leu Gln Ser Ser Gly Leu
             50                 55                 60

Tyr Ser Leu Ser Ser Val Val Thr Val Pro Ser Ser Ser Leu Gly Thr
             65                 70                 75                 80

Gln Thr Tyr Ile Cys Asn Val Asn His Lys Pro Ser Asn Thr Lys Val
                         85                 90                 95

Asp Lys Lys Val Glu Pro Lys Ser Cys Asp Lys Thr His Thr Cys Pro
                        100                105                110

Pro Cys Pro Ala Pro Glu Leu Leu Gly Gly Pro Ser Val Phe Leu Phe
                        115                120                125

Pro Pro Lys Pro Lys Asp Thr Leu Met Ile Ser Arg Thr Pro Glu Val
                        130                135                140

Thr Cys Val Val Val Asp Val Ser His Glu Asp Pro Glu Val Lys Phe
            145                150                155                160

Asn Trp Tyr Val Asp Gly Val Glu Val His Asn Ala Lys Thr Lys Pro
                        165                170                175

Arg Glu Glu Gln Tyr Asn Ser Thr Tyr Arg Val Val Ser Val Leu Thr
                        180                185                190

Val Leu His Gln Asp Trp Leu Asn Gly Lys Glu Tyr Lys Cys Lys Val
                        195                200                205

Ser Asn Lys Ala Leu Pro Ala Pro Ile Glu Lys Thr Ile Ser Lys Ala
                        210                215                220

Lys Gly Gln Pro Arg Glu Pro Gln Val Tyr Thr Leu Pro Pro Ser Arg
            225                230                235                240

Glu Glu Met Thr Lys Asn Gln Val Ser Leu Thr Cys Leu Val Lys Gly
                        245                250                255

Phe Tyr Pro Cys Asp Ile Ala Val Glu Trp Glu Ser Asn Gly Gln Pro
                        260                265                270

Glu Asn Asn Tyr Lys Thr Thr Pro Pro Val Leu Asp Ser Asp Gly Ser
                        275                280                285

Phe Phe Leu Tyr Ser Lys Leu Thr Val Asp Lys Ser Arg Trp Gln Gln
                        290                295                300

Gly Asn Val Phe Ser Cys Ser Val Met His Glu Ala Leu His Asn His
            305                310                315                320

Tyr Thr Gln Lys Ser Leu Ser Leu Ser Pro Gly Lys
                        325                330
```

<210> SEQ ID NO 309
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 309

```
            Lys Arg Thr Val Ala Ala Pro Ser Val Phe Ile Phe Pro Pro Ser Asp
            1               5                  10                 15

Glu Gln Leu Lys Ser Gly Thr Ala Ser Val Val Cys Leu Leu Asn Asn
                        20                 25                 30
```

```
Phe Tyr Pro Arg Glu Ala Lys Val Gln Trp Lys Val Asp Asn Ala Leu
        35              40              45
Gln Ser Gly Asn Ser Gln Glu Ser Val Thr Glu Gln Asp Ser Lys Asp
    50              55              60
Ser Thr Tyr Ser Leu Ser Ser Thr Leu Thr Leu Ser Lys Ala Asp Tyr
65              70              75              80
Glu Lys His Lys Val Tyr Ala Cys Glu Val Thr His Gln Gly Leu Ser
            85              90              95
Ser Pro Val Thr Lys Ser Phe Asn Arg Gly Glu Cys
            100             105
```

SPECIFIC SITES FOR MODIFYING ANTIBODIES TO MAKE IMMUNOCONJUGATES

FIELD OF THE INVENTION

This application is a continuation of U.S. patent application Ser. No. 14/764,026, filed Jul. 28, 2015, now abandoned, which is a National Stage Entry of PCT/US14/15393, filed Feb. 7, 2014, which claims priority to U.S. Provisional Application No. 61/762,563, filed Feb. 8, 2013, each of which are incorporated herein by reference in their entireties.

Due to the importance of antibodies for various therapeutic applications, there is a need for robust methods to selectively modify antibodies to introduce improved properties or additional functions. The invention provides specific sites for attaching moieties to antibodies for making modified antibodies, such as for use in preparation of antibody-drug conjugates (ADCs). The selective conjugation sites are located on constant regions of the antibody and thus are useful with various antibodies.

BACKGROUND

The value of methods for modifying antibodies is well known, and many methods for conjugation of antibodies to attach various "payload" moieties have been developed. Many of these methods rely upon the natural occurrence of specific reactive amino acid residues on the antibody, such as lysine and cysteine, which can be used to attach a payload. However, relying on the native amino acids is not always desirable, because the location and amount of payload attached depend on the number and position of those reactive amino acids: too many or too few such residues make it difficult to efficiently control loading of the payload onto the antibody. In addition, placement of the reactive amino acids may make it difficult to get complete conjugation, resulting in heterogeneous products during conjugation. Heterogeneity of a pharmaceutical active ingredient, for example, is typically undesirable because it compounds the unpredictability of administering a drug to a heterogeneous population of subjects: it is far preferable to administer a homogeneous product, and far more difficult to fully characterize and predict behavior of a heterogeneous one. Site-specific conjugation of a cytotoxic drug to an antibody through, for example, engineered cysteine residues results in homogenous immunoconjugates that exhibit improved therapeutic index (Junutula et al., (2008) Nat Biotechnol. 26(8):925-932)).

Antibodies have been engineered to add certain residues like cysteine in specific positions where these residues can be used for conjugation (Lyons et al., (1990) Protein Eng., 3:703-708), but the value of specific substitutions can vary with certain antibodies, as engineered cysteine might interfere with folding of the antibody and oxidation of the proper intra-molecular disulfide bonds (Voynov et al., (2010) Bioconjug. Chem. 21(2):385-392).

Because engineered cysteines in antibodies expressed in mammalian cells are modified through disulfide bonds with glutathione (GSH) and/or cysteine during their biosynthesis (Chen et al. (2009) *mAbs* 1:6, 563-571), the modified cysteine(s) in the antibody drug conjugate product as initially expressed is unreactive to thiol reactive reagents. Activation of the engineered cysteine(s) requires reduction of the GSH and/or cysteine adduct (which typically results in reduction of all inter-chain disulfide bonds of the antibody), followed by reoxidation and reformation of the native, inter-chain disulfide bonds prior to conjugation (Junutula et al., (2008) Nat. Biotechnol. 26(8):925-32). Some of the sites where cysteine has been inserted interfere with the process of reoxidation and subsequently result in undesirable, non-homogeneous conjugation products. It is therefore important to identify sites on the antibody where the introduced cysteine does not interfere with the reoxidation process prior to the conjugation with a thiol reactive reagent such as maleimide or bromo-, chloro- or iodo-acetamide groups.

Conjugation of cysteine residues with bromo-acetamide, iodo-acetamide or chloro-acetamide results in the formation of a stable thioether linkage. (Alley et al., (2008) Bioconjug Chem. 19(3):759-65). However, the chemistry is less efficient than maleimide conjugation chemistry. Since forming such thiol-maleimide linkages is a popular and highly efficient method to use when attaching a payload or linker to cysteine, there is a need to identify cysteine substitution sites on an antibody where maleimide linkages can be used. More importantly, site-specifically conjugated immunoconjugates can exhibit improved therapeutic index, thus there remains a need to identify specific privileged sites for cysteine substitution in antibodies that enables conjugation of payloads onto antibodies to form efficiently, and that provide conjugates having high stability. The instant invention provides such privileged cysteine substitution sites that give improved antibodies for conjugation purposes and immunoconjugates comprising such improved antibodies.

SUMMARY OF THE INVENTION

The invention provides specific sites in the constant region of an antibody or antibody fragment at which cysteine ("Cys") replacement of the native amino acid on a parental antibody or antibody fragment can be performed in order to provide a Cys residue for attachment of a chemical moiety (e.g., payload/drug moiety) to form an immunoconjugate with good efficiency and stability. The invention further provides engineered antibodies or antibody fragments having one or more Cys residues in one or more of these specific sites, as well as immunoconjugates made from such engineered antibodies or antibody fragments.

Methods for inserting Cys at specific locations of an antibody are known in the art, see, e.g., WO 2011/005481. However, the current invention discloses specific sites in the constant region of antibodies or antibody fragments where replacing one or more native amino acids of a parental antibody or antibody fragment with Cys provides one or more of the following advantages: Good reactivity to promote efficient immunoconjugation; reduced propensity for loss of payload when a Cys-maleimide conjugation linker is used; a reduced tendency to form undesired disulfide linkages, such as cross-linking between antibodies or the formation of non-native intramolecular disulfide bonds; and low hydrophobicity of the resulting ADC.

The specific privileged sites for Cys replacement of native amino acids in the constant region of a parental antibody or antibody fragment are selected to provide efficient conjugation while minimizing undesired effects. First, the specific sites for modification are selected so that replacing the native amino acid of a parental antibody or antibody fragment with Cys in one or more of the selected locations provides antibodies or antibody fragments that are readily conjugated on the new cysteine. The specific locations are selected to be sufficiently surface-accessible to allow the sulfhydryl of the cysteine residue to be reactive towards electrophiles in aqueous solutions. The identification of suitable sites for Cys replacement of native amino acids of a parental antibody or antibody fragment involved analyzing surface exposure of the native amino acids based on crystal structure data. Because the sites described herein are sufficiently accessible and reactive, they can be used to form immunoconjugates via chemistry that is well known in the art for modifying naturally-occurring cysteine residues. Conjugation of the replacement Cys residues thus uses conventional methods.

Selected modification sites can show a low propensity for reversal of conjugation when thiol-maleimide moieties are used in the conjugation. The thiol-maleimide conjugation reaction is often highly selective and extremely efficient, and may be used either to attach a payload to the thiol of a cysteine residue of a protein or as a linker elsewhere in the linkage between protein and payload. For example, a maleimide can be attached to a protein (e.g., an antibody or antibody fragment), and a payload having an attached thiol can be added to the maleimide to form a conjugate:

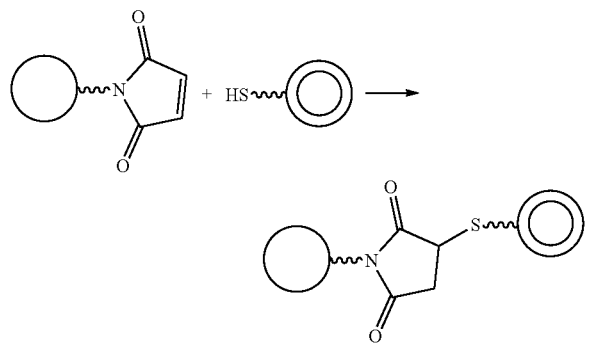

Accordingly, in this conjugation step, the protein (e.g., an antibody or antibody fragment) could be either the single circle or the double circle; the other would represent the payload. The immunoconjugate stability information here specifically relates to conjugation of the substituted cysteine by reaction with a maleimide group. In some embodiments, the thiol is from a cysteine on the protein (e.g., an antibody or antibody fragment), so the double circle represents the protein and the single circle represents a payload.

While the thiol-maleimide reaction is often used for making conjugates, reversal of the conjugation step as depicted below can result in loss of payload or scrambling of payload with other thiol-containing species:

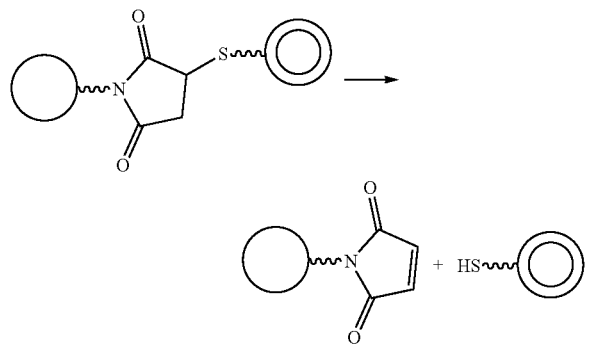

It has been reported that some sites for cysteine substitution provide more stable maleimide conjugates than others, presumably because the local chemical environment at certain points on the antibody surface around a new cysteine can promote the hydrolysis of the succinimide ring and hence prevent reversal of the thiol-maleimide linkage in the immunoconjugate (Shen et al. (2012), Nat. Biotechnol. 30(2):184-9). The identification of the advantageous sites for meeting this criterion involved inserting Cys in place of many of the native amino acids having suitable surface exposure, making immunoconjugates containing a thiol-maleimide linkage, and assessing stability of the immunoconjugate in order to eliminate sites where the stability of the conjugate was reduced by the local microenvironment around destabilizing sites. Because of this, the chemistry that can be used to attach linkers and payloads to the replacement Cys residues is not limited by the stability problems associated with the reversibility of thiol-maleimide conjugates that is discussed above. A number of methods can be used to form conjugates at cysteine, including maleimide conjugation. The sites for cysteine substitution described herein promote stability of the antibody conjugate product when using one of the most common conjugation methods, making these sites advantageous for antibody engineering, because the modified antibody can be used with the well-known and highly efficient maleimide conjugation methodology. Selection of sites based on this criterion is illustrated by data presented in Table 22 and Example 9.

Selected sites can be positioned so as to minimize undesired disulfide formation that may interfere with formation of a homogeneous conjugate. When antibodies or antibody fragments containing engineered cysteines are produced in mammalian cells, the Cys residues are typically present as disulfides to a free Cys amino acid or to glutathione (Chen el al., (2009) mAbs 16, 353-571). To free the Cys residues for conjugation with thiol reactive groups, the antibody or antibody fragment needs to be reduced, breaking all of the disulfide bonds. The antibody or antibody fragment is then reoxidized under conditions that facilitate formation of the native disulfides that stabilize the antibody or antibody fragment. Upon reoxidation, cysteine residues that are too prominently exposed on the surface of the antibody or antibody fragment can form disulfides by reaction with Cys on another antibody or antibody fragment ("inter-antibody disulfides"), or by forming undesired intra-antibody disulfides. It has been found that cysteine residues placed in the specific sites described herein are suitably accessible to be available for efficient conjugation, but are sufficiently shielded or suitably positioned to reduce or eliminate formation of inter-antibody and intra-antibody disulfide bonds that would otherwise occur during the reduction/reoxidation procedures typically needed when expressing cys-modified antibodies. Similarly, after re-oxidation some sites were found to produce non-homogenous conjugation products that appear to be due to the location of the new Cys residue engineered into the protein, and the specific sites identified herein are ones where such heterogeneity is minimized.

Conjugating drug payloads at sites where they are sequestered from solvent interactions and attachment can increase the hydrophobicity of the antibody upon drug attachment is preferred as reducing hydrophobicity of a protein drug is generally considered beneficial because it might reduce aggregation and clearance from circulation. Selecting attachment sites that result in minimal changes in hydrophobicity might be particularly beneficial when 4, 6 or 8 drugs are attached per antibody, or when particularly hydrophobic payloads are used.

Sites for Cys incorporation were evaluated using these and additional methods described in the Examples herein, leading to the selection of preferred sites for Cys incorporation for engineering antibodies or antibody fragments to introduce Cys as a site for conjugation, especially for making ADCs. Additional details regarding the selection of the specific sites for replacing a natural amino acid of an antibody with Cys are provided herein.

Cysteine substitution sites are located in the constant region of an antibody or antibody fragment, and are identified herein using standard numbering conventions. It is well known, however, that portions or fragments of antibodies can be used for many purposes instead of intact full-length antibodies, and also that antibodies can be modified in various ways that affect numbering of sites in the constant region even though they do not substantially affect the functioning of the constant region. For example, insertion of an S6 tag (a short peptide) into a loop region of an antibody has been shown to allow activity of the antibody to be retained, even though it would change the numbering of many sites in the antibody. Accordingly, while the preferred cysteine substitution sites described herein are identified by a standard numbering system based on intact antibody numbering, the invention includes the corresponding sites in antibody fragments or in antibodies containing other modifications, such as peptide tag insertion. The corresponding sites in those fragments or modified antibodies are thus preferred sites for cysteine substitution in fragments or modified antibodies, and references to the cysteine substitution sites by number include corresponding sites in modified antibodies or antibody fragments that retain the function of the relevant portion of the full-length antibody.

A corresponding site in an antibody fragment or modified antibody can readily be identified by aligning a segment of the antibody fragment or modified antibody with the full-length antibody to identify the site in the antibody fragment or modified antibody that matches one of the preferred cysteine substitution sites of the invention. Alignment may be based on a segment long enough to ensure that the segment matches the correct portion of the full-length antibody, such as a segment of at least 20 amino acid residues, or at least 50 residues, or at least 100 residues, or at least 150 residues. Alignment may also take into account other modifications that may have been engineered into the antibody fragment or modified antibody, thus differences in sequence due to engineered point mutations in the segment used for alignment, particularly for conservative substitutions, would be allowed. Thus, for example, an Fc domain can be excised from an antibody, and would contain amino acid residues that correspond to the cysteine substitution sites described herein, despite numbering differences: sites in the Fc domain corresponding to the cysteine substitution sites of the invention would also be expected to be advantageous sites for cysteine substation in the Fc domain, and are included in the scope of the invention.

In one embodiment, the invention provides an immunoconjugate of Formula (I):

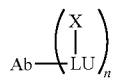

wherein Ab represents an antibody or antibody fragment comprising at least one cysteine residue at one of the preferred cysteine substitution sites described herein;

LU is a linker unit as described herein;
X is a payload or drug moiety;
and n is an integer from 1 to 16.

Typically in compounds of Formula (I), LU is attached to a cysteine at one of the cysteine substitution sites described herein, X is a drug moiety such as an anticancer drug, and n is 2-8 when Ab is an antibody, or n can be 1-8 when Ab is an antibody fragment.

In an embodiment, the invention provides an immunoconjugate comprising a modified antibody or antibody fragment thereof and a drug moiety, wherein said modified antibody or antibody fragment comprises a substitution of one or more amino acids with cysteine on its constant region chosen from positions 121, 124, 152, 171, 174, 258, 292, 333, 360, and 375 of a heavy chain of said antibody or antibody fragment, and wherein said positions are numbered according to the EU system.

In an embodiment, the invention provides an immunoconjugate comprising a modified antibody or antibody fragment thereof and a drug moiety, wherein said modified antibody or antibody fragment comprises a substitution of one or more amino acids with cysteine on its constant region chosen from positions 107, 108, 142, 145, 159, 161, and 165 of a light chain of said antibody or antibody fragment, wherein said positions are numbered according to the EU system, and wherein said light chain is human kappa light chain.

In an aspeembodimentt, the invention provides an immunoconjugate comprising a modified antibody or antibody fragment thereof and a drug moiety, wherein said modified antibody or antibody fragment comprises a substitution of one or more amino acids with cysteine on its constant region chosen from positions 143, 147, 159, 163, and 168 of a light chain of said antibody or antibody fragment, wherein said positions are numbered according to the Kabat system, and wherein said light chain is human lambda light chain.

In an embodiment, the invention provides a modified antibody or antibody fragment thereof comprising a substitution of one or more amino acids with cysteine at the positions described herein. The sites for cysteine substitution are in the constant regions of the antibody and are thus applicable to a variety of antibodies, and the sites are selected to provide stable and homogeneous conjugates. The modified antibody or fragment can have two or more cysteine substitutions, and these substitutions can be used in combination with other antibody modification and conjugation methods as described herein.

In an embodiment, the invention provides pharmaceutical compositions comprising the immunoconjugate disclosed above, and methods to use the immunoconjugates.

In an embodiment, the invention provides a nucleic acid encoding the modified antibody or antibody fragment described herein having at least one cysteine substitution at a site described herein. The invention further provides host cells comprising these nucleic acids and methods to use the nucleic acid or host cells to express and produce the antibodies or fragments described herein.

In an embodiment, the invention provides a method to select an amino acid of an antibody that is suitable for replacement by cysteine to provide a good site for conjugation, comprising:

(1) identifying amino acids in the constant region of the antibody that have a suitable surface exposure to provide a set of initial candidate sites;

(2) for each initial candidate site, expressing an antibody wherein the native amino acid at that site is replaced by cysteine;

(3) for each expressed antibody, determining whether the expressed protein is substantially homogeneous after reduction and reoxidation to provide a functional antibody having a free cysteine at the initial candidate site, (4) for each expressed protein that is substantially homogeneous and functional, conjugating the cysteine at the initial candidate site with a maleimide moiety and determining whether the thiol-maleimide linkage is stable at that site;

(5) removing from the set of initial candidate sites those sites for which the expressed antibody is not substantially homogeneous and functional, and those wherein the thiol-maleimide linkage is destabilized, to provide a set of advantaged sites for cysteine substitution.

Optionally, the method further comprises a step of determining the melting temperature for the conjugate of each advantaged cysteine substitution site, and eliminating from the set any sites where cysteine substitution and conjugation causes the melting temperature to differ by 5° C. or more from that of the native antibody.

In an embodiment, the invention provides a method to produce an immunoconjugate, which comprises attaching a Linker Unit (LU) or a Linker Unit-Payload combination (-LU-X) to a cysteine residue in an antibody or antibody fragment, wherein the cysteine is located at a cysteine substitution site selected from 121, 124, 152, 171, 174, 258, 292, 333, 360, and 375 of a heavy chain of said antibody or antibody fragment, and positions 107, 108, 142, 145, 159, 161, and 165 of a light chain of said antibody or antibody fragment, wherein said positions are numbered according to the EU system.

Other aspects and embodiments of the invention are described in greater detail herein.

1. An immunoconjugate comprising a modified antibody or antibody fragment thereof, wherein said modified antibody or antibody fragment comprises a substitution of one or more amino acids with cysteine on its constant region at a site selected from positions 121, 124, 152, 171, 174, 258, 292, 333, 334, 360, 375, and 392 of a heavy chain of said antibody or antibody fragment, and wherein said positions are numbered according to the EU system.
2. The immunoconjugate of embodiment 1, wherein the substitution of one or more amino acids with cysteine is selected from positions 121, 124, 152, 258, 334, 360, and 392.
3. The immunoconjugate of embodiments 1 or 2, wherein said antibody or antibody fragment comprises a sequence selected from the group consisting of SEQ ID NOs: 4, 5, 10, 17, 18, 29, 35, 42, 43, 48, 50, 54, 290, 291, 292, 293, 294, and 295.
4. An immunoconjugate comprising a modified antibody or antibody fragment thereof, wherein said modified antibody or antibody fragment comprises a substitution of one or more amino acids with cysteine on its constant region at a site selected from positions 107, 108, 142, 145, 159, 161, and 165 of a light chain of said antibody or antibody fragment, wherein said positions are numbered according to the EU system, and wherein said light chain is a human kappa light chain.
5. The immunoconjugate of embodiment 4, wherein the substitution of one or more amino acids with cysteine is selected from positions 145 or 165.
6. The immunoconjugate of embodiment 4, wherein said antibody or antibody fragment comprises a sequence selected from the group consisting of SEQ ID NOs: 61, 62, 69, 71, 75, 76, and 77.
7. An immunoconjugate comprising a modified antibody or antibody fragment thereof, wherein said modified antibody or antibody fragment comprises a substitution of one or more amino acids with cysteine on its constant region at a site selected from positions 143, 147, 159, 163, and 168 of a light chain of said antibody or antibody fragment, wherein said positions are numbered according to the Kabat system, and wherein said light chain is human a lambda light chain.
8. The immunoconjugate of embodiment 7, wherein said antibody or antibody fragment comprises a sequence selected from the group consisting of SEQ ID NOs: 92, 94, 96, 97, and 98.
9. The immunoconjugate of embodiment 1, 2, or 3, wherein said modified antibody or antibody fragment further comprises a substitution of one or more amino acids with cysteine on its constant region at a site selected from positions 107, 108, 142, 145, 159, 161, and 165 of a light chain of said antibody or antibody fragment, wherein said positions are numbered according to the EU system, and wherein said light chain is a human kappa light chain.
10. The immunoconjugate of embodiment 1, 2, or 3, wherein said modified antibody or antibody fragment further comprises a substitution of one or more amino acids with cysteine on its constant region selected from positions 143, 147, 159, 163, and 168 of a light chain of said antibody or antibody fragment, wherein said light chain positions are numbered according to the Kabat system, and wherein said light chain is a human kappa light chain.
11. An immunoconjugate comprising a modified antibody or antibody fragment thereof wherein said modified antibody or antibody fragment comprises a combination of substitutions of two or more amino acids with cysteine on a constant region of a heavy chain at positions 152 and 375, or at positions 327 and 375, wherein said positions are numbered according to the EU system.
12. An immunoconjugate comprising a modified antibody or antibody fragment thereof wherein said modified antibody or antibody fragment comprises a combination of substitution of two or more amino acids with cysteine on its constant regions comprising position 107 of a light chain and 360 of a heavy chain, wherein said light chain is a kappa chain, and wherein said positions are numbered according to the EU system.
13. An immunoconjugate comprising a modified antibody or antibody fragment thereof wherein said modified antibody or antibody fragment comprises a substitution of one or more amino acids with cysteine on its constant region selected from positions 117, 119, 121, 124, 139, 152, 153, 155, 157, 164, 169, 171, 174, 189, 205, 207, 246, 258, 269, 274, 286, 288, 290, 292, 293, 320, 322, 326, 333, 334, 335, 337, 344, 355, 360, 375, 382, 390, 392, 398, 400 and 422 of a heavy chain of said antibody or antibody fragment, and wherein said positions are numbered according to the EU system.
14. An immunoconjugate comprising a modified antibody or antibody fragment thereof wherein said modified antibody or antibody fragment comprises a substitution of one or more amino acids with cysteine on its constant region selected from positions 107, 108, 109, 114, 129, 142, 143, 145, 152, 154, 156, 159, 161, 165, 168, 169, 170, 182, 183, 197, 199, and 203 of a light chain of said antibody or antibody fragment, wherein said positions are numbered according to the EU system, and wherein said light chain is a human kappa light chain.

15. An immunoconjugate comprising a modified antibody or antibody fragment thereof, wherein said modified antibody or antibody fragment comprises a substitution of one or more amino acids with cysteine selected from positions 143, 145, 147, 156, 159, 163, and 168 on its constant region of a light chain of said antibody or antibody fragment, wherein said positions are numbered according to the Kabat system, and wherein said light chain is a human lambda light chain.

16. An immunoconjugate comprising a modified antibody or antibody fragment thereof, wherein said modified antibody or antibody fragment comprises a combination of substitution of two or more amino acids with cysteine on its constant regions wherein the combinations comprise substitutions at positions 375 of an antibody heavy chain and position 165 of an antibody light chain, or at position 334 of an antibody heavy chain at position 165 of an antibody light chain, and wherein said light chain is a kappa chain, and wherein said positions are numbered according to the EU system.

17. The immunoconjugate of any of embodiments 11, 12, and 16 wherein the drug antibody ratio is about 4.

18. An immunoconjugate comprising a modified antibody or antibody fragment thereof, wherein said modified antibody or antibody fragment comprises a combination of substitution of three or more amino acids with cysteine on its constant regions wherein the combinations comprise substitutions selected from
    a. positions 375 and 392 of the an antibody heavy chain and position 165 of an antibody light chain,
    b. positions 334 and 375 of an antibody heavy chain and position 165 of an antibody light chain, and
    c. positions 334 and 392 of an antibody heavy chain and position 165 of an antibody light chain,
    and wherein said light chain is a kappa chain, and wherein said positions are numbered according to the EU system.

19. An immunoconjugate comprising a modified antibody or antibody fragment thereof, wherein said modified antibody or antibody fragment comprises a combination of substitution of three or more amino acids with cysteine on its constant regions wherein the combinations comprise substitutions selected from
    a. positions 152, 375 and 392 of the an antibody heavy chain,
    b. positions 152, 334 and 375 of an antibody heavy chain, and
    c. positions 152, 334 and 392 of an antibody heavy chain,
    and wherein said positions are numbered according to the EU system.

20. The immunoconjugates of embodiments 18 or 19 wherein the drug antibody ratio is about 6.

21. An immunoconjugate comprising a modified antibody or antibody fragment thereof, wherein said modified antibody or antibody fragment thereof comprises a combination of substitution of four or more amino acids with cysteine on its constant regions wherein the combinations comprise substitutions at positions 334, 375, and 392 of an antibody heavy chain and position 165 of an antibody light chain, or at positions 333, 375, and 392 of an antibody heavy chain and at position 165 of an antibody light chain, and wherein said light chain is a kappa chain, and wherein said positions are numbered according to the EU system.

22. An immunoconjugate comprising a modified antibody or antibody fragment thereof, wherein said modified antibody or antibody fragment thereof comprises a combination of substitution of four or more amino acids with cysteine on its constant regions wherein the combinations comprise substitutions at positions 152, 334, 375, and 392 of an antibody heavy chain, or at positions 152, 333, 375, and 392 of an antibody heavy chain, and wherein said positions are numbered according to the EU system.

23. The immunoconjugates of embodiment 21 or 22 wherein the drug antibody ratio is about 8.

24. The immunoconjugate of any of embodiments 1-23 further comprising a drug moiety.

25. The immunoconjugate of embodiment 24, wherein a drug moiety is attached to the modified antibody or antibody fragment through the sulfur of said cysteine and an optional linker.

26. The immunoconjugate of embodiment 25, wherein said drug moiety is connected to said sulfur of said cysteine through a cleavable or non-cleavable linker.

27. The immunoconjugate of embodiment 25, wherein said drug moiety is connected to said sulfur of said cysteine through a non-cleavable linker.

28. The immunoconjugate of embodiment 25, wherein said immunoconjugate comprises a thiol-maleimide linkage.

29. The immunoconjugate of embodiment 25, wherein said immunoconjugate comprises a —S—CH$_2$—C(═O)— linkage or a disulfide linkage.

30. The immunoconjugate of any of embodiments 25-29, wherein said drug moiety is a cytotoxic agent.

31. The immunoconjugate of embodiment 30, wherein said drug moiety is selected from the group consisting of taxanes, DNA-alkylating agents (e.g., CC-1065 analogs), anthracyclines, tubulysin analogs, duocarmycin analogs, auristatin E, auristatin F, and maytansinoids.

32. The immunoconjugate of any of embodiments 1-31, wherein said antibody is a monoclonal antibody.

33. The immunoconjugate of any of embodiments 1-31, wherein said antibody is a chimeric antibody.

34. The immunoconjugate of embodiment 31, wherein said antibody is a humanized or fully human antibody.

35. The immunoconjugate of embodiment 31, wherein said antibody is a bispecific or multi-specific antibody.

36. The immunoconjugate of any of embodiments 1-32, wherein said antibody or antibody fragment specifically binds to a cell surface marker characteristic of a tumor.

37. A pharmaceutical composition comprising the immunoconjugate of any of embodiments 1-36.

38. A modified antibody or antibody fragment thereof comprising a substitution of one or more amino acids with cysteine on its constant region selected from positions 117, 119, 121, 124, 139, 152, 153, 155, 157, 164, 169, 171, 174, 189, 205, 207, 246, 258, 269, 274, 286, 288, 290, 292, 293, 320, 322, 326, 333, 334, 335, 337, 344, 355, 360, 375, 382, 390, 392, 398, 400, and 422 of a heavy chain of said antibody or antibody fragment, and wherein said positions are numbered according to the EU system.

39. A modified antibody or antibody fragment thereof comprising a substitution of one or more amino acids with cysteine on its constant region selected from positions 107, 108, 109, 114, 129, 142, 143, 145, 152, 154, 156, 159, 161, 165, 168, 169, 170, 182, 183, 197, 199, and 203 of a light chain of said antibody or antibody fragment, wherein said positions are numbered according to the EU system, and wherein said light chain is human kappa light chain.

40. A modified antibody or antibody fragment thereof comprising a substitution of one or more amino acids with cysteine on its constant region selected from positions 143, 145, 147, 156, 159, 163, 168 on its constant region of a light chain of said antibody or antibody fragment, wherein said positions are numbered according to the Kabat system, and wherein light chain is human lambda light chain.

41. The modified antibody or antibody fragment of embodiment 38, wherein said substitution is at least one cysteine, selected from positions 121, 124, 152, 171, 174, 258, 292, 333, 360, and 375 of the heavy chain, and wherein said positions are numbered according to the EU system.

42. The modified antibody or antibody fragment of embodiment 39, wherein said substitution is two to six cysteines, wherein said cysteines are at positions selected from 121, 124, 152, 171, 174, 258, 292, 333, 360, and 375 of a heavy chain, and wherein said positions are numbered according to the EU system.

43. The modified antibody or antibody fragment of embodiment 39, wherein said substitution is at least one cysteine, selected from positions 107, 108, 142, 145, 159, 161, and 165 of a light chain, wherein said positions are numbered according to the EU system, and wherein said light chain is a human kappa light chain.

44. The modified antibody or antibody fragment of embodiment 40, wherein said substitution is two to six cysteines, wherein said cysteines are at positions selected from positions 107, 108, 142, 145, 159, 161, and 165 of a light chain, wherein said positions are numbered according to the EU system, and wherein said light chain is a human kappa light chain.

45. The modified antibody or antibody fragment of embodiment 40, wherein said substitution is at least one cysteine, selected from positions 143, 147, 159, 163, and 168 of a light chain, wherein said positions are numbered according to the Kabat system, and wherein said light chain is a human lambda light chain.

46. The modified antibody or antibody fragment of embodiment 40, wherein said substitution is two to six cysteines, wherein said cysteines are at positions selected from positions 143, 147, 159, 163, and 168 of a light chain, wherein said positions are numbered according to the Kabat system, and wherein said light chain is a human lambda light chain.

47. The modified antibody or antibody fragment of any of embodiment 11, 12, 14-22, 38-47 which is further attached to a drug moiety, and wherein said drug moiety is attached to the modified antibody or antibody fragment through the sulfur of said cysteine and an optional linker.

48. The modified antibody or antibody fragment of embodiment 47, wherein said drug moiety is attached to the sulfur of said cysteine through a Linker Unit 49. The modified antibody or antibody fragment of any of embodiment 38-48, further comprising at least one Pcl or unnatural amino acid substitution or a peptide tag for enzyme-mediated conjugation and/or combinations thereof.

50. A nucleic acid encoding the modified antibody or antibody fragment of any of embodiment 38-49.

51. A host cell comprising the nucleic acid of embodiment 50.

52. A method of producing a modified antibody or antibody fragment comprising incubating the host cell of embodiment 49 under suitable conditions for expressing the antibody or antibody fragment, and isolating said antibody or antibody fragment.

53. A method to select an amino acid of an antibody that is suitable for replacement by cysteine to provide a suitable site for conjugation, comprising
  (1) identifying amino acids in the constant region of the antibody that have a suitable surface exposure to provide a set of initial candidate sites;
  (2) for each initial candidate site, expressing an antibody wherein the native amino acid at that site is replaced by cysteine;
  (3) for each expressed antibody, determining whether the expressed protein is substantially homogeneous after reduction and reoxidation to provide a functional antibody having a free cysteine at the initial candidate site,
  (4) for each expressed protein that is substantially homogeneous and functional, conjugating the cysteine at the initial candidate site with a maleimide moiety and determining whether the thiol-maleimide linkage is destabilized at that site;
  (5) removing from the set of initial candidate sites those sites for which the expressed antibody is not substantially homogeneous and functional, and those wherein the thiol-maleimide linkage is destabilized, to provide a set of advantaged sites for cysteine substitution.

54. The method of embodiment 53, further comprising a step of determining the melting temperature for the conjugate of each advantaged cysteine substitution site, and eliminating from the set any sites where cysteine substitution and conjugation causes the melting temperature to differ by 5° C. or more from that of the parental antibody.

55. The method of embodiment 53 or 54, further comprising producing an antibody or antibody fragment containing cysteine at one or more of the substitution sites identified.

56. A method to produce an immunoconjugate, which comprises attaching a Linker Unit (LU) or a Linker Unit-Payload combination (-LU-X) to a cysteine residue in an antibody or antibody fragment, wherein the cysteine is located at a cysteine substitution site selected from 121, 124, 152, 171, 174, 258, 292, 333, 360, and 375 of a heavy chain of said antibody or antibody fragment, and positions 107, 108, 142, 145, 159, 161, and 165 of a light chain of said antibody or antibody fragment, wherein said positions are numbered according to the EU system.

57. The method of embodiment 56, wherein the immunoconjugate is of Formula (I):

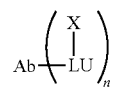

wherein Ab represents an antibody or antibody fragment comprising at least one cysteine residue at one of the preferred cysteine substitution sites described herein;

LU is a linker unit as described herein;

X is a payload or drug moiety;

and n is an integer from 1 to 16.

Definitions

The term "amino acid" refers to canonical, synthetic, and unnatural amino acids, as well as amino acid analogs and amino acid mimetics that function in a manner similar to the canonical amino acids. Canonical amino acids are proteidogenous amino acids encoded by the genetic code and include alanine, arginine, asparagine, aspartic acid, cysteine, glutamine, glutamic acid, glycine, histidine, isoleucine, leucine, lysine, methionine, phenylalanine, proline serine, threonine, tryptophan, tyrosine, valine, as well as selenocysteine, pyrrolysine and its analog pyrroline-carboxy-lysine. Amino acid analogs refer to compounds that have the same basic chemical structure as a canonical amino acid, i.e., an α-carbon that is bound to a hydrogen, a carboxyl group, an amino group, and an R group, e.g., citrulline, homoserine, norleucine, methionine sulfoxide, methionine methyl sulfonium. Such analogs have modified R groups (e.g., norleucine) or modified peptide backbones, but retain the same basic chemical structure as a canonical amino acid.

Amino acid mimetics refer to chemical compounds that have a structure that is different from the general chemical structure of an amino acid, but that function in a manner similar to a canonical amino acid. The term "unnatural amino acid", as used herein, is intended to represent amino acid structures that cannot be generated biosynthetically in any organism using unmodified or modified genes from any organism, whether the same or different. In addition, such "unnatural amino acids" typically require a modified tRNA and a modified tRNA synthetase (RS) for incorporation into a protein. This tRNA/RS pair preferentially incorporates the unnatural amino acid over canonical amino acids. Such orthogonal tRNA/RS pair is generated by a selection process as developed by Schultz et al. (see, e.g., Liu et al., (2010) Annu. Rev. Biochem. 79:413-444) or a similar procedure. The term "unnatural amino acid" does not include the natural occurring $22^{nd}$ proteinogenic amino acid pyrrolysine (Pyl) as well as its demethylated analog pyrroline-carboxy-lysine (Pcl), because incorporation of both residues into proteins is mediated by the unmodified, naturally occurring pyrrolysyl-tRNA/tRNA synthetase pair and because Pyl and Pcl are generated biosynthetically (see, e.g., On et al., (2011) Proc. Natl. Acad. Sci. USA, 108:10437-10442; Cellitti et al., (2011) Nat. Chem. Biol. 27; 7(8):528-30). See also U.S. provisional application 61/762,36, incorporated by reference, that sites specific amino acid residues in antibody light and heavy chains that can be substituted with Pcl.

The term "antibody" as used herein refers to a polypeptide of the immunoglobulin family that is capable of binding a corresponding antigen non-covalently, reversibly, and in a specific manner. For example, a naturally occurring IgG antibody is a tetramer comprising at least two heavy (H) chains (also referred to as "antibody heavy chain") and two light (L) chains (also referred to as "antibody light chain") inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hyper variability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antibody" includes, but is not limited to, monoclonal antibodies, human antibodies, humanized antibodies, camelid antibodies, chimeric antibodies, and anti-idiotypic (anti-Id) antibodies (including, e.g., anti-Id antibodies to antibodies of the invention). The antibodies can be of any isotype/class (e.g., IgG, IgE, IgM, IgD, IgA and IgY), or subclass (e.g., IgG1, IgG2, IgG3, IgG4, IgA1 and IgA2).

Both the light and heavy chains are divided into regions of structural and functional homology. The terms "constant" and "variable" are used functionally. In this regard, it will be appreciated that the variable domains of both the light ($V_L$) and heavy ($V_H$) chain portions determine antigen recognition and specificity. Conversely, the constant domains of the light chain ($C_L$) and the heavy chain (CH1, CH2 or CH3) confer important biological properties such as secretion, transplacental mobility, Fc receptor binding, complement binding, and the like. By convention, the numbering of the constant region domains increases as they become more distal from the antigen binding site or amino-terminus of the antibody. The N-terminus is a variable region and at the C-terminus is a constant region; the CH3 and $C_L$ domains actually comprise the carboxy-terminal domains of the heavy and light chain, respectively.

The term "antibody fragment" as used herein refers to either an antigen binding fragment of an antibody or a non-antigen binding fragment (e.g., Fc) of an antibody. The term "antigen binding fragment", as used herein, refers to one or more portions of an antibody that retain the ability to specifically interact with (e.g., by binding, steric hindrance, stabilizing/destabilizing, spatial distribution) an epitope of an antigen. Examples of binding fragments include, but are not limited to, single-chain Fvs (scFv), disulfide-linked Fvs (sdFv), Fab fragments, F(ab') fragments, a monovalent fragment consisting of the $V_L$, $V_H$, $C_L$ and CH1 domains; a $F(ab)_2$ fragment, a bivalent fragment comprising two Fab fragments linked by a disulfide bridge at the hinge region; a Fd fragment consisting of the $V_H$ and CH1 domains; a Fv fragment consisting of the $V_L$ and $V_H$ domains of a single arm of an antibody; a dAb fragment (Ward et al., Nature 341:544-546, 1989), which consists of a $V_H$ domain; and an isolated complementarity determining region (CDR), or other epitope-binding fragments of an antibody.

Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv ("scFv"); see, e.g., Bird et al., Science 242:423-426, 1988; and Huston et al., Proc. Natl. Acad. Sci. 85:5879-5883, 1988). Such single chain antibodies are also intended to be encompassed within the term "antigen binding fragment." These antigen binding fragments are obtained using conventional techniques known to those of skill in the art, and the fragments are screened for utility in the same manner as are intact antibodies.

Antigen binding fragments can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen binding fragments can be grafted into scaffolds based on polypeptides such as fibronectin type III (Fn3) (see U.S. Pat. No. 6,703,199, which describes fibronectin polypeptide monobodies).

Antigen binding fragments can be incorporated into single chain molecules comprising a pair of tandem Fv segments ($V_H$-CH1-$V_H$-CH1) which, together with complementary light chain polypeptides, form a pair of antigen binding regions (Zapata et al., *Protein Eng.* 8:1057-1062, 1995; and U.S. Pat. No. 5,641,870).

The term "monoclonal antibody" or "monoclonal antibody composition" as used herein refers to polypeptides, including antibodies and antibody fragments that have substantially identical amino acid sequence or are derived from the same genetic source. This term also includes preparations of antibody molecules of single molecular composition. A monoclonal antibody composition displays a single binding specificity and affinity for a particular epitope.

The term "human antibody", as used herein, includes antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences or antibody containing consensus framework sequences derived from human framework sequences analysis, for example, as described in Knappik et al., *J. Mol. Biol.* 296:57-86, 2000).

The human antibodies of the invention may include amino acid residues not encoded by human sequences (e.g., mutations introduced by random or site-specific mutagenesis in vitro or by somatic mutation in vivo, or a conservative substitution to promote stability or manufacturing).

The term "humanized" antibody, as used herein, refers to an antibody that retains the reactivity of a non-human antibody while being less immunogenic in humans. This can be achieved, for instance, by retaining the non-human CDR regions and replacing the remaining parts of the antibody with their human counterparts. See, e.g., Morrison et al., *Proc. Natl. Acad. Sci. USA,* 81:6851-6855 (1984); Morrison and Oi, *Adv. Immunol.,* 44:65-92 (1988); Verhoeyen et al., *Science,* 239:1534-1536 (1988); Padlan, *Molec. Immun.,* 28:489-498 (1991); Padlan, *Molec. Immun.,* 31(3):169-217 (1994).

The term "recognize" as used herein refers to an antibody or antigen binding fragment thereof that finds and interacts (e.g., binds) with its epitope, whether that epitope is linear or conformational. The term "epitope" refers to a site on an antigen to which an antibody or antigen binding fragment of the invention specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include techniques in the art, for example, x-ray crystallography and 2-dimensional nuclear magnetic resonance (see, e.g., Epitope Mapping Protocols in Methods in Molecular Biology, Vol. 66, G. E. Morris, Ed. (1996)).

The term "affinity" as used herein refers to the strength of interaction between antibody and antigen at single antigenic sites. Within each antigenic site, the variable region of the antibody "arm" interacts through weak non-covalent forces with antigen at numerous sites; the more interactions, the stronger the affinity.

The term "isolated antibody" refers to an antibody that is substantially free of other antibodies having different antigenic specificities. An isolated antibody that specifically binds to one antigen may, however, have cross-reactivity to other antigens. Moreover, an isolated antibody may be substantially free of other cellular material and/or chemicals.

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). In some embodiments, the term "conservative sequence modifications" are used to refer to amino acid modifications that do not significantly affect or alter the binding characteristics of the antibody containing the amino acid sequence.

The term "optimized" as used herein refers to a nucleotide sequence has been altered to encode an amino acid sequence using codons that are preferred in the production cell or organism, generally a eukaryotic cell, for example, a yeast cell, a *Pichia* cell, a fungal cell, a *Trichoderma* cell, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence.

The terms "percent identical" or "percent identity," in the context of two or more nucleic acids or polypeptide sequences, refers to two or more sequences or subsequences that are the same. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 30 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman, Adv. Appl. Math. 2:482c (1970), by the homology alignment algorithm of Needleman and Wunsch, J. Mol. Biol. 48:443 (1970), by the search for similarity method of Pearson and Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., Current Protocols in Molecular Biology, 2003).

Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: The cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=−4 and a comparison of both strands. For amino acid sequences, the BLASTP program uses as defaults a word length of 3, and expectation (E) of 10, and the BLOSUM62 scoring matrix (see Henikoff and Henikoff, (1989) Proc. Natl. Acad. Sci. USA 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul, Proc. Natl. Acad. Sci. USA 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The percent identity between two amino acid sequences can also be determined using the algorithm of E. Meyers and W. Miller, Comput. Appl. Biosci. 4:11-17, 1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch, J. Mol. Biol. 48:444-453, 1970) algorithm which has been incorporated into the GAP program in the GCG software package (available at www.gcg.com), using either a Blossom 62 matrix or a PAM250 matrix, and a gap weight of 16, 14, 12, 10, 8, 6, or 4 and a length weight of 1, 2, 3, 4, 5, or 6.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses silent variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., (1991) Nucleic Acid Res. 19:5081; Ohtsuka et al., (1985) J. Biol. Chem. 260:2605-2608; and Rossolini et al., (1994) Mol. Cell. Probes 8:91-98).

The term "operably linked" in the context of nucleic acids refers to a functional relationship between two or more polynucleotide (e.g., DNA) segments. Typically, it refers to the functional relationship of a transcriptional regulatory sequence to a transcribed sequence.

For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The terms "polypeptide" and "protein" are used interchangeably herein to refer to a polymer of amino acid residues. The terms apply to canonical amino acid polymers as well as to non-canonical amino acid polymers. Unless otherwise indicated, a particular polypeptide sequence also implicitly encompasses conservatively modified variants thereof.

The term "immunoconjugate" or "antibody conjugate" as used herein refers to the linkage of an antibody or an antibody fragment thereof with another agent, such as a chemotherapeutic agent, a toxin, an immunotherapeutic agent, an imaging probe, a spectroscopic probe, and the like. The linkage can be through one or multiple covalent bonds, or non-covalent interactions, and can include chelation. Various linkers, many of which are known in the art, can be employed in order to form the immunoconjugate. Additionally, the immunoconjugate can be provided in the form of a fusion protein that may be expressed from a polynucleotide encoding the immunoconjugate. As used herein, "fusion protein" refers to proteins created through the joining of two or more genes or gene fragments which originally coded for separate proteins (including peptides and polypeptides). Fusion proteins may be created by joining at the N- or C-terminus, or by insertions of genes or gene fragments into permissible regions of one of the partner proteins. Translation of the fusion gene results in a single protein with functional properties derived from each of the original proteins.

The term "subject" includes human and non-human animals. Non-human animals include all vertebrates, e.g., mammals and non-mammals, such as non-human primates, sheep, dog, cow, chickens, amphibians, and reptiles. Except when noted, the terms "patient" or "subject" are used herein interchangeably.

The term "cytotoxin", or "cytotoxic agent" as used herein, refer to any agent that is detrimental to the growth and proliferation of cells and may act to reduce, inhibit, or destroy a cell or malignancy.

The term "anti-cancer agent" as used herein refers to any agent that can be used to treat a cell proliferative disorder such as cancer, including but not limited to, cytotoxic agents, chemotherapeutic agents, radiotherapy and radiotherapeutic agents, targeted anti-cancer agents, and immunotherapeutic agents.

The term "drug moiety" or "payload" are used interchangeably and refers to a chemical moiety that is conjugated to the antibody or antibody fragment of the invention, and can include any moiety that is useful to attach to an antibody or antibody fragment. For example, a drug moiety or payload can be an anti-cancer agent, an anti-inflammatory agent, an antifungal agent, an antibacterial agent, an anti-parasitic agent, an anti-viral agent, an anesthetic agent. In certain embodiments a drug moiety is selected from a V-ATPase inhibitor, a HSP90 inhibitor, an IAP inhibitor, an mTor inhibitor, a microtubule stabilizer, a microtubule destabilizers, an auristatin, a dolastatin, a maytansinoid, a MetAP (methionine aminopeptidase), an inhibitor of nuclear export of proteins CRM1, a DPPIV inhibitor, an inhibitor of phosphoryl transfer reactions in mitochondria, a protein synthesis inhibitor, a kinase inhibitor, a CDK2 inhibitor, a CDK9 inhibitor, a proteasome inhibitor, a kinesin inhibitor, an HDAC inhibitor, a DNA damaging agent, a DNA alkylating agent, a DNA intercalator, a DNA minor groove binder and a DHFR inhibitor. Suitable examples include auristatins such as MMAE and MMAF; calicheamycins such as gamma-calicheamycin; and maytansinoids such as DM1 and DM4. Methods for attaching each of these to a linker compatible with the antibodies and method of the invention are known in the art. See, e.g., Singh et al., (2009) Therapeutic Antibodies: Methods and Protocols, vol. 525, 445-457. In addition, a payload can be a biophysical probe, a fluorophore, a spin label, an infrared probe an affinity probe, a chelator, a spectroscopic probe, a radioactive probe, a lipid molecule, a polyethylene glycol, a polymer, a spin label, DNA, RNA, a protein, a peptide, a surface, an antibody, an antibody fragment, a nanoparticle, a quantum dot, a liposome, a PLGA particle, a saccharide or a polysaccharide, a reactive functional group, or a binding agent that can connect the conjugate to another moiety, surface, etc.

The term "drug antibody ratio" (also referred to as "DAR"), refers to the number or payload or drug moieties linked to an antibody of the immunoconjugate. For example a drug antibody of ratio of 2 means that average of two drug moieties bound to an each antibody in a sample of immunoconjugates. Some individual immunoconjugates will in a sample with a drug antibody ratio of two might have none or only one drug moiety linked; others immunoconjugates in that sample will have two, three, four, or even more moieties on individual antibody. But the average in the sample will be two. There are different methods known in the art for measuring drug antibody ratios of immunoconjugates.

In an embodiment of this invention, the DAR in a sample of immunoconjugates can be "homogenous". A "homogenous conjugation sample" is a sample with a narrow distribution of DAR. As an illustrative embodiment, in a homogenous conjugation sample having a DAR of 2, can contain within that sample antibodies that are not conjugated, and some antibodies having more than two moieties conjugated at about a DAR of two. "Most of the sample" means have at least over 70%, or at least over 80% or at least over 90% of the antibodies in the sample will be conjugated to two moieties.

As an illustrative embodiment, in a homogenous conjugation sample having a DAR of 4, can contain within that sample antibodies that have more or fewer than four moieties conjugated at about a DAR of four. "Most of the sample" means have at least over 70%, or at least over 80% or at least over 90% of the antibodies in the sample will be conjugated to four moieties.

As an illustrative embodiment, in a homogenous conjugation sample having a DAR of 6, can contain within that sample antibodies that are have more or fewer than six moieties conjugated at about a DAR of six. "Most of the sample" means have at least over 70%, or at least over 80% or at least over 90% of the antibodies in the sample will be conjugated to six moieties.

As an illustrative embodiment, in a homogenous conjugation sample having a DAR of 8, can contain within that sample antibodies that has some antibodies having fewer or more than eight moieties conjugated at about a DAR of four. "Most of the sample" means have at least over 70%, or at least over 80% or at least over 90% of the antibodies in the sample will be conjugated to eight moieties.

An immunoconjugate having a "drug antibody ratio of about 2" refers to sample of immunoconjugates where in the drug antibody ratio can range from about 1.6-2.4 moieties/antibody, 1.8-2.3 moieties/antibody, or 1.9-2.1 moieties/antibody.

An immunoconjugate having a "drug antibody ratio of about 4" refers to sample of immunoconjugates where in the drug antibody ratio can range from about 3.6-4.4 moieties/antibody, 3.8-4.3 moieties/antibody, or 3.9-4.1 moieties/antibody.

An immunoconjugate having a "drug antibody ratio of about 6" refers to sample of immunoconjugates where in the drug antibody ratio can range from about 5.6-6.4 moieties/antibody, 5.8-6.3 moieties/antibody, or 5.9-6.1 moieties/antibody.

An immunoconjugate having a "drug antibody ratio of about 8" refers to sample of immunoconjugates where in the drug antibody ratio can range from about 7.6-84 moieties/antibody, 7.8-8.3 moieties/antibody, or 7.9-8.1 moieties/antibody.

"Tumor" refers to neoplastic cell growth and proliferation, whether malignant or benign, and all pre-cancerous and cancerous cells and tissues.

The term "anti-tumor activity" means a reduction in the rate of tumor cell proliferation, viability, or metastatic activity. A possible way of showing anti-tumor activity is to show a decline in growth rate of abnormal cells that arises during therapy or tumor size stability or reduction. Such activity can be assessed using accepted in vitro or in vivo tumor models, including but not limited to xenograft models, allograft models, MMTV models, and other known models known in the art to investigate anti-tumor activity.

The term "malignancy" refers to a non-benign tumor or a cancer. As used herein, the term "cancer" includes a malignancy characterized by deregulated or uncontrolled cell growth. Exemplary cancers include: carcinomas, sarcomas, leukemias, and lymphomas.

The term "cancer" includes primary malignant tumors (e.g., those whose cells have not migrated to sites in the subject's body other than the site of the original tumor) and secondary malignant tumors (e.g., those arising from metastasis, the migration of tumor cells to secondary sites that are different from the site of the original tumor).

As used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or may be resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlorotheophyllinate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulfate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholanate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled compounds as defined herein, for example those into which radioactive isotopes, such as $^3H$ and $^{14}C$, or those into which non-radioactive isotopes, such as $^2H$ and $^{13}C$ are present. Such isotopically labeled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of a compound of the present invention that, when administered to a subject, is effective to at least partially alleviate, inhibit, prevent and/or ameliorate a condition, or a disorder or a disease, or at least partially inhibit activity of a targeted enzyme or receptor.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

The term "thiol-maleimide" as used herein describes a group formed by reaction of a thiol with maleimide, having this general formula

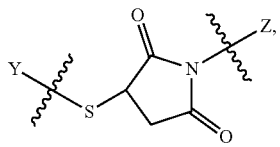

where Y and Z are groups to be connected via the thiol-maleimide linkage and can be linker units, and can be attached to antibodies or payloads. In some instances, Y is an engineered antibody according to the invention, and the sulfur atom shown in the formula is from a cysteine at one of the substitution sites described herein; while Z represents a linker unit connected to a payload.

"Linker Unit" (LU) as used herein refers to a covalent chemical connection between two moieties, such as an antibody and a payload. Each LU can be comprised of one or more components described herein as $L_1$, $L_2$, $L_3$, $L_4$, $L_5$ and $L_6$. The linker unit can be selected to provide suitable spacing between the connected moieties, or to provide certain physicochemical properties, or to allow cleavage of the linker unit under certain conditions.

"Cleavable" as used herein refers to a linker or linker unit (LU) that connects two moieties by covalent connections, but breaks down to sever the covalent connection between the moieties under physiological conditions. Cleavage may be enzymatic or non-enzymatic, but generally releases a payload from an antibody without degrading the antibody.

"Non-cleavable" as used herein refers to a linker or linker unit (LU) that is not susceptible to breaking down under physiological conditions. While the linker may be modified physiologically, it keeps the payload connected to the antibody until the antibody is substantially degraded, i.e., the antibody degradation precedes cleavage of the linker in vivo.

"Cyclooctyne" as used herein refers to an 8-membered ring containing a carbon-carbon triple bond (acetylene). The ring is optionally fused to one or two phenyl rings, which may be substituted with 1-4 $C_{1-4}$ alkyl, $C_{1-4}$ alkoxy, halo, hydroxyl, COOH, $COOL_1$, —C(O)NH-$L_1$, O-$L_1$, or similar groups, and which may contain N, O or S as a ring member. In preferred embodiments, cyclooctyne can be a $C_8$ hydrocarbon ring, particularly an isolated ring that is saturated aside from the triple bond, and may be substituted with F or Hydroxy, and may be linked to a linker or LU via —O—, —C(O), C(O)NH, or C(O)O.

"Cyclooctene" as used herein refers to an 8-membered ring containing at least one double bond, especially a trans-double bond. The ring is optionally fused to one or two phenyl rings, which may be substituted with 1-4 $C_{1-4}$ alkyl, $C_{1-4}$ alkoxy, halo, hydroxyl, COOH, $COOL_1$, —C(O)NH-$L_1$, O-$L_1$, or similar groups, and which may contain N, O or S as a ring member. In preferred embodiments, cyclooctene can be an isolated $C_8$ hydrocarbon ring that is saturated aside from the trans double bond and is optionally substituted with F or Hydroxy, and may be linked to a linker or LU via —O—, —C(O), C(O)NH, or C(O)O.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

BRIEF DESCRIPTION OF THE DRAWINGS

FIG. 2. Location of selected 92 TAG mutations in the structure of a human IgG1 with a kappa light chain. Selected residues for TAG mutations are shown in black on only one of the two heavy chains and for one of the two kappa light chains (1HZH.pdb). Structures are shown using PyMOL, an open-source molecular modeling package (The PyMOL Molecular Graphics System, Version 1.5.0. Schrödinger. LLC).

FIG. 3. The amino acid sequence alignment of the heavy chain constant regions of trastuzumab and antibody 14090. Residues mutated to Cys in the trastuzumab antibody and in antibody 14090 are underlined. Amino acid residues in heavy chain are numbered by Eu numbering system (Edelman et al., 1969).

FIG. 4. Amino acid sequence alignment of constant regions of trastuzumab, human IgG1, IgG2, IgG3 and IgG4.

FIG. 5A-FIG. 5B. The amino acid sequence alignment of the constant regions of human kappa and lambda light chains. A. Residues mutated to Cys in the kappa light chain of trastuzumab and in the lambda light chain of antibody 14090 are underlined. B. Residues selected for Cys mutations are shown in a PyMOL structure model of a human lambda light chain (Protein Structure Databank entry 3G6D.pdb)

FIG. 24A-FIG. 24C. Location of selected payload sites in the structure of a human IgG1 with a kappa light chain. Selected residues are shown in black on only one of the two heavy chains and for one of the two kappa light chains (1HZH.pdb). Three rotations of the structure are shown using PyMOL, an open-source molecular modeling package (The PyMOL Molecular Graphics System, Version 1.5.0. Schrödinger, LLC).

DETAILED DESCRIPTION

Figure 1A:
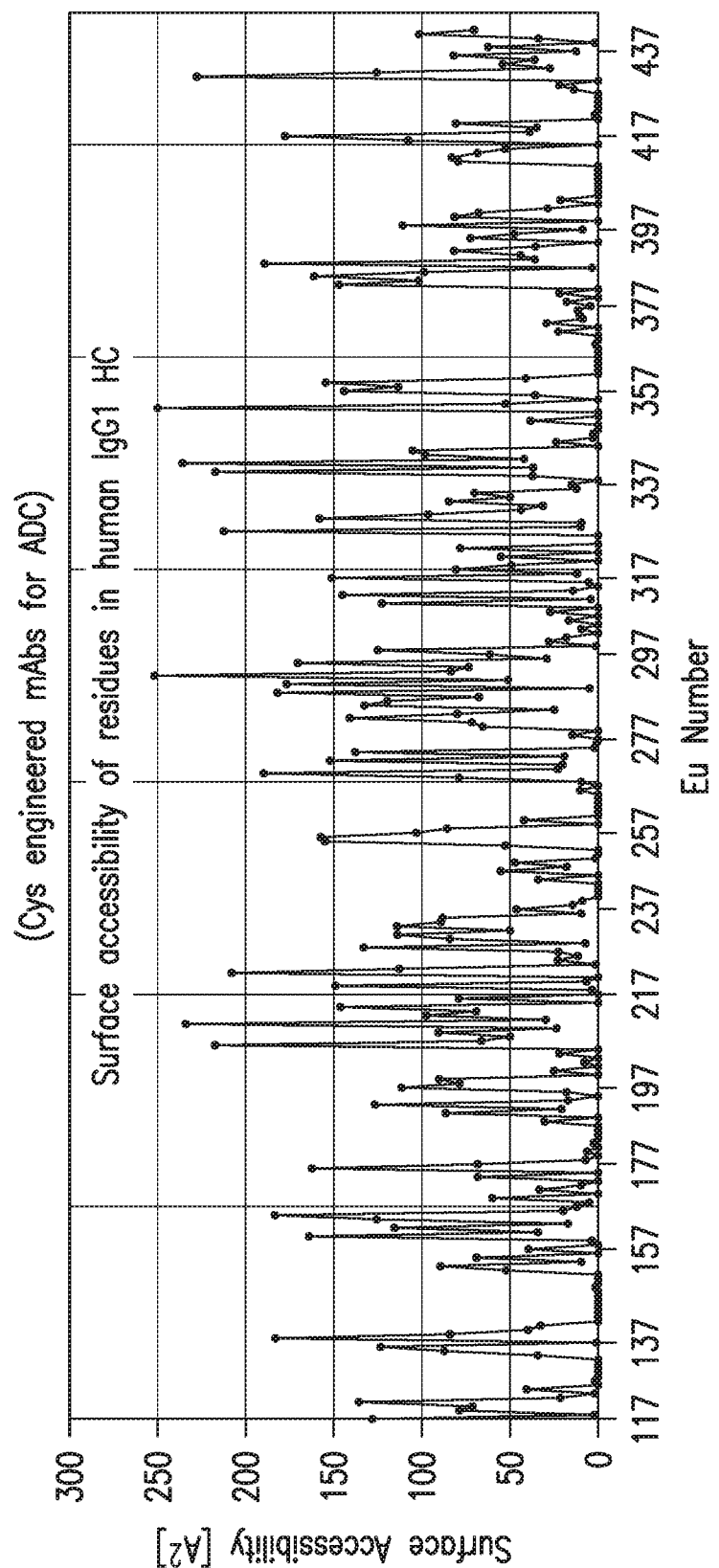
FIG. 1A-FIG. 1B. Surface accessibility plot of amino acid residues in human IgG1 heavy chain (A) and kappa light chain (B). Surface accessibility was calculated using Surface Racer 5.0 and is expressed as Angstrom square [$Å^2$].

The present invention provides methods of site-specific labeling of antibodies or antibody fragments by replacing one or more amino acids of a parental antibody or antibody fragment at specific positions with cysteine amino acids ("Cys"), such that the engineered antibodies or antibody fragments are capable of conjugation to various agents (e.g., cytotoxic agents). The present invention also provides immunoconjugates that are produced by using the methods described herein.

When a cysteine is engineered into a parental antibody or antibody fragment, the modified antibody or antibody fragment is first recovered from the expression medium with cysteine or glutathione (GSH) attached at the engineered cysteine site(s) via a disulfide linkage (Chen et al., (2009) mAbs 16, 353-571). The attached cysteine or GSH is then removed in a reduction step, which also reduces all native inter-chain disulfide bonds of the parental antibody or antibody fragment. In a second step these disulfide bonds are re-oxidized before conjugation occurs. The present disclosure shows that when cysteine is engineered at certain sites, the re-oxidation step does not proceed well, presumably due to formation of the incorrect disulfide bonds. Accordingly, the present invention provides unique sets of sites on the antibody heavy chain constant region and antibody light chain constant region, respectively, where Cys substitution as described herein produces modified antibodies or antibody fragments that perform well in the re-oxidation process, and also produce stable and well behaved immunoconjugates.

The site-specific antibody labeling according to the present invention can be achieved with a variety of chemically accessible labeling reagents, such as anti-cancer agents, fluorophores, peptides, sugars, detergents, polyethylene glycols, immune potentiators, radio-imaging probes, prodrugs, and other molecules.

Accordingly, the present invention provides methods of preparation of homogeneous immunoconjugates with a defined drug-to-antibody ratio for use in cancer therapy and other indications as well as imaging reagents. The present invention also provides immunoconjugates prepared thereby, as well as pharmaceutical compositions comprising these immunoconjugates. The methods of the instant invention can be used in combination with other conjugation methods known in the art.

The following enumerated embodiments represent certain aspects and variations of the invention:

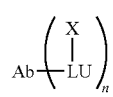

wherein Ab represents an antibody or antibody fragment comprising at least one cysteine residue at one of the preferred cysteine substitution sites described herein;

LU is a linker unit as described herein;

X is a payload or drug moiety;

and n is an integer from 1 to 16. In these embodiments, n is preferably about 2, about 4, about 6, or about 8. LU is typically a group of formula -$L_1$-$L_2$-$L_3$-$L_4$-$L_5$-$L_6$-, wherein $L_1$, $L_2$, $L_3$, $L_4$, $L_5$ and $L_6$ are independently selected from -$A_1$-, -$A_1X^2$— and —$X^2$—;

wherein:

$A_1$ is —C(=O)NH—, —C(=O)NH(CH$_2$)$_n$—, —C(=O)NH(C(R$^4$)$_2$)$_n$—, —(O(CH$_2$)$_n$)$_m$—, —(O(C(R$^4$)$_2$)$_n$)$_m$—, —((CH$_2$)$_n$O)$_m$—, —((C(R$^4$)$_2$)$_n$O)$_m$—, —((CH$_2$)$_n$O)$_m$(CH$_2$)$_n$—, —((C(R$^4$)$_2$)$_n$O)$_m$C(R$^4$)$_2$)$_n$—, —(CH$_2$)$_n$C(=O)NH—, —(C(R$^4$)$_2$)$_n$C(=O)NH—, —(CH$_2$)$_n$NHC(=O)—, —(C(R$^4$)$_2$)$_n$NHC(=O)—, —NHC(=O)(CH$_2$)$_n$—, —NHC(=O)(C(R$^4$)$_2$)$_n$—, —C(=O)NH(CH$_2$)$_n$S—, —C(=O)NH(C(R$^4$)$_2$)$_n$S—, —S(CH$_2$)$_n$C(=O)NH—, —S(C(R$^4$)$_2$)$_n$C(=O)NH—, —C(=O)NH(CH$_2$)$_n$NHC(=O)(CH$_2$)$_n$—, —C(=O)NH(C(R$^4$)$_2$)$_n$NHC(=O)(C(R$^4$)$_2$)$_n$—, —C(=O)(CH$_2$)$_n$—, —C(=O)(C(R$^4$)$_2$)$_n$—, —(CH$_2$)$_n$C(=O)—, —(C(R$^4$)$_2$)$_n$C(=O)—, —(CH$_2$)$_n$(O(CH$_2$)$_n$)$_m$NHC(=O)(CH$_2$)$_n$—, —(C(R$^4$)$_2$)$_n$(O(C(R$^4$)$_2$)$_n$)$_m$NHC(=O)(C(R$^4$)$_2$)$_n$—, —(CH$_2$)$_n$NHC(=O)(CH$_2$)$_n$—, —(C(R$^4$)$_2$)$_n$NHC(=O)(C(R$^4$)$_2$)$_n$—, —(CH$_2$)$_n$NH((CH$_2$)$_n$O)$_m$(CH$_2$)$_n$—, —(C(R$^4$)$_2$)$_n$NH((C(R$^4$)$_2$)$_n$O)$_m$(C(R$^4$)$_2$)$_n$—, —(O(CH$_2$)$_n$)$_m$NHC(=O)(CH$_2$)$_n$—, or —(O(C(R$^4$)$_2$)$_n$)$_m$NHC(=O)(C(R$^4$)$_2$)$_n$—;

each $X^2$ is independently selected from a bond, $R^8$,

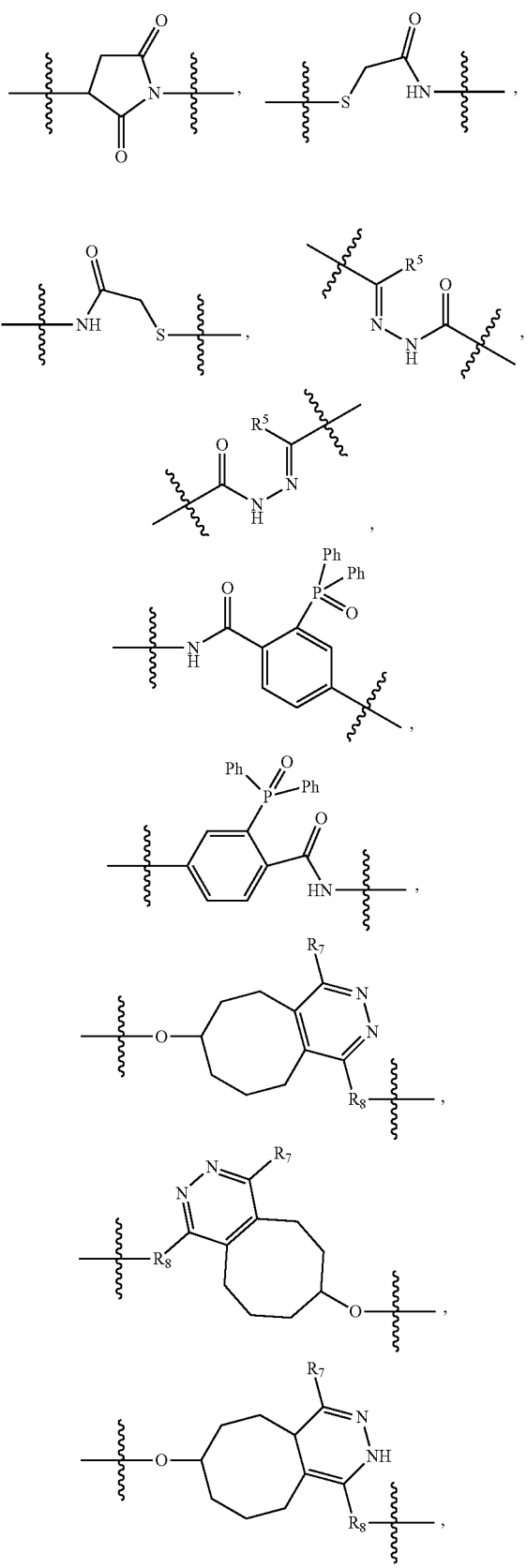

-continued

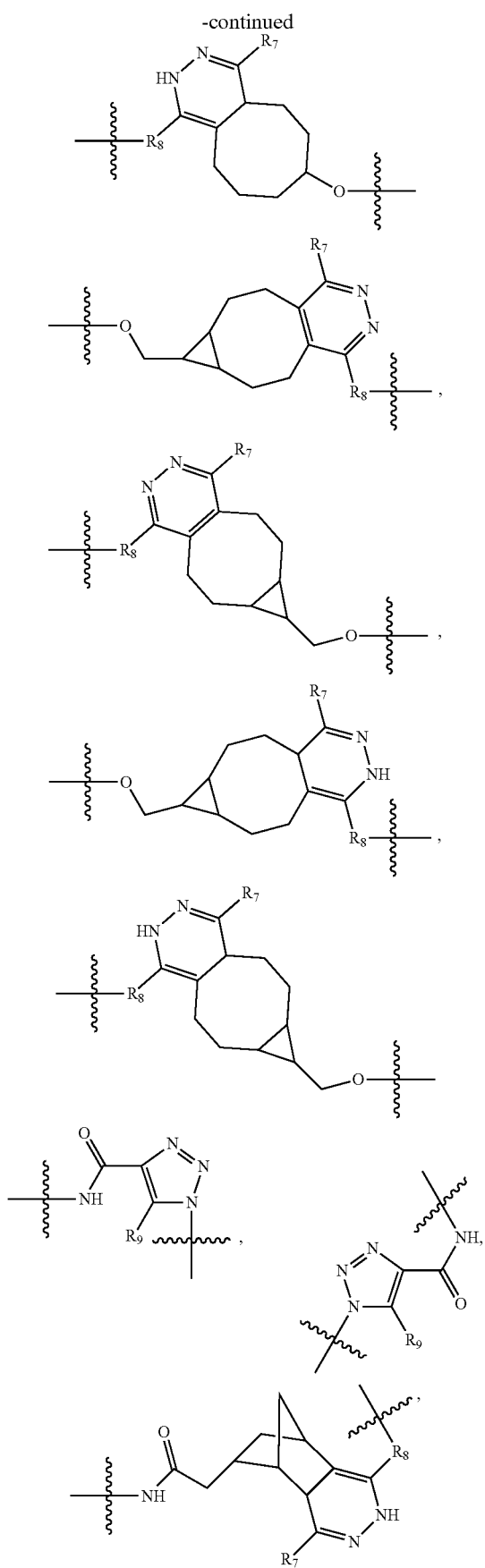

-continued

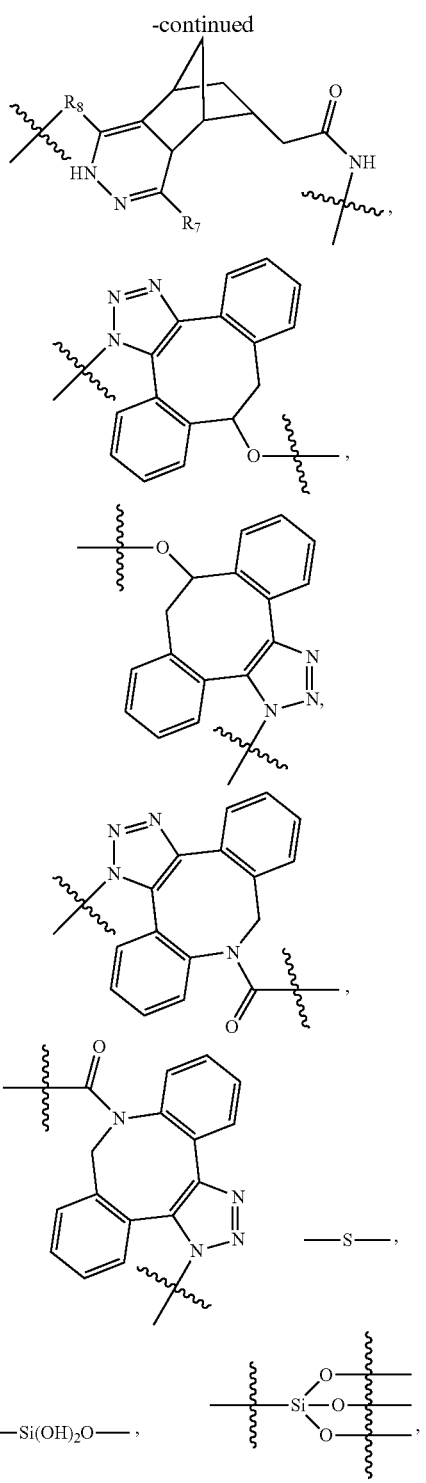

—CHR⁴(CH₂)ₙC(=O)NH—, —CHR⁴(CH₂)ₙNHC(=O)—, —C(=O)NH— and —NHC(=O)—;

each $R^4$ is independently selected from H, $C_{1-4}$alkyl, side chains of known amino acids, —C(=O)OH and —OH, each $R^5$ is independently selected from H, $C_{1-4}$alkyl, phenyl or $C_{1-4}$alkyl substituted with 1 to 3 —OH groups;

each $R^6$ is independently selected from H, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;

$R^7$ is independently selected from H, $C_{1-4}$alkyl, phenyl, pyrimidine and pyridine;

$R^8$ is independently selected from

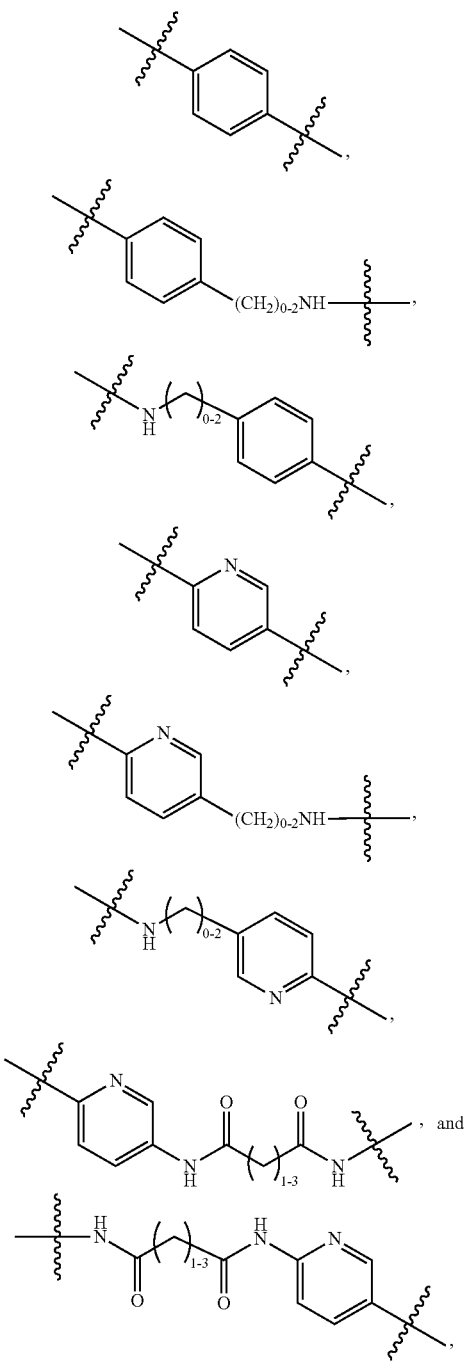

$R^9$ is independently selected from H and $C_{1-6}$haloalkyl;
each n is independently selected from 1, 2, 3, 4, 5, 6, 7, 8 and 9, and
each n is independently selected from 1, 2, 3, 4, 5, 6, 7, 8 and 9.

In some of these embodiments, the immunoconjugate comprises a group of the formula

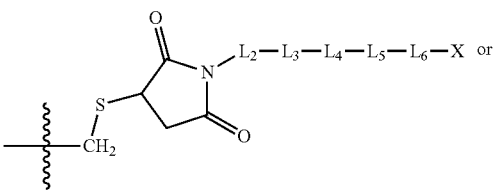

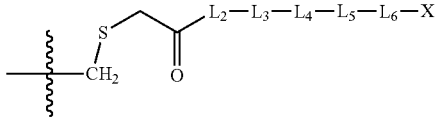

wherein the sulfur atom is the sulfur of a cysteine residue in a modified antibody or antibody fragment and is located at one of the substitution sites identified herein.

In any of the foregoing embodiments, the cysteine substitution site may be a position that corresponds to one of the sites identified by a position number, even though the position of the site in the sequence has been changed by a modification or truncation of the full-length antibody. Corresponding sites can be readily identified by alignment of an antibody or fragment with a full-length antibody.

1. Site-Specific Cysteine Engineered Antibodies

Site-Specific Labeling

The antibodies (e.g., a parent antibody, optionally containing one or more non-canonical amino acids) of the present invention are numbered according to the EU numbering system as set forth in Edelman et al., (1969) Proc. Natl. Acad. USA 63:78-85, except that the lambda light chain is numbered according to the Kabat numbering system as set forth in Kabat et al., (1991) Fifth Edition. NIH Publication No. 91-3242. Human IgG1 constant region is used as a representative throughout the application. However, the invention is not limited to human IgG1; corresponding amino acid positions can be readily deduced by sequence alignment. For example, FIG. 4 shows sequence alignment of human IgG1, IgG2, IgG3 and IgG4 heavy chain constant regions, so that an identified Cys engineering site in the IgG1 constant region can be readily identified for IgG2, IgG3, and IgG4 as shown in FIG. 4. For the light chain constant region, IgG1, IgG2, IgG3 and IgG4 are the same. Table 1 below lists the amino acid positions in the constant region of the heavy chain of an antibody that can be replaced by a cysteine. Table 2 lists the amino acid positions in the constant region of the kappa light chain of an antibody that can be replaced by a cysteine. Table 3 lists the amino acid positions in the constant region of the lambda light chain of an antibody that can be replaced by a cysteine.

TABLE 1

Identified cysteine substitution sites in the heavy chain constant region of human IgG1 (Sites numbered according to EU numbering system).

| EU number | Residue | Surface accessibility [Å$^2$] | Selected HC Cys | SEQ ID NO. |
|---|---|---|---|---|
| 117 | SER | 128.0 | HC-S117C | 2 |
| 119 | SER | 79.1 | HC-S119C | 3 |

TABLE 1-continued

Identified cysteine substitution sites in the heavy chain constant region of human IgG1 (Sites numbered according to EU numbering system).

| EU number | Residue | Surface accessibility [Å²] | Selected HC Cys | SEQ ID NO. |
|---|---|---|---|---|
| 121 | LYS | 135.9 | HC-K121C | 4 |
| 124 | SER | 40.2 | HC-S124C | 5 |
| 132 | SER | 34.4 | HC-S132C | 6 |
| 134 | SER | 123.3 | HC-S134C | 7 |
| 136 | SER | 182.9 | HC-S136C | 8 |
| 139 | THR | 32.9 | HC-T139C | 9 |
| 152 | GLU | 52.1 | HC-E152C | 10 |
| 153 | PRO | 89.1 | HC-P153C | 11 |
| 155 | THR | 69.0 | HC-T155C | 12 |
| 157 | SER | 39.0 | HC-S157C | 13 |
| 164 | THR | 125.4 | HC-T164C | 14 |
| 165 | SER | 183.2 | HC-S165C | 15 |
| 169 | THR | 60.0 | HC-T169C | 16 |
| 171 | PRO | 33.3 | HC-P171C | 17 |
| 174 | LEU | 68.1 | HC-L174C | 18 |
| 176 | SER | 161.9 | HC-S176C | 19 |
| 177 | SER | 68.1 | HC-S177C | 20 |
| 189 | PRO | 86.4 | HC-P189C | 21 |
| 191 | SER | 126.8 | HC-S191C | 22 |
| 195 | THR | 111.3 | HC-T195C | 23 |
| 197 | THR | 89.8 | HC-T197C | 24 |
| 205 | LYS | 217.1 | HC-K205C | 25 |
| 207 | SER | 50.0 | HC-S207C | 26 |
| 212 | ASP | 97.0 | HC-D212C | 27 |
| 246 | LYS | 55.1 | HC-K246C | 28 |
| 258 | GLU | 42.1 | HC-E258C | 29 |
| 269 | GLU | 189.2 | HC-E269C | 30 |
| 274 | LYS | 137.8 | HC-K274C | 31 |
| 286 | ASN | 119.4 | HC-N286C | 32 |
| 288 | LYS | 181.8 | HC-K288C | 33 |
| 290 | LYS | 177.0 | HC-K290C | 34 |
| 292 | ARG | 251.5 | HC-R292C | 35 |
| 293 | GLU | 83.3 | HC-E293C | 36 |
| 294 | GLN | 73.5 | HC-E294C | 37 |
| 320 | LYS | 55.0 | HC-K320C | 38 |
| 322 | LYS | 78.3 | HC-K322C | 39 |
| 326 | LYS | 212.7 | HC-K326C | 40 |
| 330 | ALA | 96.3 | HC-A330C | 41 |
| 333 | GLU | 84.7 | HC-E333C | 42 |
| 334 | LYS | 49.6 | HC-K334C | 43 |
| 335 | THR | 70.1 | HC-T335C | 44 |
| 337 | SER | 15.1 | HC-S337C | 45 |
| 344 | ARG | 98.2 | HC-R344C | 46 |
| 355 | ARG | 249.4 | HC-R355C | 47 |
| 360 | LYS | 113.9 | HC-K360C | 48 |
| 362 | GLN | 40.8 | HC-Q362C | 49 |
| 375 | SER | 28.9 | HC-S375C | 50 |
| 382 | GLU | 21.8 | HC-E382C | 51 |
| 389 | ASN | 189.5 | HC-N389C | 52 |
| 390 | ASN | 36.4 | HC-N390C | 53 |
| 392 | LYS | 81.8 | HC-K392C | 54 |
| 393 | THR | 35.8 | HC-T393C | 55 |
| 398 | LEU | 110.9 | HC-L398C | 56 |
| 400 | SER | 81.3 | HC-S400C | 57 |
| 413 | ASP | 79.6 | HC-D413C | 58 |
| 415 | SER | 69.0 | HC-S415C | 59 |
| 422 | VAL | 80.8 | HC-V422C | 60 |

TABLE 2

Identified cysteine substitution sites in the kappa light chain constant region of human IgG1 (Sites numbered according to EU numbering system).

| EU number | Residue | Surface accessibility [Å²] | Selected LC Cys | SEQ ID NO. |
|---|---|---|---|---|
| 107 | LYS | 90 | LC-K107C | 61 |
| 108 | ARG | 49 | LC-R108C | 62 |
| 109 | THR | 148 | LC-T109C | 63 |
| 112 | ALA | 50 | LC-A112C | 64 |
| 114 | SER | 39 | LC-S114C | 65 |
| 122 | ASP | 90 | LC-D122C | 66 |
| 123 | GLU | 51 | LC-E123C | 67 |
| 129 | THR | 41 | LC-T129C | 68 |
| 142 | ARG | 55 | LC-R142C | 69 |
| 143 | GLU | 117 | LC-E143C | 70 |
| 145 | LYS | 160 | LC-K145C | 71 |
| 152 | ASN | 157 | LC-N152C | 72 |
| 154 | LEU | 117 | LC-L154C | 73 |
| 156 | SER | 122 | LC-S156C | 74 |
| 159 | SER | 22 | LC-S159C | 75 |
| 161 | GLU | 66 | LC-E161C | 76 |
| 165 | GLU | 74 | LC-E165C | 77 |
| 168 | SER | 170 | LC-S168C | 78 |
| 169 | LYS | 241 | LC-K169C | 79 |
| 170 | ASP | 48 | LC-D170C | 80 |
| 182 | SER | 59 | LC-S182C | 81 |
| 183 | LYS | 131 | LC-K183C | 82 |
| 188 | LYS | 201 | LC-K188C | 83 |
| 190 | LYS | 167 | LC-K190C | 84 |
| 191 | VAL | 58 | LC-V191C | 85 |
| 197 | THR | 38 | LC-T197C | 86 |
| 199 | GLN | 127 | LC-Q199C | 87 |
| 203 | SER | 110 | LC-S203C | 88 |
| 206 | THR | 70 | LC-T206C | 89 |

TABLE 3

Identified cysteine substitution sites on the lambda light chain of human IgG1.

| Kabat number | Residue | Surface accessibility [Å²] | Selected LC Cys | SEQ ID NO. |
|---|---|---|---|---|
| 143 | ALA | 82 | LC-A143C | 92 |
| 145 | THR | 106 | LC-T145C | 93 |
| 147 | ALA | 14 | LC-A147C | 94 |
| 156 | LYS | 233 | LC-K156C | 95 |
| 159 | VAL | 28 | LC-V159C | 96 |
| 163 | THR | 157 | LC-T163C | 97 |
| 168 | SER | 166 | LC-S168C | 98 |

Because of the high sequence homology of constant regions of IgG1, IgG2, IgG3 and IgG4 antibodies, findings of the invention are not limited to any specific antibodies or antibody fragments.

In one embodiment, the present invention provides immunoconjugates comprising a modified antibody or an antibody fragment thereof, and a drug moiety, wherein said modified antibody or antibody fragment thereof comprises a substitution of one or more (e.g., 1, 2, 3, 4, 5, 6, 7, 8, 9, or 10) amino acids on its heavy chain constant region chosen from positions identified in Table 1. In a specific embodiment, the present invention provides an immunoconjugate comprising a modified antibody or antibody fragment thereof and a drug moiety, wherein said modified antibody or antibody fragment comprises a substitution of one or more amino acids with cysteine on its constant region chosen from positions 121, 124, 152, 171, 174, 258, 292, 333, 334, 360, 375, and 392 of the heavy chain. For example, an immunoconjugate of the invention comprises a modified antibody or antibody fragment thereof and a drug moiety, wherein said modified antibody or antibody fragment comprises a substitution of two amino acids with cysteine on its constant region chosen from positions 121 and 124, 121 and 152, 121 and 171, 121 and 174, 121 and 258, 121 and 292, 121 and 333, 121 and 334, 121 and 360, 121 and 375, 121 and 392, 124 and 152, 124 and 171, 124 and 174, 124 and 258, 124 and 292, 124 and 333, 124 and 334, 124 and 360, 124 and 375, 124 and 392,152 and 171, 152 and 174, 152 and 258, 152 and 292, 152 and 333, 152 and 334, 152 and 360, 152 and 375, 152 and 392, 171 and 174, 171 and 258, 171 and 292, 171 and 333, 171 and 360, 171 and 375, 174 and 258, 174 and 292, 174 and 333, 174 and 334, 174 and 360, 174 and 375, 174 and 392, 258 and 292, 258 and 333, 258 and 334, 258 and 360, 258 and 375, 258 and 392, 292 and 333, 292 and 334, 292 and 360, 292 and 375, 292 and 392, 333 and 334, 333 and 360, 333 and 375, 333 and 392; 334 and 360, 334 and 375, 334 and 392, 360 and 375, 360 and 392, or 375 and 392 of the heavy chain.

In another embodiment, an immunoconjugate of the invention comprises a modified antibody or antibody fragment thereof and a drug moiety, wherein said modified antibody or antibody fragment comprises a substitution of three amino acids with cysteine on its constant region chosen from positions 121, 124 and 152; 121, 124 and 171; 121, 124 and 174; 121, 124 and 258; 121, 124 and 292; 121, 124 and 333; 121, 124 and 334; 121, 124 and 360; 121, 124 and 375; 121, 124 and 392; 121, 152 and 171; 121, 152 and 174; 121, 152 and 258; 121, 152 and 292; 121, 152 and 333; 121, 152 and 334; 121, 152 and 360; 121, 152 and 375; 121, 152 and 392; 121, 171 and 174; 121, 171 and 258; 121, 171 and 292; 121, 171 and 333; 121, 171 and 334; 121, 171 and 360; 121, 171 and 375; 121, 171 and 392; 121, 174 and 258, 121, 174 and 292; 121, 174 and 333; 121, 174 and 334; 121, 174 and 360; 121, 174 and 375; 121, 174 and 392; 121, 258 and 292; 121, 258 and 333; 121, 258 and 334; 121, 258 and 360; 121, 258 and 375; 121, 258 and 392; 121, 292 and 333; 121, 292 and 334; 121, 292 and 360; 121, 292 and 375; 121, 292 and 392; 121, 333 and 334; 121, 333 and 360; 121, 333 and 375; 121, 333 and 392; 121, 334 and 360; 121, 334 and 375; 121, 334 and 392; 121, 360 and 375; 121, 360 and 392; 121, 375 and 392; 124, 152 and 171; 124, 152 and 174; 124, 152 and 258; 124, 152 and 292; 124, 152 and 333; 124, 152 and 334; 124, 152 and 360; 124, 152 and 375; 124, 152 and 392; 124, 171 and 174; 124, 171 and 258; 124, 171 and 292; 124, 171 and 333; 124, 171 and 334; 124, 171 and 360; 124, 171 and 375; 124, 171 and 392; 124, 174 and 258; 124, 174 and 292; 124, 174 and 333; 124, 174 and 334; 124, 174 and 360; 124, 174 and 375; 124, 174 and 392; 124, 258 and 292; 124, 258 and 333; 124, 258 and 334; 124, 258 and 360; 124, 258 and 375; 124, 258 and 392; 124, 292 and 333; 124, 292 and 334; 124, 292 and 360; 124, 292 and 375; 124, 292 and 392; 124, 333 and 360; 124, 333 and 334; 124, 333 and 375; 124, 333 and 392; 124, 334 and 360; 124, 334 and 375; 124, 334 and 392; 124, 360 and 375; 124, 360 and 392; 124, 375 and 392; 152, 171 and 174; 152, 171 and 258; 152, 171 and 292; 152, 171 and 333; 152, 171 and 334; 152, 171 and 360; 152, 171 and 375; 152, 171 and 392; 152, 174 and 258; 152, 174 and 292; 152, 174 and 333; 152, 174 and 334; 152, 174 and 360; 152, 174 and 375; 152, 174 and 392; 152, 258 and 292; 152, 258 and 333; 152, 258 and 334; 152, 258 and 360; 152, 258 and 375; 152, 258 and 392; 152, 292 and 333; 152, 292 and 334; 152, 292 and 360; 152, 292 and 375; 152, 292 and 392; 152, 333 and 334; 152, 333 and 360; 152, 333 and 375; 152, 333 and 392; 152, 334 and 360; 152, 334 and 375; 152, 334 and 392; 152, 360 and 375; 152, 360 and 392; 152, 375 and 392; 171, 174 and 258; 171, 174 and 292; 171, 174 and 333; 171, 174 and 334; 171, 174 and 360; 171, 174 and 375; 171, 174 and 392; 171, 258 and 292; 171, 258 and 292; 171, 258 and 333; 171, 258 and 334; 171, 258 and 360; 171, 258 and 375; 171, 258 and 392; 171, 292 and 333; 171, 292 and 334; 171, 292 and 360; 171, 292 and 375; 171, 292 and 392; 171, 333 and 334; 171, 333 and 360; 171, 333 and 375; 171, 333 and 392; 171, 334 and 360; 171, 334 and 392; 171, 360 and 375; 171, 360 and 392; 171, 375 and 392; 174, 258 and 292; 174, 258 and 333; 174, 258 and 334; 174, 258 and 360; 174, 258 and 375; 174, 258 and 392; 174, 292 and 333; 174, 292 and 334; 174, 292 and 360; 174, 292 and 375; 174, 292 and 392; 174, 333 and 334; 174, 333 and 360; 174, 333 and 375; 174, 333 and 392; 174, 334 and 360; 174, 334 and 375; 174, 334 and 392; 174, 360 and 375; 174, 360 and 392; 174, 375 and 392; 258, 292 and 333; 258, 292 and 334; 258, 292 and 360; 258, 292 and 375; 258, 292 and 392; 258, 333 and 360; 258, 333 and 375; 258, 333 and 392; 258, 334 and 360; 258, 334 and 375; 258, 334 and 392; 258, 360 and 375; 258, 360 and 392; 258, 375 and 392; 292, 333 and 334; 292, 333 and 360; 292, 333 and 375; 292, 333 and 392; 292, 334 and 360; 292, 334 and 375; 292, 334 and 392; 292, 360 and 375; 292, 360 and 392; 292, 375 and 392; 333, 334 and 360; 333, 334 and 375; 333, 334 and 392; 333, 360 and 375, 333, 360 and 392; 333, 375 and 392; 334, 360 and 375; 334, 360 and 392; or 360, 375 and 392 of the heavy chain.

In an embodiment, an immunoconjugate of the invention comprises a modified antibody or antibody fragment thereof and a drug moiety, wherein said modified antibody or antibody fragment comprises a substitution of four amino acids with cysteine on its constant region chosen from positions 152, 333, 375 and 392; or 152, 334, 375 and 392 of the heavy chain.

In a specific embodiment, the present invention provides an immunoconjugate comprising a modified antibody or antibody fragment thereof, and a drug moiety, wherein said modified antibody or antibody fragment thereof comprises SEQ ID NO: 2, 3, 9, 11, 12, 13, 14, 16, 21, 25, 26, 28, 30, 31, 32, 33, 34, 36, 38, 39, 40, 43, 44, 45, 46, 47, 51, 53, 54, 56, 57, or 60. In another specific embodiment, the present invention provides an immunoconjugate comprising a modified antibody or an antibody fragment thereof, and a drug moiety, wherein said modified antibody or antibody fragment thereof comprises SEQ ID NO: 6, 7, 8, 15, 19, 20, 22, 23, 24, 27, 36, 37, 41, 49, 52, 55, 58, or 59.

In another embodiment, the present invention provides immunoconjugates comprising a modified antibody or an antibody fragment thereof, and a drug moiety, wherein said modified antibody or antibody fragment thereof comprises a substitution of one or more amino acids (e.g., 1, 2, 3, 4, 5, 6, 7, 8, 9, or 10) on its light chain constant region chosen from positions identified in Table 2. In a specific embodiment, the present invention provides an immunoconjugate comprising a modified antibody or antibody fragment thereof and a drug moiety, wherein said modified antibody or antibody fragment comprises a substitution of one or more amino acids with cysteine on its constant region chosen from positions 107, 108, 142, 145, 159, 161, and 165 of the light chain, wherein said light chain is human kappa light chain. For example, an immunoconjugate of the invention comprises a modified antibody or antibody fragment thereof and a drug moiety, wherein said modified antibody or antibody fragment comprises a substitution of two amino acids with cysteine on its constant region chosen from positions 107 and 108; 107 and 142; 107 and 145; 107 and 159; 107 and 161; 107 and 165; 108 and 142; 108 and 145; 108 and 159; 108 and 161; 108 and 165; 142 and 145; 142 and 159; 142 and 161; 142 and 165; 145 and 159; 145 and 161; 145 and 165; 159 and 161; 159 and 165; 161 and 165 of the light chain, wherein said light chain is human kappa light chain. In another embodiment, an immunoconjugate of the invention comprises a modified antibody or antibody fragment thereof and a drug moiety, wherein said modified antibody or antibody fragment comprises a substitution of three amino acids with cysteine on its constant region chosen from positions 107, 108 and 142; 107, 108 and 145; 107, 108 and 159; 107, 108 and 161; 107, 108 and 165; 107, 142 and 145; 107, 142 and 159; 107, 142 and 161; 107, 142 and 165; 107, 145 and 159; 107, 145 and 161; 107, 145 and 165; 107, 159 and 161; 107, 159 and 165; 107, 161 and 165; 108, 142 and 145; 108, 142 and 159; 108, 142 and 161; 108, 142 and 165; 108, 145 and 159; 108, 145 and 161; 108, 145 and 165; 108, 159 and 161; 108, 159 and 165; 108, 161 and 165; 142, 145 and 159; 142, 145 and 161; 142, 145 and 165; 142, 159 and 161; 142, 159 and 165; 142, 161 and 165; 145, 159 and 161; 145, 159 and 165; 145, 161 and 165; or 159, 161 and 165 of the light chain, wherein said light chain is human kappa light chain.

In a specific embodiment, the present invention provides an immunoconjugate comprising a modified antibody or antibody fragment thereof, and a drug moiety, wherein said modified antibody or antibody fragment thereof comprises SEQ ID NO: 63, 65, 68, 70, 72, 73, 74, 78, 79, 80, 81, 82, 83, 86, 87, or 88. In another specific embodiment, the present invention provides an immunoconjugate comprising a modified antibody or antibody fragment thereof, and a drug moiety, wherein said modified antibody or antibody fragment thereof comprises SEQ ID NO: 64, 66, 67, 84, 85, or 89 63, 64, 65, 66, 67, 68, 70, 72, 73, 74, 78, 79, 80, 81, 82, 83, 84, 85, 86, 87, 88, or 89.

In another embodiment, the present invention provides immunoconjugates comprising a modified antibody or an antibody fragment thereof, and a drug moiety, wherein said modified antibody or antibody fragment thereof comprises a substitution of one or more amino acids on its light chain constant region chosen from positions identified in Table 3. In a specific embodiment, the present invention provides an immunoconjugate comprising a modified antibody or antibody fragment thereof and a drug moiety, wherein said modified antibody or antibody fragment comprises a substitution of one or more amino acids with cysteine on its constant region chosen from positions 143, 147, 159, 163, and 168 of the light chain, wherein said light chain positions are numbered according to the Kabat system, and wherein said light chain is human lambda light chain. For example, an immunoconjugate of the invention comprises a modified antibody or antibody fragment thereof and a drug moiety, wherein said modified antibody or antibody fragment comprises a substitution of two amino acids with cysteine on its constant region chosen from positions 143 and 147; 143 and 159; 143 and 163; 143 and 168; 147 and 159; 147 and 163; 147 and 168; 159 and 163; 159 and 168; or 163 and 168 of the light chain, wherein said light chain positions are numbered according to the Kabat system, and wherein said light chain is human lambda light chain. In another embodiment, an immunoconjugate of the invention comprises a modified antibody or antibody fragment thereof and a drug moiety, wherein said modified antibody or antibody fragment comprises a substitution of three amino acids with cysteine on its constant region chosen from positions 143, 147 and 159; 143, 147 and 163; 143, 147 and 168; 143, 159 and 163; 143, 159 and 168; 143, 163 and 168; 147, 159 and 163; 147, 159 and 168; 147, 163 and 168; or 159, 163 and 168 of the light chain, wherein said light chain positions are numbered according to the Kabat system, and wherein said light chain is human lambda light chain.

In an embodiment, the present invention provides an immunoconjugate comprising a modified antibody or antibody fragment thereof, and a drug moiety, wherein said modified antibody or antibody fragment thereof comprises SEQ ID NO: 92, 94, 96, 97 or 98. In another specific embodiment, the present invention provides an immunoconjugate comprising a modified antibody or antibody fragment thereof, and a drug moiety, wherein said modified antibody or antibody fragment thereof comprises SEQ ID NO: 93 or 95.

In an embodiment, the immunoconjugate can have an DAR of about 2 or about 4. In an embodiment, the present invention provides immunoconjugates comprising a modified antibody or antibody fragment thereof, and a drug moiety, wherein said modified antibody or antibody fragment comprises a Cys substitution of one or more (e.g., 1, 2, 3, 4, 5, 6, 7, 8, 9, or 10) amino acids on its heavy chain constant region chosen from positions identified in Table 1, and a Cys substitution of one or more (e.g., 1, 2, 3, 4, 5, 6, 7, 8, 9, or 10) amino acids on its light chain constant region chosen from positions identified in Table 2 or Table 3. In one embodiment, the present invention provides immunoconjugates comprising a modified antibody or antibody fragment thereof, and a drug moiety, wherein said modified antibody or antibody fragment comprises a Cys substitution of one or more amino acids in its heavy chain constant region chosen from positions 121, 124, 152, 171, 174, 258, 292, 333, 334, 360, 375 and 392; and a Cys substitution of one or more amino acids in its light chain constant region chosen from positions 107, 108, 142, 145, 159, 161, and 165, wherein said light chain is human kappa light chain. In an embodiment, a modified antibody or antibody fragment according to the present invention may comprise a Cys substitution on position 121 of a heavy chain, and a Cys substitution on position 107 of a human kappa light chain; or a Cys substitution on position 121 of a heavy chain, and a Cys substitution on position 108 of a human kappa light chain; or a Cys substitution on position 121 of a heavy chain, and a Cys substitution on position 142 of a human kappa light chain; or a Cys substitution on position 121 of a heavy chain, and a Cy s substitution on position 145 of a human kappa light chain; or a Cys substitution on position 121 of a heavy chain, and a Cys substitution on position 159 of a human kappa light chain; or a Cys substitution on position 121 of a heavy chain, and a Cys substitution on position 161 of a human kappa light chain; or a Cys substitution on position 121 of a heavy chain, and a Cys substitution on position 165 of a human kappa light chain; or a Cys substitution on position 124 of a heavy chain, and a Cys substitution on position 107 of a human kappa light chain; or a Cys substitution on position 124 of a heavy chain, and a Cys substitution on position 108 of a human kappa light chain; or a Cys substitution on position 124 of a heavy chain, and a Cys substitution on position 142 of a human kappa light chain; or a Cys substitution on position 124 of a heavy chain, and a Cys substitution on position 145 of a human kappa light chain; or a Cys substitution on position 124 of a heavy chain, and a Cys substitution on position 159 of a human kappa light chain; or a Cys substitution on position 124 of a heavy chain, and a Cys substitution on position 161 of a human kappa light chain; or a Cys substitution on position 124 of a heavy chain, and a Cys substitution on position 165 of a human kappa light chain; or a Cy s substitution on position 152 of a heavy chain, and a Cys substitution on position 107 of a human kappa light chain; or a Cys substitution on position 152 of a heavy chain, and a Cys substitution on position 108 of a human kappa light chain; or a Cys substitution on position 152 of a heavy chain, and a Cys substitution on position 142 of a human kappa light chain; or a Cys substitution on position 152 of a heavy chain, and a Cys substitution on position 145 of a human kappa light chain; or a Cys substitution on position 152 of a heavy chain, and a Cys substitution on position 159 of a human kappa light chain; or a Cys substitution on position 152 of a heavy chain, and a Cys substitution on position 161 of a human kappa light chain; or a Cys substitution on position 152 of a heavy chain, and a Cys substitution on position 165 of a human kappa light chain; or a Cys substitution on position 171 of a heavy chain, and a Cys substitution on position 107 of a human kappa light chain; or a Cys substitution on position 171 of a heavy chain, and a Cys substitution on position 108 of a human kappa light chain; or a Cys substitution on position 171 of a heavy chain, and a Cys substitution on position 142 of a human kappa light chain; or a Cys substitution on position 171 of a heavy chain, and a Cys substitution on position 145 of a human kappa light chain; or a Cys substitution on position 171 of a heavy chain, and a Cys substitution on position 159 of a human kappa light chain; or a Cys substitution on position 171 of a heavy chain, and a Cys substitution on position 161 of a human kappa light chain; or a Cys substitution on position 171 of a heavy chain, and a Cys substitution on position 165 of a human kappa light chain; or a Cys substitution on position 174 of a heavy chain, and a Cys substitution on position 107 of a human kappa light chain; or a Cys substitution on position 174 of a heavy chain, and a Cys substitution on position 108 of a human kappa light chain; or a Cys substitution on position 174 of a heavy chain, and a Cys substitution on position 142 of a human kappa light chain; or a Cys substitution on position 174 of a heavy chain, and a Cys substitution on position 145 of a human kappa light chain; or a Cys substitution on position 174 of a heavy chain, and a Cys substitution on position 159 of a human kappa light chain; or a Cys substitution on position 174 of a heavy chain, and a Cys substitution on position 161 of a human kappa light chain; or a Cys substitution on position 174 of a heavy chain, and a Cys substitution on position 165 of a human kappa light chain; or a Cys substitution on position 258 of a heavy chain, and a Cys substitution on position 107 of a human kappa light chain; or a Cys substitution on position 258 of a heavy chain, and a Cys substitution on position 108 of a human kappa light chain; or a Cys substitution on position 258 of a heavy chain, and a Cys substitution on position 142 of a human kappa light chain; or a Cys substitution on position 258 of a heavy chain, and a Cys substitution on position 145 of a human kappa light chain; or a Cys substitution on position 258 of a heavy chain, and a Cys substitution on position 159 of a human kappa light chain; or a Cys substitution on position 258 of a heavy chain, and a Cys substitution on position 161 of a human kappa light chain; or a Cys substitution on position 258 of a heavy chain, and a Cys substitution on position 165 of a human kappa light chain; or a Cys substitution on position 292 of a heavy chain, and a Cys substitution on position 107 of a human kappa light chain; or a Cys substitution on position 292 of a heavy chain, and a Cys substitution on position 108 of a human kappa light chain; or a Cys substitution on position 292 of a heavy chain, and a Cys substitution on position 142 of a human kappa light chain; or a Cys substitution on position 292 of a heavy chain, and a Cys substitution on position 145 of a human kappa light chain; or a Cys substitution on position 292 of a heavy chain, and a Cys substitution on position 159 of a human kappa light chain; or a Cys substitution on position 292 of a heavy chain, and a Cys substitution on position 161 of a human kappa light chain; or a Cys substitution on position 292 of a heavy chain, and a Cys substitution on position 165 of a human kappa light chain; or a Cys substitution on position 333 of a heavy chain, and a Cys substitution on position 107 of a human kappa light chain; or a Cys substitution on position 333 of a heavy chain, and a Cys substitution on position 108 of a human kappa light chain; or a Cys substitution on position 333 of a heavy chain, and a Cys substitution on position 142 of a human kappa light chain; or a Cys substitution on position 333 of a heavy chain, and a Cys substitution on position 145 of a human kappa light chain; or a Cys substitution on position 333 of a heavy chain, and a Cys substitution on position 159 of a human kappa light chain; or a Cys substitution on position 333 of a heavy chain, and a Cys substitution on position 161 of a human kappa light chain; or a Cys substitution on position 333 of a heavy chain, and a Cys substitution on position 165 of a human kappa light chain; or a Cys substitution on position 334 of a heavy chain, and a Cys substitution on position 107 of a human kappa light chain; or a Cys substitution on position 334 of a heavy chain, and a Cys substitution on position 108 of a human kappa light chain; or a Cys substitution on position 334 of a heavy chain, and a Cys substitution on position 142 of a human kappa light chain; or a Cys substitution on position 334 of a heavy chain, and a Cys substitution on position 145 of a human kappa light chain; or a Cys substitution on position 334 of a heavy chain, and a Cys substitution on position 159 of a human kappa light chain; or a Cys substitution on position 334 of a heavy chain, and a Cys substitution on position 161 of a human kappa light chain; or a Cys substitution on position 334 of a heavy chain, and a Cys substitution on position 165 of a human kappa light chain; or a Cys substitution on position 360 of a heavy chain, and a Cys substitution on position 107 of a human kappa light chain; or a Cys substitution on position 360 of a heavy chain, and a Cys substitution on position 108 of a human kappa light chain; or a Cys substitution on position 360 of a heavy chain, and a Cys substitution on position 142 of a human kappa light chain; or a Cys substitution on position 360 of a heavy chain, and a Cys substitution on position 145 of a human kappa light chain; or a Cys substitution on position 360 of a heavy chain, and a Cys substitution on position 159 of a human kappa light chain; or a Cys substitution on position 360 of a heavy chain, and a Cys substitution on position 161 of a human kappa light chain; or a Cys substitution on position 360 of a heavy chain, and a Cys substitution on position 165 of a human kappa light chain; or a Cys substitution on position 375 of a heavy chain, and a Cys substitution on position 107 of a human kappa light chain; or a Cys substitution on position 375 of a heavy chain, and a Cys substitution on position 108 of a human kappa light chain; or a Cys substitution on position 375 of a heavy chain, and a Cys substitution on position 142 of a human kappa light chain; or a Cys substitution on position 375 of a heavy chain, and a Cys substitution on position 145 of a human kappa light chain; or a Cys substitution on position 375 of a heavy chain, and a Cys substitution on position 159 of a human kappa light chain; or a Cys substitution on position 375 of a heavy chain, and a Cys substitution on position 161 of a human kappa light chain; or a Cys substitution on position 375 of a heavy chain, and a Cys substitution on position 165 of a human kappa light chain; or a Cys substitution on position 392 of a heavy chain, and a Cys substitution on position 107 of a human kappa light chain; or a Cys substitution on position 392 of a heavy chain, and a Cys substitution on position 108 of a human kappa light chain; or a Cys substitution on position 392 of a heavy chain, and a Cys substitution on position 142 of a human kappa light chain; or a Cys substitution on position 392 of a heavy chain, and a Cys substitution on position 145 of a human kappa light chain; or a Cys substitution on position 392 of a heavy chain, and a Cys substitution on position 159 of a human kappa light chain; or a Cys substitution on position 392 of a heavy chain, and a Cys substitution on position 161 of a human kappa light chain; or a Cys substitution on position 392 of a heavy chain, and a Cys substitution on position 165 of a human kappa light chain. In a embodiment, a modified antibody or antibody fragment according to the present invention comprises a Cys substitution on position 375 and on position 392 of a heavy chain, and a Cys substitution on position 165 of a human kappa light chain. In an embodiment a modified antibody or antibody fragment according to the present invention may comprise a Cys substitution on position 334 and on position 375 of a heavy chain, and a Cys substitution on position 165 of a human kappa light chain. In another example, a modified antibody or antibody fragment according to the present invention may comprise a Cys substitution on position 334 and on position 392 of a heavy chain, and a Cys substitution on position 165 of a human kappa light chain. In an embodiment, an immunoconjugates of those combinations can have a DAR of about 4 or about 6.

In an embodiment, a modified antibody or antibody fragment according to the present invention may comprise a Cys substitution on position 334, on position 375 and on position 392 of a heavy chain, and a Cys substitution on position 165 of a human kappa light chain. In an embodiment, a modified antibody or antibody fragment according to the present invention may comprise a Cys substitution on position 333, on position 375 and on position 392 of a heavy chain, and a Cys substitution on position 165 of a human kappa light chain. In an embodiment, those combinations can have a DAR of about 4, 6, or 8.

In an embodiment, the present invention provides immunoconjugates comprising a modified antibody or antibody fragment thereof, and a drug moiety, wherein said modified antibody or antibody fragment comprises a Cys substitution of one or more amino acids in its heavy chain constant region chosen from positions 121, 124, 152, 171, 174, 258, 292, 333, 334 360, 375 and 392; and a Cys substitution of one or more amino acids in its light chain constant region chosen from positions 143, 147, 159, 163, and 168, wherein said light chain is human lambda light chain. For example, a modified antibody or antibody fragment according to the present invention may comprise a Cys substitution on position 121 of a heavy chain, and a Cys substitution on position 143 of a human lambda light chain; or a Cys substitution on position 121 of a heavy chain, and a Cys substitution on position 147 of a human lambda light chain; or a Cys substitution on position 121 of a heavy chain, and a Cys substitution on position 159 of a human lambda light chain; or a Cys substitution on position 121 of a heavy chain, and a Cys substitution on position 163 of a human lambda light chain; or a Cys substitution on position 121 of a heavy chain, and a Cys substitution on position 168 of a human lambda light chain; or a Cys substitution on position 124 of a heavy chain, and a Cys substitution on position 143 of a human lambda light chain; or a Cys substitution on position 124 of a heavy chain, and a Cys substitution on position 147 of a human lambda light chain; or a Cys substitution on position 124 of a heavy chain, and a Cys substitution on position 159 of a human lambda light chain; or a Cys substitution on position 124 of a heavy chain, and a Cys substitution on position 163 of a human lambda light chain; or a Cys substitution on position 124 of a heavy chain, and a Cys substitution on position 168 of a human lambda light chain; or a Cys substitution on position 152 of a heavy chain, and a Cys substitution on position 143 of a human lambda light chain; or a Cys substitution on position 152 of a heavy chain, and a Cys substitution on position 147 of a human lambda light chain; or a Cys substitution on position 152 of a heavy chain, and a Cys substitution on position 159 of a human lambda light chain; or a Cys substitution on position 152 of a heavy chain, and a Cys substitution on position 163 of a human lambda light chain; or a Cys substitution on position 152 of a heavy chain, and a Cys substitution on position 168 of a human lambda light chain; or a Cys substitution on position 171 of a heavy chain, and a Cys substitution on position 143 of a human lambda light chain; or a Cys substitution on position 171 of a heavy chain, and a Cys substitution on position 147 of a human lambda light chain; or a Cys substitution on position 171 of a heavy chain, and a Cys substitution on position 159 of a human lambda light chain; or a Cys substitution on position 171 of a heavy chain, and a Cys substitution on position 163 of a human lambda light chain; or a Cys substitution on position 171 of a heavy chain, and a Cys substitution on position 168 of a human lambda light chain; or a Cys substitution on position 174 of a heavy chain, and a Cys substitution on position 143 of a human lambda light chain; or a Cys substitution on position 174 of a heavy chain, and a Cys substitution on position 147 of a human lambda light chain; or a Cys substitution on position 174 of a heavy chain, and a Cys substitution on position 159 of a human lambda light chain; or a Cys substitution on position 174 of a heavy chain, and a Cys substitution on position 163 of a human lambda light chain; or a Cys substitution on position 174 of a heavy chain, and a Cys substitution on position 168 of a human lambda light chain; or a Cys substitution on position 258 of a heavy chain, and a Cys substitution on position 143 of a human lambda light chain; or a Cys substitution on position 258 of a heavy chain, and a Cys substitution on position 147 of a human lambda light chain; or a Cys substitution on position 258 of a heavy chain, and a Cys substitution on position 159 of a human lambda light chain; or a Cys substitution on position 258 of a heavy chain, and a Cys substitution on position 163 of a human lambda light chain; or a Cys substitution on position 258 of a heavy chain, and a Cys substitution on position 168 of a human lambda light chain; or a Cys substitution on position 292 of a heavy chain, and a Cys substitution on position 143 of a human lambda light chain; or a Cys substitution on position 292 of a heavy chain, and a Cys substitution on position 147 of a human lambda light chain; or a Cys substitution on position 292 of a heavy chain, and a Cys substitution on position 159 of a human lambda light chain; or a Cys substitution on position 292 of a heavy chain, and a Cys substitution on position 163 of a human lambda light chain; or a Cys substitution on position 292 of a heavy chain, and a Cys substitution on position 168 of a human lambda light chain; or a Cys substitution on position 333 of a heavy chain, and a Cys substitution on position 143 of a human lambda light chain; or a Cys substitution on position 333 of a heavy chain, and a Cys substitution on position 147 of a human lambda light chain; or a Cys substitution on position 333 of a heavy chain, and a Cys substitution on position 159 of a human lambda light chain;

or a Cys substitution on position 333 of a heavy chain, and a Cys substitution on position 163 of a human lambda light chain; or a Cys substitution on position 333 of a heavy chain, and a Cys substitution on position 168 of a human lambda light chain; or a Cys substitution on position 334 of a heavy chain, and a Cys substitution on position 143 of a human lambda light chain; or a Cys substitution on position 334 of a heavy chain, and a Cys substitution on position 147 of a human lambda light chain; or a Cys substitution on position 334 of a heavy chain, and a Cys substitution on position 159 of a human lambda light chain; or a Cys substitution on position 334 of a heavy chain, and a Cys substitution on position 163 of a human lambda light chain; or a Cys substitution on position 334 of a heavy chain, and a Cys substitution on position 168 of a human lambda light chain; or a Cys substitution on position 360 of a heavy chain, and a Cys substitution on position 143 of a human lambda light chain; or a Cys substitution on position 360 of a heavy chain, and a Cys substitution on position 147 of a human lambda light chain; or a Cys substitution on position 360 of a heavy chain, and a Cys substitution on position 159 of a human lambda light chain; or a Cys substitution on position 360 of a heavy chain, and a Cys substitution on position 163 of a human lambda light chain; or a Cys substitution on position 360 of a heavy chain, and a Cys substitution on position 168 of a human lambda light chain; or a Cys substitution on position 375 of a heavy chain, and a Cys substitution on position 143 of a human lambda light chain; or a Cys substitution on position 375 of a heavy chain, and a Cys substitution on position 147 of a human lambda light chain; or a Cys substitution on position 375 of a heavy chain, and a Cys substitution on position 159 of a human lambda light chain; or a Cys substitution on position 375 of a heavy chain, and a Cys substitution on position 163 of a human lambda light chain; or a Cys substitution on position 375 of a heavy chain, and a Cys substitution on position 168 of a human lambda light chain; or a Cys substitution on position 392 of a heavy chain, and a Cys substitution on position 143 of a human lambda light chain; or a Cys substitution on position 392 of a heavy chain, and a Cys substitution on position 147 of a human lambda light chain; or a Cys substitution on position 392 of a heavy chain, and a Cys substitution on position 159 of a human lambda light chain; or a Cys substitution on position 392 of a heavy chain, and a Cys substitution on position 163 of a human lambda light chain; or a Cys substitution on position 392 of a heavy chain, and a Cys substitution on position 168 of a human lambda light chain;

In an embodiment of the invention, the amino acid substitution described herein is cysteine comprising a thiol group. In some aspects of the invention, the thiol group is utilized for chemical conjugation, and is attached to a linker unit (LU) and/or drug moiety. In some embodiments, the immunoconjugates of the invention comprise a drug moiety selected from the group consisting of a V-ATPase inhibitor, a HSP90 inhibitor, an IAP inhibitor, an mTor inhibitor, a microtubule stabilizer, a microtubule destabilizers, an auristatin, a dolastatin, a maytansinoid, a MetAP (methionine aminopeptidase), an inhibitor of nuclear export of proteins CRM1, a DPPIV inhibitor, proteasome inhibitors, an inhibitors of phosphoryl transfer reactions in mitochondria, a protein synthesis inhibitor, a kinase inhibitor, a CDK2 inhibitor, a CDK9 inhibitor, an kinesin inhibitor, an HDAC inhibitor, a DNA damaging agent, a DNA alkylating agent, a DNA intercalator, a DNA minor groove binder and a DHFR inhibitor. In some embodiments, the immunoconjugates of the invention comprise a drug moiety that is an anti-cancer agent. The modified antibody or antibody fragments of the present invention can be any formats known in the art, such as a monoclonal, chimeric, humanized, fully human, bispecific, or multispecific antibody or antibody fragment thereof.

According to the present invention, the modified antibody heavy chain and/or light chain (or antibody fragment thereof) may contain 1, 2, 3, 4, 5, 6, 7, 8, or more cysteine substitutions in its constant regions. In one embodiment, the modified antibodies or antibody fragments contain 2, 4, 6, 8, or more cysteine substitutions in its constant regions. In some embodiments, the modified antibody, antibody fragment or immunoconjugate thereof comprises 2 or 4 Cys substitutions.

In one embodiment, the parental antibody (antibody without cysteine substitution) is an IgG, IgM, IgE, or IgA antibody. In a specific embodiment, the parental antibody is an IgG1 antibody. In another specific embodiment, the parental antibody is an IgG2, IgG3, or IgG4 antibody.

The present invention also provides modified antibodies or antibody fragments thereof comprising a substitution of one or more amino acids on its heavy chain constant region chosen from positions identified in Table 1. In some embodiments, the present invention provides modified antibodies or antibody fragments thereof comprising a substitution of one or more amino acids on its light chain constant region chosen from positions identified in Table 2 or Table 3.

In certain embodiments, the modified antibodies or antibody fragments provided herein are labeled using the methods of the invention in combination with other conjugation methods known in the art including, but not limited to, chemoselective conjugation through lysine, histidine, tyrosine, formyl-glycine, pyrrolysine, pyrroline-carboxy-lysine, unnatural amino acids, and protein tags for enzyme-mediated conjugation (e.g., S6 tags).

2. Conjugation Chemistry

The conjugated antibody or antibody fragment thereof provided herein is produced by post-translational modification of at least one cysteine residue that was incorporated into the antibody or antibody fragment thereof as described above by site-specific labeling methods. The conjugated antibody or antibody fragment can be prepared by methods known in the art for conjugation of a payload of interest to cysteine residues that occur naturally in proteins, and by methods described for conjugation to proteins engineered to contain an additional cysteine residue substituted for another amino acid of a natural protein sequence.

In certain embodiments the modified antibodies or antibody fragment thereof provided herein are conjugated using known methods wherein the incorporated cysteine (cys) is conjugated to a maleimide derivative as Scheme Ia below. Modified antibodies of the invention that undergo this type of conjugation contain a thiol-maleimide linkage.

Scheme Ia. Conjugation via thiol-maleimide adduct formation.

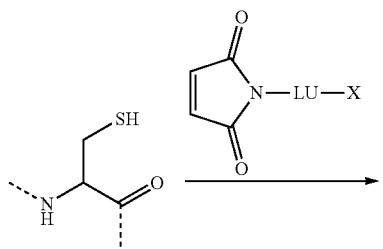

-continued

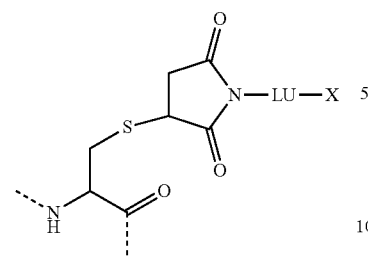

where:
LU is a Linker Unit (LU), and
X is a payload or drug moiety.

In other embodiments, the Cys incorporated into the modified antibodies or antibody fragment is conjugated by reaction with an alpha-halo carbonyl compound such as a chloro-, bromo-, or iodo-acetamide as shown in Scheme Ib below. It is understood that other leaving groups besides halogen, such as tosylate, triflate and other alkyl or aryl sulfonates, can be used as the leaving group Y. While Scheme Ib depicts reaction of a Cys thiol with an alpha-halo acetamide, the method includes any alkylation of a sulfur of an incorporated Cys with a group of the formula Y—CHR—C(=O)—, where R is H or $C_{1-4}$alkyl, Y is a leaving group (typically Cl, Br, or I, and optionally an alkylsulfonate or arylsulfonate); it is not limited to amides.

Scheme Ib. Conjugation via reaction with an alpha-halo carbonyl compound.

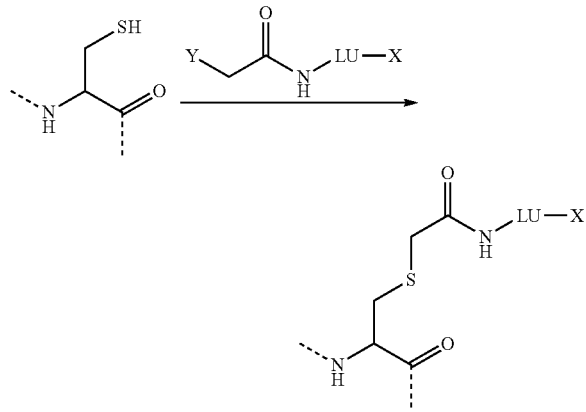

Y is a leaving group (Cl, Br, I, OTs, OTf, and the like)
LU is a linker unit
X is a payload or drug moiety Alternatively, the Cys incorporated into the modified antibodies or antibody fragment can be conjugated by reaction with an external thiol under conditions that induce formation of a disulfide bond between the external thiol and the sulfur atom of the incorporated cysteine residue as shown in Scheme Ic below. In these examples, R can be H; however, compounds where one or both R groups represent an alkyl group, e.g., Methyl, have been found to increase the stability of the disulfide.

Scheme Ic. Conjugation via disulfide formation.

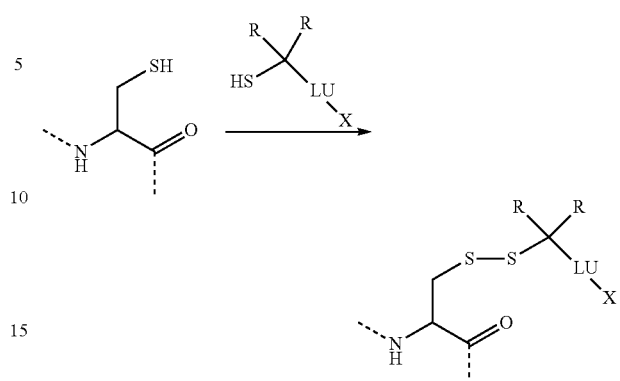

each R is independently H or $C_{1-4}$alkyl
LU is a linker unit
X is a payload or drug moiety By way of example only, such post-translational modifications are illustrated in Schemes (Ia)-(Ic) above, where the starting structure represents a cysteine incorporated into a light chain or heavy chain of an antibody at one of the specific sites identified herein. Methods for performing each of these conjugation methods are well known in the art. An antibody can be modified by these methods in its light chains, or its heavy chains, or in both light and heavy chains. An antibody in which each light chain or each heavy chain has been modified to contain a single incorporated cysteine will generally contain two conjugation sites, since an antibody typically contains two light and two heavy chains.

Upon conjugation, the modified antibodies of the invention typically contain 1-12, frequently 2-8, and preferably 2, 4 or 6-LU-X (Linker Unit-Payload) moieties. In some embodiments, an antibody light or heavy chain is modified to incorporate two new Cys residues at two of the specific sites identified herein for Cys substitutions (or alternatively one Cys is incorporated in the light chain and one in the heavy chain), so the tetrameric antibody ultimately contains four conjugation sites. Similarly the antibody can be modified by replacement of 3 or 4 of its native amino acids with Cys at the specific sites identified herein, in light chain or heavy chain or a combination thereof, resulting in 6 or 8 conjugation sites in the tetrameric antibody.

X in these conjugates represents a payload, which can be any chemical moiety that is useful to attach to an antibody. In some embodiments, X is a drug moiety selected from a cytotoxin, an anti-cancer agent, an anti-inflammatory agent, an antifungal agent, an antibacterial agent, an anti-parasitic agent, an anti-viral agent, an immune potentiator, and an anesthetic agent or any other therapeutic, or biologically active moiety or drug moiety. In other embodiments, X is a label such as a biophysical probe, a fluorophore, an affinity probe, a spectroscopic probe, a radioactive probe, a spin label, or a quantum dot. In other embodiments, X is a chemical moiety that modifies the antibody's physicochemical properties such as a lipid molecule, a polyethylene glycol, a polymer, a polysaccharide, a liposome, or a chelator. In other embodiments, X is a functional or detectable biomolecule such as a nucleic acid, a ribonucleic acid, a protein, a peptide (e.g., an enzyme or receptor), a sugar or polysaccharide, an antibody, or antibody fragment. In other embodiments, X is an anchoring moiety such as a nanoparticle, a PLGA particle, or a surface, or any binding moiety for specifically binding the conjugate to another moiety, such as a histidine tag, poly-G, biotin, avidin, streptavidin, and the like. In other embodiments, X is a reactive functional group that can be used to attach the antibody conjugate to another chemical moiety, such as a drug moiety, a label, another antibody, another chemical moiety, or a surface.

The Linker Unit (LU) can be any suitable chemical moiety that covalently attaches the thiol-reactive group (e.g., maleimide, alpha-halo carbonyl, vinyl carbonyl (e.g., acrylate or acrylamide), vinyl sulfone, vinylpyridine, or thiol) to a payload. Many suitable LUs are known in the art. For example, LU can be comprised of one, two, three, four, five, six, or more than six linkers referred to herein as $L_1$, $L_2$, $L_3$, $L_4$, $L_5$ and $L_6$. In certain embodiments the LU comprises a linker selected from a non-enzymatically cleavable linker, a non-cleavable linker, an enzymatically cleavable linker, a photo-stable linker, a photo-cleavable linker or any combination thereof, and the LU optionally contains a self-immolative spacer.

In some embodiments, LU is a group of the formula -$L_1$-$L_2$-$L_3$-$L_4$- or -$L_1$-L-$L_3$-$L_4$-$L_5$-$L_6$-. Linking groups $L_1$, $L_2$, $L_3$, $L_4$, $L_5$ and $L_6$ for use in LU include alkylene groups —$(CH_2)_n$— (where n is 1-20, typically 1-10 or 1-6), ethylene glycol units (—$CH_2CH_2O$—)$_n$ (where n is 1-20, typically 1-10 or 1-6), amides —C(=O)—NH— or —NH—C(=O)—, esters —C(=O)—O— or —O—C(=O)—, rings having two available points of attachment such as divalent phenyl, $C_{3-8}$cycloalkyl or $C_{4-8}$ heterocyclyl groups, amino acids NH—CHR*—C=O— or C(=O)—CHR*—NH—, where R* is the side chain of a known amino acid (frequently one of the canonical amino acids, but also including e.g. norvaline, norleucine, homoserine, homocysteine, phenylglycine, citrulline, and other named alpha-amino acids), polypeptides of known amino acids (e.g., dipeptides, tripeptides, tetrapeptides, etc.), thiol-maleimide linkages (from addition of —SH to maleimide). —S—$CR_2$— and other thiol ethers such as —S—$CR_2$—C(=O)— or —C(=O)—$CR_2$—S—, where R is as defined above for Scheme Ic, —$CH_2$—C(=O)—, and disulfides (—S—S—), as well as combinations of any of these with other linkers described below, e.g., a bond, a non-enzymatically cleavable linker, a non-cleavable linker, an enzymatically cleavable linker, a photo-stable linker, a photo-cleavable linker or a linker that comprises a self-immolative spacer.

In some embodiments when LU is -$L_1$-L-$L_3$-$L_4$-$L_5$-$L_6$-, $L_1$, $L_2$, $L_3$, $L_4$, $L_5$ and $L_6$ can be selected from: -$A_1$-, -$A_1X^2$— and —$X^2$—; wherein:

$A_1$ is —C(=O)NH—, —C(=O)NH($CH_2$)$_n$—, —C(=O)NH(C($R^4$)$_2$)$_n$—, —(O($CH_2$)$_n$)$_m$—, —(O(C($R^4$)$_2$)$_n$)$_m$—, —(($CH_2$)$_n$O)$_m$—, —((C($R^4$)$_2$)$_n$O)$_m$—, —(($CH_2$)$_n$O)$_m$($CH_2$)$_n$—, —((C($R^4$)$_2$)$_n$O)$_m$C($R^4$)$_2$)$_n$—, —($CH_2$)$_n$C(=O)NH—, —(C($R^4$)$_2$)$_n$C(=O)NH—, —($CH_2$)$_n$NHC(=O)—, —(C($R^4$)$_2$)$_n$NHC(=O)—, —NHC(=O)($CH_2$)$_n$—, —NHC(=O)(C($R^4$)$_2$)$_n$—, —C(=O)NH($CH_2$)$_n$S—, —C(=O)NH(C($R^4$)$_2$)$_n$S—, —S($CH_2$)$_n$C(=O)NH—, —S(C($R^4$)$_2$)$_n$C(=O)NH—, —C(=O)NH($CH_2$)$_n$NHC(=O)($CH_2$)$_n$—, —C(=O)NH(C($R^4$)$_2$)$_n$NHC(=O)(C($R^4$)$_2$)$_n$—, —C(=O)($CH_2$)$_n$—, —C(=O)(C($R^4$)$_2$)$_n$—, —($CH_2$)$_n$C(=O)—, —(C($R^4$)$_2$)$_n$C(=O)—, —($CH_2$)$_n$(O($CH_2$)$_n$)$_m$NHC(=O)($CH_2$)$_n$—, —(C($R^4$)$_2$)$_n$(O(C($R^4$)$_2$)$_n$)$_m$NHC(=O)(C($R^4$)$_2$)$_n$—, —($CH_2$)$_n$NHC(=O)($CH_2$)$_n$—, —(C($R^4$)$_2$)$_n$NHC(=O)(C($R^4$)$_2$)$_n$—, —($CH_2$)$_n$NH(($CH_2$)$_n$O)$_m$($CH_2$)$_n$—, —(C($R^4$)$_2$)$_n$NH((C($R^4$)$_2$)$_n$O)$_m$(C($R^4$)$_2$)$_n$—, —(O($CH_2$)$_n$)$_m$NHC(=O)($CH_2$)$_n$—, or —(O(C($R^4$)$_2$)$_n$)$_m$NHC(=O)(C($R^4$)$_2$)$_n$—;

each $X^2$ is independently selected from a bond, $R^8$,

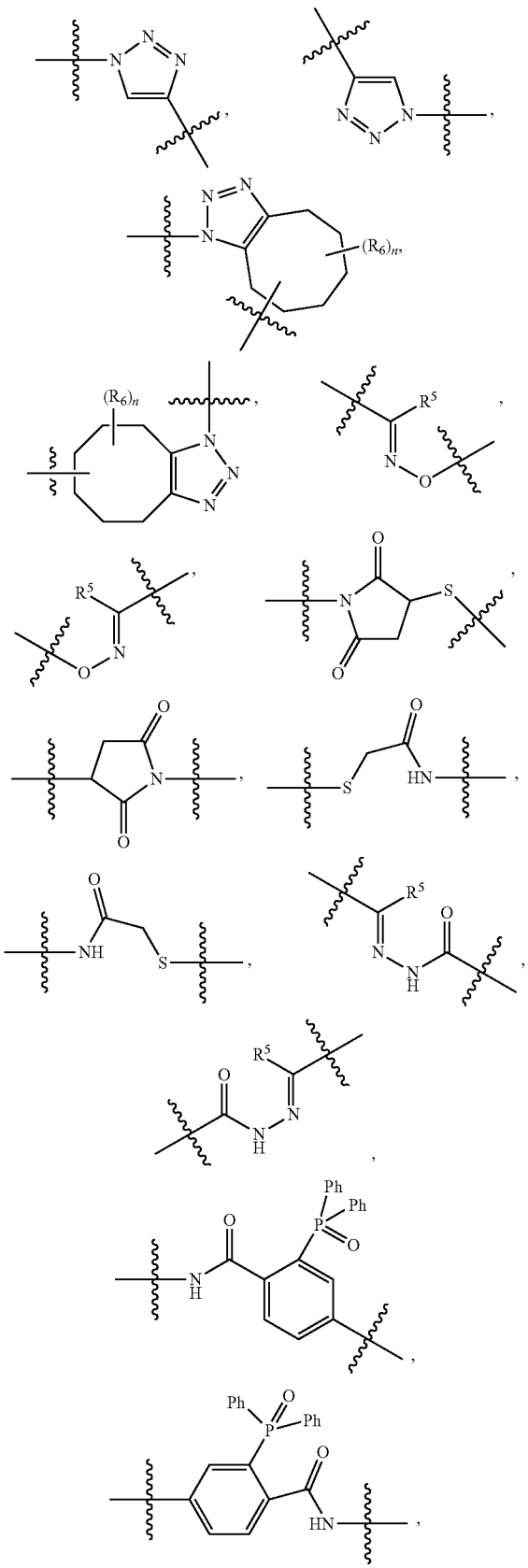

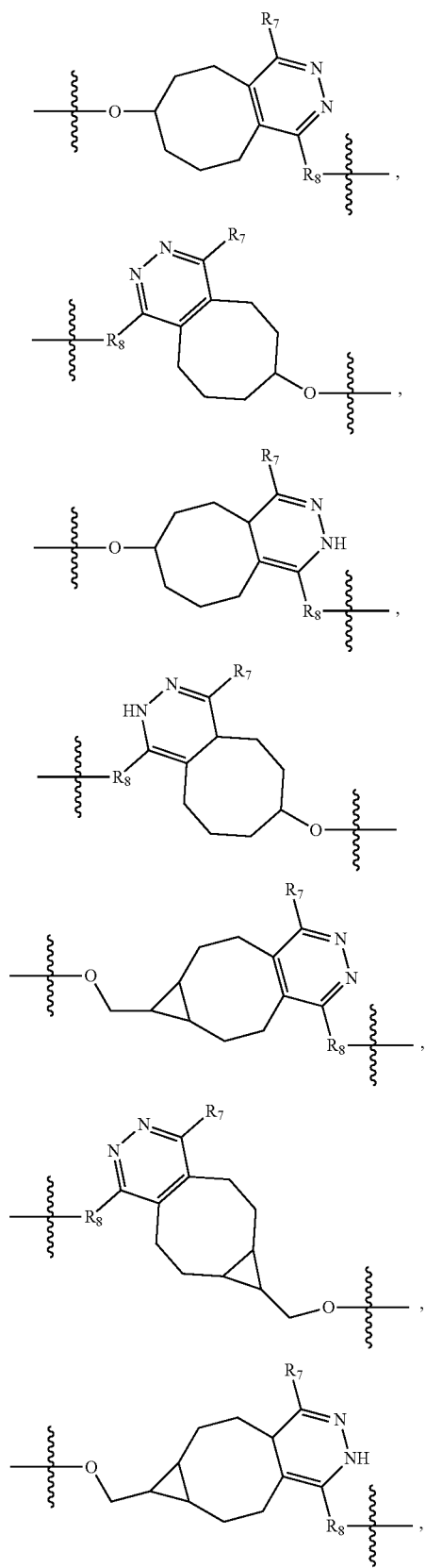
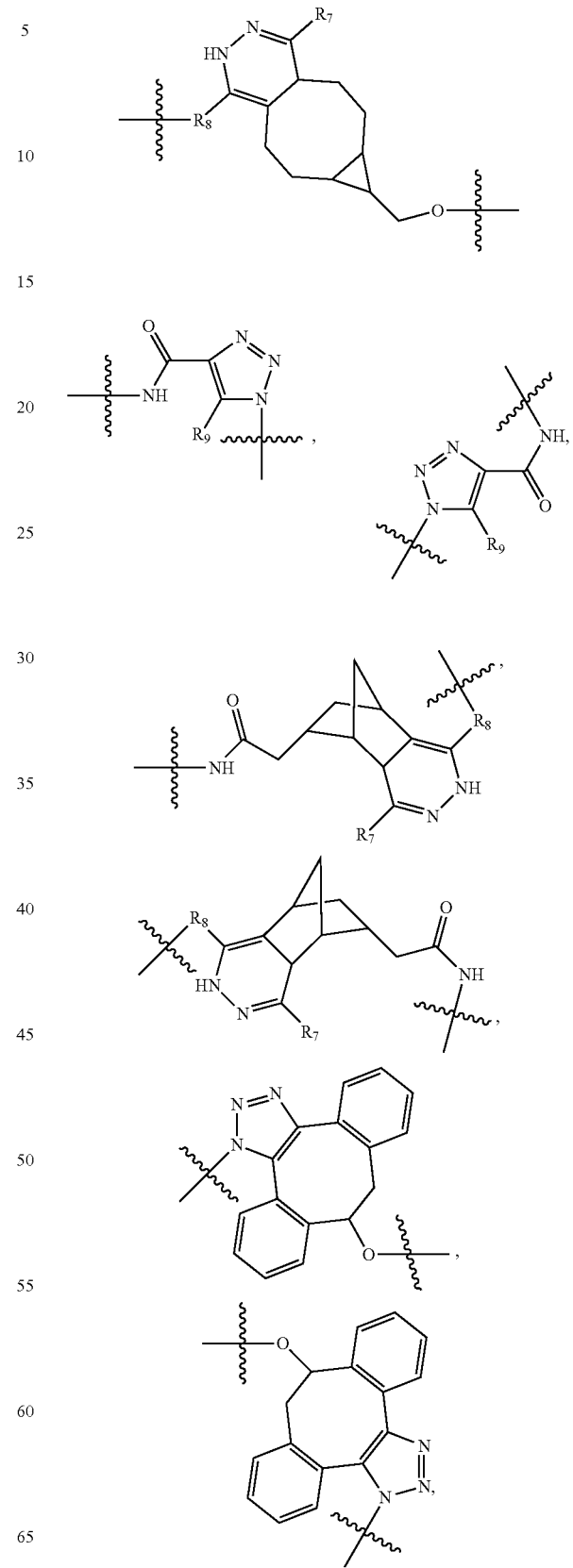

-continued

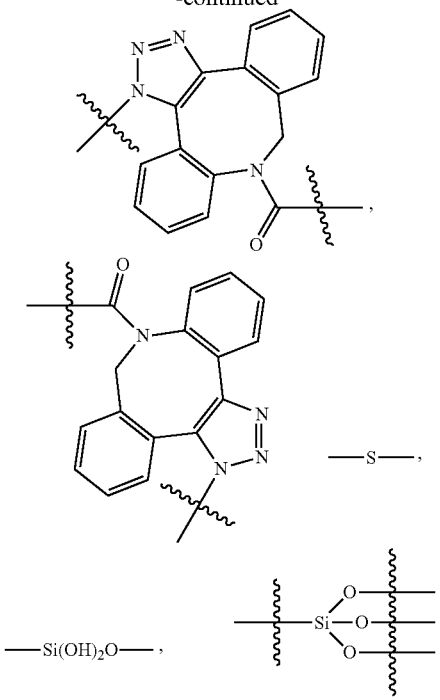

—CHR⁴(CH₂)ₙC(=O)NH—, —CHR⁴(CH₂)ₙNHC(=O)—, —C(=O)NH— and —NHC(=O)—;

each R⁴ is independently selected from H, $C_{1-4}$alkyl, side chains of known amino acids, —C(=O)OH and —OH, each R⁵ is independently selected from H, $C_{1-4}$alkyl, phenyl or $C_{1-4}$alkyl substituted with 1 to 3 —OH groups;

each R⁶ is independently selected from H, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;

R⁷ is independently selected from H, $C_{1-4}$alkyl, phenyl, pyrimidine and pyridine;

R⁸ is independently selected from

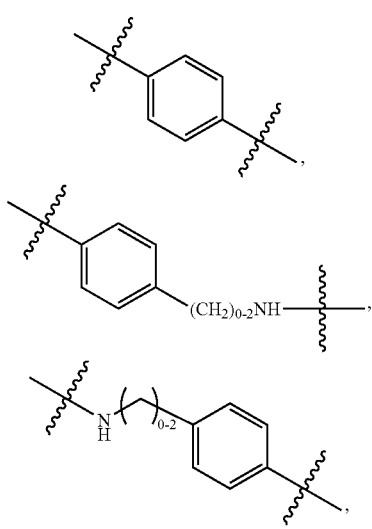

-continued

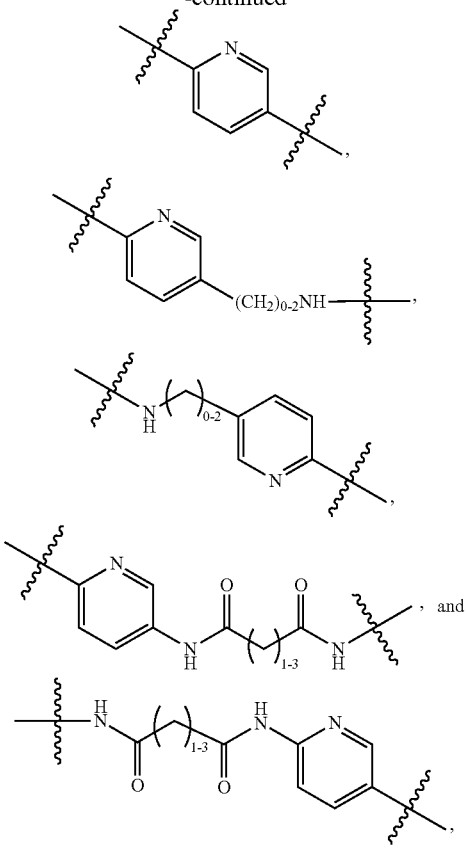

R⁹ is independently selected from H and $C_{1-6}$haloalkyl;

each n is independently selected from 1, 2, 3, 4, 5, 6, 7, 8 and 9, and each n is independently selected from 1, 2, 3, 4, 5, 6, 7, 8 and 9.

In some embodiments, at least one of $L_1$, $L_2$, $L_3$, $L_4$, $L_5$ and $L_6$ is a stable, or non-cleavable, linker. In some embodiments, at least one of $L_1$, $L_2$, $L_3$, $L_4$, $L_5$ and $L_6$ is a cleavable linker, which may be chemically cleavable (hydrazones, disulfides) or enzymatically cleavable. In some embodiments, the enzymatically cleavable linker is one readily cleaved by a peptidase: The Val-Cit linker (valine-citrulline), a dipeptide of two known amino acids, is one such linker. In other embodiments, the enzymatically cleavable linker is one that is triggered by activity of a glucuronidase:

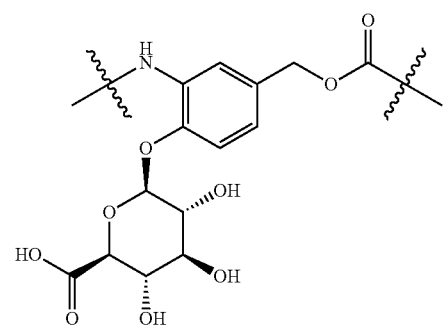 [SMILES: *Nc1cc(COC(*)=O)ccc1O[C@@H]1O[C@H](C(=O)O)[C@@H](O)[C@H](O)[C@H]1O]

is an example of such a linker, which also comprises a self-immolative spacer that falls apart spontaneously under physiological conditions once glucuronidase cleaves the glycosidic linkage.

In some embodiments, the immunoconjugate of the invention comprises a modified cysteine residue of the formula IIA or IIB:

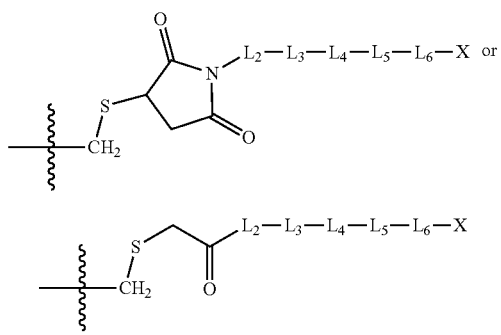

wherein —$CH_2$—S— represents the side chain of Cys incorporated at one of the selected Cys substitution sites described herein, and $L_2$-$L_6$ and X represent linking groups and payloads, respectively, as further described herein. In some embodiments of IIA, $L_2$ is a bond. In some embodiments of IIB, $L_2$ is NH or O. In some embodiments of both IIA and IIB, $L_3$ is selected from $(CH_2)_{1-10}$ and $(CH_2CH_2O)_{1-6}$. $L_4$, $L_5$ and $L_6$ are additional optional linkers selected from those described herein. In certain embodiments, $L_6$ can be a carbonyl (C=O) or a linker that comprises a self-immolative spacer.

In certain embodiments the Linker Unit (LU) is -$L_1$-$L_2$-$L_3$-$L_4$-, wherein:
$L_1$ is a bond, a non-enzymatically cleavable linker, a non-cleavable linker, an enzymatically cleavable linker, a photo-stable linker or a photo-cleavable linker;
$L_2$ is a bond, a non-enzymatically cleavable linker, a non-cleavable linker, an enzymatically cleavable linker, a photo-stable linker or a photo-cleavable linker;
$L_3$ is a bond, a non-enzymatically cleavable linker, a non-cleavable linker, an enzymatically cleavable linker, a photo-stable linker or a photo-cleavable linker, and
$L_4$ is a bond, a non-enzymatically cleavable linker, a non-cleavable linker, an enzymatically cleavable linker, a photo-stable linker, a photo-cleavable linker or a linker that comprises a self-immolative spacer.

In certain embodiments the Linker Unit (LU) is -$L_1$-$L_2$-$L_3$-$L_4$-, wherein
$L_1$ is a non-enzymatically cleavable linker, a non-cleavable linker, an enzymatically cleavable linker, a photo-stable linker or a photo-cleavable linker;
$L_2$ is a bond, a non-enzymatically cleavable linker, a non-cleavable linker, an enzymatically cleavable linker, a photo-stable linker or a photo-cleavable linker;
$L_3$ is a bond, a non-enzymatically cleavable linker, a non-cleavable linker, an enzymatically cleavable linker, a photo-stable linker or a photo-cleavable linker, and
$L_4$ is a bond, a non-enzymatically cleavable linker, a non-cleavable linker, an enzymatically cleavable linker, a photo-stable linker, a photo-cleavable linker or a linker that comprises a self-immolative spacer.

In some of the embodiments of LU at least one of $L_1$, $L_2$, $L_3$, $L_4$, $L_5$ and $L_6$ is a cleavable linker, and LU is considered cleavable. Similarly, in some of the embodiments of LU at least one of $L_1$, $L_2$, $L_3$, $L_4$, $L_5$ and $L_6$ is a non-cleavable linker. In certain of these embodiments, each linker of LU is non-cleavable, and LU is considered non-cleavable.

In some of the foregoing embodiments wherein LU is-$L_1$-$L_2$-$L_3$-$L_4$-, at least one of $L_1$, $L_2$, $L_3$ and $L_4$ is a linker selected from -$A_1$-, -$A_1X^2$— and —$X^2$—; wherein:

$A_1$ is —C(=O)NH—, —C(=O)NH$(CH_2)_n$—, —C(=O)NH$(C(R^4)_2)_n$—, —$(O(CH_2)_n)_m$—, —$(O(C(R^4)_2)_n)_m$—, —$((CH_2)_nO)_m$—, —$((C(R^4)_2)_nO)_m$—, —$((CH_2)_nO)_m(CH_2)_n$—, —$(((C(R^4)_2)_nO)_mC(R^4)_2)_n$—, —$(CH_2)_nC(=O)NH$—, —$(C(R^4)_2)_nC(=O)NH$—, —$(CH_2)_nNHC(=O)$—, —$(C(R^4)_2)_nNHC(=O)$—, —NHC(=O)$(CH_2)_n$—, —NHC(=O)$(C(R^4)_2)_n$—, —C(=O)NH$(CH_2)_nS$—, —C(=O)NH$(C(R^4)_2)_nS$—, —S$(CH_2)_n$C(=O)NH—, —S$(C(R^4)_2)_nC(=O)NH$—, —C(=O)NH$(CH_2)_n$NHC(=O)$(CH_2)_n$—, —C(=O)NH$(C(R^4)_2)_n$NHC(=O)$(C(R^4)_2)_n$—, —C(=O)$(CH_2)_n$—, —C(=O)$(C(R^4)_2)_n$—, —$(CH_2)_nC(=O)$—, —$(C(R^4)_2)_nC(=O)$—, —$(CH_2)_n(O(CH_2)_a)_m$NHC(=O)$(CH_2)_n$—, —$(C(R^4)_2)_n(O(C(R^4)_2)_n)_m$NHC(=O)$(C(R^4)_2)_n$—, —$(CH_2)_n$NHC(=O)$(CH_2)_n$—, —$(C(R^4)_2)_n$NHC(=O)$(C(R^4)_2)_n$—, —$(CH_2)_n$NH$((CH_2)_nO)_m(CH_2)_n$—, —$(C(R^4)_2)_n$NH$((C(R^4)_2)_nO)_m(C(R^4)_2)_n$—, —$(O(CH_2)_n)_m$NHC(=O)$(CH_2)_n$—, or —$(O(C(R^4)_2)_n)_m$NHC(=O)$(C(R^4)_2)_n$—;

each $X^2$ is independently selected from a bond, $R^8$,

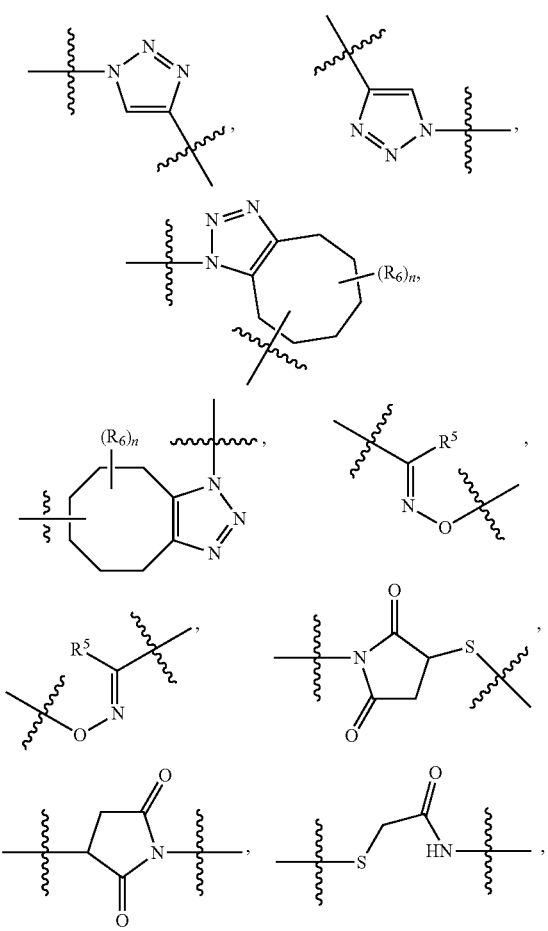

-continued
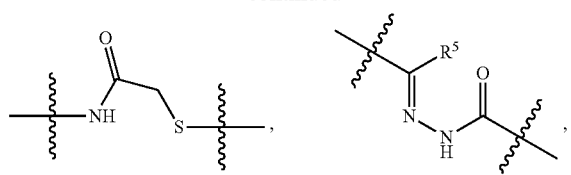
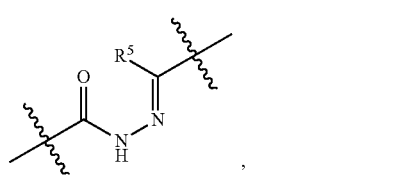
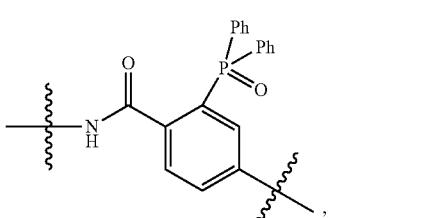
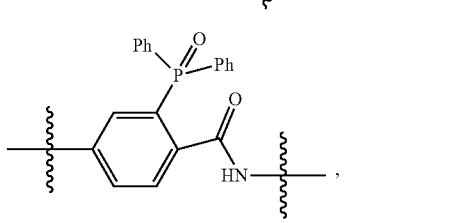
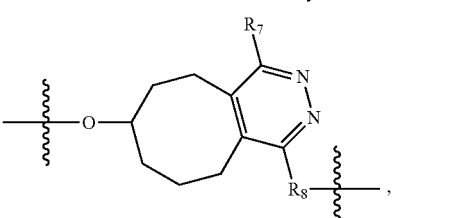
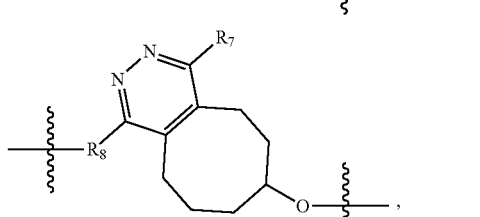
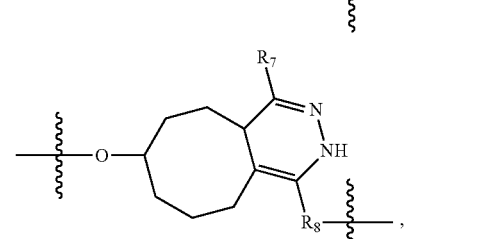
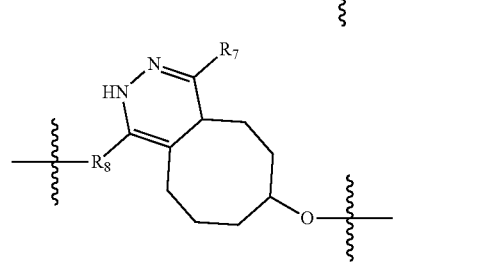
-continued
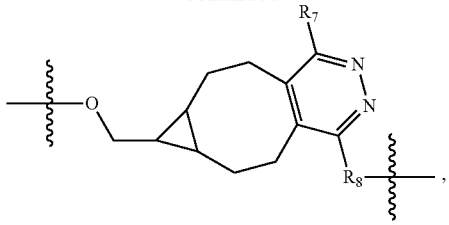
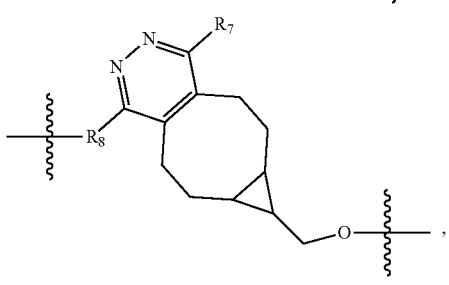
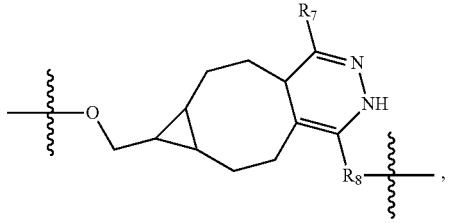
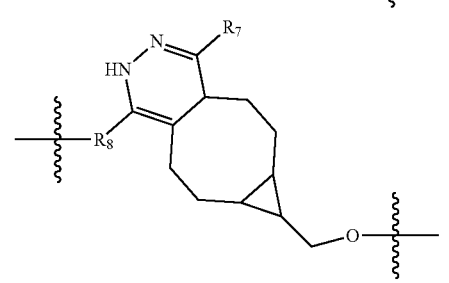
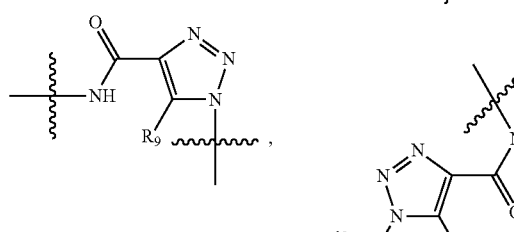
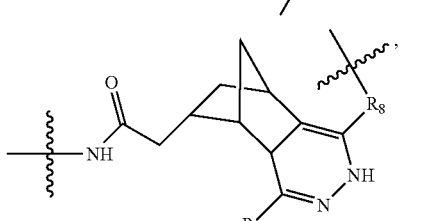
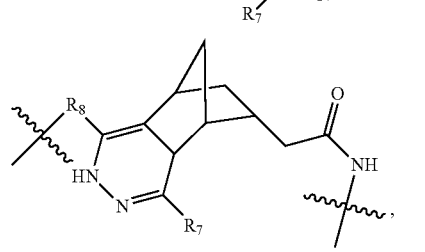

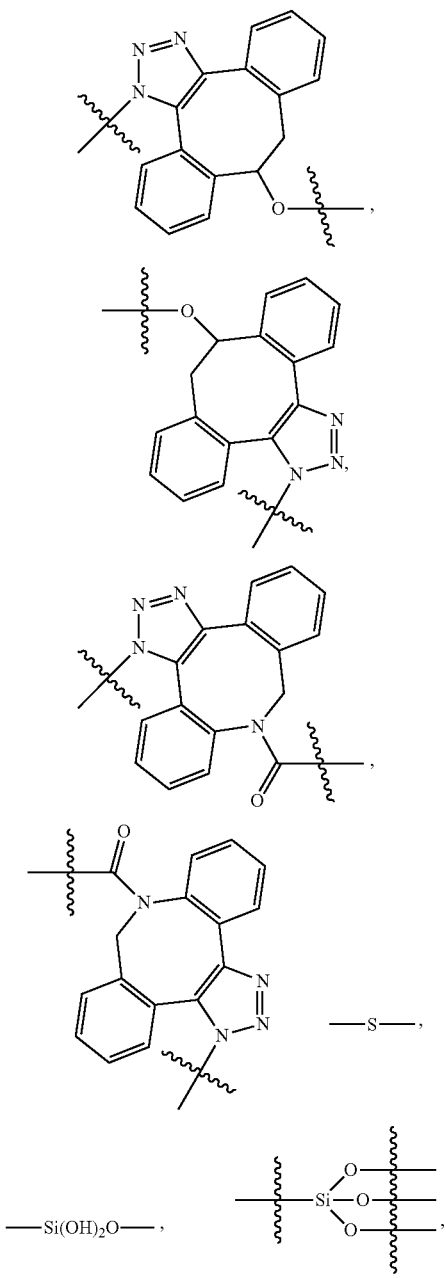

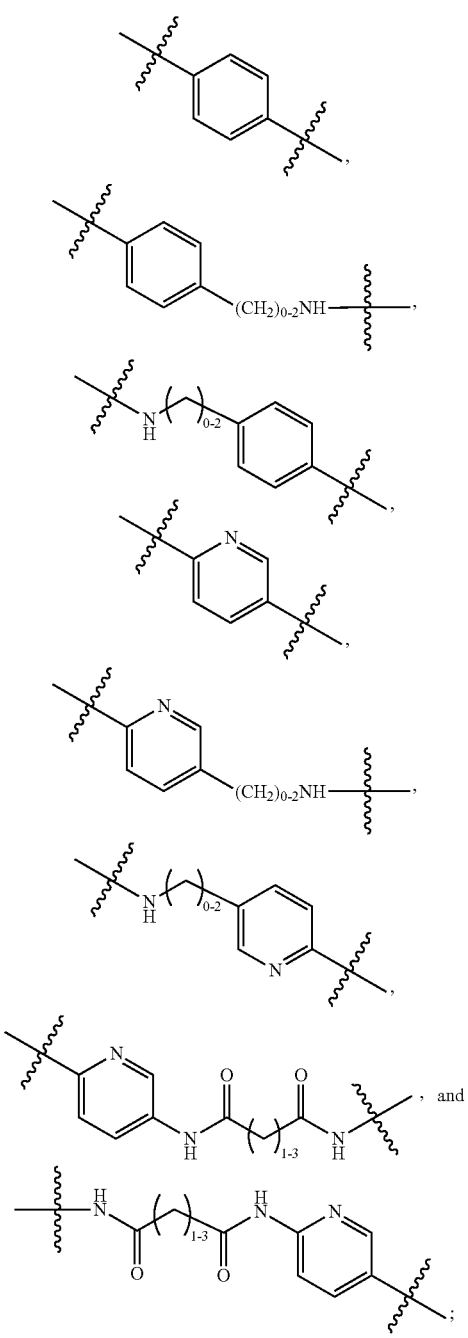

—CHR⁴(CH₂)ₙC(=O)NH—, —CHR⁴(CH₂)ₙNHC(=O)—, —C(=O)NH— and —NHC(=O)—;

each R⁴ is independently selected from H, C₁₋₄alkyl, side chains of known amino acids, —C(=O)OH and —OH, each R⁵ is independently selected from H, C₁₋₄alkyl, phenyl or C₁₋₄alkyl substituted with 1 to 3 —OH groups;

each R⁶ is independently selected from H, fluoro, benzyloxy substituted with —C(=O)OH, benzyl substituted with —C(=O)OH, C₁₋₄alkoxy substituted with —C(=O)OH and C₁₋₄alkyl substituted with —C(=O)OH;

R⁷ is independently selected from H, C₁₋₄alkyl, phenyl, pyrimidine and pyridine;

R⁸ is independently selected

R⁹ is independently selected from H and C₁₋₆haloalkyl;

each n is independently selected from 1, 2, 3, 4, 5, 6, 7, 8 and 9, and each m is independently selected from 1, 2, 3, 4, 5, 6, 7, 8 and 9.

In these embodiments, the other linkers of LU are independently selected from a bond, -A¹-, -A₁X²—, —X²—, a non-enzymatically cleavable linker, a non-cleavable linker, an enzymatically cleavable linker, a photo-stable linker, a photo-cleavable linker and a linker that comprises a self-immolative spacer.

In certain embodiments the Linker Unit (LU) is -L₁-L₂-L₃-L₄-, wherein $L_1$ is a bond, $-A_1-$, $-A_1X^2-$ or $-X^2-$; where:

$A_1$ is $-C(=O)NH-$, $-C(=O)NH(CH_2)_n-$, $-C(=O)NH(C(R^4)_2)_n-$, $-(O(CH_2)_n)_m-$, $-(O(C(R^4)_2)_n)_m-$, $-((CH_2)_nO)_n-$, $-((C(R^4)_2)_nO)_m-$, $-((CH_2)_nO)_m(CH_2)_n-$, $-(((C(R^4)_2)_nO)_mC(R^4)_2)_n-$, $-(CH_2)_nC(=O)NH-$, $-(C(R^4)_2)_nC(=O)NH-$, $-(CH_2)_nNHC(=O)-$, $-(C(R^4)_2)_nNHC(=O)-$, $-NHC(=O)(CH_2)_n-$, $-NHC(=O)(C(R^4)_2)_n-$, $-C(=O)NH(CH_2)_nS-$, $-C(=O)NH(C(R^4)_2)_nS-$, $-S(CH_2)_nC(=O)NH-$, $-S(C(R^4)_2)_nC(=O)NH-$, $-C(=O)NH(CH_2)_nNHC(=O)(CH_2)_n-$, $-C(=O)NH(C(R^4)_2)_nNHC(=O)(C(R^4)_2)_n-$, $-C(=O)(CH_2)_n-$, $-C(=O)(C(R^4)_2)_n-$, $-(CH_2)_nC(=O)-$, $-(C(R^4)_2)_nC(=O)-$, $-(CH_2)_n(O(CH_2)_n)_mNHC(=O)(CH_2)_n-$, $-(C(R^4)_2)_n(O(C(R^4)_2)_n)_mNHC(=O)(C(R^4)_2)_n-$, $-(CH_2)_nNHC(=O)(CH_2)_n-$, $-(C(R^4)_2)_nNHC(=O)(C(R^4)_2)_n-$, $-(CH_2)_nNH((CH_2)_nO)_m(CH_2)_n-$, $-(C(R^4)_2)_nNH((C(R^4)_2)_nO)_m(C(R^4)_2)_n-$, $-(O(CH_2)_n)_mNHC(=O)(CH_2)_n-$, or $-(O(C(R^4)_2)_n)_mNHC(=O)(C(R^4)_2)_n-$;

each $X^2$ is independently selected from a bond, $R^8$

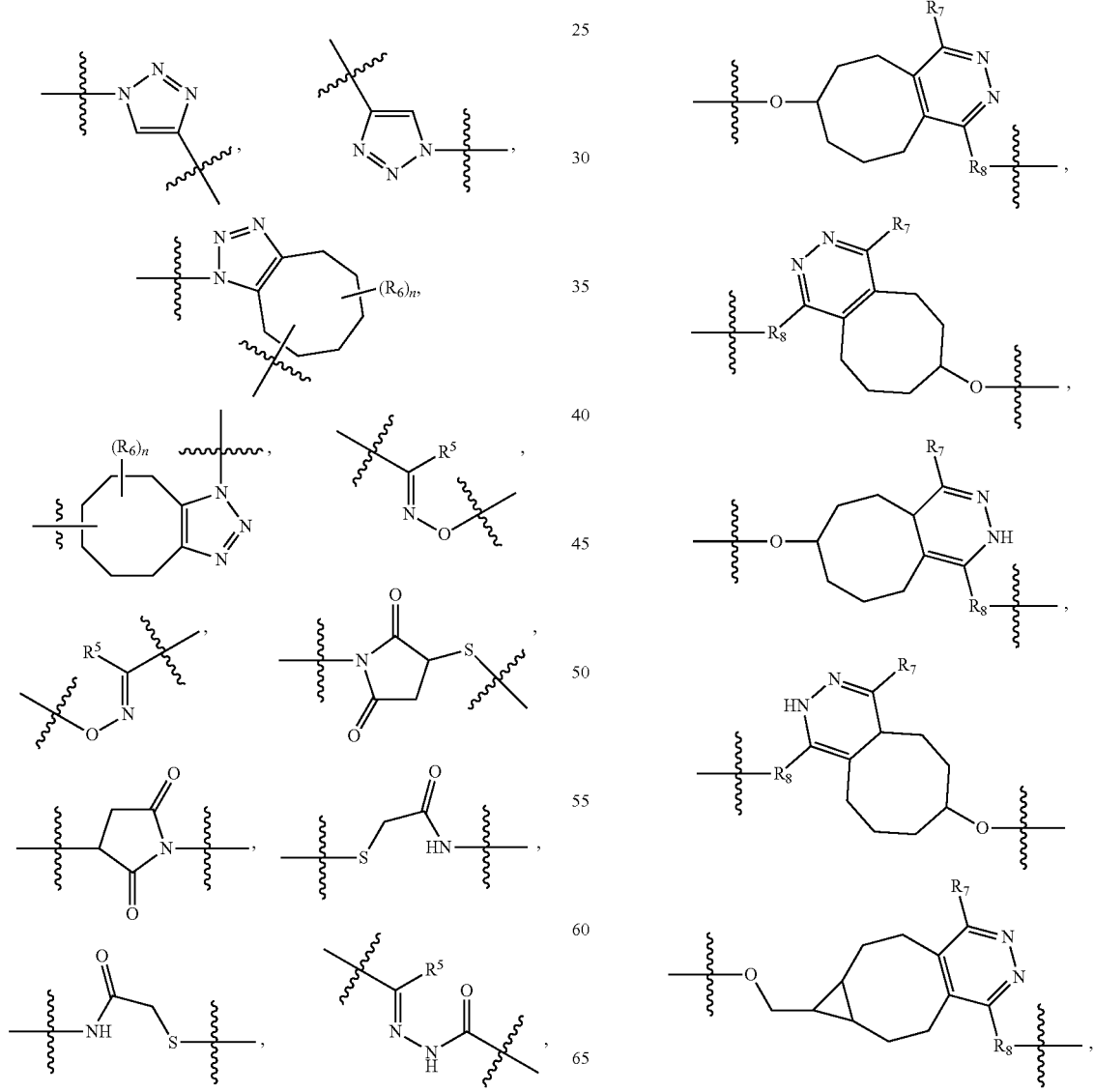

63
-continued

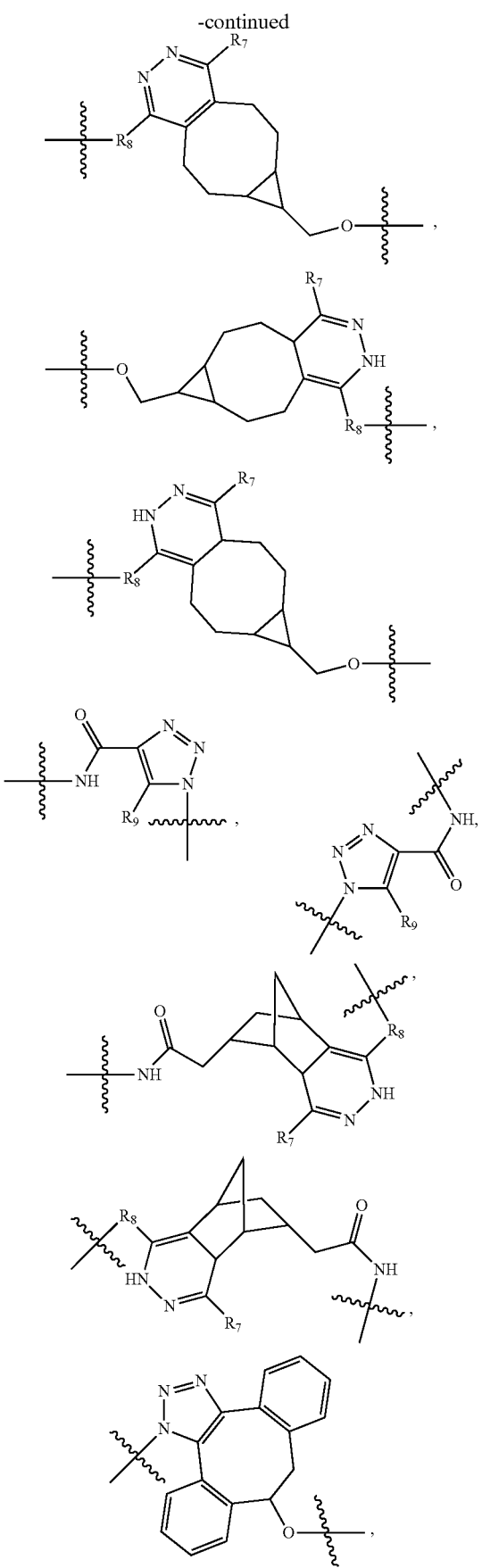

64
-continued

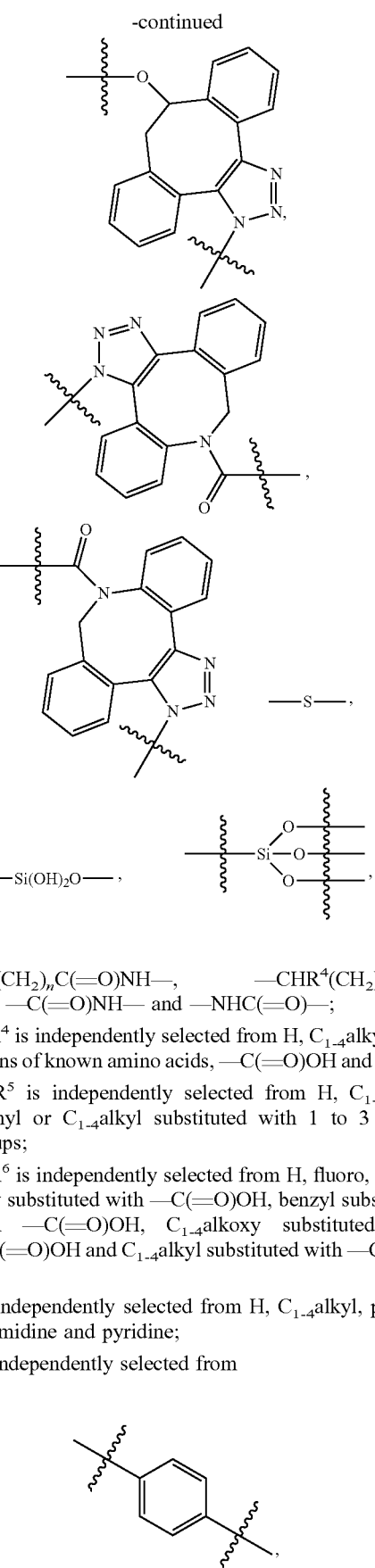

—CHR⁴(CH₂)ₙC(=O)NH—, —CHR⁴(CH₂)ₙNHC(=O)—, —C(=O)NH— and —NHC(=O)—;

each $R^4$ is independently selected from H, $C_{1-4}$alkyl, side chains of known amino acids, —C(=O)OH and —OH, each $R^5$ is independently selected from H, $C_{1-4}$alkyl, phenyl or $C_{1-4}$alkyl substituted with 1 to 3 —OH groups;

each $R^6$ is independently selected from H, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;

$R^7$ is independently selected from H, $C_{1-4}$alkyl, phenyl, pyrimidine and pyridine;

$R^8$ is independently selected from

-continued

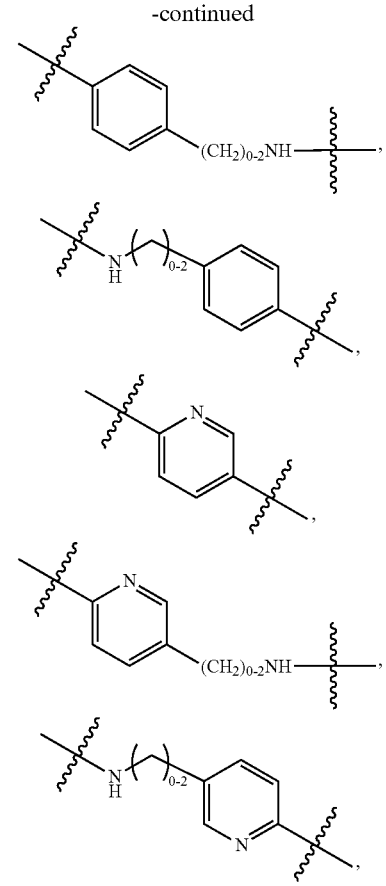

$R^9$ is independently selected from H and $C_{1-6}$haloalkyl;
each n is independently selected from 1, 2, 3, 4, 5, 6, 7, 8 and 9, and
each m is independently selected from 1, 2, 3, 4, 5, 6, 7, 8 and 9;
$L_2$ is a bond, a non-enzymatically cleavable linker, a non-cleavable linker, an enzymatically cleavable linker, a photo-stable linker or a photo-cleavable linker;
$L_3$ is a bond, a non-enzymatically cleavable linker, a non-cleavable linker, an enzymatically cleavable linker, a photo-stable linker or a photo-cleavable linker, and
$L_4$ is a bond, a non-enzymatically cleavable linker, a non-cleavable linker, an enzymatically cleavable linker, a photo-stable linker, a photo-cleavable linker or a linker that comprises a self-immolative spacer.
In certain embodiments, $L_1$ is C(=O)—$CH_2CH_2$—NH—C(=O)—$CH_2CH_2$—S—, so LU is —C(=O)—$CH_2CH_2$—NH—C(=O)—$CH_2CH_2$—S-$L_2$-$L_3$-$L_4$-.
In certain embodiments the Linker Unit (LU) is -$L_1$-$L_2$-$L_3$-$L_4$-, wherein $L_1$ is a bond, -$A_1$-, -$A_1X^2$— or —$X^2$—; where:

$A_1$ is —C(=O)NH—, —C(=O)NH$(CH_2)_n$—, —(O$(CH_2)_n)_m$—, —$((CH_2)_nO)_m$—, —$((CH_2)_nO)_m(CH_2)_n$—, —$(CH_2)_nC$(=O)NH—, —$(CH_2)_n$NHC(=O)—, —NHC(=O)$(CH_2)_n$—, —C(=O)NH$(CH_2)_nS$—, —S$(CH_2)_nC$(=O)NH—, —C(=O)NH$(CH_2)_n$NHC(=O)$(CH_2)_n$—, —C(=O)$(CH_2)_n$—, —$(CH_2)_nC$(=O)—, —$(CH_2)_n(O(CH_2)_n)_m$NHC(=O)$(CH_2)_n$—, —$(CH_2)_n$NHC(=O)$(CH_2)_n$—, —$(CH_2)_n$NH$((CH_2)_nO)_m(CH_2)_n$—, or —$(O(CH_2)_n)_m$NHC(=O)$(CH_2)_n$—;

each $X^2$ is independently selected from a bond, $R^8$

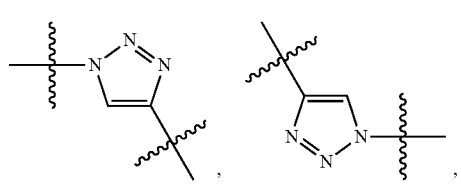

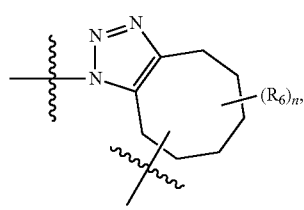

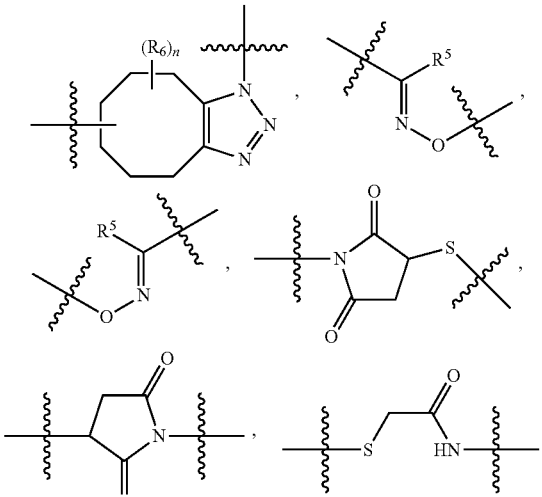

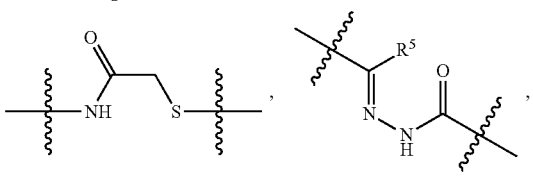

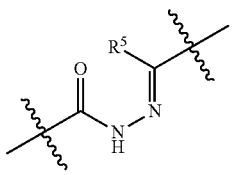

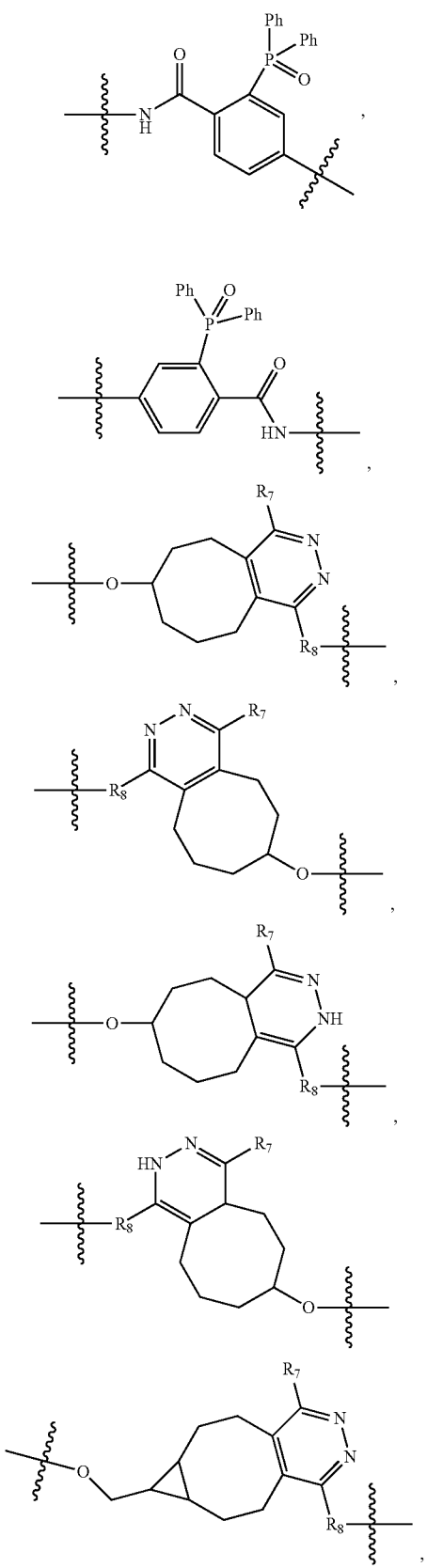
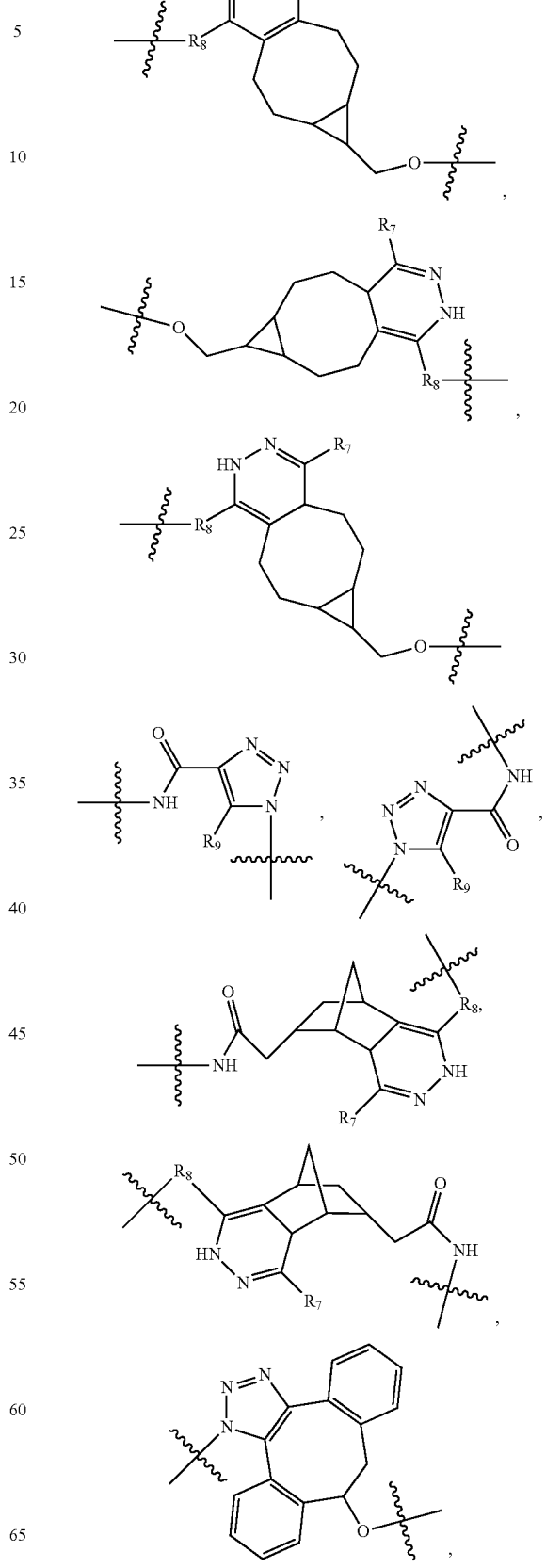

69
-continued

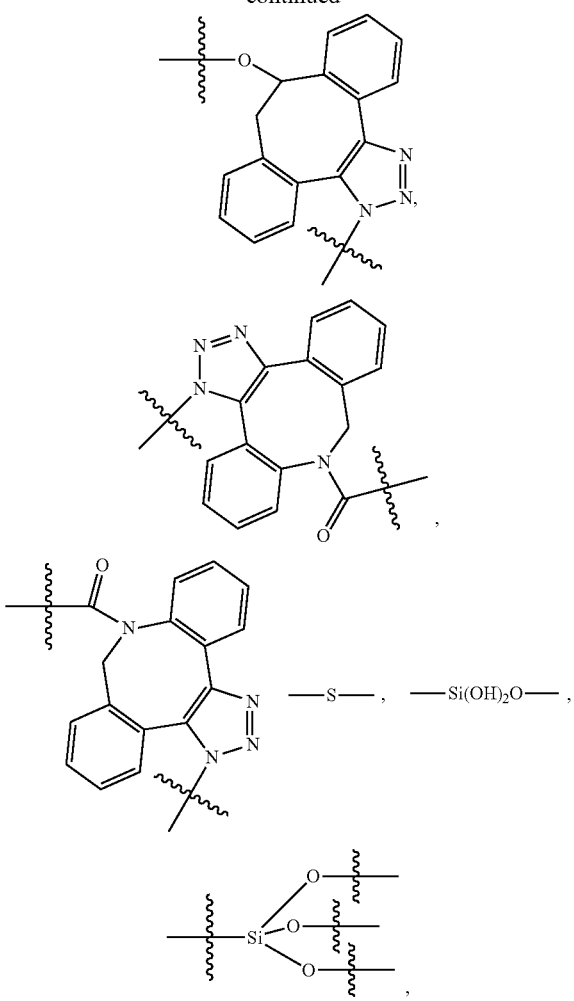

—S—, —Si(OH)₂O—, $$\text{structure with Si and three O groups}$$

CHR⁴(CH₂)ₙC(=O)NH—, —CHR⁴(CH₂)ₙNHC(=O)—, —C(=O)NH— and —NHC(=O)—;

each $R^4$ is independently selected from H, $C_{1-4}$alkyl, side chains of known amino acids, —C(=O)OH and —OH, each $R^5$ is independently selected from H, $C_{1-4}$alkyl, phenyl or $C_{1-4}$alkyl substituted with 1 to 3 —OH groups;

each $R^6$ is independently selected from H, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;

$R^7$ is independently selected from H, $C_{1-4}$alkyl, phenyl, pyrimidine and pyridine;

$R^8$ is independently selected

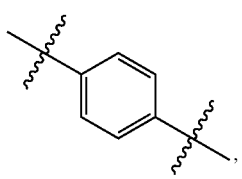

70
-continued

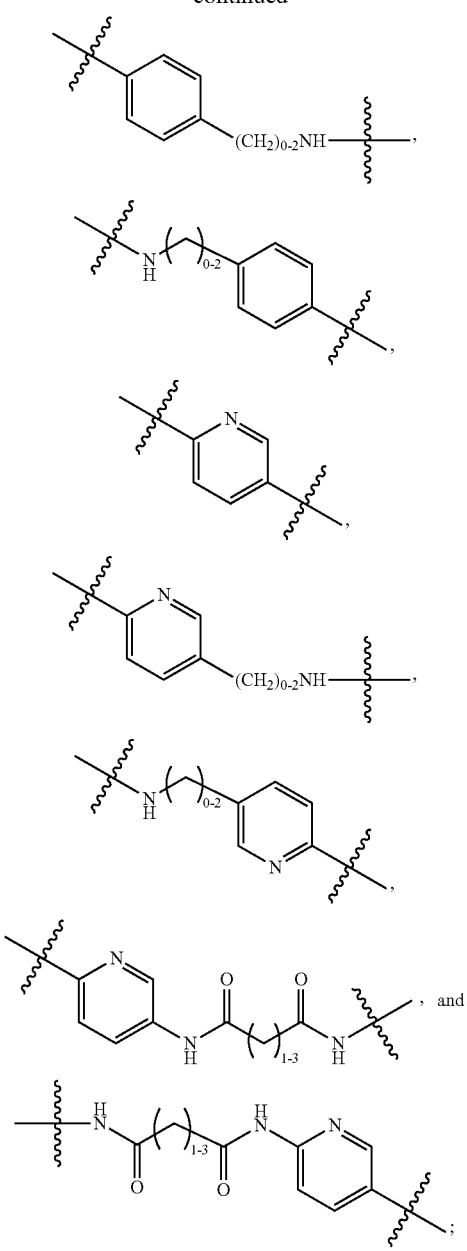

$R^9$ is independently selected from H and $C_{1-6}$haloalkyl;

each n is independently selected from 1, 2, 3, 4, 5, 6, 7, 8 and 9, and each m is independently selected from 1, 2, 3, 4, 5, 6, 7, 8 and 9;

$L_2$ is a bond, a non-enzymatically cleavable linker, a non-cleavable linker, an enzymatically cleavable linker, a photo-stable linker or a photo-cleavable linker;

$L_3$ is a bond, a non-enzymatically cleavable linker, a non-cleavable linker, an enzymatically cleavable linker, a photo-stable linker or a photo-cleavable linker;

$L_4$ is a bond, a non-enzymatically cleavable linker, a non-cleavable linker, an enzymatically cleavable linker, a photo-stable linker, a photo-cleavable linker or a linker that comprises a self-immolative spacer.

In certain embodiments the Linker Unit (LU) is -L$_1$-L$_2$-L$_3$-L$_4$-, wherein
L$_1$ is a bond, -A$_1$-, -A$_1$X$^2$— or —X$^2$—; where:
A$_1$ is —C(=O)NH—, —C(=O)NH(CH$_2$)$_n$—, —C(=O)NH(CH$_2$)$_n$S—, —(O(CH$_2$)$_n$)$_m$—, —((CH$_2$)$_n$O)$_m$(CH$_2$)$_n$—, —NHC(=O)(CH$_2$)$_n$—, —C(=O)NH(CH$_2$)$_n$NHC(=O)(CH$_2$)$_n$—, —(CH$_2$)$_n$NH((CH$_2$)$_n$O)$_m$(CH$_2$)$_n$— or —(O(CH$_2$)$_n$)$_m$NHC(=O)(CH$_2$)$_n$—;
each X$^2$ is independently selected from a bond, R$^8$
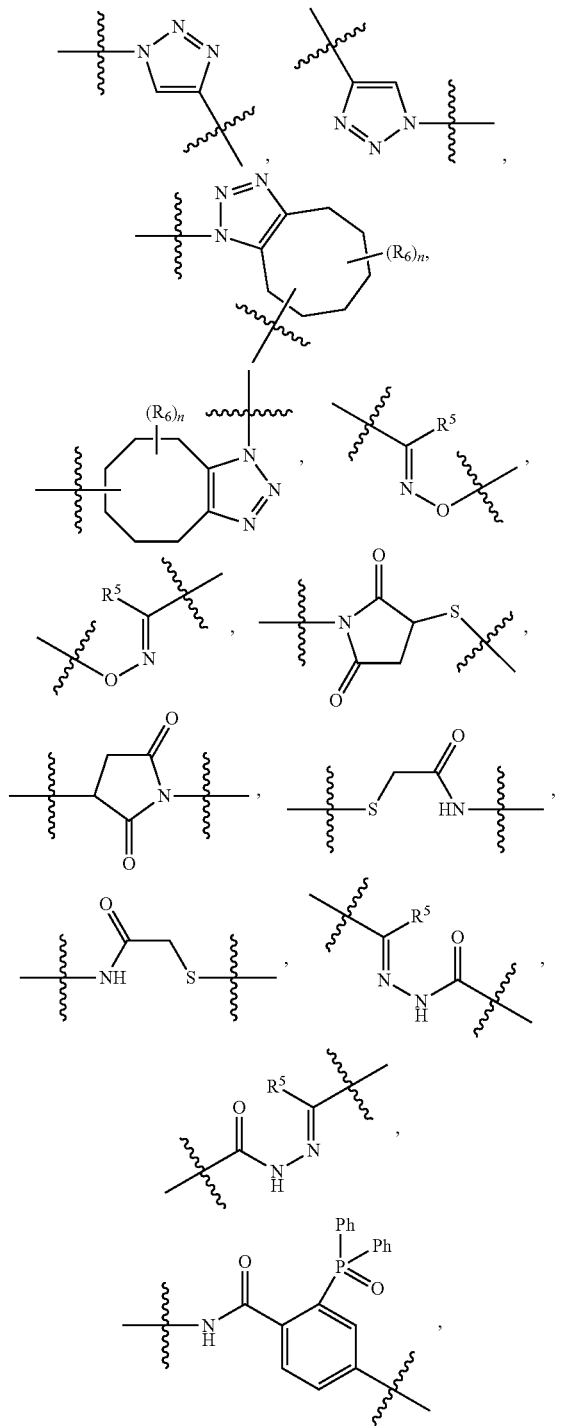
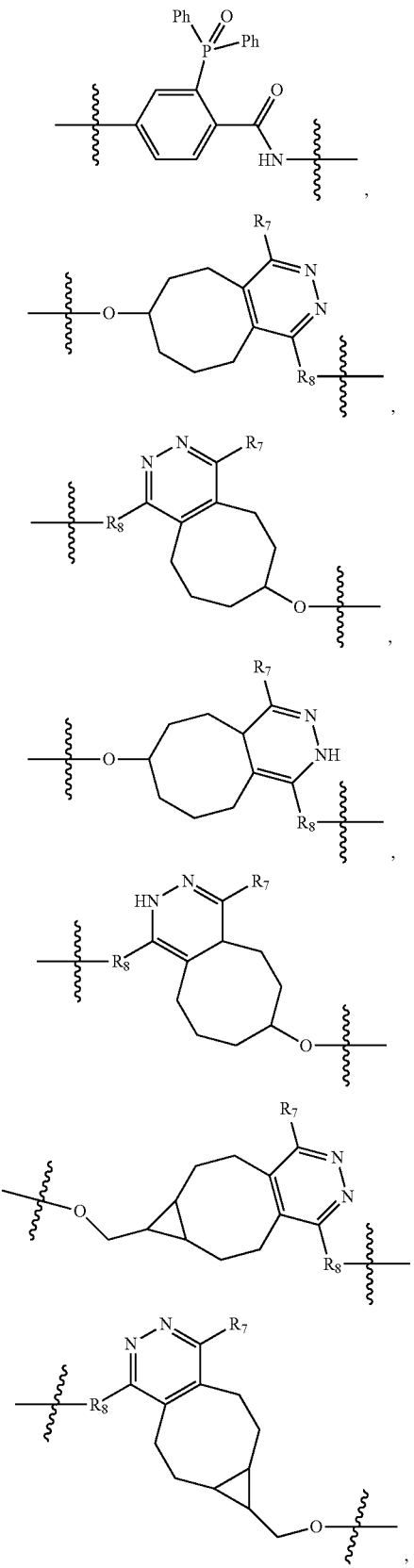

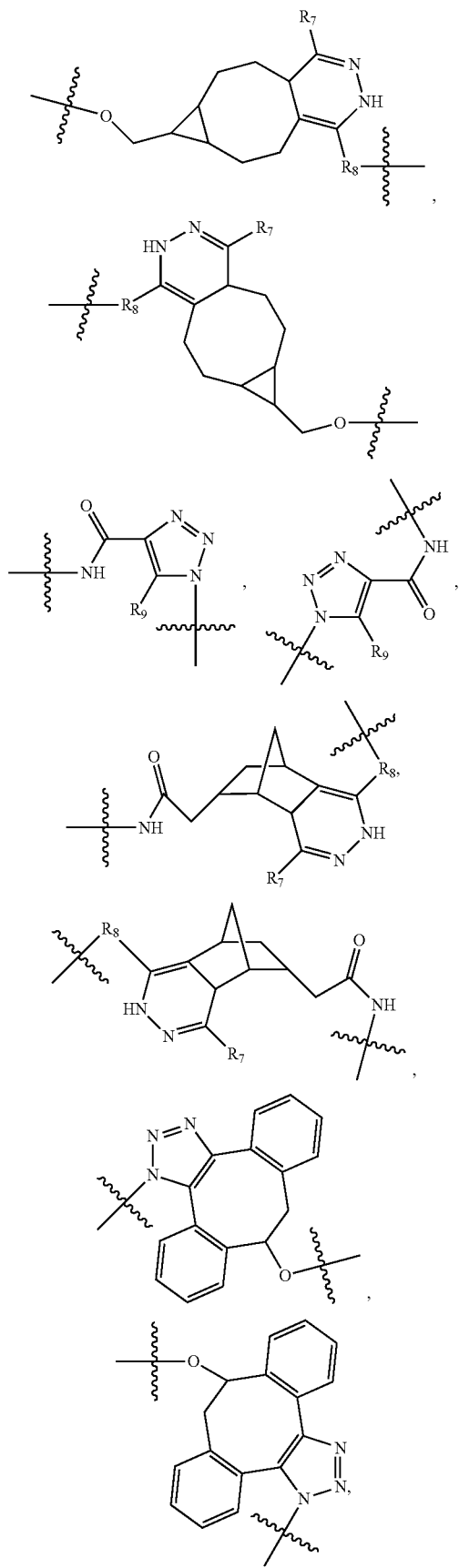

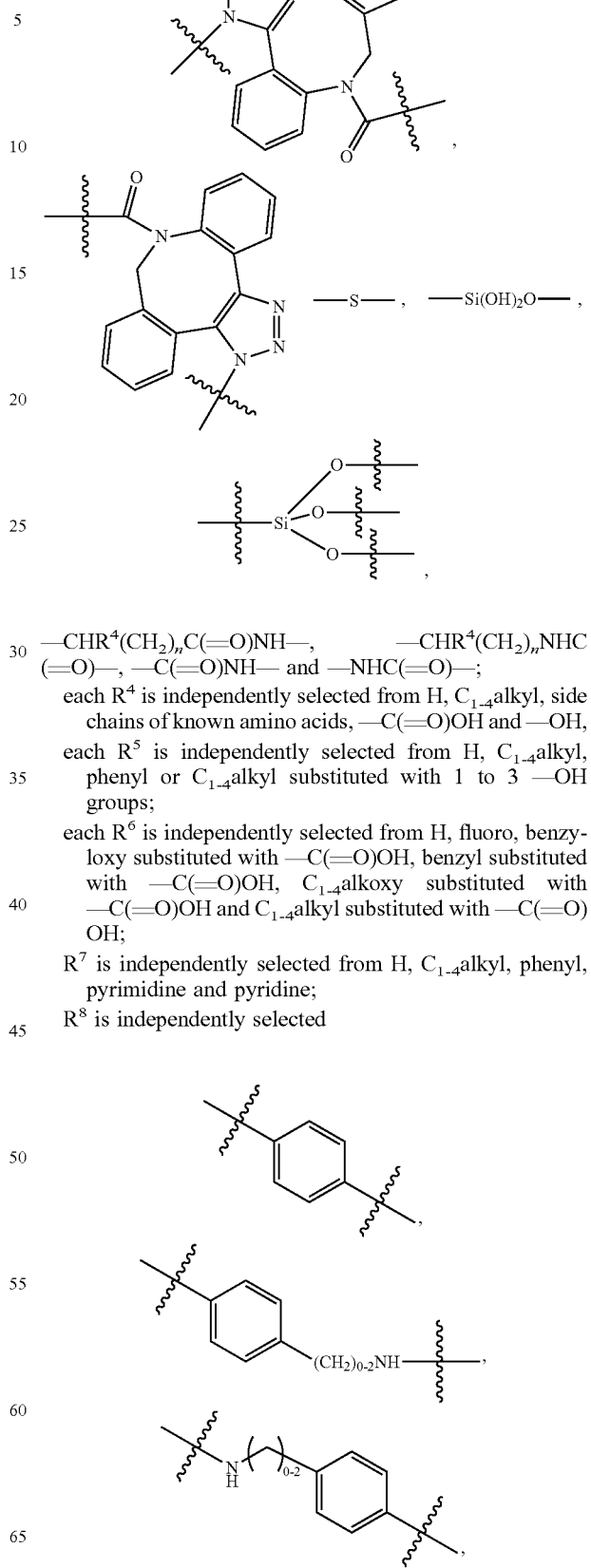

—CHR⁴(CH₂)ₙC(=O)NH—, —CHR⁴(CH₂)ₙNHC(=O)—, —C(=O)NH— and —NHC(=O)—;

each $R^4$ is independently selected from H, $C_{1-4}$alkyl, side chains of known amino acids, —C(=O)OH and —OH, each $R^5$ is independently selected from H, $C_{1-4}$alkyl, phenyl or $C_{1-4}$alkyl substituted with 1 to 3 —OH groups;

each $R^6$ is independently selected from H, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;

$R^7$ is independently selected from H, $C_{1-4}$alkyl, phenyl, pyrimidine and pyridine;

$R^8$ is independently selected

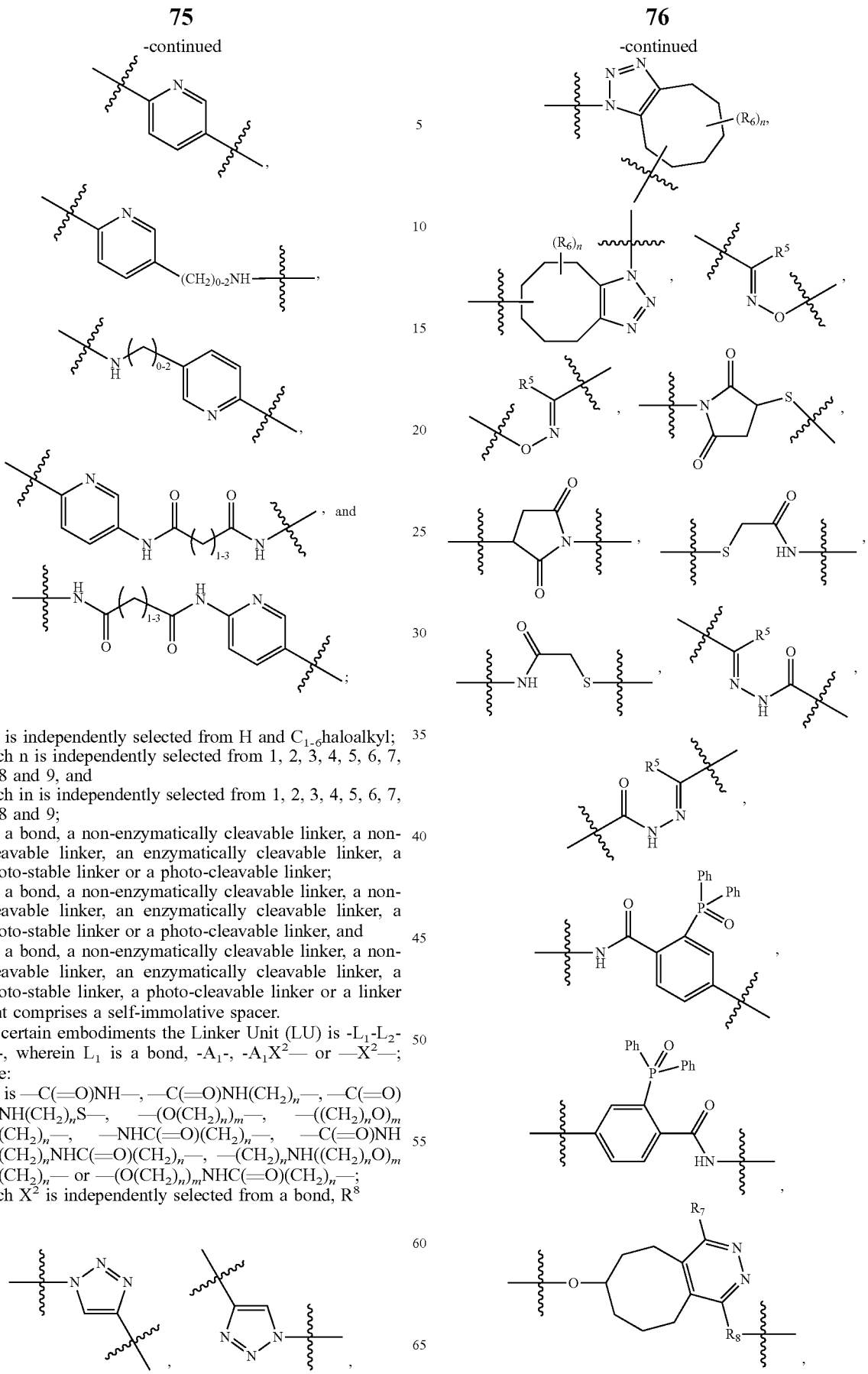

$R^9$ is independently selected from H and $C_{1-6}$haloalkyl; each n is independently selected from 1, 2, 3, 4, 5, 6, 7, 8 and 9, and
each m is independently selected from 1, 2, 3, 4, 5, 6, 7, 8 and 9;

$L_2$ is a bond, a non-enzymatically cleavable linker, a non-cleavable linker, an enzymatically cleavable linker, a photo-stable linker or a photo-cleavable linker;

$L_3$ is a bond, a non-enzymatically cleavable linker, a non-cleavable linker, an enzymatically cleavable linker, a photo-stable linker or a photo-cleavable linker, and $L_4$ is a bond, a non-enzymatically cleavable linker, a non-cleavable linker, an enzymatically cleavable linker, a photo-stable linker, a photo-cleavable linker or a linker that comprises a self-immolative spacer.

In certain embodiments the Linker Unit (LU) is -$L_1$-$L_2$-$L_3$-L-, wherein $L_1$ is a bond, -$A_1$-, -$A_1X^2$— or —$X^2$—; where:

$A_1$ is —C(=O)NH—, —C(=O)NH(CH$_2$)$_n$—, —C(=O)NH(CH$_2$)$_n$S—, —(O(CH$_2$)$_n$)$_m$—, —((CH$_2$)$_n$O)$_m$(CH$_2$)$_n$—, —NHC(=O)(CH$_2$)$_n$—, —C(=O)NH(CH$_2$)$_n$NHC(=O)(CH$_2$)$_n$—, —(CH$_2$)$_n$NH((CH$_2$)$_n$O)$_m$(CH$_2$)$_n$— or —(O(CH$_2$)$_n$)$_m$NHC(=O)(CH$_2$)$_n$—;

each $X^2$ is independently selected from a bond, $R^8$

77
-continued
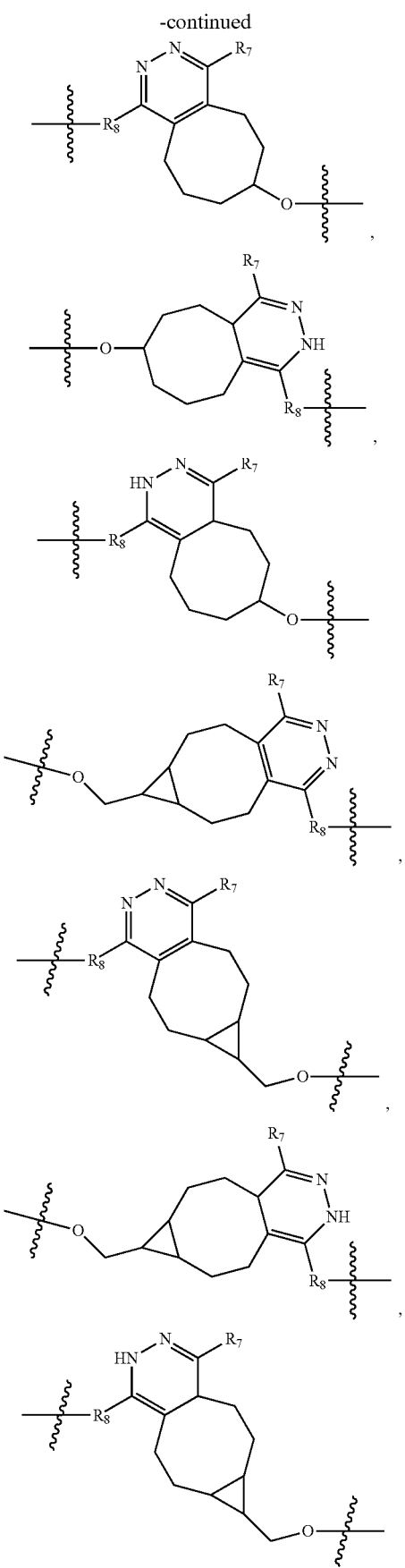
78
-continued
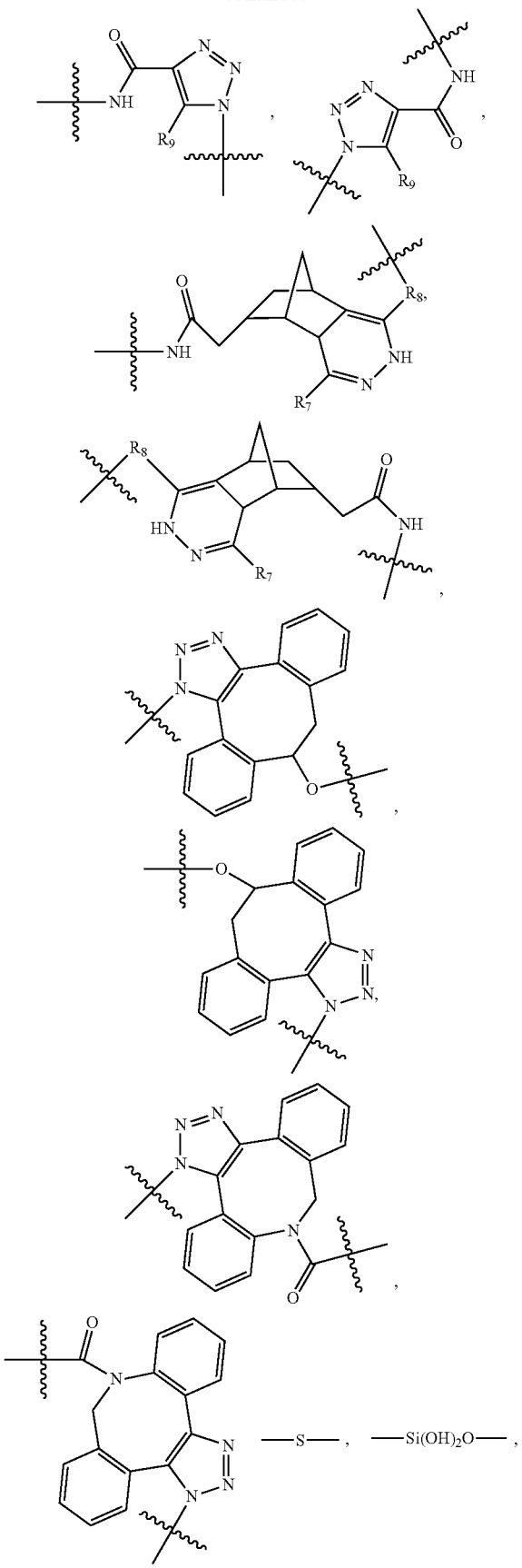

-continued

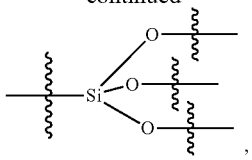

—CHR⁴(CH₂)ₙC(=O)NH—, —CHR⁴(CH₂)ₙNHC(=O)—, —C(=O)NH— and —NHC(=O)—;

each R⁴ is independently selected from H, C₁₋₄alkyl, side chains of known amino acids, —C(=O)OH and —OH, each R⁵ is independently selected from H, C₁₋₄alkyl, phenyl or C₁₋₄alkyl substituted with 1 to 3 —OH groups;

each R⁶ is independently selected from H, fluoro, benzyloxy substituted with —C(=O)OH, benzyl substituted with —C(=O)OH, C₁₋₄alkoxy substituted with —C(=O)OH and C₁₋₄alkyl substituted with —C(=O)OH;

R⁷ is independently selected from H, C₁₋₄alkyl, phenyl, pyrimidine and pyridine;

R⁸ is independently selected from

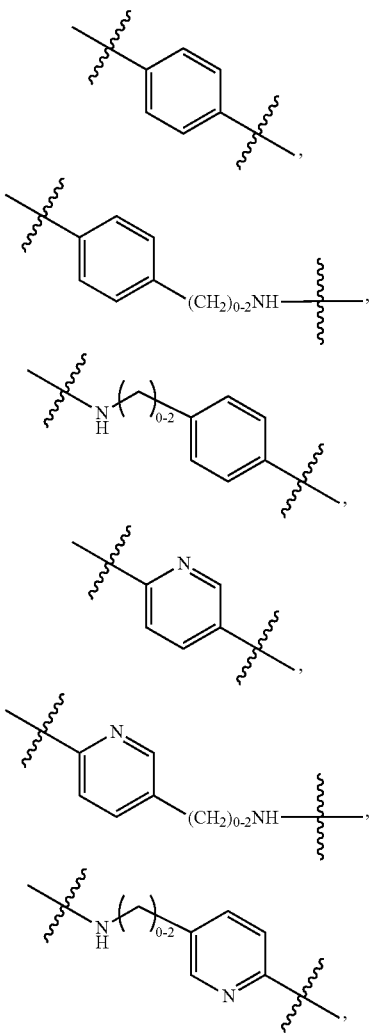

-continued

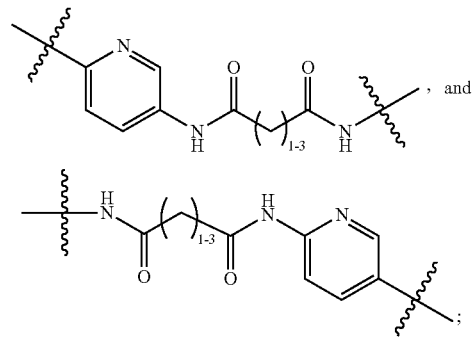

R⁹ is independently selected from H and C₁₋₆haloalkyl;

each n is independently selected from 1, 2, 3, 4, 5, 6, 7, 8 and 9, and each in is independently selected from 1, 2, 3, 4, 5, 6, 7, 8 and 9;

L₂ is a bond, a non-enzymatically cleavable linker or a non-cleavable linker;

L₃ is a bond, a non-enzymatically cleavable linker or a non-cleavable linker;

L₄ is a bond, an enzymatically cleavable linker or a linker that comprises a self-immolative spacer.

In certain embodiments the Linker Unit (LU) is -L₁-L₂-L₃-L₄-, wherein

L₁ is a bond, -A₁-, -A₁X²— or —X²—;

L₂ is a bond, -A₂-, or -A₂X²—;

L₃ is a bond, -A₃-, or -A₃X²—;

L₄ is a bond, -A₄-, -A₄X²—,

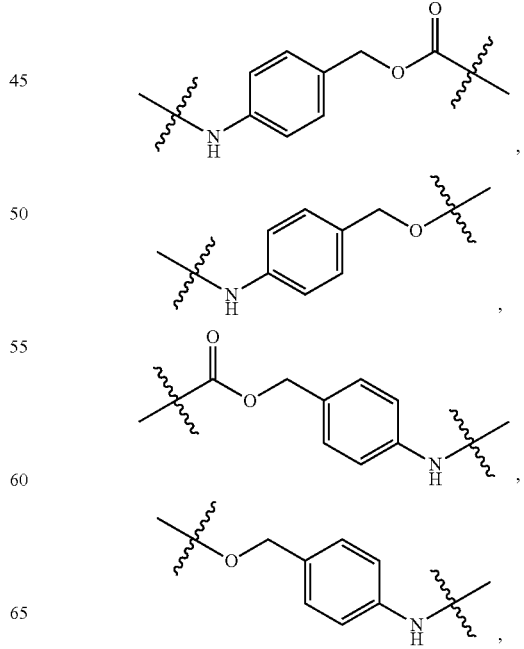

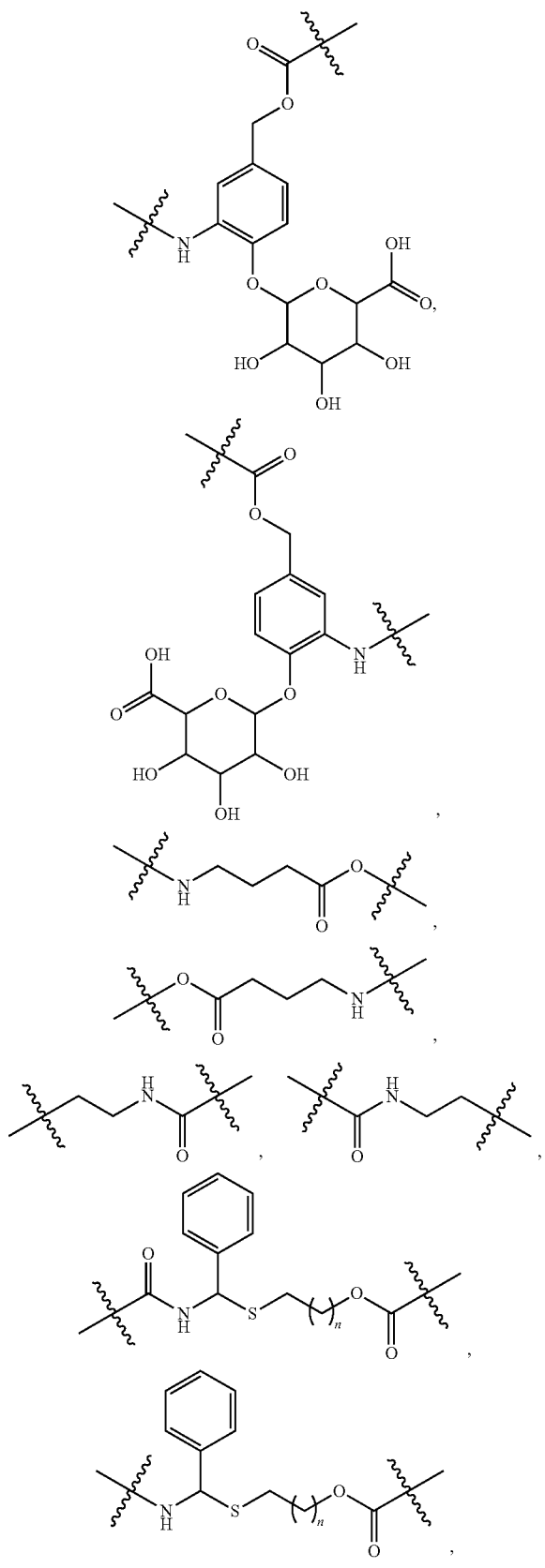

$A_1$ is —C(=O)NH—, —NHC(=O)—, —C(=O)NH$(CH_2)_n$—, —C(=O)NH$(C(R^4)_2)_n$—, —$(O(CH_2)_n)_m$—, —$(O(C(R^4)_2)_n)_m$—, —$((CH_2)_nO)_m$—, —$((C(R^4)_2)_nO)_m$—, —$((CH_2)_nO)_m(CH_2)_n$—, —$(((C(R^4)_2)_nO)_mC(R^4)_2)_n$—, —$(CH_2)_nC(=O)NH$—, —$(C(R^4)_2)_nC(=O)NH$—, —$(CH_2)_nNHC(=O)$—, —$(C(R^4)_2)_nNHC(=O)$—, —NHC(=O)$(CH_2)_n$—, —NHC(=O)$(C(R^4)_2)_n$—, —C(=O)NH$(CH_2)_nS$—, —C(=O)NH$(C(R^4)_2)_nS$—, —S$(CH_2)_nC(=O)NH$—, —S$(C(R^4)_2)_nC(=O)NH$—, —C(=O)NH$(CH_2)_nNHC(=O)(CH_2)_n$—, —C(=O)NH$(C(R^4)_2)_nNHC(=O)(C(R^4)_2)_n$—, —C(=O)$(CH_2)_n$—, —C(=O)$(C(R^4)_2)_n$—, —$(CH_2)_nC(=O)$—, —$(C(R^4)_2)_nC(=O)$—, —$(CH_2)_n(O(CH_2)_n)_mNHC(=O)(CH_2)_n$—, —$(C(R^4)_2)_n(O(C(R^4)_2)_n)_mNHC(=O)(C(R^4)_2)_n$—, —$(CH_2)_nNHC(=O)(CH_2)_n$—, —$(C(R^4)_2)_nNHC(=O)(C(R^4)_2)_n$—, —$(CH_2)_nNH((CH_2)_nO)_m(CH_2)_n$—, —$(C(R^4)_2)_nNH((C(R^4)_2)_nO)_m(C(R^4)_2)_n$—, —$(O(CH_2)_n)_mNHC(=O)(CH_2)_n$—, or —$(O(C(R^4)_2)_n)_mNHC(=O)(C(R^4)_2)_n$—;

$A_2$ is —C(=O)NH—, —C(=O)NH$(CH_2)_n$—, —C(=O)NH$(C(R^4)_2)_n$—, —$(O(CH_2)_n)_m$—, —$(O(C(R^4)_2)_n)_m$—, —$((CH_2)_nO)_m$—, —$((C(R^4)_2)_nO)_m$—, —$((CH_2)_nO)_m(CH_2)_n$—, —$(((C(R^4)_2)_nO)_mC(R^4)_2)_n$—, —$(CH_2)_nC(=O)NH$—, —$(C(R^4)_2)_nC(=O)NR^4$—, —$(CH_2)_nNHC(=O)$—, —$(C(R^4)_2)_nNHC(=O)$—, —NHC(=O)$(CH_2)_n$—, —NHC(=O)$(C(R^4)_2)_n$—, —C(=O)NH$(CH_2)_nS$—, —C(=O)NH$(C(R^4)_2)_nS$—, —S$(CH_2)_nC(=O)NH$—, —S$(C(R^4)_2)_nC(=O)NH$—, —$(CH_2)_nS$—, —$(C(R^4)_2)_nS$—, —S$(CH_2)_n$—, —S$(C(R^4)_2)_n$—, —$(CH_2)_nNH$—, —$(C(R^4)_2)_nNH$—, —C(=O)NH$(CH_2)_nNHC(=O)(CH_2)_n$—, —C(=O)NH$(C(R^4)_2)_nNHC(=O)(C(R^4)_2)_n$—, —C(=O)$(CH_2)_n$—, —C(=O)$(C(R^4)_2)_n$—, —$(CH_2)_nC(=O)$—, —$(C(R^4)_2)_nC(=O)$—, —$(CH_2)_n(O(CH_2)_n)_mNHC(=O)(CH_2)_n$—, —$(C(R^4)_2)_n(O(C(R^4)_2)_n)_mNHC(=O)(C(R^4)_2)_n$—, —$(CH_2)_n(O(CH_2)_n)_mOC(=O)NH(CH_2)_n$—, —$(C(R^4)_2)_n(O(C(R^4)_2)_n)_mOC(=O)NH(C(R^4)_2)_n$—, —$(CH_2)_nNHC(=O)(CH_2)_n$—, —$(C(R^4)_2)_nNHC(=O)(C(R^4)_2)_n$—, —$(CH_2)_nNH((CH_2)_nO)_m(CH_2)_n$—, —$(C(R^4)_2)_nNH((C(R^4)_2)_nO)_m(C(R^4)_2)_n$—, —$(O(CH_2))_n)_mNHC(=O)(CH_2)_n$—, —$(O(C(R^4)_2)_n)_mNHC(=O)(C(R^4)_2)_n$—,

83

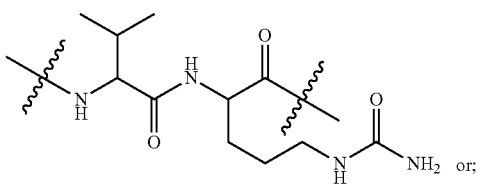 or;

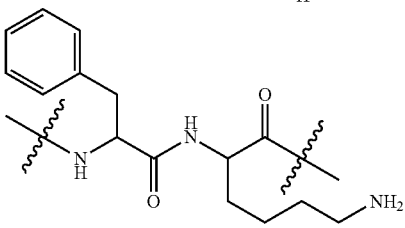

$A_3$ is —C(=O)NH—, —C(=O)NH(CH$_2$)$_n$—, —C(=O)NH(C(R$^4$)$_2$)$_n$—, —(O(CH$_2$)$_n$)$_m$—, —(O(C(R$^4$)$_2$)$_n$)$_m$—, —((CH$_2$)$_n$O)$_m$—, —((C(R$^4$)$_2$)$_n$O)$_m$—, —((CH$_2$)$_n$O)$_m$(CH$_2$)$_n$—, —(((C(R$^4$)$_2$)$_n$O)$_m$C(R$^4$)$_2$)$_n$—, —(CH$_2$)$_n$C(=O)NH—, —(C(R$^4$)$_2$)$_n$C(=O)NH—, —(CH$_2$)$_n$NHC(=O)—, —(C(R$^4$)$_2$)$_n$NHC(=O)—, —NHC(=O)(CH$_2$)$_n$—, —NHC(=O)(C(R$^4$)$_2$)$_n$—, —C(=O)NH(CH$_2$)$_n$S—, —C(=O)NH(C(R$^4$)$_2$)$_n$S—, —S(CH$_2$)$_n$C(=O)NH—, —S(C(R$^4$)$_2$)$_n$C(=O)NH—, —(CH$_2$)$_n$S—, —(C(R$^4$)$_2$)$_n$S—, —S(CH$_2$)$_n$—, —S(C(R$^4$)$_2$)$_n$—, —C(=O)NH(CH$_2$)$_n$NHC(=O)(CH$_2$)$_n$—, —C(=O)NH(C(R$^4$)$_2$)$_n$NHC(=O)(C(R$^4$)$_2$)$_n$—, —C(=O)(CH$_2$)$_n$—, —C(=O)(C(R$^4$)$_2$)$_n$—, —(CH$_2$)$_n$C(=O)—, —(C(R$^4$)$_2$)$_n$C(=O)—, —(CH$_2$)$_n$(O(CH$_2$)$_n$)$_m$NHC(=O)(CH$_2$)$_n$—, —(C(R$^4$)$_2$)$_n$(O(C(R$^4$)$_2$)$_n$)$_m$NHC(=O)(C(R$^4$)$_2$)$_n$—, —(CH$_2$)$_n$(O(CH$_2$)$_n$)$_m$OC(=O)NH(CH$_2$)$_n$—, —(C(R$^4$)$_2$)$_n$(O(C(R$^4$)$_2$)$_n$)$_m$OC(=O)NH(C(R$^4$)$_2$)$_n$—, —(CH$_2$)$_n$(O(CH$_2$)$_n$)$_m$OC(=O)—, —(C(R$^4$)$_2$)$_n$(O(C(R$^4$)$_2$)$_n$)$_m$OC(=O)—, —(CH$_2$)$_n$(O(CH$_2$)$_n$)$_m$C(=O)—, —(C(R$^4$)$_2$)$_n$(O(C(R$^4$)$_2$)$_n$)$_m$C(=O)—, —(CH$_2$)$_n$NHC(=O)(CH$_2$)$_n$—, —(C(R$^4$)$_2$)$_n$NHC(=O)(C(R$^4$)$_2$)$_n$—, —(O(CH$_2$)$_n$)$_m$NHC(=O)(CH$_2$)$_n$—, —(O(C(R$^4$)$_2$)$_n$)$_m$NHC(=O)(C(R$^4$)$_2$)$_n$—,

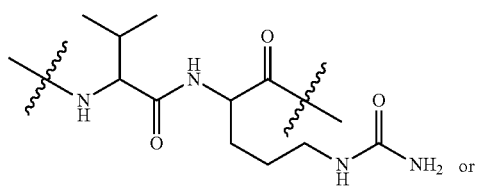 or

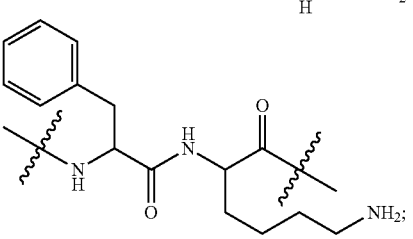

$A_4$ is —C(=O)NH—, —C(=O)NH(CH$_2$)$_n$—, —C(=O)NH(C(R$^4$)$_2$)$_n$—, —(O(CH$_2$)$_n$)$_m$—, —(O(C(R$^4$)$_2$)$_n$)$_m$—, —((CH$_2$)$_n$O)$_m$—, —((C(R$^4$)$_2$)$_n$O)$_m$—, —((CH$_2$)$_n$O)$_m$(CH$_2$)$_n$—, —(((C(R$^4$)$_2$)$_n$O)$_m$C(R$^4$)$_2$)$_n$—, —(CH$_2$)$_n$C(=O)NH—, —(C(R$^4$)$_2$)$_n$C(=O)NH—, —(CH$_2$)$_n$NHC(=O)—, —(C(R$^4$)$_2$)$_n$NHC(=O)—, —NHC(=O)(CH$_2$)$_n$—, —NHC(=O)(C(R$^4$)$_2$)$_n$—, —C(=O)NH(CH$_2$)$_n$S—, —C(=O)NH(C(R$^4$)$_2$)$_n$S—, —S(CH$_2$)$_n$C(=O)NH—, —S(C(R$^4$)$_2$)$_n$C(=O)NH—, —C(=O)NH(CH$_2$)$_n$NHC(=O)(CH$_2$)$_n$—, —C(=O)NH(C(R$^4$)$_2$)$_n$NHC(=O)(C(R$^4$)$_2$)$_n$—, —C(=O)(CH$_2$)$_n$—, —C(=O)(C(R$^4$)$_2$)$_n$—, —(CH$_2$)$_n$C(=O)—, —(C(R$^4$)$_2$)$_n$C(=O)—, —(CH$_2$)$_n$(O(CH$_2$)$_n$)$_m$NHC(=O)(CH$_2$)$_n$—, —(C(R$^4$)$_2$)$_n$(O(C(R$^4$)$_2$)$_n$)$_m$NHC(=O)(C(R$^4$)$_2$)$_n$—, —(CH$_2$)$_n$NHC(=O)(CH$_2$)$_n$—, —(C(R$^4$)$_2$)$_n$NHC(=O)(C(R$^4$)$_2$)$_n$—, —(CH$_2$)$_n$NH((CH$_2$)$_n$O)$_m$(CH$_2$)$_n$—, —(C(R$^4$)$_2$)$_n$NH((C(R$^4$)$_2$)$_n$O)$_m$(C(R$^4$)$_2$)$_n$—, —(O(CH$_2$)$_n$)$_m$NHC(=O)(CH$_2$)$_n$—, or —(O(C(R$^4$)$_2$)$_n$)$_m$NHC(=O)(C(R$^4$)$_2$)$_n$—;

each $X^2$ is independently selected from a bond, $R^8$

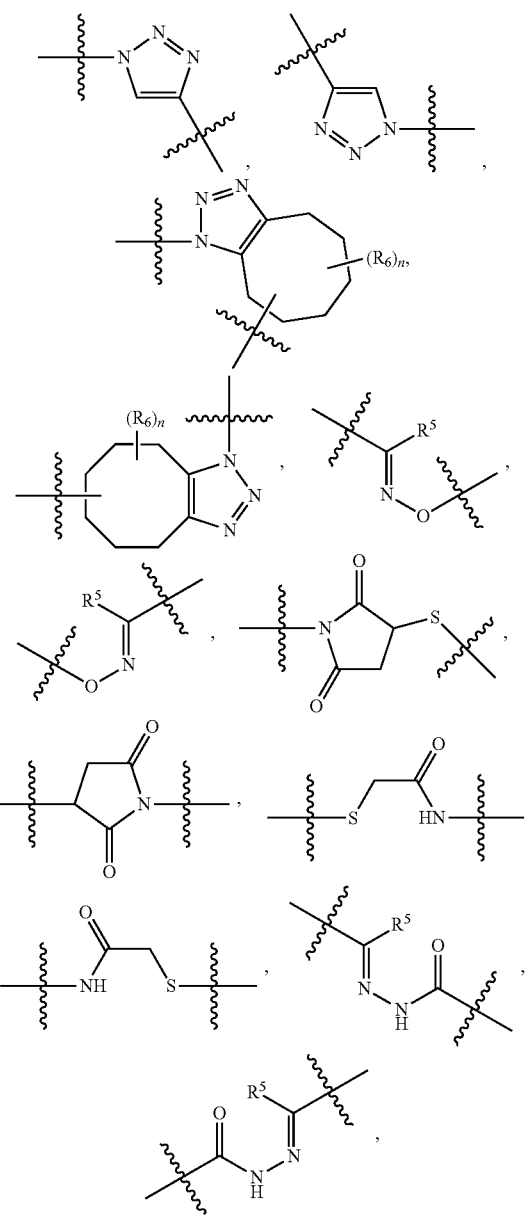

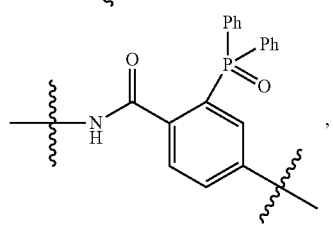

-continued
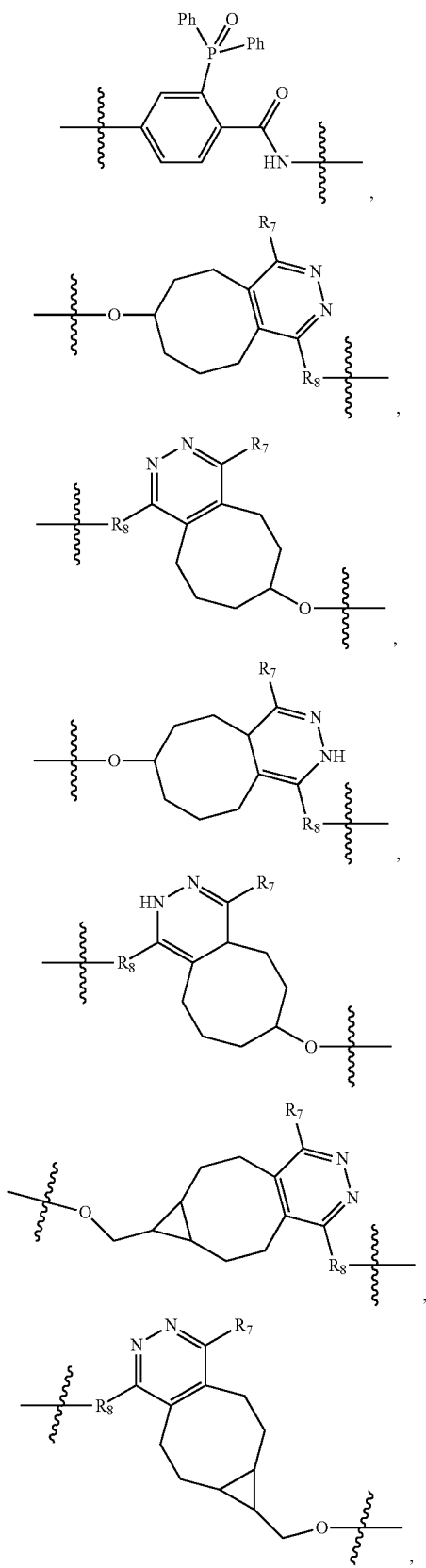
-continued
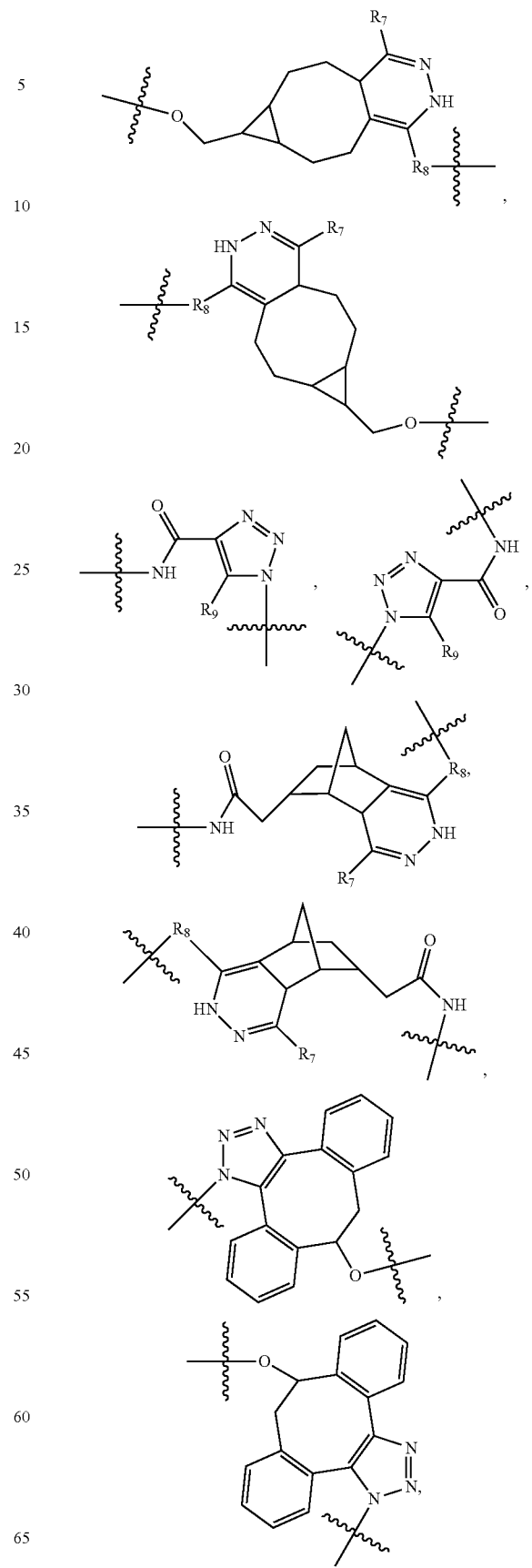

-continued

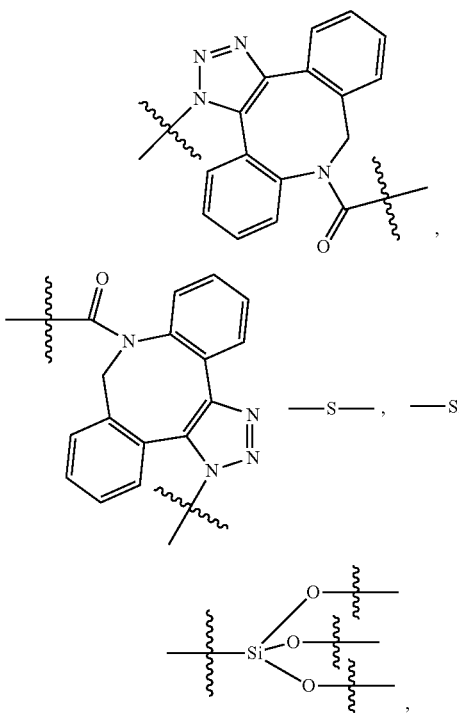

—CHR⁴(CH₂)ₙC(=O)NH—,   —CHR⁴(CH₂)ₙNHC(=O)—, —C(=O)NH— and —NHC(=O)—;

each R⁴ is independently selected from H, $C_{1-4}$alkyl, side chains of known amino acids, —C(=O)OH and —OH, each R⁵ is independently selected from H, $C_{1-4}$alkyl, phenyl or $C_{1-4}$alkyl substituted with 1 to 3 —OH groups;

each R⁶ is independently selected from H, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;

R⁷ is independently selected from H, $C_{1-4}$alkyl, phenyl, pyrimidine and pyridine;

R⁸ is independently selected from

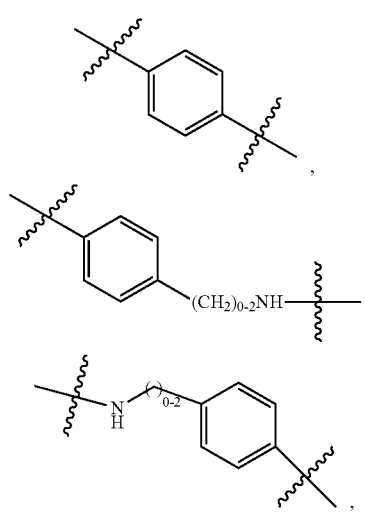

-continued

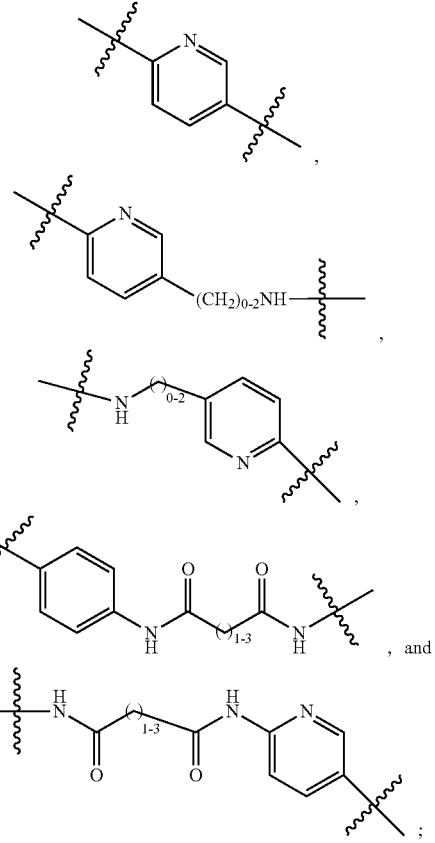

R⁹ is independently selected from H and $C_{1-6}$haloalkyl;

each n is independently selected from 1, 2, 3, 4, 5, 6, 7, 8 and 9, and each m is independently selected from 1, 2, 3, 4, 5, 6, 7, 8 and 9.

In certain embodiments the Linker Unit (LU) is -L₁-L₂-L₃-L₄-, wherein

L₁ is a bond, -A₁-, -A₁X²— or —X²—;

L₂ is a bond, -A₂-, or -A₂X²—;

L₃ is a bond, -A₃-, or -A₃X²—;

L₄ is a bond, -A₄-, -A₄X²—,

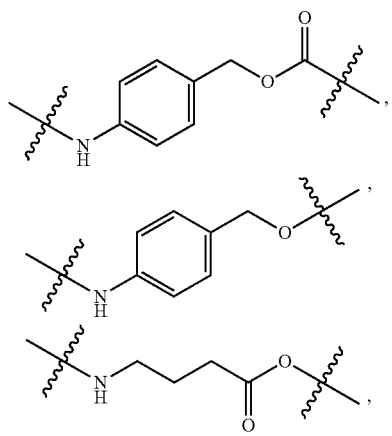

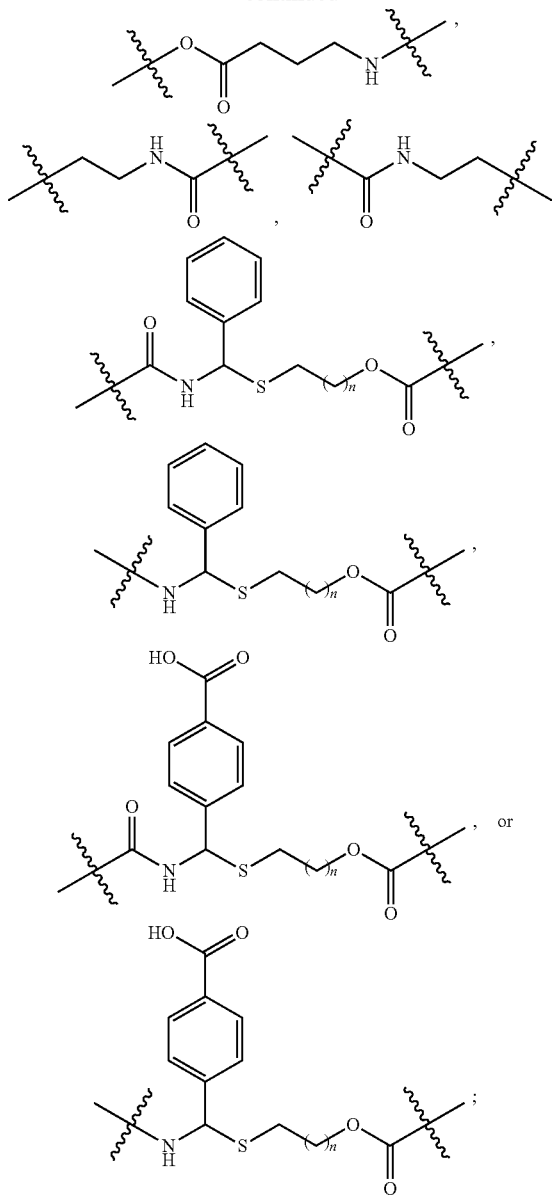

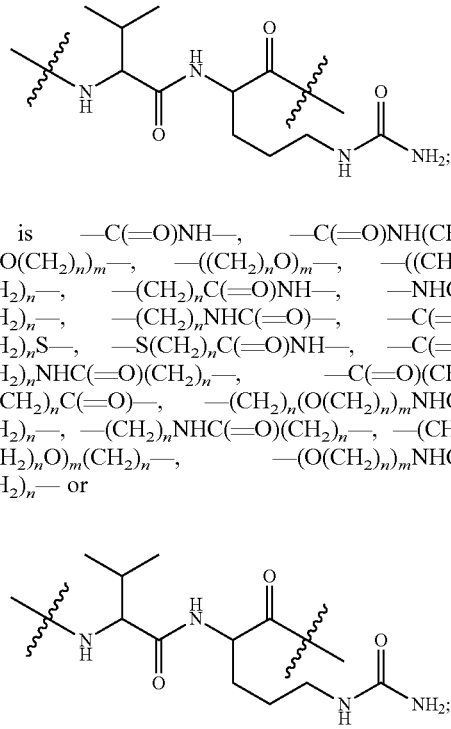

$A_3$ is —C(=O)NH—, —C(=O)NH(CH$_2$)$_n$—, —(O(CH$_2$)$_n$)$_m$—, —((CH$_2$)$_n$O)$_m$—, —((CH$_2$)$_n$O)$_m$(CH$_2$)$_n$—, —(CH$_2$)$_n$C(=O)NH—, —NHC(=O)(CH$_2$)$_n$—, —(CH$_2$)$_n$NHC(=O)—, —C(=O)NH(CH$_2$)$_n$S—, —S(CH$_2$)$_n$C(=O)NH—, —C(=O)NH(CH$_2$)$_n$NHC(=O)(CH$_2$)$_n$—, —C(=O)(CH$_2$)$_n$—, —(CH$_2$)$_n$C(=O)—, —(CH$_2$)$_n$(O(CH$_2$)$_n$)$_m$NHC(=O)(CH$_2$)$_n$—, —(CH$_2$)$_n$NHC(=O)(CH$_2$)$_n$—, —(CH$_2$)$_n$NH((CH$_2$)$_n$O)$_m$(CH$_2$)$_n$—, —(O(CH$_2$)$_n$)$_m$NHC(=O)(CH$_2$)$_n$— or $A_4$ —C(=O)NH—, —C(=O)NH(CH$_2$)$_n$—, —(O(CH$_2$)$_n$)$_m$—, —((CH$_2$)$_n$O)$_m$—, —((CH$_2$)$_n$O)$_m$(CH$_2$)$_n$—, —(CH$_2$)$_n$C(=O)NH—, —NHC(=O)(CH$_2$)$_n$—, —(CH$_2$)$_n$NHC(=O)—, —C(=O)NH(CH$_2$)$_n$S—, —S(CH$_2$)$_n$C(=O)NH—, —C(=O)NH(CH$_2$)$_n$NHC(=O)(CH$_2$)$_n$—, —C(=O)(CH$_2$)$_n$—, —(CH$_2$)$_n$C(=O)—, —(CH$_2$)$_n$(O(CH$_2$)$_n$)$_m$NHC(=O)(CH$_2$)$_n$—, —(CH$_2$)~NHC(=O)(CH$_2$)$_n$—, —(CH$_2$)$_n$NH((CH$_2$)$_n$O)$_m$(CH$_2$)$_n$— or —(O(CH$_2$)$_n$)$_m$NHC(=O)(CH$_2$)$_n$—;

each $X^2$ is independently selected from a bond,

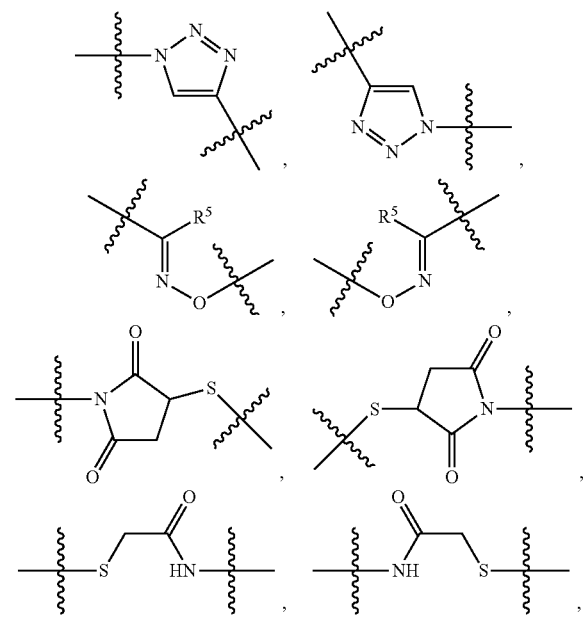

$A_1$ is —C(=O)NH—, —C(=O)NH(CH$_2$)$_n$—, —(O(CH$_2$)$_n$)$_m$—, —((CH$_2$)$_n$O)$_m$—, —((CH$_2$)$_n$O)$_m$(CH$_2$)$_n$—, —(CH$_2$)$_n$C(=O)NH—, —NHC(=O)(CH$_2$)$_n$—, —(CH$_2$)$_n$NHC(=O)—, —C(=O)NH(CH$_2$)$_n$S—, —S(CH$_2$)$_n$C(=O)NH—, —C(=O)NH(CH$_2$)$_n$NHC(=O)(CH$_2$)$_n$—, —C(=O)(CH$_2$)$_n$—, —(CH$_2$)$_n$C(=O)—, —(CH$_2$)$_n$(O(CH$_2$)$_n$)$_m$NHC(=O)(CH$_2$)$_n$—, —(CH$_2$)~NHC(=O)(CH$_2$)$_n$—, —(CH$_2$)$_n$NH((CH$_2$)$_n$O)$_m$(CH$_2$)$_n$— or —(O(CH$_2$)$_n$)$_m$NHC(=O)(CH$_2$)$_n$—;

$A_2$ is —C(=O)NH—, —C(=O)NH(CH$_2$)$_n$—, —(O(CH$_2$)$_n$)$_m$—, —((CH$_2$)$_n$O)$_m$—, —((CH$_2$)$_n$O)$_m$(CH$_2$)$_n$—, —(CH$_2$)$_n$C(=O)NH—, —NHC(=O)(CH$_2$)$_n$—, —(CH$_2$)$_n$NHC(=O)—, —C(=O)NH(CH$_2$)$_n$S—, —S(CH$_2$)$_n$C(=O)NH—, —C(=O)NH(CH$_2$)$_n$NHC(=O)(CH$_2$)$_n$—, —C(=O)(CH$_2$)$_n$—, —(CH$_2$)~C(=O)—, —(CH$_2$)$_n$(O(CH$_2$)$_n$)$_m$NHC(=O)(CH$_2$)$_n$—, —(CH$_2$)$_n$NHC(=O)(CH$_2$)$_n$—, —(CH$_2$)$_n$NH((CH$_2$)$_n$O)$_m$(CH$_2$)$_n$—, —(O(CH$_2$)$_n$)$_m$NHC(=O)(CH$_2$)$_n$— or

-continued

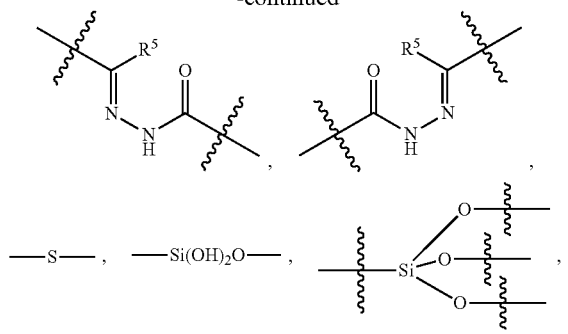

—CHR⁴(CH₂)ₙC(=O)NH—, —CHR⁴(CH₂)ₙNHC(=O)—, —C(=O)NH— and —NHC(=O)—;

each R⁴ is independently selected from H, $C_{1-4}$alkyl, side chains of known amino acids, —C(=O)OH and —OH, each R⁵ is independently selected from H, $C_{1-4}$alkyl, phenyl or $C_{1-4}$alkyl substituted with 1 to 3 —OH groups;

each n is independently selected from 1, 2, 3, 4, 5, 6, 7, 8 and 9, and each m is independently selected from 1, 2, 3, 4, 5, 6, 7, 8 and 9.

In certain embodiments the Linker Unit (LU) is -$L_1$-$L_2$-$L_3$-$L_4$-, wherein $L_1$ is a bond, -$A_1$-, -$A_1X^2$— or —$X^2$—;
$L_2$ is a bond, -$A_2$-, or -$A_2X^2$—;
$L_3$ is a bond, -$A_3$-, or -$A_3X^2$—;
$L_4$ is a bond, -$A_4$-, -$A_4X^2$—,

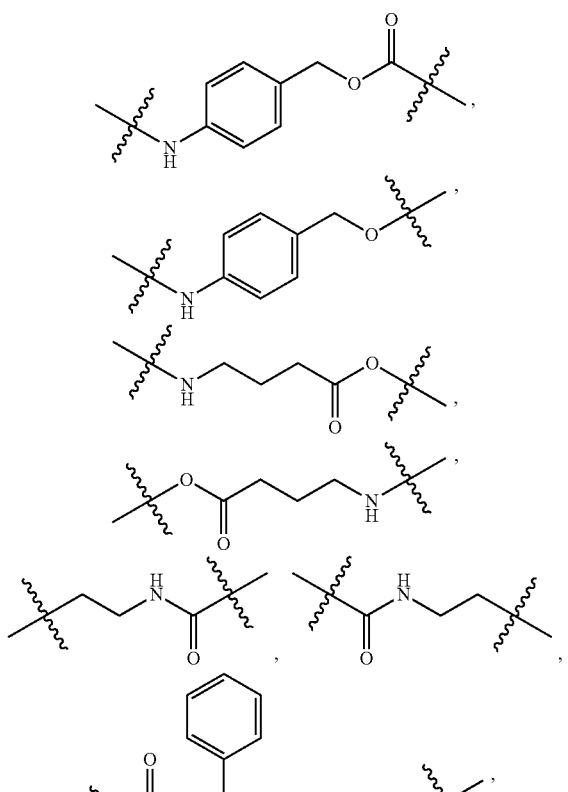

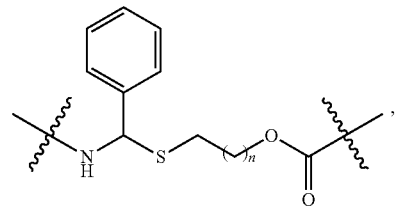

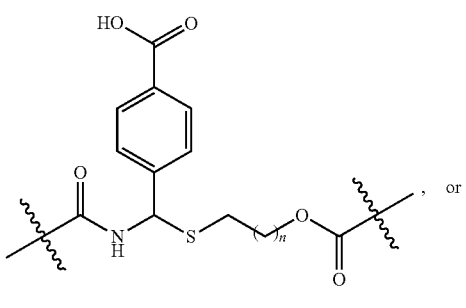

,or

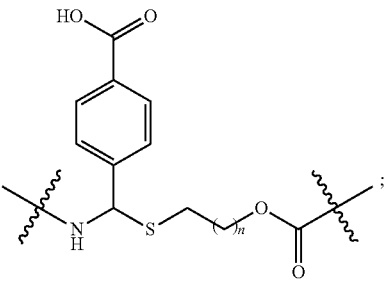

;

$A_1$ is —C(=O)NH—, —C(=O)NH(CH₂)ₙ—, —C(=O)NH(CH₂)ₙS—, —(O(CH₂)ₙ)ₘ—, —((CH₂)ₙO)ₘ(CH₂)ₙ—, —NHC(=O)(CH₂)ₙ—, —(CH₂)ₙNHC(=O)—, —C(=O)NH(CH₂)ₙNHC(=O)(CH₂)ₙ—, —(CH₂)ₙNH((CH₂)ₙO)ₘ(CH₂)ₙ— or —(O(CH₂))ₙ)ₘNHC(=O)(CH₂)ₙ—;

$A_2$ is —C(=O)NH—, —C(=O)NH(CH₂)ₙ—, —C(=O)NH(CH₂)ₙS—, —(O(CH₂)ₙ)ₘ—, —((CH₂)ₙO)ₘ(CH₂)ₙ—, —NHC(=O)(CH₂)ₙ—, —(CH₂)ₙNHC(=O)—, —C(=O)NH(CH₂)ₙNHC(=O)(CH₂)ₙ—, —(CH₂)ₙNH((CH₂)ₙO)ₘ(CH₂)ₙ—, —(O(CH₂)ₙ)ₘNHC(=O)(CH₂)ₙ— or

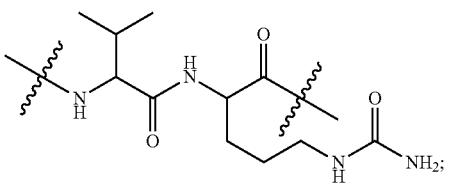 [SMILES: *NC(C(=O)NC(CCCNC(N)=O)C(*)=O)C(C)C]

$A_3$ is —C(=O)NH—, —C(=O)NH(CH₂)ₙ—, —C(=O)NH(CH₂)ₙS—, —(O(CH₂)ₙ)ₘ—, —((CH₂)ₙO)ₘ(CH₂)ₙ—, —NHC(=O)(CH₂)ₙ—, —(CH₂)ₙNHC(=O)—, —C(=O)NH(CH₂)ₙNHC(=O)(CH₂)ₙ—, —(CH₂)ₙNH((CH₂)ₙO)ₘ(CH₂)ₙ—, —(O(CH₂)ₙ)ₘNHC(=O)(CH₂)ₙ— or

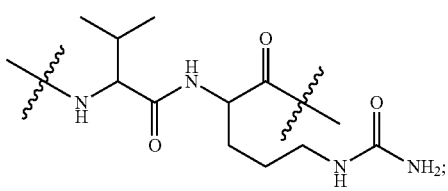 [SMILES: *NC(C(=O)NC(CCCNC(N)=O)C(*)=O)C(C)C]
$A_4$ is —C(=O)NH—, —C(=O)NH(CH$_2$)$_n$—, —C(=O)NH(CH$_2$)$_n$S—, —(O(CH$_2$)$_n$)$_m$—, —((CH$_2$)$_n$O)$_m$(CH$_2$)$_n$—, —NHC(=O)(CH$_2$)$_n$—, —(CH$_2$)$_n$NHC(=O)—, —C(=O)NH(CH$_2$)$_n$NHC(=O)(CH$_2$)$_n$—, —(CH$_2$)$_n$NH((CH$_2$)$_n$O)$_m$(CH$_2$)$_n$— or —(O(CH$_2$)$_n$)$_m$NHC(=O)(CH$_2$)$_n$—;
each $X^2$ is independently selected from a bond, $R^8$
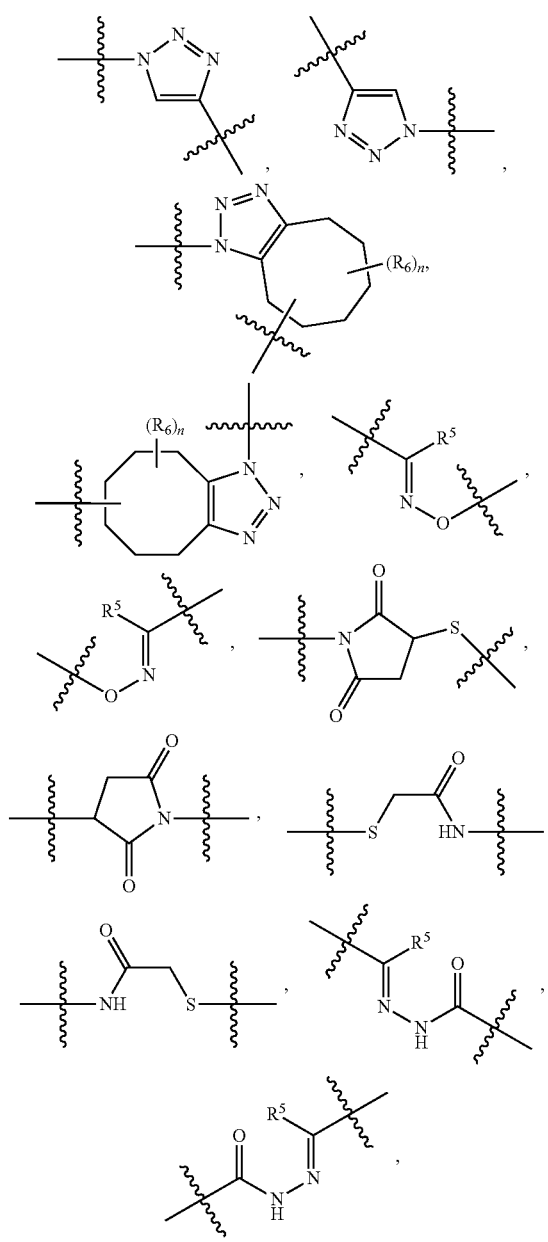
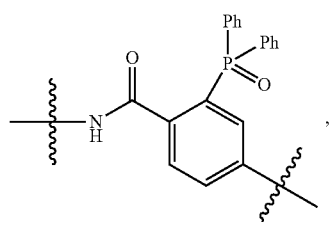
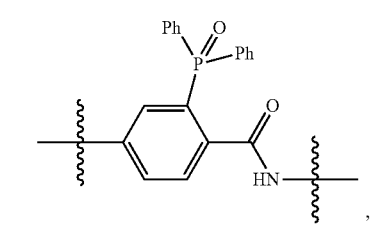
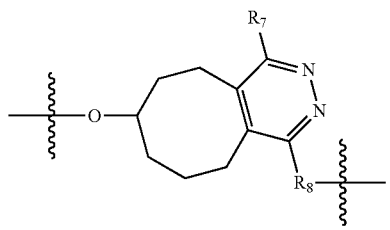
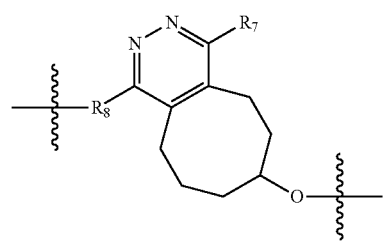
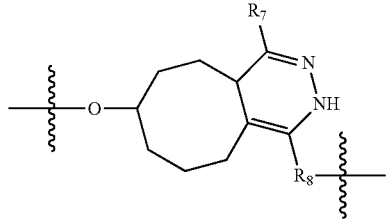
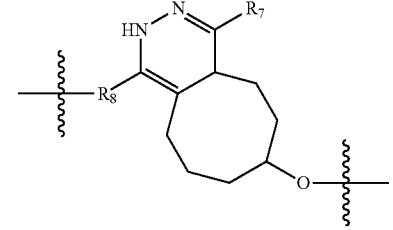
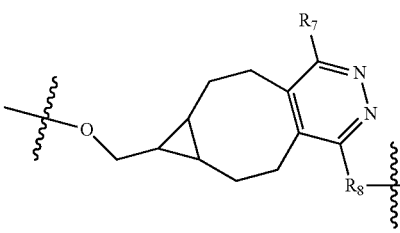

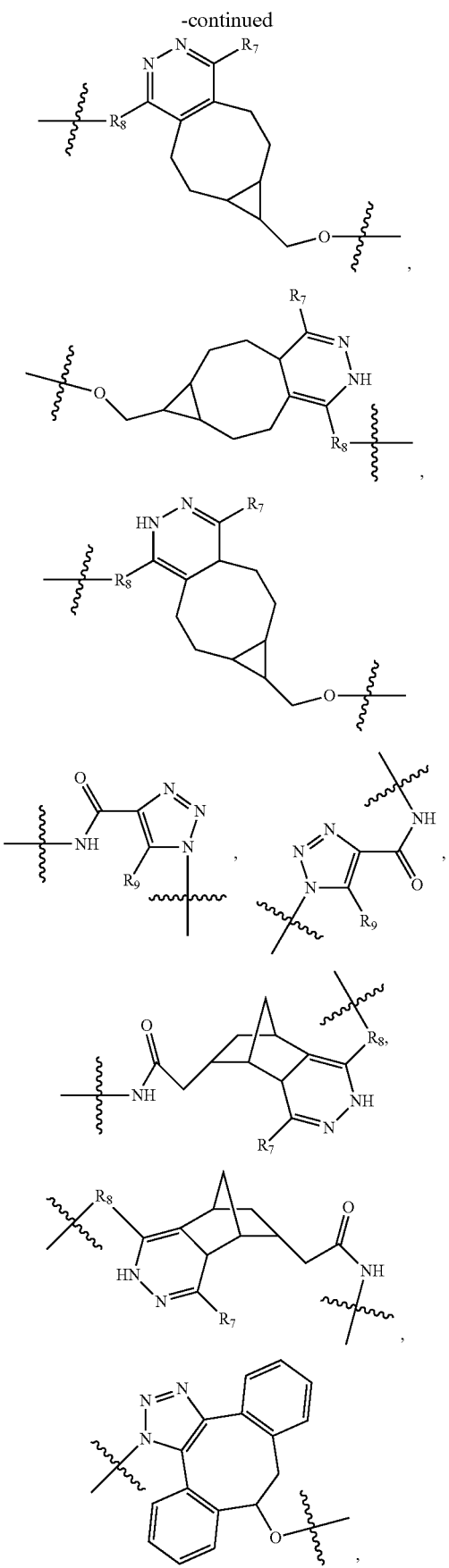

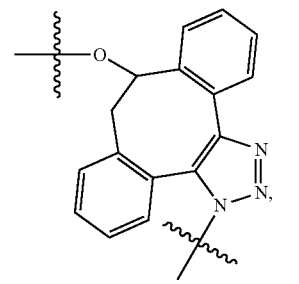

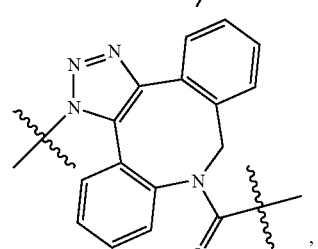

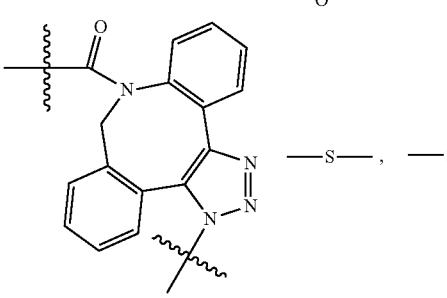

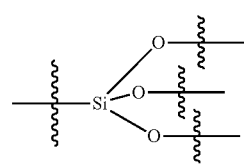

—CHR⁴(CH₂)ₙC(=O)NH—, —CHR⁴(CH₂)ₙNHC(=O)—, —C(=O)NH— and —NHC(=O)—;

each $R^4$ is independently selected from H, $C_{1-4}$alkyl, side chains of known amino acids, —C(=O)OH and —OH, each $R^5$ is independently selected from H, $C_{1-4}$alkyl, phenyl or $C_{1-4}$alkyl substituted with 1 to 3 —OH groups;

each $R^6$ is independently selected from H, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;

$R^7$ is independently selected from H, $C_{1-4}$alkyl, phenyl, pyrimidine and pyridine;

$R^8$ is independently selected from

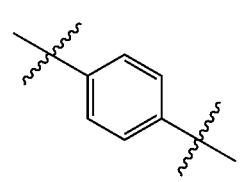

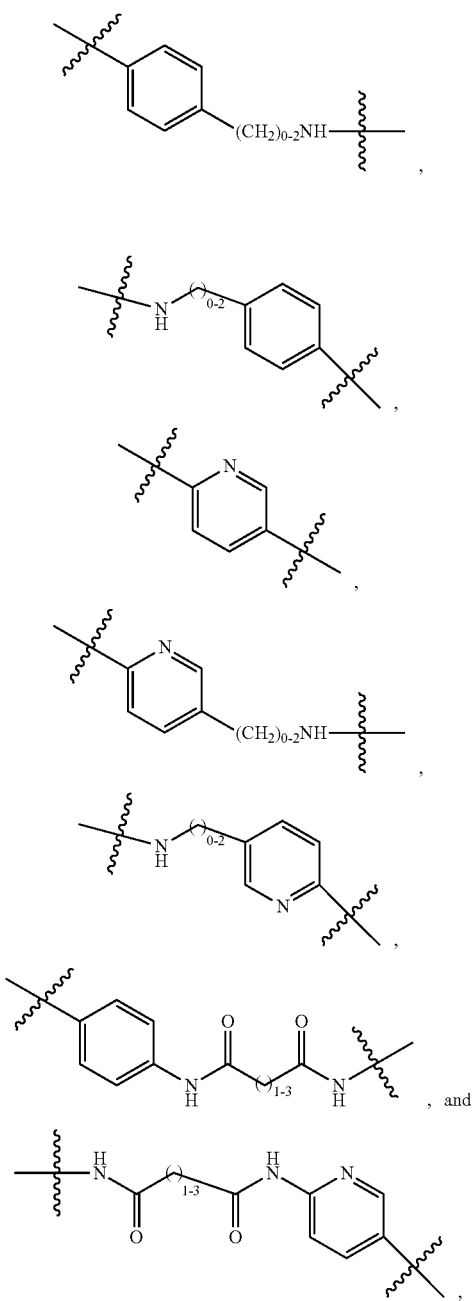

R[9] is independently selected from H and $C_{1-6}$haloalkyl;

each n is independently selected from 1, 2, 3, 4, 5, 6, 7, 8 and 9, and each m is independently selected from 1, 2, 3, 4, 5, 6, 7, 8 and 9.

In one embodiment, $L_1$ is —(CH$_2$)$_{1-10}$—C(=O)—, e.g., —(CH$_2$)$_5$—C(=O)—; and $L_2$, $L_3$ and $L_4$ each represent a bond.

In certain embodiments LU comprises a val-cit linker of this formula, wherein X represents a payload, typically a drug moiety such as one having anticancer activity:

When $L_4$-$L_5$-$L_6$ is a val-cit linker as shown above, $L_3$ is preferably —(CH$_2$)$_{2-6}$—C(=O)—.

In certain embodiments the X group is a maytansinoid such as DM1 or DM4, or a dolastatin analog or derivative such as dolastatin 10 or 15 and auristatins MMAF or MMAE, or a calicheamicin such as N-acetyl-γ-calicheamicin, or a label or dye such as rhodamine or tetramethylrhodamine.

As used herein, a "linker" is any chemical moiety that is capable of connecting an antibody or a fragment thereof to an X group (payload) to form an immunoconjugate. Linkers can be susceptible to cleavage, such as, acid-induced cleavage, light-induced cleavage, peptidase-induced cleavage, esterase-induced cleavage, and disulfide bond cleavage, at conditions under which the compound or the antibody remains active. Alternatively, linkers can be substantially resistant to cleavage. A linker may or may not include a self-immolative spacer.

Non-limiting examples of the non-enzymatically cleavable linkers as used herein to conjugate an X[1] group to the modified antibodies or antibody fragment thereof provided herein include, acid-labile linkers, linkers containing a disulfide moiety, linkers containing a triazole moiety, linkers containing a hydrazone moiety, linkers containing a thioether moiety, linkers containing a diazo moiety, linkers containing an oxime moiety, linkers containing an amide moiety and linkers containing an acetamide moiety.

Non-limiting examples of the enzymatically cleavable linkers as used herein to conjugate an X group to the modified antibodies or antibody fragment thereof provided herein include, but are not limited to, linkers that are cleaved by a protease, linkers that are cleaved by an amidase, and linkers that are cleaved by β-glucuronidase or another glycosidase.

In certain embodiments, such enzyme cleavable linkers are linkers which are cleaved by cathepsin, including cathepsin Z, cathepsin B, cathepsin H and cathepsin C. In certain embodiments the enzymatically cleavable linker is a dipeptide cleaved by cathepsin, including dipeptides cleaved by cathepsin Z, cathepsin B, cathepsin H or cathepsin C. In certain embodiments the enzymatically cleavable linker is a cathepsin B-cleavable peptide linker. In certain embodiments the enzymatically cleavable linker is a cathepsin B-cleavable dipeptide linker. In certain embodiments the enzymatically cleavable dipeptide linker is valine-citrulline or phenylalanine-lysine. Other non-limiting examples of the enzymatically cleavable linkers as used herein conjugate an X group to the modified antibodies or antibody fragment thereof provided herein include, but are not limited to, linkers which are cleaved by β-glucuronidase, e.g.,

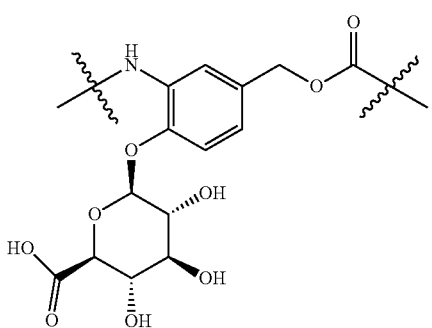 [SMILES: *Nc1cc(COC(*)=O)ccc1O[C@@H]1O[C@H](C(=O)O)[C@@H](O)[C@H](O)[C@H]1O]

See Ducry et al, Bioconjugate Chem, (2010) vol. 21(1), 5-13.

"Self-immolative spacers" are bifunctional chemical moieties covalently linked at one terminus to a first chemical moiety and at the other terminus to a second chemical moiety, thereby forming a stable tripartite molecule. A linker can comprise a self-immolative spacer bonded to a third chemical moiety that is cleavable from the spacer either chemically or enzymatically. Upon cleavage of a bond between the self-immolative spacer and the first chemical moiety or the third chemical moiety, self-immolative spacers undergo rapid and spontaneous intramolecular reactions and thereby separate from the second chemical moiety. These intramolecular reactions generally involve electronic rearrangements such as 1,4, or 1,6, or 1,8 elimination reactions or cyclizations to form highly favored five- or six-membered rings. In certain embodiments of the present invention, the first or third moiety is an enzyme cleavable group, and this cleavage results from an enzymatic reaction, while in other embodiments the first or third moiety is an acid labile group and this cleavage occurs due to a change in pH. As applied to the present invention, the second moiety is the "Payload" group as defined herein. In certain embodiments, cleavage of the first or third moiety from the self-immolative spacer results from cleavage by a proteolytic enzyme, while in other embodiments it results from cleaved by a hydrolase. In certain embodiments, cleavage of the first or third moiety from the self-immolative spacer results from cleavage by a cathepsin enzyme or a glucuronidase.

In certain embodiments, the enzyme cleavable linker is a peptide linker and the self-immolative spacer is covalently linked at one of its ends to the peptide linker and covalently linked at its other end to a drug moiety. This tripartite molecule is stable and pharmacologically inactive in the absence of an enzyme, but which is enzymatically cleavable by enzyme at a bond covalently linking the spacer moiety and the peptide moiety. The peptide moiety is cleaved from the tripartite molecule which initiates the self-immolating character of the spacer moiety, resulting in spontaneous cleavage of the bond covalently linking the spacer moiety to the drug moiety, to thereby effect release of the drug in pharmacologically active form.

In other embodiments, a linker comprises a self-immolative spacer that connects to the peptide, either directly or indirectly at one end, and to a payload at the other end; and the spacer is attached to a third moiety that can be cleaved from the spacer enzymatically, such as by a glucuronidase. Upon cleavage of the third moiety, the spacer degrades or rearranges in a way that causes the payload to be released. An example of a linker with this type of self-immolative spacer is this glucuronidase-cleavable linker, where hydrolysis of the acetal catalyzed by glucuronidase releases a phenolic compound that spontaneously decomposes under physiological conditions:

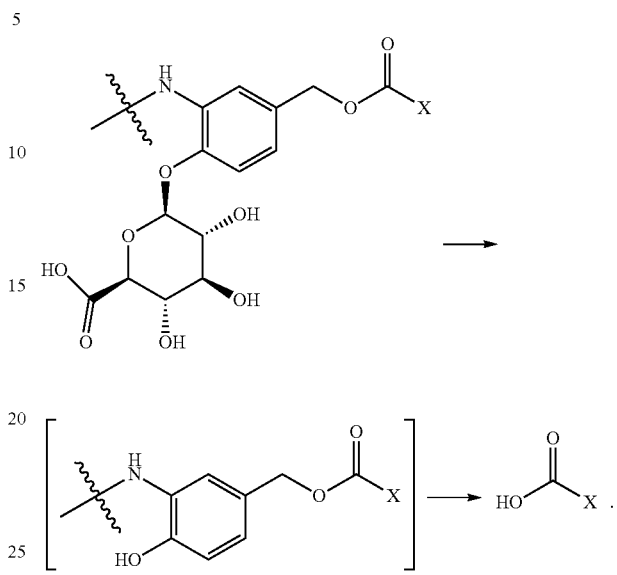

Non-limiting examples of the self-immolative spacer optionally used in the conjugation of an $X^1$ group to the modified antibodies or antibody fragment thereof provided herein include, but are not limited to, moieties which include a benzyl carbonyl moiety, a benzyl ether moiety, a 4-aminobutyrate moiety, a hemithioaminal moiety or a N-acyl-hemithioaminal moiety.

Other examples of self-immolative spacers include, but are not limited to, p-aminobenzyloxycarbonyl groups, aromatic compounds that are electronically similar to the p-aminobenzyloxycarbonyl group, such as 2-aminoimidazol-5-methanol derivatives and ortho or para-aminobenzylacetals. In certain embodiments, self-immolative spacers used herein which undergo cyclization upon amide bond hydrolysis, include substituted and unsubstituted 4-aminobutyric acid amides and 2-aminophenylpropionic acid amides.

In certain embodiments, the self-immolative spacer is

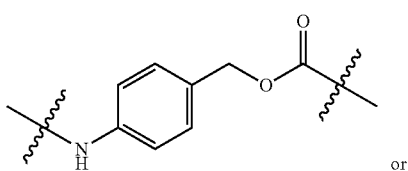

or

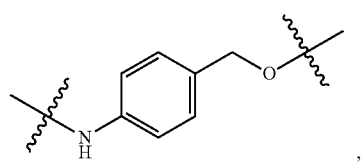

, while in other embodiments the self-immolative spacer is

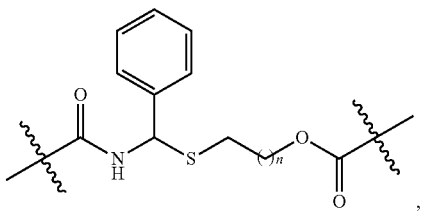

where n is 1 or 2. In other embodiments the self-immolative spacer is

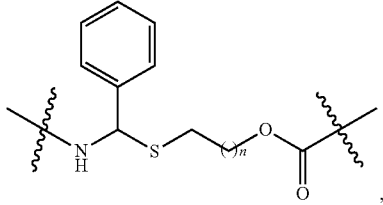

where n is 1 or 2. In other embodiments the self-immolative spacer is

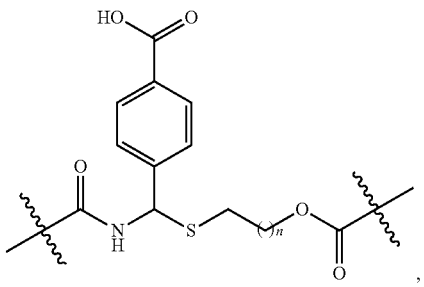

where n is 1 or 2. In other embodiments the self-immolative spacer is

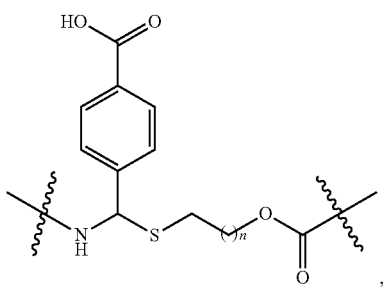

where n is 1 or 2. In other embodiments the self-immolative spacer is

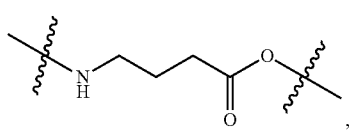

where n is 1 or 2.

Schemes (2a-2c) illustrate the post-translational modification of the modified antibodies or antibody fragment thereof provided herein wherein the Linker Unit (LU) is $-L_1-L_2-L_3-L_4-$, and L1 in each case is the group that reacts with the new Cys.

Scheme 2a.

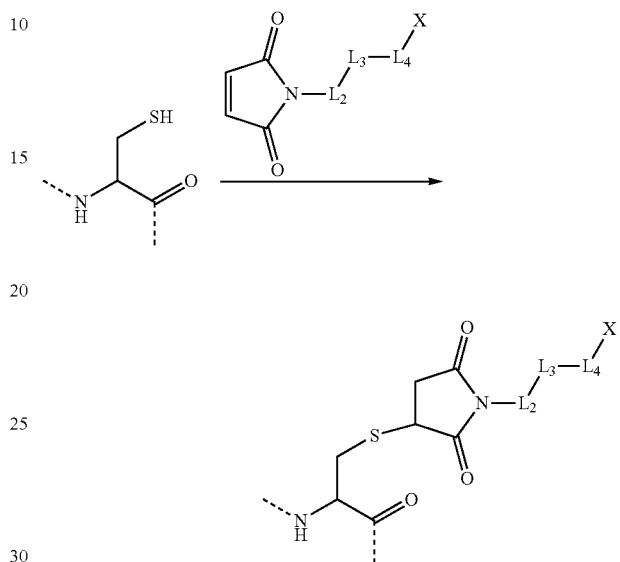

Scheme 2b.

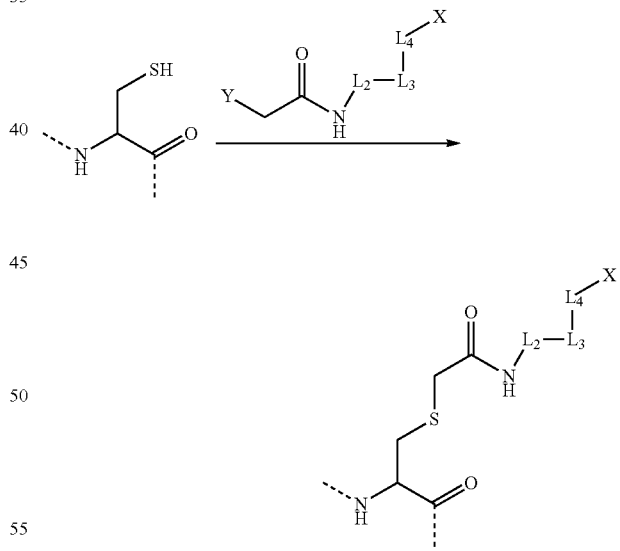

Scheme 3c.

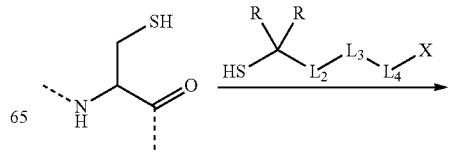

-continued

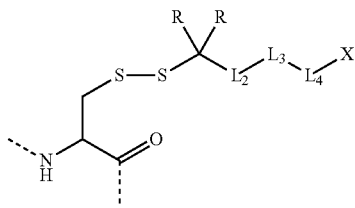

In each of Schemes 2ab 2c, the starting material is the replacement Cys residue in an antibody or antibody fragment modified as described herein, where the dashed bonds indicate connection to adjoining residues of the antibody or antibody fragment; each R is H or $C_{1-4}$alkyl, typically H or methyl; $L_2$, $L_3$ and $L_4$ are components of the linking unit LU, such as those described above; X is the payload; and the group connecting $L_2$ to the sulfur of the substitute Cys of the invention is $L_1$.

In some embodiments of the invention, X is a reactive functional group that can be used to connect the conjugated antibody to another chemical moiety, by interacting with a suitable complementary functional group. Table 4 depicts some examples of reactive functional groups that X can represent, along with a complementary functional group that can be used to connect a conjugate comprising X to another compound. Methods for using X to connect to the corresponding complementary functional group are well known in the art. Connections using azide are typically done using 'Click' or copper-free click chemistry; reactions involving hydrazines, alkoxyamines or acyl hydrazines typically proceed through the formation of a Schiff base with one of the carbonyl functional groups.

TABLE 4

| X | Complementary Reactive Functional Group for X |
|---|---|
| a thiol | a thiol, a maleimide, a haloacetamide, a vinyl sulfone, or a vinylpyridine |
| an azide | an alkene, alkyne, a phosphine-(thio)ester, a cyclooctyne, a cyclooctene or an oxanobornadiene |
| a phosphine-(thio)ester | an azide |
| an oxanobornadiene | an azide or a tetrazine |
| an alkyne | an azide or a tetrazine |
| an alkene | a tetrazine |
| a cyclooctyne | an azide or a tetrazine |
| a cyclooctene | a tetrazine |
| a norbornene | a tetrazine |
| a tetrazine | a norbornene, an alkene, alkyne, a cyclooctyne or an oxanobornadiene |
| an aldehyde | a hydroxylamine, a hydrazine or $NH_2$—NH—C(=O)— |
| a ketone | a hydroxylamine, a hydrazine or $NH_2$—NH—C(=O)— |
| a hydroxylamine | an aldehyde or a ketone |
| a hydrazine | an aldehyde or a ketone |
| $NH_2$—NH—C(=O)— | an aldehyde or a ketone |
| a haloacetamide | a thiol |
| a thiol | a thiol |
| a maleimide | a thiol |
| a vinyl sulfone | a thiol |
| a vinylpyridine | a thiol |

Exemplary products of the connections made using these components are depicted in Table 5, where $Y^1$ represents an antibody of the invention, $A_1$ represents a linking unit (LU) connecting the antibody to payload $X^a$, -$L_2$-$L_3$-$L_4$- in Formula II-a represents a linker unit that can be present in a molecule to be connected to the conjugated antibody via $X^a$, and $X^1$ represents a payload. Payload $X^a$ is a reactive functional group, and $X^b$ on Formula II-a is the corresponding complementary functional group, and Formula II-a itself represents a molecule to be connected to the conjugated antibody. The third column in Table 5 depicts a product from reaction of $X^a$ with $X^b$.

TABLE 5

| $Y^1$—$A_1$—$X^a$ | $X^b$—$L_2$—$L_3$—$L_4$—$X^1$ Formula (II-a) | $Y^1$—$A_1$—$X^2$—$L_2$—$L_3$—$L_4$—$X^1$ |
|---|---|---|
| $Y^1$—$A_1$—$N_3$ | HC≡C—$L_2$—$L_3$—$L_4$—$X^1$ | triazole with $Y^1$—$A_1$ on N, $L_2$—$L_3$—$L_4$—$X^1$ on C |
| $Y^1$—$A_1$—$N_3$ | HC≡C—$L_2$—$L_3$—$L_4$—$X^1$ | triazole (regioisomer) with $Y^1$—$A_1$ on N, $L_2$—$L_3$—$L_4$—$X^1$ on C |
| $Y^1$—$A_1$—C≡CH | $N_3$—$L_2$—$L_3$—$L_4$—$X^1$ | triazole with $Y^1$—$A_1$ on C, $L_2$—$L_3$—$L_4$—$X^1$ on N |
| $Y^1$—$A_1$—C≡CH | $N_3$—$L_2$—$L_3$—$L_4$—$X^1$ | triazole (regioisomer) with $Y^1$—$A_1$ on C, $L_2$—$L_3$—$L_4$—$X^1$ on N |

TABLE 5-continued

| $Y^1-A_1-X^a$ | $X^b-L_2-L_3-L_4-X^1$ Formula (II-a) | $Y^1-A_1-X^2-L_2-L_3-L_4-X^1$ |
|---|---|---|

(table content consists of chemical structure diagrams)

TABLE 5-continued

| $Y^1-A_1-X^a$ | $X^b-L_2-L_3-L_4-X^1$ Formula (II-a) | $Y^1-A_1-X^2-L_2-L_3-L_4-X^1$ |
|---|---|---|
| $Y^1-A_1$ with C=O (ketone) | $NH_2-NH-C(=O)-L_2-L_3-L_4-X^1$ | hydrazone product with $Y^1-A_1$ C=N-NH-C(=O)-$L_2-L_3-L_4-X^1$ |
| $Y^1-A_1$-CHO (aldehyde) | $NH_2-NH-C(=O)-L_2-L_3-L_4-X^1$ | hydrazone product with $Y^1-A_1$-CH=N-NH-C(=O)-$L_2-L_3-L_4-X^1$ |
| $Y^1-A_1-C(=O)-NHNH_2$ | $R_5C(=O)-L_2-L_3-L_4-X^1$ | $Y^1-A_1-C(=O)-NH-N=C(R_5)-L_2-L_3-L_4-X^1$ |
| $Y^1-A_1-C(=O)-NHNH_2$ | $HC(=O)-L_2-L_3-L_4-X^1$ | $Y^1-A_1-C(=O)-NH-N=CH-L_2-L_3-L_4-X^1$ |
| $Y^1-A_1-SH$ | $HS-L_2-L_3-L_4-X^1$ | $Y^1-A_1-S-S-L_2L_3L_4-X^1$ |
| $Y^1-A_1-N_3$ | cyclooctyne with $(R_6)_n$ and $L_2-L_3-L_4-X^1$ | triazole product |
| $Y^1-A_1$ with cyclooctyne $(R_6)_n$ | $N_3-L_2-L_3-L_4-X^1$ | triazole product |
| $Y^1-A_1-N_3$ | Staudinger reagent: $Ph_2P$-phenyl-C(=O)-OMe with $L_2-L_3-L_4-X^1$ | $Y^1-A_1-NH-C(=O)$-phenyl-$P(=O)Ph_2$ with $L_2-L_3-L_4-X^1$ |

TABLE 5-continued

| $Y^1-A_1-X^a$ | $X^b-L_2-L_3-L_4-X^1$<br>Formula (II-a) | $Y^1-A_1-X^2-L_2-L_3-L_4-X^1$ |
|---|---|---|

TABLE 5-continued

| $Y^1$—$A_1$—$X^a$ | $X^b$—$L_2$—$L_3$—$L_4$—$X^1$<br>Formula (II-a) | $Y^1$—$A_1$—$X^2$—$L_2$—$L_3$—$L_4$—$X^1$ |
|---|---|---|
| 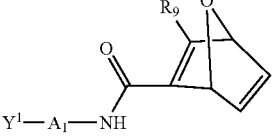 | $N_3$—$L_2$—$L_3$—$L_4$—$X^1$ | 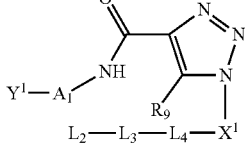 |
| $Y^1$—$A_1$—$N_3$ | 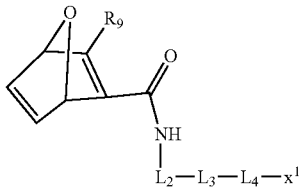 | 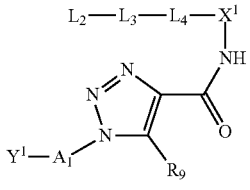 |
| 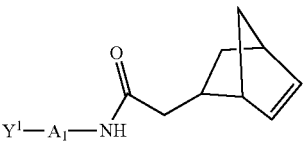 | 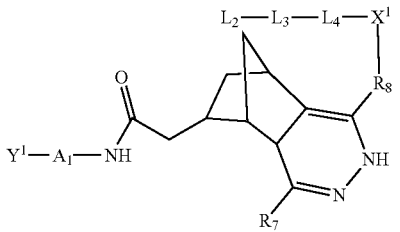 | 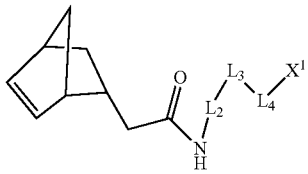 |
| 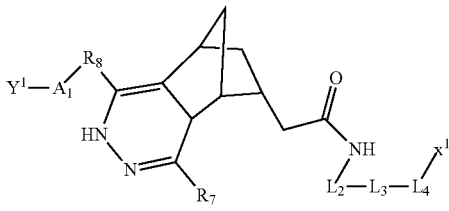 | 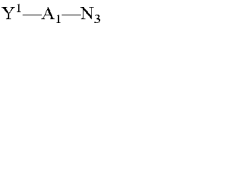 | 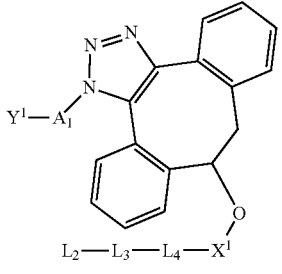 |
| $Y^1$—$A_1$—$N_3$ |  | 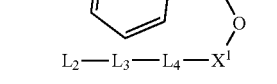 |
| 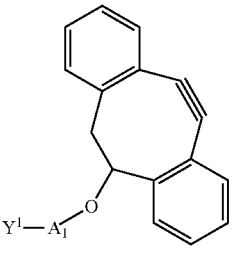 | $N_3$—$L_2$—$L_3$—$L_4$—$X^1$ | 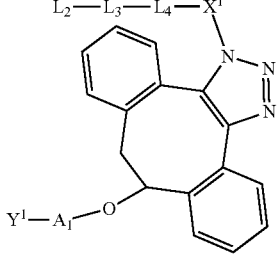 |

In certain embodiments, the modified antibody or antibody fragment thereof provided herein is conjugated with an "X group-to-antibody" (payload to antibody) ratio between about 1 and 16, such as 1-12, or 1, 2, 3, 4, 5, 6, 7, or 8, wherein the modified antibody or antibody fragment thereof contains 1, 2, 3, 4, 5, 6, 7, or 8 cysteine residues incorporated at the specific sites disclosed herein. For example, an "X group-to-antibody" ratio of 4 can be achieved by incorporating two Cys residues into the heavy chain of an antibody, which will contain 4 conjugation sites, two from each heavy chain. Immunoconjugates of such antibodies will contain up to 4 payload groups, which may be alike or different and are preferably all alike. In another example, an "X group-to-antibody" ratio of 4 can be achieved by incorporating one Cys residue into the heavy chain and a second Cys residue into the light chain of an antibody resulting in 4 conjugation sites, two in the two heavy chains and two in the two light chains. A ratio 6, 8 or higher can be achieved by combinations of 3, 4 or more cysteine substitutions of the invention in heavy and light chain of the antibody. Substituting multiple cysteine groups into an antibody can lead to inappropriate disulfide formation and other problems. Thus for loading more than 4 payload groups onto one antibody molecule, the methods of the invention can alternatively be combined with methods that do not rely upon reactions at cysteine sulfur, such as acylations at lysine, or conjugation via S6 tags or Pcl methodology.

While the payload to antibody ratio has an exact value for a specific conjugate molecule, it is understood that the value will often be an average value when used to describe a sample containing many molecules, due to some degree of inhomogeneity, typically in the conjugation step. The average loading for a sample of an immunoconjugate is referred to herein as the drug to antibody ratio, or DAR. In some embodiments, the DAR is between about 1 and about 16, and typically is about 1, 2, 3, 4, 5, 6, 7, or 8. In some embodiments, at least 50% of a sample by weight is compound having the average ratio plus or minus 2, and preferably at least 50% of the sample is a conjugate that contains the average ratio plus or minus 1. Preferred embodiments include immunoconjugates wherein the DAR is about 2 or about 8, e.g., about 2, about 4, about 6 or about 8. In some embodiments, a DAR of 'about n' means the measured value for DAR is within 10% of n (in Formula (I)).

3. Further Alteration of the Framework of Fc Region

The present invention provides site-specific labeled immunoconjugates. The immunoconjugates of the invention may comprise modified antibodies or antibody fragments thereof that further comprise modifications to framework residues within $V_H$ and/or $V_L$, e.g. to improve the properties of the antibody. Typically such framework modifications are made to decrease the immunogenicity of the antibody. For example, one approach is to "back-mutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "back-mutated" to the germline sequence by, for example, site-directed mutagenesis. Such "back-mutated" antibodies are also intended to be encompassed by the invention.

Another type of framework modification involves mutating one or more residues within the framework region, or even within one or more CDR regions, to remove T-cell epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In yet other embodiments, the Fe region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in, e.g., U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in, e.g., U.S. Pat. No. 6,194,551 by Idusogie et al.

In another embodiment, one or more amino acid residues are altered to thereby alter the ability of the antibody to fix complement. This approach is described in, e.g., the PCT Publication WO 94/29351 by Bodmer el al. In a specific embodiment, one or more amino acids of an antibody or antibody fragment thereof of the present invention are replaced by one or more allotypic amino acid residues, such as those shown in FIG. 4 for the IgG1 subclass and the kappa isotype. Allotypic amino acid residues also include, but are not limited to, the constant region of the heavy chain of the IgG1, IgG2, and IgG3 subclasses as well as the constant region of the light chain of the kappa isotype as described by Jefferis et al., MAbs. 1:332-338 (2009).

In yet another embodiment, the Fc region is modified to increase the ability of the antibody to mediate antibody dependent cellular cytotoxicity (ADCC) and/or to increase the affinity of the antibody for an Fey receptor by modifying one or more amino acids. This approach is described in, e.g., the PCT Publication WO 00/42072 by Presta. Moreover, the binding sites on human IgG1 for FcγRI, FcγRII, FcγRIII and FcRn have been mapped and variants with improved binding have been described (see Shields et al., J. Biol. Chem. 276:6591-6604, 2001).

In still another embodiment, the glycosylation of an antibody is modified. For example, an aglycosylated antibody can be made (i.e., the antibody lacks glycosylation). Glycosylation can be altered to, for example, increase the affinity of the antibody for "antigen." Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in, e.g., U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lecl3 cells, with reduced ability to attach fucose to Asn(297)-linked carbohydrates, also resulting in hypofucosylation of antibodies expressed in that host cell (see also Shields et al., (2002) J. Biol. Chem. 277: 26733-26740). PCT Publication WO 99/54342 by Umana et al. describes cell lines engineered to express glycoprotein-modifying glycosyl transferases (e.g., beta(1,4)-N acetylglucosaminyltransferase III (GnTIII)) such that antibodies expressed in the engineered cell lines exhibit increased bisecting GlcNac structures which results in increased ADCC activity of the antibodies (see also Umana et al., Nat. Biotech. 17:176-180, 1999).

In another embodiment, the antibody is modified to increase its biological half-life. Various approaches are possible. For example, one or more of the following mutations can be introduced: T252L, T254S, or T256F, as described in U.S. Pat. No. 6,277,375 to Ward. Alternatively, to increase the biological half-life, the antibody can be altered within the CH1 or $C_L$ region to contain a salvage receptor binding epitope taken from two loops of a CH2 domain of an Fc region of an IgG, as described in U.S. Pat. Nos. 5,869,046 and 6,121,022 by Presta et al.

4. Antibody Conjugates

The present invention provides site-specific labeling methods, modified antibodies and antibody fragments thereof, and immunoconjugates prepared accordingly. Using the methods of the invention, a modified antibody or antibody fragments thereof can be conjugated to a label, such as a drug moiety, e.g., an anti-cancer agent, an autoimmune treatment agent, an anti-inflammatory agent, an antifungal agent, an antibacterial agent, an anti-parasitic agent, an anti-viral agent, or an anesthetic agent, or an imaging reagent, such as a chelator for PET imaging, or a fluorescent label, or a MRI contrast reagent. An antibody or antibody fragments can also be conjugated using several identical or different labeling moieties combining the methods of the invention with other conjugation methods.

In certain embodiments, the immunoconjugates of the present invention comprise a drug moiety selected from a V-ATPase inhibitor, a HSP90 inhibitor, an IAP inhibitor, an mTor inhibitor, a microtubule stabilizer, a microtubule destabilizer, an auristatin, a dolastatin, a maytansinoid, a MetAP (methionine aminopeptidase), an inhibitor of nuclear export of proteins CRM1, a DPPIV inhibitor, proteasome inhibitors, an inhibitor of phosphoryl transfer reactions in mitochondria, a protein synthesis inhibitor, a kinase inhibitor, a CDK2 inhibitor, a CDK9 inhibitor, an HDAC inhibitor, a DNA damaging agent, a DNA alkylating agent, a DNA intercalator, a DNA minor groove binder, topoisomerase inhibitors, RNA synthesis inhibitors, kinesin inhibitors, inhibitors of protein-protein interactions, and a DHFR inhibitor.

Further, the modified antibodies or antibody fragments of the present invention may be conjugated to a drug moiety that modifies a given biological response. Drug moieties are not to be construed as limited to classical chemical therapeutic agents. For example, the drug moiety may be an immune modulator, such as an immune potentiator, a small molecule immune potentiator, a TLR agonist, a CpG oligomer, a TLR2 agonist, a TLR4 agonist, a TLR7 agonist, a TLR9 agonist, a TLR8 agonist, a T-cell epitope peptide or a like. The drug moiety may also be an oligonucleotide, a siRNA, a shRNA, a cDNA or a like. Alternatively, the drug moiety may be a protein, peptide, or polypeptide possessing a desired biological activity. Such proteins may include, for example, a toxin such as abrin, ricin A, pseudomonas exotoxin, cholera toxin, or diphtheria toxin, a protein such as tumor necrosis factor, α-interferon, β-interferon, nerve growth factor, platelet derived growth factor, tissue plasminogen activator, a cytokine, an apoptotic agent, an anti-angiogenic agent, or, a biological response modifier such as, for example, a lymphokine.

In one embodiment, the modified antibodies or antibody fragments of the present invention are conjugated to a drug moiety, such as a cytotoxin, a drug (e.g., an immunosuppressant) or a radiotoxin. Examples of cytotoxin include but not limited to, taxanes (see, e.g., International (PCT) Patent Application Nos. WO 01/38318 and PCT/US03/02675), DNA-alkylating agents (e.g., CC-1065 analogs), anthracyclines, tubulysin analogs, duocarmycin analogs, auristatin E, auristatin F, maytansinoids, and cytotoxic agents comprising a reactive polyethylene glycol moiety (see, e.g., Sasse el al., J. Antibiot. (Tokyo), 53, 879-85 (2000), Suzawa el al., Bioorg. Med. Chem., 8, 2175-84 (2000), Ichimura et al., J. Antibiot. (Tokyo), 44, 1045-53 (1991), Francisco et al., Blood (2003) (electronic publication prior to print publication), U.S. Pat. Nos. 5,475,092, 6,340,701, 6,372,738, and 6,436,931, U.S. Patent Application Publication No. 2001/0036923 A1, Pending U.S. patent application Ser. Nos. 10/024,290 and 10/116,053, and International (PCT) Patent Application No. WO 01/49698), taxol, cytochalasin B, gramicidin D, ethidium bromide, emetine, mitomycin, etoposide, tenoposide, colchicine, doxorubicin, daunorubicin, dihydroxy anthracin dione, mitoxantrone, mithramycin, actinomycin D, 1-dehydrotestosterone, glucocorticoids, and puromycin and analogs or homologs thereof. Therapeutic agents also include, for example, anti-metabolites (e.g., methotrexate, 6-mercaptopurine, 6-thioguanine, cytarabine, 5-fluorouracil decarbazine), ablating agents (e.g., mechlorethamine, thiotepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin, anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). (See e.g., Seattle Genetics US20090304721).

Other examples of therapeutic cytotoxins that can be conjugated to the modified antibodies or antibody fragments of the invention include duocarmycins, calicheamicins, maytansines and auristatins, and derivatives thereof. An example of a calicheamicin antibody conjugate is commercially available (Mylotarg™; Wyeth-Ayerst).

For further discussion of types of cytotoxins, linkers and methods for conjugating therapeutic agents to antibodies, see also Saito et al., (2003) Adv. Drug Deliv. Rev. 55:199-215; Trail et al., (2003) Cancer Immunol. Immunother. 52:328-337; Payne, (2003) Cancer Cell 3:207-212; Allen, (2002) Nat. Rev. Cancer 2:750-763; Pastan and Kreitman, (2002) Curr. Opin. Investig. Drugs 3:1089-1091; Senter and Springer, (2001) Adv. Drug Deliv. Rev. 53:247-264.

According to the present invention, modified antibodies or antibody fragments thereof can also be conjugated to a radioactive isotope to generate cytotoxic radiopharmaceuticals, referred to as radioimmunoconjugates. Examples of radioactive isotopes that can be conjugated to antibodies for use diagnostically or therapeutically include, but are not limited to, iodine$^{131}$, indium$^{111}$, yttrium$^{90}$, and lutetium$^{177}$. Methods for preparing radioimmunoconjugates are established in the art. Examples of radioimmunoconjugates are commercially available, including Zevalin™ (DEC Pharmaceuticals) and Bexxar™ (Corixa Pharmaceuticals), and similar methods can be used to prepare radioimmunoconjugates using the antibodies of the invention. In certain embodiments, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al., (1998) Clin. Cancer Res. 4(10):2483-90; Peterson et al., (1999) Bioconjug. Chem. 10(4):553-7; and Zimmerman el al., (1999) Nucl. Med. Biol. 26(8):943-50, each incorporated by reference in their entireties.

The present invention further provides modified antibodies or fragments thereof that specifically bind to an antigen. The modified antibodies or fragments may be conjugated or fused to a heterologous protein or polypeptide (or fragment thereof, preferably to a polypeptide of at least 10, at least 20, at least 30, at least 40, at least 50, at least 60, at least 70, at least 80, at least 90 or at least 100 amino acids) to generate fusion proteins. In particular, the invention provides fusion proteins comprising an antibody fragment described herein (e.g., a Fab fragment, Fd fragment, Fv fragment, F(ab)2 fragment, a $V_H$ domain, a $V_H$ CDR, a $V_L$ domain or a $V_L$ CDR) and a heterologous protein, polypeptide, or peptide.

In some embodiments, modified antibody fragments without antigen binding specificity, such as but not limited to, modified Fc domains with engineered cysteine residue(s) according to the present invention, are used to generate fusion proteins comprising such an antibody fragment (e.g., engineered Fc) and a heterologous protein, polypeptide, or peptide.

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of antibodies of the invention or fragments thereof (e.g., antibodies or fragments thereof with higher affinities and lower dissociation rates). See, generally, U.S. Pat. Nos. 5,605,793, 5,811,238, 5,830,721, 5,834,252, and 5,837,458; Patten et al., (1997) Curr. Opinion Biotechnol. 8:724-33; Harayama, (1998) Trends Biotechnol. 16(2):76-82; Hansson el al., (1999) J. Mol. Biol. 287:265-76; and Lorenzo and Blasco, (1998) Biotechniques 24(2):308-313 (each of these patents and publications are hereby incorporated by reference in its entirety). Antibodies or fragments thereof, or the encoded antibodies or fragments thereof, may be altered by being subjected to random mutagenesis by error-prone PCR, random nucleotide insertion or other methods prior to recombination. A polynucleotide encoding an antibody or fragment thereof that specifically binds to an antigen may be recombined with one or more components, motifs, sections, parts, domains, fragments, etc. of one or more heterologous molecules.

Moreover, the modified antibodies or antibody fragments thereof of the present invention can be conjugated to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., (1989) Proc. Natl. Acad. Sci. USA 86:821-824, for instance, hexa-histidine provides for convenient purification of the fusion protein. Other peptide tags useful for purification include, but are not limited to, the hemagglutinin ("HA") tag, which corresponds to an epitope derived from the influenza hemagglutinin protein (Wilson el al., (1984) Cell 37:767), and the "FLAG" tag (A. Einhauer et al., J. Biochem. Biophys. Methods 49: 455-465, 2001). According to the present invention, antibodies or antibody fragments can also be conjugated to tumor-penetrating peptides in order to enhance their efficacy.

In other embodiments, modified antibodies or antibody fragments of the present invention are conjugated to a diagnostic or detectable agent. Such immunoconjugates can be useful for monitoring or prognosing the onset, development, progression and/or severity of a disease or disorder as part of a clinical testing procedure, such as determining the efficacy of a particular therapy. Such diagnosis and detection can accomplished by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, Alexa Fluor 750, umbelliferone, fluorescein, fluorescein isothiocyanate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine ($^{131}$I, $^{125}$I, $^{123}$I, and $^{121}$I), carbon ($^{14}$C), sulfur ($^{35}$S), tritium ($^{3}$H), indium ($^{115}$In, $^{113}$In, $^{112}$In, and $^{111}$In), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, 47Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{64}$Cu, $^{113}$Sn, and $^{117}$Sn; and positron emitting metals using various positron emission tomographies, and non-radioactive paramagnetic metal ions.

Modified antibodies or antibody fragments of the invention may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

5. Pharmaceutical Composition

To prepare pharmaceutical or sterile compositions including immunoconjugates, the immunoconjugates of the invention are mixed with a pharmaceutically acceptable carrier or excipient. The compositions can additionally contain one or more other therapeutic agents that are suitable for treating or preventing cancer (breast cancer, colorectal cancer, lung cancer, multiple myeloma, ovarian cancer, liver cancer, gastric cancer, pancreatic cancer, acute myeloid leukemia, chronic myeloid leukemia, osteosarcoma, squamous cell carcinoma, peripheral nerve sheath tumors (e.g., schwannoma), head and neck cancer, bladder cancer, esophageal cancer, Barretts esophageal cancer, glioblastoma, clear cell sarcoma of soft tissue, malignant mesothelioma, neurofibromatosis, renal cancer, melanoma, prostate cancer, benign prostatic hyperplasia (BPH), gynacomastica, and endometriosis).

Formulations of therapeutic and diagnostic agents can be prepared by mixing with physiologically acceptable carriers, excipients, or stabilizers in the form of, e.g., lyophilized powders, slurries, aqueous solutions, lotions, or suspensions (see, e.g., Hardman et al., Goodman and Gilman's The Pharmacological Basis of Therapeutics, McGraw-Hill, New York, N.Y., 2001; Gennaro, Remington: The Science and Practice of Pharmacy, Lippincott, Williams, and Wilkins, New York, N.Y., 2000; Avis, et al. (eds.), Pharmaceutical Dosage Forms: Parenteral Medications, Marcel Dekker, N Y, 1993; Lieberman, el al. (eds.), Pharmaceutical Dosage Forms: Tablets, Marcel Dekker, N Y, 1990; Lieberman, et al. (eds.) Pharmaceutical Dosage Forms: Disperse Systems, Marcel Dekker, N Y, 1990; Weiner and Kotkoskie, Excipient Toxicity and Safety, Marcel Dekker, Inc., New York, N.Y., 2000).

Selecting an administration regimen for a therapeutic depends on several factors, including the serum or tissue turnover rate of the entity, the level of symptoms, the immunogenicity of the entity, and the accessibility of the target cells in the biological matrix. In certain embodiments, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules is available (see, e.g., Wawrzynczak, Antibody Therapy, Bios Scientific Pub. Ltd, Oxfordshire, U K, 1996; Kresina (ed.), Monoclonal Antibodies, Cytokines and Arthritis, Marcel Dekker, New York, N.Y., 1991; Bach (ed.), Monoclonal Antibodies and Peptide Therapy in Autoimmune Diseases, Marcel Dekker, New York, N.Y., 1993; Baert el al., New Engl. J. Med. 348:601-608, 2003; Milgrom el al., New Engl. J. Med. 341:1966-1973, 1999; Slamon et al., New Engl. J. Med. 344:783-792, 2001; Beniaminovitz et al., New Engl. J. Med. 342:613-619, 2000; Ghosh el al., New Engl. J. Med. 348:24-32, 2003; Lipsky el al., New Engl. J. Med. 343:1594-1602, 2000).

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors known in the medical arts.

Compositions comprising antibodies or fragments thereof of the invention can be provided by continuous infusion, or by doses at intervals of, e.g., one day, one week, or 1-7 times per week. Doses may be provided intravenously, subcutaneously, topically, orally, nasally, rectally, intramuscular, intracerebrally, or by inhalation. A specific dose protocol is one involving the maximal dose or dose frequency that avoids significant undesirable side effects.

For the immunoconjugates of the invention, the dosage administered to a patient may be 0.0001 mg/kg to 100 mg/kg of the patient's body weight. The dosage may be between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. The dosage of the antibodies or fragments thereof of the invention may be calculated using the patient's weight in kilograms (kg) multiplied by the dose to be administered in mg/kg.

Doses of the immunoconjugates the invention may be repeated and the administrations may be separated by at least 1 day, 2 days, 3 days, 5 days, 10 days, 15 days, 30 days, 45 days, 2 months, 75 days, 3 months, or at least 6 months. In a specific embodiment, does of the immunoconjugates of the invention are repeated every 3 weeks.

An effective amount for a particular patient may vary depending on factors such as the condition being treated, the overall health of the patient, the method route and dose of administration and the severity of side effects (see, e.g., Maynard et al., A Handbook of SOPs for Good Clinical Practice, Interpharm Press, Boca Raton, Fla., 1996; Dent, Good Laboratory and Good Clinical Practice, Urch Publ., London, U K, 2001).

The route of administration may be by, e.g., topical or cutaneous application, injection or infusion by intravenous, intraperitoneal, intracerebral, intramuscular, intraocular, intraarterial, intracerobrospinal, intralesional, or by sustained release systems or an implant (see, e.g., Sidman et al., Biopolymers 22:547-556, 1983; Langer et al., J. Biomed. Mater. Res. 15:167-277, 1981; Langer, Chem. Tech. 12:98-105, 1982; Epstein et al., Proc. Natl. Acad. Sci. USA 82:3688-3692, 1985; Hwang et al., Proc. Natl. Acad. Sci.

USA 77:4030-4034, 1980; U.S. Pat. Nos. 6,350,466 and 6,316,024). Where necessary, the composition may also include a solubilizing agent and a local anesthetic such as lidocaine to ease pain at the site of the injection. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety.

A composition of the present invention may also be administered via one or more routes of administration using one or more of a variety of methods known in the art. As will be appreciated by the skilled artisan, the route and/or mode of administration will vary depending upon the desired results. Selected routes of administration for the immunoconjugates of the invention include intravenous, intramuscular, intradermal, intraperitoneal, subcutaneous, spinal or other parenteral routes of administration, for example by injection or infusion. Parenteral administration may represent modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, a composition of the invention can be administered via a non-parenteral route, such as a topical, epidermal or mucosal route of administration, for example, intranasally, orally, vaginally, rectally, sublingually or topically. In one embodiment, the immunoconjugates of the invention is administered by infusion. In another embodiment, the immunoconjugates of the invention is administered subcutaneously.

If the immunoconjugates of the invention are administered in a controlled release or sustained release system, a pump may be used to achieve controlled or sustained release (see Langer, supra; Sefton, CRC Crit. Ref Biomed. Eng. 14:20, 1987; Buchwald et al., Surgery 88:507, 1980; Saudek et al., N. Engl. J. Med. 321:574, 1989). Polymeric materials can be used to achieve controlled or sustained release of the therapies of the invention (see e.g., Medical Applications of Controlled Release, Langer and Wise (eds.), CRC Pres., Boca Raton, Fla., 1974; Controlled Drug Bioavailability, Drug Product Design and Performance, Smolen and Ball (eds.), Wiley, New York, 1984; Ranger and Peppas, J. Macromol. Sci. Rev. Macromol. Chem. 23:61, 1983; see also Levy et al., Science 228:190, 1985; During el al., Ann. Neurol. 25:351, 1989; Howard et al., J. Neurosurg. 7 1:105, 1989; U.S. Pat. Nos. 5,679,377; 5,916,597; 5,912,015; 5,989,463; 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), poly anhydrides, poly(N-vinyl pyrrolidone), poly(vinyl alcohol), poly acrylamide, poly(ethylene glycol), polylactides (PLA), poly(lactide-co-glycolides) (PLGA), and polyorthoesters. In one embodiment, the polymer used in a sustained release formulation is inert, free of leachable impurities, stable on storage, sterile, and biodegradable. A controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138, 1984).

Controlled release systems are discussed in the review by Langer, Science 249:1527-1533, 1990). Any technique known to one of skill in the art can be used to produce sustained release formulations comprising one or more immunoconjugates of the invention. See, e.g., U.S. Pat. No. 4,526,938, PCT publication WO 91/05548, PCT publication WO 96/20698, Ning et al., Radiotherapy & Oncology 39:179-189, 1996; Song et al., PDA Journal of Pharmaceutical Science & Technology 50:372-397, 1995; Cleek et al., Pro. Int'l. Symp. Control. Rel. Bioact. Mater. 24:853-854, 1997; and Lam el al., Proc. Int'l. Symp. Control Rel. Bioact. Mater. 24:759-760, 1997, each of which is incorporated herein by reference in their entirety.

If the immunoconjugates of the invention are administered topically, they can be formulated in the form of an ointment, cream, transdermal patch, lotion, gel, shampoo, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity, in some instances, greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, in some instances, in combination with a solid or liquid inert carrier, is packaged in a mixture with a pressurized volatile (e.g., a gaseous propellant, such as Freon™) or in a squeeze bottle. Moisturizers or humectants can also be added to pharmaceutical compositions and dosage forms if desired. Examples of such additional ingredients are well-known in the art.

If the compositions comprising the immunoconjugates are administered intranasally, it can be formulated in an aerosol form, spray, mist or in the form of drops. In particular, prophylactic or therapeutic agents for use according to the present invention can be conveniently delivered in the form of an aerosol spray presentation from pressurized packs or a nebulizer, with a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

Methods for co-administration or treatment with a second therapeutic agent, e.g., a cytokine, steroid, chemotherapeutic agent, antibiotic, or radiation, are known in the art (see, e.g., Hardman et al., (eds.) (2001) Goodman and Gilman's The Pharmacological Basis of Therapeutics, 10.sup.th ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.). An effective amount of therapeutic may decrease the symptoms by at least 10%; by at least 20%; at least about 30%; at least 40%, or at least 50%.

Additional therapies (e.g., prophylactic or therapeutic agents), which can be administered in combination with the immunoconjugates of the invention may be administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart from the immunoconjugates of the invention. The two or more therapies may be administered within one same patient visit.

In certain embodiments, the immunoconjugates of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., Ranade, (1989) J. Clin. Pharmacol. 29:685). Exemplary targeting moieties include folate or biotin (see, e.g., U.S. Pat. No. 5,416,016 to Low et al.); mannosides (Umezawa el al., (1988) Biochem. Biophys. Res. Commun. 153:1038); antibodies (Bloeman et al., (1995) FEBS Lett. 357:140; Owais el al., (1995) Antimicrob. Agents Chemother. 39:180); surfactant protein A receptor (Briscoe et al., (1995) Am. J. Physiol. 1233:134); p 120 (Schreier et al, (1994) J. Biol. Chem. 269:9090); see also K. Keinanen; M. L. Laukkanen (1994) FEBS Lett. 346:123; J. J. Killion; I. J. Fidler (1994) Immunomethods 4:273.

The invention provides protocols for the administration of pharmaceutical composition comprising immunoconjugates of the invention alone or in combination with other therapies to a subject in need thereof. The therapies (e.g., prophylactic or therapeutic agents) of the combination therapies of the present invention can be administered concomitantly or sequentially to a subject. The therapy (e.g., prophylactic or therapeutic agents) of the combination therapies of the present invention can also be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time and repeating this sequential administration, i.e., the cycle, in order to reduce the development of resistance to one of the therapies (e.g., agents) to avoid or reduce the side effects of one of the therapies (e.g., agents), and/or to improve, the efficacy of the therapies.

The therapies (e.g., prophylactic or therapeutic agents) of the combination therapies of the invention can be administered to a subject concurrently.

The term "concurrently" is not limited to the administration of therapies (e.g., prophylactic or therapeutic agents) at exactly the same time, but rather it is meant that a pharmaceutical composition comprising antibodies or fragments thereof the invention are administered to a subject in a sequence and within a time interval such that the antibodies of the invention can act together with the other therapy or therapies to provide an increased benefit than if they were administered otherwise. For example, each therapy may be administered to a subject at the same time or sequentially in any order at different points in time; however, if not administered at the same time, they should be administered sufficiently close in time so as to provide the desired therapeutic or prophylactic effect. Each therapy can be administered to a subject separately, in any appropriate form and by any suitable route. In various embodiments, the therapies (e.g., prophylactic or therapeutic agents) are administered to a subject less than 15 minutes, less than 30 minutes, less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, 24 hours apart, 48 hours apart, 72 hours apart, or 1 week apart. In other embodiments, two or more therapies (e.g., prophylactic or therapeutic agents) are administered to a within the same patient visit.

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

The invention having been fully described, it is further illustrated by the following examples and claims, which are illustrative and are not meant to be further limiting.

EXAMPLES

Figure 1B:
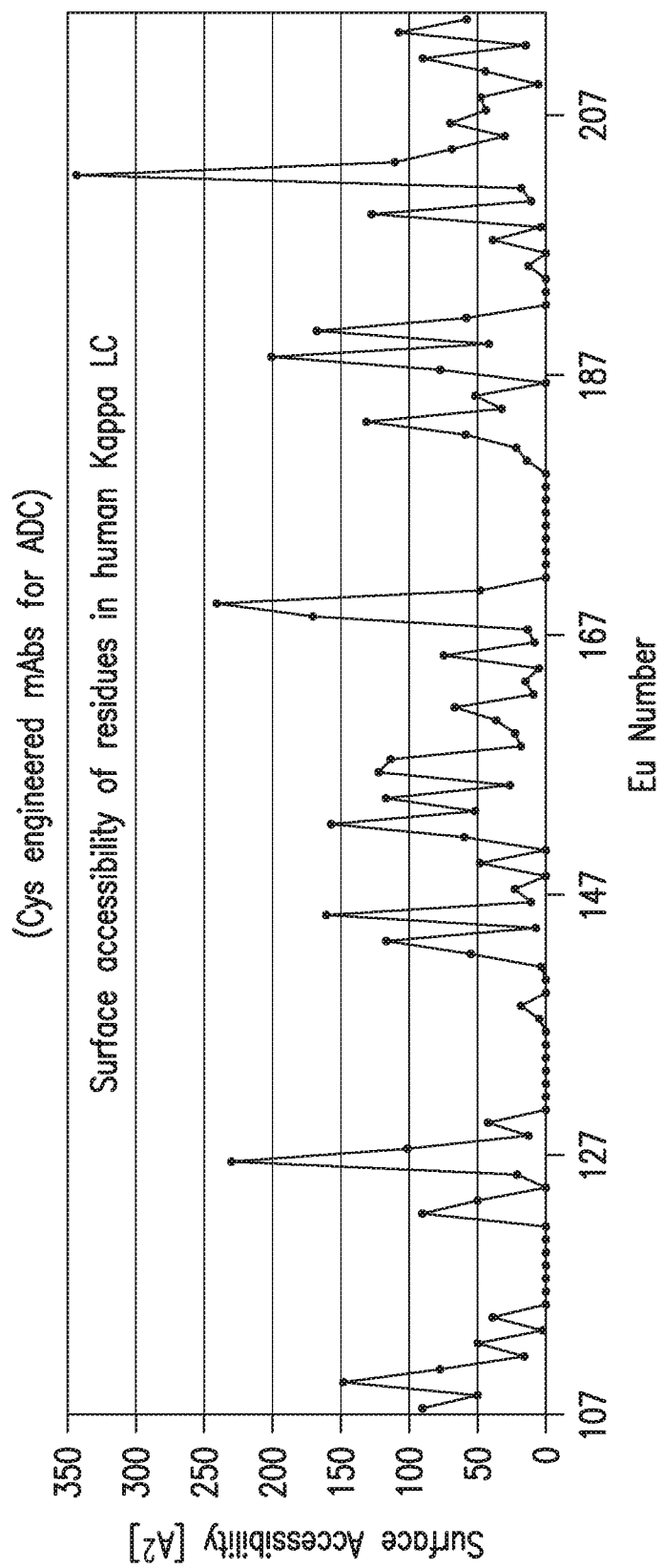

Example 1. Selection of Surface Accessible Sites for Cys Mutation in Human IgG1 Heavy Chain and Kappa Light Chain Surface exposed residues in the constant region of human IgG1 heavy and human kappa light chains were identified in a crystal structure of an hIgG1/kappa antibody (Protein Databank structure entry 1HZH.pdb, Table 6, Table 7. FIG. 1) using the computer program Surface Racer 5.0, as described by Tsodikov et al, "A novel computer program for fast exact calculation of accessible and molecular surface areas and average surface curvature," *J. Comput. Chem.*, 23, 600-609 (2002). 88 residues were selected for Cys substitution, 59 sites in hIgG heavy chain and 29 in human kappa light chain, based on the following criteria: 1) select residues in CH1, CH2 and CH3 domains of the constant regions of heavy chain and the constant regions of light chain; 2) select surface exposed residues but circumvent globally exposed residues and the C-terminal region to avoid inter-antibody dimer formation; 3) focus on polar or charged residues such as Ser, Thr, Lys, Arg, Glu, and Asp; and 4) exclude residues in FcRn binding domain, Protein A binding domain, and heavy chain hinge region.

Criterion 1) namely the selection of Cys substitution sites in the constant region of the antibody, assures transferability of the conjugation sites to many different antibodies. Criterion 2) is based on observation of inter-antibody dimer formation for Cys substitutions of prominently exposed residues (residues excluded based on this criteria are listed in Table 6). Based on the IgG crystal structure, the putative orientation of the Cys side chain was taking into consideration: residues for which the Cys side chain may be partially shielded from interactions with another antibody but may still be reactive with a small molecular payload, were favored over residues with larger surface accessibility but with an orientation that may enable interactions with a large macromolecule such as dimer formation. Criterion 3) was implemented to favor conservative mutations in order to minimize destabilizing effects of the mutations on the antibody. Similarly, criterion 4) was used to avoid functional changes to the antibody such as effects on FcRn and Protein A binding which may affect the antibody's pharmacokinetic properties or may result in the loss of a purification handle, respectively. Residues excluded based on criterion 4 are listed in Table 6. The location of the 88 selected mutation sites in the structure model of hIgG1/kappa indicates that the selected sites are surface accessible (FIG. 2).

TABLE 6

Surface accessibility of amino acid residues in human IgG1 heavy chain. Surface accessibility was calculated using Surface Racer 5.0 and is expressed as Angstrom square [Å$^2$]. "Excluded sites" indicate the sites that are excluded from selection due to the reasons mentioned in example 1. "Selected sites" are the sites that are selected for substitution to Cys in the invention.

| Eu number | Residue | Surface accessibility [Å$^2$] | Reason for exclusion (if applicable) | Selected sites |
|---|---|---|---|---|
| 117 | SER | 128 | | HC-S117C |
| 118 | ALA | 2 | | |
| 119 | SER | 79 | | HC-S119C |
| 120 | THR | 71 | | |
| 121 | LYS | 136 | | HC-K121C |
| 122 | GLY | 21 | | |
| 123 | PRO | 2 | | |
| 124 | SER | 40 | | HC-S124C |
| 125 | VAL | 0 | | |
| 126 | PHE | 1 | | |
| 127 | PRO | 0 | | |
| 128 | LEU | 0 | | |
| 129 | ALA | 0 | | |
| 130 | PRO | 0 | | |
| 131 | SER | 0 | | |
| 132 | SER | 34 | | HC-S132C |
| 133 | LYS | 87 | | |
| 134 | SER | 123 | | HC-S134C |
| 135 | THR | 1 | | |
| 136 | SER | 183 | | HC-S136C |
| 137 | GLY | 84 | | |
| 138 | GLY | 40 | | |
| 139 | THR | 33 | | HC-T139C |
| 140 | ALA | 0 | | |
| 141 | ALA | 0 | | |
| 142 | LEU | 0 | | |
| 143 | GLY | 0 | | |
| 144 | CYS | 0 | | |
| 145 | LEU | 0 | | |
| 146 | VAL | 0 | | |
| 147 | LYS | 0 | | |
| 148 | ASP | 1 | | |
| 149 | TYR | 0 | | |
| 150 | PHE | 0 | | |
| 151 | PRO | 0 | | |
| 152 | GLU | 52 | | HC-E152C |
| 153 | PRO | 89 | | HC-P153C |
| 154 | VAL | 10 | | |
| 155 | THR | 69 | | HC-T155C |
| 156 | VAL | 0 | | |
| 157 | SER | 39 | | HC-S157C |

TABLE 6-continued

Surface accessibility of amino acid residues in human IgG1 heavy chain. Surface accessibility was calculated using Surface Racer 5.0 and is expressed as Angstrom square [Å$^2$]. "Excluded sites" indicate the sites that are excluded from selection due to the reasons mentioned in example 1. "Selected sites" are the sites that are selected for substitution to Cys in the invention.

| Eu number | Residue | Surface accessibility [Å$^2$] | Reason for exclusion (if applicable) | Selected sites |
|---|---|---|---|---|
| 158 | TRP | 0 | | |
| 159 | ASN | 4 | | |
| 160 | SER | 164 | Dimer | |
| 161 | GLY | 35 | Dimer | |
| 162 | ALA | 115 | Dimer | |
| 163 | LEU | 17 | | |
| 164 | THR | 125 | | HC-T164C |
| 165 | SER | 183 | | HC-S165C |
| 166 | GLY | 20 | | |
| 167 | VAL | 12 | | |
| 168 | HIS | 5 | | |
| 169 | THR | 60 | | HC-T169C |
| 170 | PHE | 0 | | |
| 171 | PRO | 33 | | HC-P171C |
| 172 | ALA | 9 | | |
| 173 | VAL | 0 | | |
| 174 | LEU | 68 | | HC-L174C |
| 175 | GLN | 0 | | |
| 176 | SER | 162 | | HC-S176C |
| 177 | SER | 68 | | HC-S177C |
| 178 | GLY | 8 | | |
| 179 | LEU | 0 | | |
| 180 | TYR | 6 | | |
| 181 | SER | 0 | | |
| 182 | LEU | 2 | | |
| 183 | SER | 0 | | |
| 184 | SER | 0 | | |
| 185 | VAL | 0 | | |
| 186 | VAL | 0 | | |
| 187 | THR | 30 | | |
| 188 | VAL | 0 | | |
| 189 | PRO | 86 | | HC-P189C |
| 190 | SER | 21 | | |
| 191 | SER | 127 | | HC-S191C |
| 192 | SER | 17 | | |
| 193 | LEU | 0 | | |
| 194 | GLY | 18 | | |
| 195 | THR | 111 | | HC-T195C |
| 196 | GLN | 79 | | |
| 197 | THR | 90 | | HC-T197C |
| 198 | TYR | 0 | | |
| 199 | ILE | 25 | | |
| 200 | CYS | 0 | | |
| 201 | ASN | 8 | | |
| 202 | VAL | 0 | | |
| 203 | ASN | 22 | | |
| 204 | HIS | 0 | | |
| 205 | LYS | 217 | | HC-K205C |
| 206 | PRO | 66 | | |
| 207 | SER | 50 | | HC-S207C |
| 208 | ASN | 91 | | |
| 209 | THR | 24 | | |
| 210 | LYS | 234 | Dimer | |
| 211 | VAL | 30 | | |
| 212 | ASP | 97 | | HC-D212C |
| 213 | LYS | 70 | | |
| 214 | LYS | 146 | | |
| 215 | ALA | 0 | | |
| 216 | GLU | 79 | | |
| 217 | PRO | 0 | | |
| 218 | LYS | 4 | | |
| 219 | SER | 149 | | |
| 220 | CYS | 7 | | |
| 221 | ASP | 0 | Hinge | |
| 222 | LYS | 208 | Hinge | |
| 223 | THR | 112 | Hinge | |
| 224 | HIS | 1 | Hinge | |
| 225 | THR | 22 | Hinge | |
| 226 | CYS | 12 | Hinge | |

TABLE 6-continued

Surface accessibility of amino acid residues in human IgG1 heavy chain. Surface accessibility was calculated using Surface Racer 5.0 and is expressed as Angstrom square [Å²]. "Excluded sites" indicate the sites that are excluded from selection due to the reasons mentioned in example 1. "Selected sites" are the sites that are selected for substitution to Cys in the invention.

| Eu number | Residue | Surface accessibility [Å²] | Reason for exclusion (if applicable) | Selected sites |
|---|---|---|---|---|
| 227 | PRO | 22 | Hinge | |
| 228 | PRO | 133 | Hinge | |
| 229 | CYS | 7 | Hinge | |
| 230 | PRO | 84 | Hinge | |
| 231 | ALA | 114 | Hinge | |
| 232 | PRO | 49 | Hinge | |
| 233 | GLU | 114 | Hinge | |
| 234 | LEU | 90 | | |
| 235 | LEU | 88 | | |
| 236 | GLY | 9 | | |
| 237 | GLY | 46 | | |
| 238 | PRO | 14 | | |
| 239 | SER | 9 | | |
| 240 | VAL | 0 | | |
| 241 | PHE | 0 | | |
| 242 | LEU | 0 | | |
| 243 | PHE | 1 | | |
| 244 | PRO | 34 | | |
| 245 | PRO | 0 | | |
| 246 | LYS | 55 | | HC-K246C |
| 247 | PRO | 18 | | |
| 248 | LYS | 47 | | |
| 249 | ASP | 1 | | |
| 250 | THR | 0 | FcRn binding | |
| 251 | LEU | 0 | | |
| 252 | MET | 53 | Protein A, FcRn binding | |
| 253 | ILE | 155 | Protein A binding | |
| 254 | SER | 157 | Protein A, FcRn binding | |
| 255 | ARG | 103 | | |
| 256 | THR | 86 | FcRn binding | |
| 257 | PRO | 0 | FcRn binding | |
| 258 | GLU | 42 | | HC-E258C |
| 259 | VAL | 0 | FcRn binding | |
| 260 | THR | 0 | | |
| 261 | CYS | 0 | | |
| 262 | VAL | 0 | | |
| 263 | VAL | 0 | | |
| 264 | VAL | 0 | | |
| 265 | ASP | 11 | FcRn binding | |
| 266 | VAL | 0 | | |
| 267 | SER | 10 | | |
| 268 | HIS | 79 | | |
| 269 | GLU | 189 | | HC-E269C |
| 270 | ASP | 23 | | |
| 271 | PRO | 20 | | |
| 272 | GLU | 152 | | |
| 273 | VAL | 19 | | |
| 274 | LYS | 138 | | HC-K274C |
| 275 | PHE | 2 | | |
| 276 | ASN | 1 | | |
| 277 | TRP | 0 | | |
| 278 | TYR | 14 | | |
| 279 | VAL | 0 | | |
| 280 | ASP | 66 | | |
| 281 | GLY | 72 | | |
| 282 | VAL | 141 | | |
| 283 | GLU | 80 | | |
| 284 | VAL | 25 | | |
| 285 | HIS | 133 | | |
| 286 | ASN | 119 | | HC-N286C |
| 287 | ALA | 67 | | |
| 288 | LYS | 182 | | HC-K288C |
| 289 | THR | 5 | | |
| 290 | LYS | 177 | | HC-K290C |
| 291 | PRO | 51 | | |
| 292 | ARG | 252 | | HC-R292C |
| 293 | GLU | 83 | | HC-E293C |
| 294 | GLU | 73 | | HC-E294C |
| 295 | GLN | 170 | | |
| 296 | TYR | 29 | | |
| 297 | ASN | 61 | Glycosylation | |
| 298 | SER | 125 | Glycosylation | |
| 299 | THR | 2 | Glycosylation | |
| 300 | TYR | 28 | | |
| 301 | ARG | 18 | | |
| 302 | VAL | 0 | | |
| 303 | VAL | 10 | | |
| 304 | SER | 0 | | |
| 305 | VAL | 17 | | |
| 306 | LEU | 0 | | |
| 307 | THR | 27 | FcRn binding | |
| 308 | VAL | 0 | FcRn binding | |
| 309 | LEU | 122 | | |
| 310 | HIS | 4 | Protein A binding | |
| 311 | GLN | 145 | Protein A, FcRn binding | |
| 312 | ASP | 14 | | |
| 313 | TRP | 0 | | |
| 314 | LEU | 6 | Protein A binding | |
| 315 | ASN | 151 | Protein A binding | |
| 316 | GLY | 12 | | |
| 317 | LYS | 81 | | |
| 318 | GLU | 49 | | |
| 319 | TYR | 0 | | |
| 320 | LYS | 55 | | HC-K320C |
| 321 | CYS | 0 | | |
| 322 | LYS | 78 | | HC-K322C |
| 323 | VAL | 0 | | |
| 324 | SER | 0 | | |
| 325 | ASN | 0 | | |
| 326 | LYS | 213 | | HC-K326C |
| 327 | ALA | 10 | | |
| 328 | LEU | 9 | | |
| 329 | PRO | 158 | | |
| 330 | ALA | 96 | | HC-A330C |
| 331 | PRO | 44 | | |
| 332 | ILE | 32 | | |
| 333 | GLU | 85 | | HC-E333C |
| 334 | LYS | 50 | | HC-K334C |
| 335 | THR | 70 | | HC-T335C |
| 336 | ILE | 13 | | |
| 337 | SER | 15 | | HC-S337C |
| 338 | LYS | 0 | | |
| 339 | ALA | 37 | | |
| 340 | LYS | 217 | Protein A binding | |
| 341 | GLY | 37 | | |
| 342 | GLN | 235 | | |
| 343 | PRO | 42 | | |
| 344 | ARG | 98 | | HC-R344C |
| 345 | GLU | 105 | | |
| 346 | PRO | 0 | | |
| 347 | GLN | 24 | | |
| 348 | VAL | 3 | | |
| 349 | TYR | 3 | | |
| 350 | THR | 0 | | |
| 351 | LEU | 0 | | |
| 352 | PRO | 38 | | |
| 353 | PRO | 0 | | |
| 354 | SER | 0 | | |
| 355 | ARG | 249 | | HC-R355C |
| 356 | ASP | 53 | | |

TABLE 6-continued

Surface accessibility of amino acid residues in human IgG1 heavy chain. Surface accessibility was calculated using Surface Racer 5.0 and is expressed as Angstrom square [Å²]. "Excluded sites" indicate the sites that are excluded from selection due to the reasons mentioned in example 1. "Selected sites" are the sites that are selected for substitution to Cys in the invention.

| Eu number | Residue | Surface accessibility [Å²] | Reason for exclusion (if applicable) | Selected sites |
|---|---|---|---|---|
| 357 | GLU | 0 | | |
| 358 | LEU | 36 | | |
| 359 | THR | 144 | Dimer | |
| 360 | LYS | 114 | | HC-K360C |
| 361 | ASN | 155 | | |
| 362 | GLN | 41 | | HC-Q362C |
| 363 | VAL | 0 | | |
| 364 | SER | 0 | | |
| 365 | LEU | 0 | | |
| 366 | THR | 0 | | |
| 367 | CYS | 0 | | |
| 368 | LEU | 0 | | |
| 369 | VAL | 0 | | |
| 370 | LYS | 1 | | |
| 371 | GLY | 0 | | |
| 372 | PHE | 0 | | |
| 373 | TYR | 23 | | |
| 374 | PRO | 0 | | |
| 375 | SER | 29 | | HC-S375C |
| 376 | ASP | 9 | | |
| 377 | ILE | 11 | | |
| 378 | ALA | 11 | | |
| 379 | VAL | 4 | | |
| 380 | GLU | 18 | FcRn binding | |
| 381 | TRP | 0 | | |
| 382 | GLU | 22 | | HC-E382C |
| 383 | SER | 1 | | |
| 384 | ASN | 147 | | |
| 385 | GLY | 102 | Dimer | |
| 386 | GLN | 161 | | |
| 387 | PRO | 99 | | |
| 388 | GLU | 4 | | |
| 389 | ASN | 189 | | HC-N389C |
| 390 | ASN | 36 | | HC-N390C |
| 391 | TYR | 44 | | |
| 392 | LYS | 82 | | HC-K392C |
| 393 | THR | 36 | | HC-T393C |
| 394 | THR | 0 | | |
| 395 | PRO | 72 | | |
| 396 | PRO | 47 | | |
| 397 | VAL | 9 | | |
| 398 | LEU | 111 | | HC-L398C |
| 399 | ASP | 0 | | |
| 400 | SER | 81 | | HC-S400C |
| 401 | ASP | 68 | | |
| 402 | GLY | 29 | | |
| 403 | SER | 0 | | |
| 404 | PHE | 22 | | |
| 405 | PHE | 0 | | |
| 406 | LEU | 0 | | |
| 407 | TYR | 0 | | |
| 408 | SER | 0 | | |
| 409 | LYS | 0 | | |
| 410 | LEU | 0 | | |
| 411 | THR | 0 | | |
| 412 | VAL | 0 | | |
| 413 | ASP | 80 | | HC-D413C |
| 414 | LYS | 83 | | |
| 415 | SER | 69 | | HC-S415C |
| 416 | ARG | 53 | | |
| 417 | TRP | 0 | | |
| 418 | GLN | 108 | | |
| 419 | GLN | 177 | | |
| 420 | GLY | 39 | | |
| 421 | ASN | 35 | | |
| 422 | VAL | 81 | | HC-V422C |
| 423 | PHE | 0 | | |
| 424 | SER | 2 | | |
| 425 | CYS | 0 | | |
| 426 | SER | 0 | | |
| 427 | VAL | 0 | | |
| 428 | MET | 0 | FcRn binding | |
| 429 | HIS | 0 | | |
| 430 | GLU | 14 | | |
| 431 | ALA | 22 | | |
| 432 | LEU | 1 | | |
| 433 | HIS | 227 | Protein A binding | |
| 434 | ASN | 126 | Protein A, FcRn binding | |
| 435 | HIS | 28 | | |
| 436 | TYR | 54 | | |
| 437 | THR | 36 | | |
| 438 | GLN | 82 | | |
| 439 | LYS | 12 | | |
| 440 | SER | 62 | | |
| 441 | LEU | 2 | | |
| 442 | SER | 34 | | |
| 443 | LEU | 101 | | |
| 444 | SER | 70 | Dimer | |

TABLE 7

Surface accessibility of amino acid residues in human kappa light chain. Surface accessibility was calculated using Surface Racer 5.0 and is expressed as Angstrom squared [Å²]. "Selected sites" indicate the sites selected for substitution to Cys in the invention.

| EU number | Residue | Surface accessibility [Å²] | Selected sites |
|---|---|---|---|
| 107 | LYS | 90 | LC-K107C |
| 108 | ARG | 49 | LC-R108C |
| 109 | THR | 148 | LC-T109C |
| 110 | VAL | 77 | |
| 111 | ALA | 16 | |
| 112 | ALA | 50 | LC-A112C |
| 113 | PRO | 2 | |
| 114 | SER | 39 | LC-S114C |
| 115 | VAL | 0 | |
| 116 | PHE | 0 | |
| 117 | ILE | 0 | |
| 118 | PHE | 0 | |
| 119 | PRO | 0 | |
| 120 | PRO | 0 | |
| 121 | SER | 0 | |
| 122 | ASP | 90 | LC-D122C |
| 123 | GLU | 51 | LC-E123C |
| 124 | GLN | 0 | |
| 125 | LEU | 21 | |
| 126 | LYS | 230 | |
| 127 | SER | 101 | |
| 128 | GLY | 12 | |
| 129 | THR | 41 | LC-T129C |
| 130 | ALA | 0 | |
| 131 | SER | 0 | |
| 132 | VAL | 0 | |
| 133 | VAL | 0 | |
| 134 | CYS | 0 | |
| 135 | LEU | 0 | |
| 136 | LEU | 0 | |
| 137 | ASN | 5 | |
| 138 | ASN | 18 | |
| 139 | PHE | 0 | |

TABLE 7-continued

Surface accessibility of amino acid residues in human kappa light chain. Surface accessibility was calculated using Surface Racer 5.0 and is expressed as Angstrom squared [Å²]. "Selected sites" indicate the sites selected for substitution to Cys in the invention.

| EU number | Residue | Surface accessibility [Å²] | Selected sites |
|---|---|---|---|
| 140 | TYR | 0 | |
| 141 | PRO | 3 | |
| 142 | ARG | 55 | LC-R142C |
| 143 | GLU | 117 | LC-E143C |
| 144 | ALA | 7 | |
| 145 | LYS | 160 | LC-K145C |
| 146 | VAL | 11 | |
| 147 | GLN | 22 | |
| 148 | TRP | 0 | |
| 149 | LYS | 48 | |
| 150 | VAL | 0 | |
| 151 | ASP | 59 | |
| 152 | ASN | 157 | LC-N152C |
| 153 | ALA | 51 | |
| 154 | LEU | 117 | LC-L154C |
| 155 | GLN | 26 | |
| 156 | SER | 122 | LC-S156C |
| 157 | GLY | 114 | |
| 158 | ASN | 19 | |
| 159 | SER | 22 | LC-S159C |
| 160 | GLN | 36 | |
| 161 | GLU | 66 | LC-E161C |
| 162 | SER | 8 | |
| 163 | VAL | 14 | |
| 164 | THR | 5 | |
| 165 | GLU | 74 | LC-E165C |
| 166 | GLN | 8 | |
| 167 | ASP | 13 | |
| 168 | SER | 170 | LC-S168C |
| 169 | LYS | 241 | LC-K169C |
| 170 | ASP | 48 | LC-D170C |
| 171 | SER | 1 | |
| 172 | THR | 0 | |
| 173 | TYR | 0 | |
| 174 | SER | 0 | |
| 175 | LEU | 0 | |
| 176 | SER | 0 | |
| 177 | SER | 0 | |
| 178 | THR | 0 | |
| 179 | LEU | 0 | |
| 180 | THR | 13 | |
| 181 | LEU | 21 | |
| 182 | SER | 59 | LC-S182C |
| 183 | LYS | 131 | LC-K183C |
| 184 | ALA | 32 | |
| 185 | ASP | 52 | |
| 186 | TYR | 0 | |
| 187 | GLU | 77 | |
| 188 | LYS | 201 | LC-K188C |
| 189 | HIS | 42 | |
| 190 | LYS | 167 | LC-K190C |
| 191 | VAL | 58 | LC-V191C |
| 192 | TYR | 0 | |
| 193 | ALA | 0 | |
| 194 | CYS | 0 | |
| 195 | GLU | 12 | |
| 196 | VAL | 0 | |
| 197 | THR | 38 | LC-T197C |
| 198 | HIS | 4 | |
| 199 | GLN | 127 | LC-Q199C |
| 200 | GLY | 11 | |
| 201 | LEU | 17 | |
| 202 | ARG | 343 | |
| 203 | SER | 110 | LC-S203C |
| 204 | PRO | 69 | |
| 205 | VAL | 30 | |
| 206 | THR | 70 | LC-T206C |
| 207 | LYS | 44 | |
| 208 | SER | 47 | |
| 209 | PHE | 5 | |
| 210 | ASN | 44 | |
| 211 | ARG | 89 | |
| 212 | GLY | 15 | |
| 213 | GLU | 107 | |
| 214 | CYS | 58 | |

Example 2. Preparation of Trastuzumab Cys Mutant Antibodies

DNA encoding variable regions of heavy and light chains of trastuzumab were chemically synthesized and cloned into two mammalian expression vectors, pOG-HC and pOG-LC that contain constant regions of human IgG1 and human kappa light chain, resulting in two wild-type constructs, pOG-trastuzumab HC and pOG-trastuzumab LC, respectively. In the vectors the expression of antibody heavy and light chain constructs in mammalian cells is driven by a CMV promoter. The vectors contain a synthetic 24 amino acid signal sequence: MKTFILLLWVLLLWVIFLLPGATA (SEQ ID NO: 99), in the N-terminal of heavy chain or light chain to guide their secretion from mammalian cells. The signal sequence has been validated to be efficient in directing protein secretion in hundreds of mammalian proteins in 293 Freestyle™ cells. Oligonucleotide directed mutagenesis was employed to prepare Cys mutant constructs in trastuzumab. 88 pairs of mutation primers (Table 8) were chemically synthesized that correspond to the 88 Cys mutation sites selected in the constant regions of human IgG1 heavy chain and kappa light chain as described in Example 1. The sense and anti-sense mutation primer pairs were mixed prior to PCR amplification. PCR reactions were performed by using PfuUltra II Fusion HS DNA Polymerase (Stratagene) with pOG-trastuzumab HC and pOG-trastuzumab LC as the templates. After PCR reactions, the PCR products were confirmed on agarose gels, and treated with DPN I followed by transformation in DH5a cells (Klock el al., (2009) *Methods Mol Biol.* 498:91-103).

Sequences of 88 Cys mutant constructs were confirmed by DNA sequencing. The full length amino acid sequence of wild-type trastuzumab heavy chain is shown as SEQ ID NO:1 and that of the light chain as SEQ ID NO:90. The encoded protein sequence of the constant region of 59 trastuzumab HC Cys mutant constructs (SEQ ID NO:2 through SEQ ID NO:60) and 29 trastuzumab LC Cys mutant constructs (SEQ ID NO:61 to SEQ ID NO:89) are shown in Table 9 and Table 10, respectively. Amino acid residues in human IgG1 heavy chain and human kappa light chain are numbered by Eu numbering system (Edelman et al, (1969) *Proc Natl Acad Sci USA,* 63:78-85).

TABLE 8

DNA sequences of mutation primers used to prepare 88 Cys mutations heavy and light chains of human IgG1.

| Mutation sites | Primer name | Sequence | SEQ ID NO. |
|---|---|---|---|
| LC-K107C | LC-CYS-S1 | GTGGAGATCTGTCGAACGGTGGCCGCTC CCAGCGTGTTCA | 100 |
|  | LC-CYS-A1 | ACCGTTCGACAGATCTCCACCTTGGTACC CTGTCCGAAC | 101 |
| LC-R108C | LC-CYS-S2 | GGAGATCAAATGCACGGTGGCCGCTCCC AGCGTGTTCATCT | 102 |
|  | LC-CYS-A2 | GCCACCGTGCATTTGATCTCCACCTTGGT ACCCTGTCCGA | 103 |
| LC-T109C | LC-CYS-S3 | GATCAAACGATGTGTGGCCGCTCCCAGC GTGTTCATCTTCC | 104 |
|  | LC-CYS-A3 | GCGGCCACACATCGTTTGATCTCCACCTT GGTACCCTGTC | 105 |
| LC-A112C | LC-CYS-S4 | ACGGTGGCCTGTCCCAGCGTGTTCATCTT CCCCCCCAGCGA | 106 |
|  | LC-CYS-A4 | CACGCTGGGACAGGCCACCGTTCGTTTG ATCTCCACCTTG | 107 |
| LC-S114C | LC-CYS-S5 | GCCGCTCCCTGCGTGTTCATCTTCCCCCC CAGCGACGAGCA | 108 |
|  | LC-CYS-A5 | ATGAACACGCAGGGAGCGGCCACCGTTC GTTTGATCTCCA | 109 |
| LC-D122C | LC-CYS-S6 | CCCCCAGCTGTGAGCAGCTGAAGAGCGG CACCGCCAGCGT | 110 |
|  | LC-CYS-A6 | CAGCTGCTCACAGCTGGGGGGGAAGATG AACACGCTGGGA | 111 |
| LC-E123C | LC-CYS-S7 | CCCAGCGACTGTCAGCTGAAGAGCGGCA CCGCCAGCGTG | 112 |
|  | LC-CYS-A7 | TTCAGCTGACAGTCGCTGGGGGGGAAGA TGAACACGCTG | 113 |
| LC-T129C | LC-CYS-S10 | AGAGCGGCTGTGCCAGCGTGGTGTGCCT GCTGAACAACTT | 114 |
|  | LC-CYS-A10 | CACGCTGGCACAGCCGCTCTTCAGCTGCT CGTCGCTGGGG | 115 |
| LC-R142C | LC-CYS-S11 | TCTACCCCTGTGAGGCCAAGGTGCAGTG GAAGGTGGACAA | 116 |
|  | LC-CYS-A11 | TTGGCCTCACAGGGGTAGAAGTTGTTCA GCAGGCACACCA | 117 |
| LC-E143C | LC-CYS-S12 | TACCCCCGGTGTGCCAAGGTGCAGTGGA AGGTGGACAAC | 118 |
|  | LC-CYS-A12 | ACCTTGGCACACCGGGGGTAGAAGTTGT TCAGCAGGCACA | 119 |
| LC-K145C | LC-CYS-S13 | CGGGAGGCCTGCGTGCAGTGGAAGGTGG ACAACGCCCTGC | 120 |
|  | LC-CYS-A13 | CACTGCACGCAGGCCTCCCGGGGGTAGA AGTTGTTCAGCA | 121 |
| LC-N152C | LC-CYS-S14 | AAGGTGGACTGTGCCCTGCAGAGCGGCA ACAGCCAGGAGA | 122 |
|  | LC-CYS-A14 | TGCAGGGCACAGTCCACCTTCCACTGCAC CTTGGCCTCCC | 123 |
| LC-L154C | LC-CYS-S15 | GACAACGCCTGTCAGAGCGGCAACAGCC AGGAGAGCGTCA | 124 |
|  | LC-CYS-A15 | TGCCGCTCTGACAGGCGTTGTCCACCTTC CACTGCACCTTG | 125 |
| LC-S156C | LC-CYS-S16 | GCCCTGCAGTGTGGCAACAGCCAGGAGA GCGTCACCGAGCA | 126 |
|  | LC-CYS-A16 | GCTGTTGCCACACTGCAGGGCGTTGTCCA CCTTCCACTGCA | 127 |
| LC-S159C | LC-CYS-S18 | AGCGGCAACTGTCAGGAGAGCGTCACCG AGCAGGACAGCAA | 128 |
|  | LC-CYS-A18 | CTCTCCTGACAGTTGCCGCTCTGCAGGGC GTTGTCCACCT | 129 |

TABLE 8-continued

DNA sequences of mutation primers used to prepare 88 Cys mutations heavy and light chains of human IgG1.

| Mutation sites | Primer name | Sequence | SEQ ID NO. |
|---|---|---|---|
| LC-E161C | LC-CYS-S19 | AACAGCCAGTGCAGCGTCACCGAGCAGGACAGCAAGGACT | 130 |
| | LC-CYS-A19 | GTGACGCTGCACTGGCTGTTGCCGCTCTGCAGGGCGTTGT | 131 |
| LC-E165C | LC-CYS-S20 | GAGCGTCACCTGTCAGGACAGCAAGGACTCCACCTACAGC | 132 |
| | LC-CYS-A20 | CTGTCCTGACAGGTGACGCTCTCCTGGCTGTTGCCGCTCT | 133 |
| LC-S168C | LC-CYS-S21 | GAGCAGGACTGCAAGGACTCCACCTACAGCCTGAGCAGCA | 134 |
| | LC-CYS-A21 | GAGTCCTTGCAGTCCTGCTCGGTGACGCTCTCCTGGCTGT | 135 |
| LC-K169C | LC-CYS-S22 | CAGGACAGCTGTGACTCCACCTACAGCCTGAGCAGCACC | 136 |
| | LC-CYS-A22 | GTGGAGTCACAGCTGTCCTGCTCGGTGACGCTCTCCTGG | 137 |
| LC-D170C | LC-CYS-S23 | ACAGCAAGTAGTCCACCTACAGCCTGAGCAGCACCCTGAC | 138 |
| | LC-CYS-A23 | TAGGTGGACTACTTGCTGTCCTGCTCGGTGACGCTCTCCT | 139 |
| LC-S182C | LC-CYS-S24 | TGACCCTGTGCAAGGCCGACTACGAGAAGCATAAGGTGTA | 140 |
| | LC-CYS-A24 | GTCGGCCTTGCACAGGGTCAGGGTGCTGCTCAGGCTGTAG | 141 |
| LC-K183C | LC-CYS-S25 | GACCCTGAGCTGTGCCGACTACGAGAAGCATAAGGTGTAC | 142 |
| | LC-CYS-A25 | TAGTCGGCACAGCTCAGGGTCAGGGTGCTGCTCAGGCTGT | 143 |
| LC-K188C | LC-CYS-S26 | GACTACGAGTGCCATAAGGTGTACGCCTGCGAGGTGAC | 144 |
| | LC-CYS-A26 | ACCTTATGGCACTCGTAGTCGGCCTTGCTCAGGGTCAGG | 145 |
| LC-K190C | LC-CYS-S27 | GAGAAGCATTGCGTGTACGCCTGCGAGGTGACCCACCAG | 146 |
| | LC-CYS-A27 | GGCGTACACGCAATGCTTCTCGTAGTCGGCCTTGCTCAGG | 147 |
| LC-V191C | LC-CYS-S28 | AGCATAAGTAGTACGCCTGCGAGGTGACCCACCAGGGCT | 148 |
| | LC-CYS-A28 | CAGGCGTACTACTTATGCTTCTCGTAGTCGGCCTTGCTCA | 149 |
| LC-T197C | LC-CYS-S29 | GCGAGGTGTGTCACCAGGGCCTGTCCAGCCCCGTGACCAA | 150 |
| | LC-CYS-A29 | CCCTGGTGACACACCTCGCAGGCGTACACCTTATGCTTCT | 151 |
| LC-Q199C | LC-CYS-S30 | GTGACCCACTGTGGCCTGTCCAGCCCCGTGACCAAGAGCT | 152 |
| | LC-CYS-A30 | GACAGGCCACAGTGGGTCACCTCGCAGGCGTACACCTTAT | 153 |
| LC-S203C | LC-CYS-S31 | GGCCTGTCCTGTCCCGTGACCAAGAGCTTCAACAGGGGCGA | 154 |
| | LC-CYS-A31 | GTCACGGGACAGGACAGGCCCTGGTGGGTCACCTCGCAGG | 155 |
| LC-T206C | LC-CYS-S32 | CAGCCCCGTGTGCAAGAGCTTCAACAGGGGCGAGTGCTAA | 156 |
| | LC-CYS-A32 | AAGCTCTTGCACACGGGGCTGGACAGGCCCTGGTGGGTC | 157 |

TABLE 8-continued

DNA sequences of mutation primers used to prepare 88 Cys mutations heavy and light chains of human IgG1.

| Mutation sites | Primer name | Sequence | SEQ ID NO. |
|---|---|---|---|
| HC-S117C | HC-CYS-S1 | CCGTCTCCTGCGCTAGCACCAAGGGCCCC CAGCGTGTTC | 158 |
| | HC-CYS-A1 | GGTGCTAGCGCAGGAGACGGTGACCAGG GTTCCTTGAC | 159 |
| HC-S119C | HC-CYS-S2 | TCCTCGGCTTGTACCAAGGGCCCCAGCGT GTTCCCCCTGG | 160 |
| | HC-CYS-A2 | CCCTTGGTACAAGCCGAGGAGACGGTGA CCAGGGTTCCTT | 161 |
| HC-K121C | HC-CYS-S3 | CTAGCACCTGTGGCCCCAGCGTGTTCCCC CTGGCCCCCA | 162 |
| | HC-CYS-A3 | GCTGGGGCCACAGGTGCTAGCCGAGGAG ACGGTGACCAG | 163 |
| HC-S124C | HC-CYS-S4 | AGGGCCCCTGTGTGTTCCCCCTGGCCCCC AGCAGCAAGA | 164 |
| | HC-CYS-A4 | GGGGAACACACAGGGGCCCTTGGTGCTA GCCGAGGAGACG | 165 |
| HC-S132C | HC-CYS-S5 | CCCCCAGCTGCAAGAGCACCAGCGGCGG CACAGCCGCCCT | 166 |
| | HC-CYS-A5 | GGTGCTCTTGCAGCTGGGGGCCAGGGGG AACACGCTGGGG | 167 |
| HC-S134C | HC-CYS-S6 | AGCAGCAAGTGTACCAGCGGCGGCACAG CCGCCCTGGGCT | 168 |
| | HC-CYS-A6 | CCGCTGGTACACTTGCTGCTGGGGGCCA GGGGGAACACG | 169 |
| HC-S136C | HC-CYS-S7 | AGAGCACCTGTGGCGGCACAGCCGCCCT GGGCTGCCTGGT | 170 |
| | HC-CYS-A7 | GTGCCGCCACAGGTGCTCTTGCTGCTGGG GGCCAGGGGA | 171 |
| HC-T139C | HC-CYS-S8 | AGCGGCGGCTGTGCCGCCCTGGGCTGCC TGGTGAAGGACT | 172 |
| | HC-CYS-A8 | CAGGGCGGCACAGCCGCCGCTGGTGCTC TTGCTGCTGGGG | 173 |
| HC-E152C | HC-CYS-S9 | TACTTCCCCTGTCCCGTGACCGTGTCCTG GAACAGCGGA | 174 |
| | HC-CYS-A9 | GGTCACGGGACAGGGGAAGTAGTCCTTC ACCAGGCAGC | 175 |
| HC-P153C | HC-CYS-S10 | TCCCCGAGTGCGTGACCGTGTCCTGGAAC AGCGGAGCCCT | 176 |
| | HC-CYS-A10 | CACGGTCACGCACTCGGGGAAGTAGTCC TTCACCAGGCAG | 177 |
| HC-T155C | HC-CYS-S11 | GAGCCCGTGTGCGTGTCCTGGAACAGCG GAGCCCTGACCT | 178 |
| | HC-CYS-A11 | CAGGACACGCACACGGGCTCGGGGAAGT AGTCCTTCACCA | 179 |
| HC-S157C | HC-CYS-S12 | TGACCGTGTGCTGGAACAGCGGAGCCCT GACCTCCGGCGT | 180 |
| | HC-CYS-A12 | CTGTTCCAGCACACGGTCACGGGCTCGG GGAAGTAGTCCT | 181 |
| HC-T164C | HC-CYS-S13 | GGAGCCCTGTGCTCCGGCGTGCACACCTT CCCCGCCGTGCT | 182 |
| | HC-CYS-A13 | ACGCCGGAGCACAGGGCTCCGCTGTTCC AGGACACGGTCA | 183 |
| HC-S165C | HC-CYS-S14 | CCCTGACCTGTGGCGTGCACACCTTCCCC GCCGTGCTGCA | 184 |
| | HC-CYS-A14 | TGTGCACGCCACAGGTCAGGGCTCCGCT GTTCCAGGACAC | 185 |

TABLE 8-continued

DNA sequences of mutation primers used to prepare 88 Cys mutations heavy and light chains of human IgG1.

| Mutation sites | Primer name | Sequence | SEQ ID NO. |
|---|---|---|---|
| HC-T169C | HC-CYS-S15 | GCGTGCACTGCTTCCCCGCCGTGCTGCAGAGCAGCGGCCT | 186 |
| | HC-CYS-A15 | GGCGGGGAAGCAGTGCACGCCGGAGGTCAGGGCTCCGCTG | 187 |
| HC-P171C | HC-CYS-S16 | CACACCTTCTGTGCCGTGCTGCAGAGCAGCGGCCTGTACA | 188 |
| | HC-CYS-A16 | CAGCACGGCACAGAAGGTGTGCACGCCGGAGGTCAGGGCT | 189 |
| HC-L174C | HC-CYS-S17 | CCGCCGTGTGTCAGAGCAGCGGCCTGTACAGCCTGTCCA | 190 |
| | HC-CYS-A17 | GCTGCTCTGACACACGGCGGGGAAGGTGTGCACGCCGGAG | 191 |
| HC-S176C | HC-CYS-S18 | TGCTGCAGTGCAGCGGCCTGTACAGCCTGTCCAGCGTGGT | 192 |
| | HC-CYS-A18 | ACAGGCCGCTGCACTGCAGCACGGCGGGGAAGGTGTGCACG | 193 |
| HC-S177C | HC-CYS-S19 | CTGCAGAGCTGTGGCCTGTACAGCCTGTCCAGCGTGGTGA | 194 |
| | HC-CYS-A19 | TACAGGCCACAGCTCTGCAGCACGGCGGGGAAGGTGTGCA | 195 |
| HC-P189C | HC-CYS-S21 | TGACAGTGTGCAGCAGCAGCCTGGGCACCCAGACCTACAT | 196 |
| | HC-CYS-A21 | CTGCTGCTGCACACTGTCACCACGCTGGACAGGCTGTACA | 197 |
| HC-S191C | HC-CYS-S22 | TGCCCAGCTGCAGCCTGGGCACCCAGACCTACATCTGCAA | 198 |
| | HC-CYS-A22 | CCCAGGCTGCAGCTGGGCACTGTCACCACGCTGGACAGGCT | 199 |
| HC-T195C | HC-CYS-S23 | GCCTGGGCTGTCAGACCTACATCTGCAACGTGAACCACAA | 200 |
| | HC-CYS-A23 | GTAGGTCTGACAGCCCAGGCTGCTGCTGGGCACTGTCACCA | 201 |
| HC-T197C | HC-CYS-S24 | GCACCCAGTGCTACATCTGCAACGTGAACCACAAGCCCA | 202 |
| | HC-CYS-A24 | GCAGATGTAGCACTGGGTGCCCAGGCTGCTGCTGGGCACT | 203 |
| HC-K205C | HC-CYS-S25 | TGAACCACTGTCCCAGCAACACCAAGGTGGACAAGAGAGT | 204 |
| | HC-CYS-A25 | TGTTGCTGGGACAGTGGTTCACGTTGCAGATGTAGGTCTGG | 205 |
| HC-5207C | HC-CYS-S26 | ACAAGCCCTGCAACACCAAGGTGGACAAGAGAGTGGAGC | 206 |
| | HC-CYS-A26 | CTTGGTGTTGCAGGGCTTGTGGTTCACGTTGCAGATGTAG | 207 |
| HC-D212C | HC-CYS-S27 | ACCAAGGTGTGCAAGAGAGTGGAGCCCAGAGCTGCGACA | 208 |
| | HC-CYS-A27 | CACTCTCTTGCACACCTTGGTGTTGCTGGGCTTGTGGTTCA | 209 |
| HC-K246C | HC-CYS-S28 | TCCCCCCCTGTCCCAAGGACACCCTGATGATCAGCAGGA | 210 |
| | HC-CYS-A28 | GTCCTTGGGACAGGGGGGAACAGGAACACGGAGGGTCCG | 211 |
| HC-E258C | HC-CYS-S29 | AGGACCCCTGCGTGACCTGCGTGGTGGTGGACGTGAG | 212 |
| | HC-CYS-A29 | CAGGTCACGCAGGGGTCCTGCTGATCATCAGGGTGTCCT | 213 |

TABLE 8-continued

DNA sequences of mutation primers used to prepare 88 Cys mutations heavy and light chains of human IgG1.

| Mutation sites | Primer name | Sequence | SEQ ID NO. |
|---|---|---|---|
| HC-E269C | HC-CYS-S30 | TGAGCCACTGTGACCCAGAGGTGAAGTTCAACTGGTACG | 214 |
|  | HC-CYS-A30 | CTCTGGGTCACAGTGGCTCACGTCCACCACCACGCAGGTC | 215 |
| HC-K274C | HC-CYS-S32 | CCAGAGGTGTGCTTCAACTGGTACGTGGACGGCGTGGAGG | 216 |
|  | HC-CYS-A32 | CCAGTTGAAGCACACCTCTGGGTCCTCGTGGCTCACGTCCA | 217 |
| HC-N286C | HC-CYS-S35 | GAGGTGCACTGTGCCAAGACCAAGCCCAGAGAGGAGCAGT | 218 |
|  | HC-CYS-A35 | GGTCTTGGCACAGTGCACCTCCACGCCGTCCACGTACCAGT | 219 |
| HC-K288C | HC-CYS-S36 | CACAACGCCTGTACCAAGCCCAGAGAGGAGCAGTACAACA | 220 |
|  | HC-CYS-A36 | GGCTTGGTACAGGCGTTGTGCACCTCCACGCCGTCCACGT | 221 |
| HC-K290C | HC-CYS-S37 | GCCAAGACCTGTCCCAGAGAGGAGCAGTACAACAGCACCT | 222 |
|  | HC-CYS-A37 | CTCTCTGGGACAGGTCTTGGCGTTGTGCACCTCCACGCCGT | 223 |
| HC-R292C | HC-CYS-S38 | ACCAAGCCCTGTGAGGAGCAGTACAACAGCACCTACAGGGT | 224 |
|  | HC-CYS-A38 | CTGCTCCTCACAGGGCTTGGTCTTGGCGTTGTGCACCTCCA | 225 |
| HC-E293C | HC-CYS-S39 | CAAGCCCAGATGCGAGCAGTACAACAGCACCTACAGGGTG | 226 |
|  | HC-CYS-A39 | GTACTGCTCGCATCTGGGCTTGGTCTTGGCGTTGTGCACCT | 227 |
| HC-E294C | HC-CYS-S40 | GCCCAGAGAGTGTCAGTACAACAGCACCTACAGGGTGGT | 228 |
|  | HC-CYS-A40 | TTGTACTGACACTCTCTGGGCTTGGTCTTGGCGTTGTGCA | 229 |
| HC-K320C | HC-CYS-S41 | CAAGGAATACTGCTGCAAGGTCTCCAACAAGGCCCTGCCA | 230 |
|  | HC-CYS-A41 | GACCTTGCAGCAGTATTCCTTGCCGTTCAGCCAGTCCTGGT | 231 |
| HC-K322C | HC-CYS-S42 | TACAAGTGCTGCGTCTCCAACAAGGCCCTGCCAGCCCCCA | 232 |
|  | HC-CYS-A42 | GTTGGAGACGCAGCACTTGTATTCCTTGCCGTTCAGCCAGT | 233 |
| HC-K326C | HC-CYS-S43 | GGTCTCCAACTGTGCCCTGCCAGCCCCCATCGAAAAGACC | 234 |
|  | HC-CYS-A43 | GGCAGGGCACAGTTGGAGACCTTGCACTTGTATTCCTTGC | 235 |
| HC-A330C | HC-CYS-S44 | GCCCTGCCATGTCCCATCGAAAAGACCATCAGCAAGGCCA | 236 |
|  | HC-CYS-A44 | TTCGATGGGACATGGCAGGGCCTTGTTGGAGACCTTGCACT | 237 |
| HC-E333C | HC-CYS-S45 | GCCCCCATCTGCAAGACCATCAGCAAGGCCAAGGGCCAGC | 238 |
|  | HC-CYS-A45 | GATGGTCTTGCAGATGGGGGCTGGCAGGGCCTTGTTGGAGA | 239 |
| HC-K334C | HC-CYS-S46 | CCCATCGAATGCACCATCAGCAAGGCCAGGGCCAGCCA | 240 |
|  | HC-CYS-A46 | GCTGATGGTGCATTCGATGGGGGCTGGCAGGGCCTTGTTG | 241 |

TABLE 8-continued

DNA sequences of mutation primers used to prepare 88 Cys mutations heavy and light chains of human IgG1.

| Mutation sites | Primer name | Sequence | SEQ ID NO. |
|---|---|---|---|
| HC-T335C | HC-CYS-S47 | TCGAAAAGTGCATCAGCAAGGCCAAGGG CCAGCCACGGGA | 242 |
| | HC-CYS-A47 | CTTGCTGATGCACTTTTCGATGGGGCTG GCAGGGCCTTGT | 243 |
| HC-S337C | HC-CYS-S48 | AGACCATCTGCAAGGCCAAGGGCCAGCC ACGGGAGCCCCA | 244 |
| | HC-CYS-A48 | CCTTGGCCTTGCAGATGGTCTTTTCGATG GGGGCTGGCAGG | 245 |
| HC-R344C | HC-CYS-S50 | GGCCAGCCATGCGAGCCCCAGGTGTACA CCCTGCCTCCAT | 246 |
| | HC-CYS-A50 | CTGGGGCTCGCATGGCTGGCCCTTGGCCT TGCTGATGGTCT | 247 |
| HC-R355C | HC-CYS-S51 | CTCCATCCTGCGACGAGCTGACCAAGAA CCAGGTGTCCCT | 248 |
| | HC-CYS-A51 | CAGCTCGTCGCAGGATGGAGGCAGGGTG TACACCTGGGGCT | 249 |
| HC-K360C | HC-CYS-S52 | AGCTGACCTGCAACCAGGTGTCCCTGAC CTGTCTGGTGA | 250 |
| | HC-CYS-A52 | CACCTGGTTGCAGGTCAGCTCGTCCCGGG ATGGAGGCAGG | 251 |
| HC-Q362C | HC-CYS-S53 | CCAAGAACTGCGTGTCCCTGACCTGTCTG GTGAAGGGCTT | 252 |
| | HC-CYS-A53 | TCAGGGACACGCAGTTCTTGGTCAGCTCG TCCCGGGATGGA | 253 |
| HC-5375C | HC-CYS-S54 | TTCTACCCCTGCGACATCGCCGTGGAGTG GGAGAGCAACG | 254 |
| | HC-CYS-A54 | GGCGATGTCGCAGGGGTAGAAGCCCTTC ACCAGACAGGTCA | 255 |
| HC-E382C | HC-CYS-S55 | TGGAGTGGTGCAGCAACGGCCAGCCCGA GAACAACTACA | 256 |
| | HC-CYS-A55 | GGCCGTTGCTGCACCACTCCACGGCGAT GTCGCTGGGGTAG | 257 |
| HC-N389C | HC-CYS-S56 | AGCCCGAGTGCAACTACAAGACCACCCC CCCAGTGCTGGA | 258 |
| | HC-CYS-A56 | CTTGTAGTTGCACTCGGGCTGGCCGTTGC TCTCCCACTCCA | 259 |
| HC-N390C | HC-CYS-S57 | CCCGAGAACTGCTACAAGACCACCCCCC CAGTGCTGGACA | 260 |
| | HC-CYS-A57 | GGTCTTGTAGCAGTTCTCGGGCTGGCCGT TGCTCTCCCACT | 261 |
| HC-K392C | HC-CYS-S58 | GAACAACTACTGCACCACCCCCCCAGTG CTGGACAGCGAC | 262 |
| | HC-CYS-A58 | GGGGTGGTGCAGTAGTTGTTCTCGGGCTG GCCGTTGCTCT | 263 |
| HC-T393C | HC-CYS-S59 | AACTACAAGTGTACCCCCCCAGTGCTGG ACAGCGACGGCA | 264 |
| | HC-CYS-A59 | TGGGGGGGTACACTTGTAGTTGTTCTCGG GCTGGCCGTTG | 265 |
| HC-L398C | HC-CYS-S60 | CCCCAGTGTGTGACAGCGACGGCAGCTT CTTCCTGTACA | 266 |
| | HC-CYS-A60 | GTCGCTGTCACACACTGGGGGGGTGGTC TTGTAGTTGTTCT | 267 |
| HC-5400C | HC-CYS-S61 | TGCTGGACTGCGACGGCAGCTTCTTCCTG TACAGCAAGCT | 268 |
| | HC-CYS-A61 | GCTGCCGTCGCAGTCCAGCACTGGGGGG GTGGTCTTGTAGT | 269 |

TABLE 8-continued

DNA sequences of mutation primers used to prepare 88 Cys mutations heavy and light chains of human IgG1.

| Mutation sites | Primer name | Sequence | SEQ ID NO. |
|---|---|---|---|
| HC-D413C | HC-CYS-S62 | TGACCGTGTGCAAGTCCAGGTGGCAGCA GGGCAACGTGTT | 270 |
|  | HC-CYS-A62 | ACCTGGACTTGCACACGGTCAGCTTGCTG TACAGGAAGAAG | 271 |
| HC-S415C | HC-CYS-S63 | TGGACAAGTGCAGGTGGCAGCAGGGCAA CGTGTTCAGCT | 272 |
|  | HC-CYS-A63 | CTGCCACCTGCACTTGTCCACGGTCAGCT TGCTGTACAGG | 273 |
| HC-V422C | HC-CYS-S64 | AGGGCAACTGCTTCAGCTGCAGCGTGAT GCACGAGGCCCT | 274 |
|  | HC-CYS-A64 | GCAGCTGAAGCAGTTGCCCTGCTGCCAC CTGGACTTGTCCA | 275 |

TABLE 9

Amino acid sequences of the constant region of Cys mutant constructs in human IgG1 heavy chain. SEQ ID NO: 1 is the sequence for full-length trastuzumab (human IgG1). SEQ ID NO: 2 to SEQ ID NO: 60 indicate the sequence ID numbers for 59 Cys mutant constructs in human IgG1 heavy chain, showing only the sequences of the constant region.

SEQ ID NO: 1
EVQLVESGGGLVQPGGSLRLSCAASGFNIKDTYIHWVRQAPGKGLEWVARIYP
TNGYTRYADSVKGRFTISADTSKNTAYLQMNSLRAEDTAVYYCSRWGGDGF
YAMDYWGQGTLVTVSSASTKGPSVFPLAPSSKSTSGGTAALGCLVKDYFPEPV
TVSWNSGALTSGVHTFPAVLQSSGLYSLSSVVTVPSSSLGTQTYICNVNHKPSN
TKVDKKVEPKSCDKTHTCPPCPAPELLGGPSVFLFPPKPKDTLMISRTPEVTCV
VVDVSHEDPEVKFNWYVDGVEVHNAKTKPREEQYNSTYRVVSVLTVLHQDW
LNGKEYKCKVSNKALPAPIEKTISKAKGQPREPQVYTLPPSREEMTKNQVSLTC
LVKGFYPSDIAVEWESNGQPENNYKTTPPVLDSDGSFFLYSKLTVDKSRWQQG
NVFSCSVMHEALHNHYTQKSLSLSPGK

SEQ ID NO: 2
CASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTH
TCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALP
APIEKTISKAKGQPREPQVYTLPPSREEMTKNQVSLTCLVKGFYPSDIAVEWES
NGQPENNYKTTPPVLDSDGSFFLYSKLTVDKSRWQQGNVFSCSVMHEALHNH
YTQKSLSLSPGK

SEQ ID NO: 3
SACTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTH
TCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALP
APIEKTISKAKGQPREPQVYTLPPSREEMTKNQVSLTCLVKGFYPSDIAVEWES
NGQPENNYKTTPPVLDSDGSFFLYSKLTVDKSRWQQGNVFSCSVMHEALHNH
YTQKSLSLSPGK

SEQ ID NO: 4
SASTCGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTH
TCPPCPAPELLGGPSVFLFPPKPKDTLMISRTPEVTCVVVDVSHEDPEVKFNWY
SNGQPENNYKTTPPVLDSDGSFFLYSKLTVDKSRWQQGNVFSCSVMHEALHN
HYTQKSLSLSPGK

SEQ ID NO: 23
SASTKGPSVFPLAPSSKSTSGGTAALGCLVKDYFPEPVTVSWNSGALTSGVHTF
PAVLQSSGLYSLSSVVTVPSSSLGCQTYICNVNHKPSNTKVDKKVEPKSCDKT
HTCPPCPAPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKAL
PAPIEKTISKAKGQPREPQVYTLPPSREEMTKNQVSLTCLVKGFYPSDIAVEWE
SNGQPENNYKTTPPVLDSDGSFFLYSKLTVDKSRWQQGNVFSCSVMHEALHN
HYTQKSLSLSPGK

TABLE 9 -continued

Amino acid sequences of the constant region of Cys mutant constructs in human IgG1 heavy chain. SEQ ID NO: 1 is the sequence for full-length trastuzumab (human IgG1). SEQ ID NO: 2 to SEQ ID NO: 60 indicate the sequence ID numbers for 59 Cys mutant constructs in human IgG1 heavy chain, showing only the sequences of the constant region.

SEQ ID NO: 24

```
SASTKGPSVFPLAPSSKSTSGGTAALGCLVKDYFPEPVTVSWNSGALTSGVHTF
PAVLQSSGLYSLSSVVTVPSSSLGTQCYICNVNHKPSNTKVDKKVEPKSCDKT
HTCPPCPAPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKAL
PAPIEKTISKAKGQPREPQVYTLPPSREEMTKNQVSLTCLVKGFYPSDIAVEWE
SNGQPENNYKTTPPVLDSDGSFFLYSKLTVDKSRWQQGNVFSCSVMHEALHN
HYTQKSLSLSPGK
```

SEQ ID NO: 25

```
SASTKGPSVFPLAPSSKSTSGGTAALGCLVKDYFPEPVTVSWNSGALTSGVHTF
PAVLQSSGLYSLSSVVTVPSSSLGTQTYICNVNHCPSNTKVDKKVEPKSCDKTH
TCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALP
APIEKTISKAKGQPREPQVYTLPPSREEMTKNQVSLTCLVKGFYPSDIAVEWES
NGQPENNYKTTPPVLDSDGSFFLYSKLTVDKSRWQQGNVFSCSVMHEALHNH
YTQKSLSLSPGK
```

SEQ ID NO :26

```
SASTKGPSVFPLAPSSKSTSGGTAALGCLVKDYFPEPVTVSWNSGALTSGVHTF
PAVLQSSGLYSLSSVVTVPSSSLGTQTYICNVNHKPCNTKVDKKVEPKSCDKT
HTCPPCPAPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKAL
PAPIEKTISKAKGQPREPQVYTLPPSREEMTKNQVSLTCLVKGFYPSDIAVEWE
SNGQPENNYKTTPPVLDSDGSFFLYSKLTVDKSRWQQGNVFSCSVMHEALHN
HYTQKSLSLSPGK
```

SEQ ID NO: 27

```
SASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVCKKVEPKSCDKTH
TCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALP
APIEKTISKAKGQPREPQVYTLPPSREEMTKNQVSLTCLVKGFYPSDIAVEWES
NGQPENNYKTTPPVLDSDGSFFLYSKLTVDKSRWQQGNVFSCSVMHEALHNH
YTQKSLSLSPGK
```

SEQ ID NO: 28

```
SASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTH
TCPPCPAPELLGGPSVFLFPPCPKDTLMISRTPEVTCVVVDVSHEDPEVKFNWY
VDGVEVHNAKTKPREEQYNSTYRVVSVLTVLHQDWLNGKEYKCKVSNKALP
APIEKTISKAKGQPREPQVYTLPPSREEMTKNQVSLTCLVKGFYPSDIAVEWES
NGQPENNYKTTPPVLDSDGSFFLYSKLTVDKSRWQQGNVFSCSVMHEALHNH
YTQKSLSLSPGK
```

SEQ ID NO: 29

```
SASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTH
TCPPCPAPELLGGPSVFLFPPKPKDTLMISRTPCVTCVVVDVSHEDPEVKFNWY
VDGVEVHNAKTKPREEQYNSTYRVVSVLTVLHQDWLNGKEYKCKVSNKALP
APIEKTISKAKGQPREPQVYTLPPSREEMTKNQVSLTCLVKGFYPSDIAVEWES
NGQPENNYKTTPPVLDSDGSFFLYSKLTVDKSRWQQGNVFSCSVMHEALHNH
YTQKSLSLSPGK
```

SEQ ID NO: 30

```
SASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTH
TCPPCPAPELLGGPSVFLFPPKPKDTLMISRTPEVTCVVVDVSHCDPEVKFNWY
VDGVEVHNAKTKPREEQYNSTYRVVSVLTVLHQDWLNGKEYKCKVSNKALP
APIEKTISKAKGQPREPQVYTLPPSREEMTKNQVSLTCLVKGFYPSDIAVEWES
NGQPENNYKTTPPVLDSDGSFFLYSKLTVDKSRWQQGNVFSCSVMHEALHNH
YTQKSLSLSPGK
```

SEQ ID NO: 31

```
SASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTH
TCPPCPAPELLGGPSVFLFPPKPKDTLMISRTPEVTCVVVDVSHEDPEVCFNWY
VDGVEVHNAKTKPREEQYNSTYRVVSVLTVLHQDWLNGKEYKCKVSNKALP
APIEKTISKAKGQPREPQVYTLPPSREEMTKNQVSLTCLVKGFYPSDIAVEWES
NGQPENNYKTTPPVLDSDGSFFLYSKLTVDKSRWQQGNVFSCSVMHEALHNH
YTQKSLSLSPGK
```

TABLE 9 -continued

Amino acid sequences of the constant region of Cys mutant constructs in human IgG1 heavy chain. SEQ ID NO: 1 is the sequence for full-length trastuzumab (human IgG1). SEQ ID NO: 2 to SEQ ID NO: 60 indicate the sequence ID numbers for 59 Cys mutant constructs in human IgG1 heavy chain, showing only the sequences of the constant region.

SEQ ID NO: 32
```
SASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTH
TCPPCPAPELLGGPSVFLFPPKPKDTLMISRTPEVTCVVVDVSHEDPEVKFNWY
VDGVEVHCAKTKPREEQYNSTYRVVSVLTVLHQDWLNGKEYKCKVSNKALP
APIEKTISKAKGQPREPQVYTLPPSREEMTKNQVSLTCLVKGFYPSDIAVEWES
NGQPENNYKTTPPVLDSDGSFFLYSKLTVDKSRWQQGNVFSCSVMHEALHNH
YTQKSLSLSPGK
```

SEQ ID NO: 33
```
SASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTH
TCPPCPAPELLGGPSVFLFPPKPKDTLMISRTPEVTCVVVDVSHEDPEVKFNWY
VDGVEVHNACTKPREEQYNSTYRVVSVLTVLHQDWLNGKEYKCKVSNKALP
APIEKTISKAKGQPREPQVYTLPPSREEMTKNQVSLTCLVKGFYPSDIAVEWES
NGQPENNYKTTPPVLDSDGSFFLYSKLTVDKSRWQQGNVFSCSVMHEALHNH
YTQKSLSLSPGK
```

SEQ ID NO: 34
```
SASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTH
TCPPCPAPELLGGPSVFLFPPKPKDTLMISRTPEVTCVVVDVSHEDPEVKFNWY
VDGVEVHNAKTCPREEQYNSTYRVVSVLTVLHQDWLNGKEYKCKVSNKALP
APIEKTISKAKGQPREPQVYTLPPSREEMTKNQVSLTCLVKGFYPSDIAVEWES
NGQPENNYKTTPPVLDSDGSFFLYSKLTVDKSRWQQGNVFSCSVMHEALHNH
YTQKSLSLSPGK
```

SEQ ID NO: 35
```
SASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTH
TCPPCPAPELLGGPSVFLFPPKPKDTLMISRTPEVTCVVVDVSHEDPEVKFNWY
VDGVEVHNAKTKPCEEQYNSTYRVVSVLTVLHQDWLNGKEYKCKVSNKALP
APIEKTISKAKGQPREPQVYTLPPSREEMTKNQVSLTCLVKGFYPSDIAVEWES
NGQPENNYKTTPPVLDSDGSFFLYSKLTVDKSRWQQGNVFSCSVMHEALHNH
YTQKSLSLSPGK
```

SEQ ID NO: 36
```
SASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTH
TCPPCPAPELLGGPSVFLFPPKPKDTLMISRTPEVTCVVVDVSHEDPEVKFNWY
VDGVEVHNAKTKPRCEQYNSTYRVVSVLTVLHQDWLNGKEYKCKVSNKALP
APIEKTISKAKGQPREPQVYTLPPSREEMTKNQVSLTCLVKGFYPSDIAVEWES
NGQPENNYKTTPPVLDSDGSFFLYSKLTVDKSRWQQGNVFSCSVMHEALHNH
YTQKSLSLSPGK
```

SEQ ID NO: 37
```
SASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTH
TCPPCPAPELLGGPSVFLFPPKPKDTLMISRTPEVTCVVVDVSHEDPEVKFNWY
VDGVEVHNAKTKPRECQYNSTYRVVSVLTVLHQDWLNGKEYKCKVSNKALP
APIEKTISKAKGQPREPQVYTLPPSREEMTKNQVSLTCLVKGFYPSDIAVEWES
NGQPENNYKTTPPVLDSDGSFFLYSKLTVDKSRWQQGNVFSCSVMHEALHNH
YTQKSLSLSPGK
```

SEQ ID NO: 38
```
SASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTH
TCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYCCKVSNKALP
APIEKTISKAKGQPREPQVYTLPPSREEMTKNQVSLTCLVKGFYPSDIAVEWES
NGQPENNYKTTPPVLDSDGSFFLYSKLTVDKSRWQQGNVFSCSVMHEALHNH
YTQKSLSLSPGK
```

SEQ ID NO: 39
```
SASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTH
TCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCCVSNKALP
APIEKTISKAKGQPREPQVYTLPPSREEMTKNQVSLTCLVKGFYPSDIAVEWES
NGQPENNYKTTPPVLDSDGSFFLYSKLTVDKSRWQQGNVFSCSVMHEALHNH
YTQKSLSLSPGK
```

TABLE 9 -continued

Amino acid sequences of the constant region of Cys mutant constructs in human IgG1 heavy chain. SEQ ID NO: 1 is the sequence for full-length trastuzumab (human IgG1). SEQ ID NO: 2 to SEQ ID NO: 60 indicate the sequence ID numbers for 59 Cys mutant constructs in human IgG1 heavy chain, showing only the sequences of the constant region.

SEQ ID NO: 40
SASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTH
TCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNCALP
APIEKTISKAKGQPREPQVYTLPPSREEMTKNQVSLTCLVKGFYPSDIAVEWES
NGQPENNYKTTPPVLDSDGSFFLYSKLTVDKSRWQQGNVFSCSVMHEALHNH
YTQKSLSLSPGK

SEQ ID NO: 41
SASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTH
TCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALP
CPIEKTISKAKGQPREPQVYTLPPSREEMTKNQVSLTCLVKGFYPSDIAVEWES
NGQPENNYKTTPPVLDSDGSFFLYSKLTVDKSRWQQGNVFSCSVMHEALHNH
YTQKSLSLSPGK

SEQ ID NO: 42
SASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTH
TCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALP
APICKTISKAKGQPREPQVYTLPPSREEMTKNQVSLTCLVKGFYPSDIAVEWES
NGQPENNYKTTPPVLDSDGSFFLYSKLTVDKSRWQQGNVFSCSVMHEALHNH
YTQKSLSLSPGK

SEQ ID NO: 43
SASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTH
TCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALP
APIECTISKAKGQPREPQVYTLPPSREEMTKNQVSLTCLVKGFYPSDIAVEWES
NGQPENNYKTTPPVLDSDGSFFLYSKLTVDKSRWQQGNVFSCSVMEALHNH
YTQKSLSLSPGK

SEQ ID NO: 44
SASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTH
TCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALP
APIEKCISKAKGQPREPQVYTLPPSREEMTKNQVSLTCLVKGFYPSDIAVEWES
NGQPENNYKTTPPVLDSDGSFFLYSKLTVDKSRWQQGNVFSCSVMHEALHNH
YTQKSLSLSPGK

SEQ ID NO: 45
SASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTH
TCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALP
APIEKTICKAKGQPREPQVYTLPPSREEMTKNQVSLTCLVKGFYPSDIAVEWES
NGQPENNYKTTPPVLDSDGSFFLYSKLTVDKSRWQQGNVFSCSVMHEALHNH
YTQKSLSLSPGK

SEQ ID NO: 46
SASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTH
TCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALP
APIEKTISKAKGQPCEPQVYTLPPSREEMTKNQVSLTCLVKGFYPSDIAVEWES
NGQPENNYKTTPPVLDSDGSFFLYSKLTVDKSRWQQGNVFSCSVMHEALHNH
YTQKSLSLSPGK

SEQ ID NO: 47
SASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTH
TCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALP
APIEKTISKAKGQPREPQVYTLPPSCEEMTKNQVSLTCLVKGFYPSDIAVEWES
NGQPENNYKTTPPVLDSDGSFFLYSKLTVDKSRWQQGNVFSCSVMHEALHNH
YTQKSLSLSPGK

TABLE 9 -continued

Amino acid sequences of the constant region of Cys mutant constructs in human IgG1 heavy chain. SEQ ID NO: 1 is the sequence for full-length trastuzumab (human IgG1). SEQ ID NO: 2 to SEQ ID NO: 60 indicate the sequence ID numbers for 59 Cys mutant constructs in human IgG1 heavy chain, showing only the sequences of the constant region.

SEQ ID NO: 48
```
SASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTH
TCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALP
APIEKTISKAKGQPREPQVYTLPPSREEMTCNQVSLTCLVKGFYPSDIAVEWES
NGQPENNYKTTPPVLDSDGSFFLYSKLTVDKSRWQQGNVFSCSVMHEALHNH
YTQKSLSLSPGK
```

SEQ ID NO: 49
```
SASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTH
TCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALP
APIEKTISKAKGQPREPQVYTLPPSREEMTKNCVSLTCLVKGFYPSDIAVEWES
NGQPENNYKTTPPVLDSDGSFFLYSKLTVDKSRWQQGNVFSCSVMHEALHNH
YTQKSLSLSPGK
```

SEQ ID NO: 50
```
SASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTH
TCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALP
APIEKTISKAKGQPREPQVYTLPPSREEMTKNQVSLTCLVKGFYPCDIAVEWES
NGQPENNYKTTPPVLDSDGSFFLYSKLTVDKSRWQQGNVFSCSVMHEALHNH
YTQKSLSLSPGK
```

SEQ ID NO: 51
```
SASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTH
TCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALP
APIEKTISKAKGQPREPQVYTLPPSREEMTKNQVSLTCLVKGFYPSDIAVEWCS
NGQPENNYKTTPPVLDSDGSFFLYSKLTVDKSRWQQGNVFSCSVMHEALHNH
YTQKSLSLSPGK
```

SEQ ID NO: 52
```
SASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTH
TCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALP
APIEKTISKAKGQPREPQVYTLPPSREEMTKNQVSLTCLVKGFYPSDIAVEWES
NGQPECNYKTTPPVLDSDGSFFLYSKLTVDKSRWQQGNVFSCSVMHEALHNH
YTQKSLSLSPGK
```

SEQ ID NO: 53
```
SASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTH
TCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALP
APIEKTISKAKGQPREPQVYTLPPSREEMTKNQVSLTCLVKGFYPSDIAVEWES
NGQPENCYKTTPPVLDSDGSFFLYSKLTVDKSRWQQGNVFSCSVMHEALHNH
YTQKSLSLSPGK
```

SEQ ID NO: 54
```
SASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTH
TCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALP
APIEKTISKAKGQPREPQVYTLPPSREEMTKNQVSLTCLVKGFYPSDIAVEWES
NGQPENNYCTTPPVLDSDGSFFLYSKLTVDKSRWQQGNVFSCSVMHEALHNH
YTQKSLSLSPGK
```

SEQ ID NO: 55
```
SASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTH
TCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALP
```

TABLE 9 -continued

Amino acid sequences of the constant region of Cys mutant constructs in human IgG1 heavy chain. SEQ ID NO: 1 is the sequence for full-length trastuzumab (human IgG1). SEQ ID NO: 2 to SEQ ID NO: 60 indicate the sequence ID numbers for 59 Cys mutant constructs in human IgG1 heavy chain, showing only the sequences of the constant region.

APIEKTISKAKGQPREPQVYTLPPSREEMTKNQVSLTCLVKGFYPSDIAVEWES
NGQPENNYKCTPPVLDSDGSFFLYSKLTVDKSRWQQGNVFSCSVMHEALHNH
YTQKSLSLSPGK

SEQ ID NO: 56

SASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTH
TCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALP
APIEKTISKAKGQPREPQVYTLPPSREEMTKNQVSLTCLVKGFYPSDIAVEWES
NGQPENNYKTTPPVCDSDGSFFLYSKLTVDKSRWQQGNVFSCSVMHEALHNH
YTQKSLSLSPGK

SEQ ID NO: 57

SASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTH
TCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALP
APIEKTISKAKGQPREPQVYTLPPSREEMTKNQVSLTCLVKGFYPSDIAVEWES
NGQPENNYKTTPPVLDCDGSFFLYSKLTVDKSRWQQGNVFSCSVMHEALHNH
YTQKSLSLSPGK

SEQ ID NO: 58

SASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTH
TCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALP
APIEKTISKAKGQPREPQVYTLPPSREEMTKNQVSLTCLVKGFYPSDIAVEWES
NGQPENNYKTTPPVLDSDGSFFLYSKLTVCKSRWQQGNVFSCSVMHEALHNH
YTQKSLSLSPGK

SEQ ID NO: 59

SASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTH
TCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALP
APIEKTISKAKGQPREPQVYTLPPSREEMTKNQVSLTCLVKGFYPSDIAVEWES
NGQPENNYKTTPPVLDSDGSFFLYSKLTVDKCRWQQGNVFSCSVMHEALHNH
YTQKSLSLSPGK

SEQ ID NO: 60

SASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTH
TCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALP
APIEKTISKAKGQPREPQVYTLPPSREEMTKNQVSLTCLVKGFYPSDIAVEWES
NGQPENNYKTTPPVLDSDGSFFLYSKLTVDKSRWQQGNCFSCSVMHEALHNH
YTQKSLSLSPGK

SEQ ID NO: 290

SASTKGPSVFPLAPSSKSTSGGTAALGCLVKDYFPEPVTVSWNSGALTSGVHTFP
AVLQSSGLYSLSSVVTVPSSSLGTQTYICNVNHKPSNTKVDKKVEPKSCDKTHTC
PPCPAPELLGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALPAPIEC
TISKAKGQPREPQVYTLPPSREEMTKNQVSLTCLVKGFYPCDIAVEWESNGQPE
NNYKTTPPVLDSDGSFFLYSKLTVDKSRWQQGNVFSCSVMHEALHNHYTQKSL
SLSPGK

SEQ ID NO: 291

SASTKGPSVFPLAPSSKSTSGGTAALGCLVKDYFPEPVTVSWNSGALTSGVHTFP
AVLQSSGLYSLSSVVTVPSSSLGTQTYICNVNHKPSNTKVDKKVEPKSCDKTHTC
PPCPAPELLGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALPAPIEC
TISKAKGQPREPQVYTLPPSREEMTKNQVSLTCLVKGFYPSDIAVEWESNGQPEN
NYCTTPPVLDSDGSFFLYSKLTVDKSRWQQGNVFSCSVMHEALHNHYTQKSLS
LSPGK

SEQ ID NO: 292

SASTKGPSVFPLAPSSKSTSGGTAALGCLVKDYFPEPVTVSWNSGALTSGVHTFP
AVLQSSGLYSLSSVVTVPSSSLGTQTYICNVNHKPSNTKVDKKVEPKSCDKTHTC
PPCPAPELLGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALPAPIEC

TABLE 9 -continued

Amino acid sequences of the constant region of Cys mutant constructs in human IgG1 heavy chain. SEQ ID NO: 1 is the sequence for full-length trastuzumab (human IgG1). SEQ ID NO: 2 to SEQ ID NO: 60 indicate the sequence ID numbers for 59 Cys mutant constructs in human IgG1 heavy chain, showing only the sequences of the constant region.

TISKAKGQPREPQVYTLPPSREEMTCNQVSLTCLVKGFYPCDIAVEWESNGQPE
NNYKTTPPVLDSDGSFFLYSKLTVDKSRWQQGNVFSCSVMHEALHNHYTQKSL
SLSPGK

SEQ ID NO: 293

SASTKGPSVFPLAPSSKSTSGGTAALGCLVKDYFPEPVTVSWNSGA
LTSGVHTFPAVLQSSGLYSLSSVVTVPSSSLGTQTYICNVNHKPSN
TKVDKKVEPKSCDKTHTCPPCPAPELLGGPSVFLFPPKPKDTLMIS
RTPEVTCVVVDVSHEDPEVKFNWYVDGVEVHNAKTKPREEQYNS
TYRVVSVLTVLHQDWLNGKEYKCKVSNKALPAPIECTISKAKGQP
REPQVYTLPPSREEMTCNQVSLTCLVKGFYPSDIAVEWESNGQPE
NNYCTTPPVLDSDGSFFLYSKLTVDKSRWQQGNVFSCSVMHEAL
HNHYTQKSLSLSPGK

SEQ ID NO: 294

SASTKGPSVFPLAPSSKSTSGGTAALGCLVKDYFPEPVTVSWNSGA
LTSGVHTFPAVLQSSGLYSLSSVVTVPSSSLGTQTYICNVNHKPSN
TKVDKKVEPKSCDKTHTCPPCPAPELLGGPSVFLFPPKPKDTLMIS
RTPEVTCVVVDVSHEDPEVKFNWYVDGVEVHNAKTKPREEQYNS
TYRVVSVLTVLHQDWLNGKEYKCKVSNKALPAPIECTISKAKGQP
REPQVYTLPPSREEMTKNQVSLTCLVKGFYPCDIAVEWESNGQPE
NNYCTTPPVLDSDGSFFLYSKLTVDKSRWQQGNVFSCSVMHEAL
HNHYTQKSLSLSPGK

SEQ ID NO: 295

SASTKGPSVFPLAPSSKSTSGGTAALGCLVKDYFPCPVTVSWNSG
ALTSGVHTFPAVLQSSGLYSLSSVVTVPSSSLGTQTYICNVNHKPS
NTKVDKKVEPKSCDKTHTCPPCPAPELLGGPSVFLFPPKPKDTLMI
SRTPEVTCVVVDVSHEDPEVKFNWYVDGVEVHNAKTKPREEQYN
STYRVVSVLTVLHQDWLNGKEYKCKVSNKALPAPIEKTISKAKGQ
PREPQVYTLPPSREEMTKNQVSLTCLVKGFYPCDIAVEWESNGQP
ENNYKTTPPVLDSDGSFFLYSKLTVDKSRWQQGNVFSCSVMHEA
LHNHYTQKSLSLSPGK

TABLE 10

Amino acid sequences of the constant region of 29 human kappa light chain Cys mutant constructs. SEQ ID NO: 61 is the sequence of the constant region of wild-type human kappa light chain SEQ ID NO: 62 to SEQ ID NO: 90 indicate the sequence ID numbers for 29 Cys mutant constructs in the constant region of human kappa light chain

SEQ ID NO: 61

CRTVAAPSVFIFPPSDEQLKSGTASVVCLLNNFYPREAKVQWKVDNALQSG
NSQESVTEQDSKDSTYSLSSTLTLSKADYEKHKVYACEVTHQGLSSPVTKSF
NRGEC

SEQ ID NO: 62

KCTVAAPSVFIFPPSDEQLKSGTASVVCLLNNFYPREAKVQWKVDNALQSG
NSQESVTEQDSKDSTYSLSSTLTLSKADYEKHKVYACEVTHQGLSSPVTKSF
NRGEC

SEQ ID NO: 63

KRCVAAPSVFIFPPSDEQLKSGTASVVCLLNNFYPREAKVQWKVDNALQSG
NSQESVTEQDSKDSTYSLSSTLTLSKADYEKHKVYACEVTHQGLSSPVTKSF
NRGEC

SEQ ID NO: 64

KRTVACPSVFIFPPSDEQLKSGTASVVCLLNNFYPREAKVQWKVDNALQSG
NSQESVTEQDSKDSTYSLSSTLTLSKADYEKHKVYACEVTHQGLSSPVTKSF
NRGEC

SEQ ID NO: 65

KRTVAAPCVFIFPPSDEQLKSGTASVVCLLNNFYPREAKVQWKVDNALQSG
NSQESVTEQDSKDSTYSLSSTLTLSKADYEKHKVYACEVTHQGLSSPVTKSF
NRGEC

SEQ ID NO: 66

KRTVAAPSVFIFPPSCEQLKSGTASVVCLLNNFYPREAKVQWKVDNALQSG
NSQESVTEQDSKDSTYSLSSTLTLSKADYEKHKVYACEVTHQGLSSPVTKSF
NRGEC

TABLE 10-continued

Amino acid sequences of the constant region of 29 human kappa light chain Cys mutant constructs. SEQ ID NO: 61 is the sequence of the constant region of wild-type human kappa light chain SEQ ID NO: 62 to SEQ ID NO: 90 indicate the sequence ID numbers for 29 Cys mutant constructs in the constant region of human kappa light chain KRTVAAPSVFIFPPSDCQLKSGTASVVCLLNNFYPREAKVQWKVDNALQSG
NSQESVTEQDSKDSTYSLSSTLTLSKADYEKHKVYACEVTHQGLSSPVTKSF
NRGEC
SEQ ID NO: 67

KRTVAAPSVFIFPPSDEQLKSGCASVVCLLNNFYPREAKVQWKVDNALQSG
NSQESVTEQDSKDSTYSLSSTLTLSKADYEKHKVYACEVTHQGLSSPVTKSF
NRGEC
SEQ ID NO: 68

KRTVAAPSVFIFPPSDEQLKSGTASVVCLLNNFYPCEAKVQWKVDNALQSG
NSQESVTEQDSKDSTYSLSSTLTLSKADYEKHKVYACEVTHQGLSSPVTKSF
NRGEC
SEQ ID NO: 69

KRTVAAPSVFIFPPSDEQLKSGTASVVCLLNNFYPRCAKVQWKVDNALQSG
NSQESVTEQDSKDSTYSLSSTLTLSKADYEKHKVYACEVTHQGLSSPVTKSF
NRGEC
SEQ ID NO: 70

KRTVAAPSVFIFPPSDEQLKSGTASVVCLLNNFYPREACVQWKVDNALQSG
NSQESVTEQDSKDSTYSLSSTLTLSKADYEKHKVYACEVTHQGLSSPVTKSF
NRGEC
SEQ ID NO: 71

KRTVAAPSVFIFPPSDEQLKSGTASVVCLLNNFYPREAKVQWKVDCALQSG
NSQESVTEQDSKDSTYSLSSTLTLSKADYEKHKVYACEVTHQGLSSPVTKSF
NRGEC
SEQ ID NO: 72

KRTVAAPSVFIFPPSDEQLKSGTASVVCLLNNFYPREAKVQWKVDNACQSG
NSQESVTEQDSKDSTYSLSSTLTLSKADYEKHKVYACEVTHQGLSSPVTKSF
NRGEC
SEQ ID NO: 73

KRTVAAPSVFIFPPSDEQLKSGTASVVCLLNNFYPREAKVQWKVDNALQCG
NSQESVTEQDSKDSTYSLSSTLTLSKADYEKHKVYACEVTHQGLSSPVTKSF
NRGEC
SEQ ID NO: 74

KRTVAAPSVFIFPPSDEQLKSGTASVVCLLNNFYPREAKVQWKVDNALQSG
NCQESVTEQDSKDSTYSLSSTLTLSKADYEKHKVYACEVTHQGLSSPVTKSF
NRGEC
SEQ ID NO: 75

KRTVAAPSVFIFPPSDEQLKSGTASVVCLLNNFYPREAKVQWKVDNALQSG
NSQCSVTEQDSKDSTYSLSSTLTLSKADYEKHKVYACEVTHQGLSSPVTKSF
NRGEC
SEQ ID NO: 76

KRTVAAPSVFIFPPSDEQLKSGTASVVCLLNNFYPREAKVQWKVDNALQSG
NSQESVTCQDSKDSTYSLSSTLTLSKADYEKHKVYACEVTHQGLSSPVTKSF
NRGEC
SEQ ID NO: 77

KRTVAAPSVFIFPPSDEQLKSGTASVVCLLNNFYPREAKVQWKVDNALQSG
NSQESVTEQDCKDSTYSLSSTLTLSKADYEKHKVYACEVTHQGLSSPVTKSF
NRGEC
SEQ ID NO: 78

KRTVAAPSVFIFPPSDEQLKSGTASVVCLLNNFYPREAKVQWKVDNALQSG
NSQESVTEQDSCDSTYSLSSTLTLSKADYEKHKVYACEVTHQGLSSPVTKSF
NRGEC
SEQ ID NO: 79

KRTVAAPSVFIFPPSDEQLKSGTASVVCLLNNFYPREAKVQWKVDNALQSG
NSQESVTEQDSKCSTYSLSSTLTLSKADYEKHKVYACEVTHQGLSSPVTKSF
NRGEC
SEQ ID NO: 80

TABLE 10-continued

Amino acid sequences of the constant region of 29 human kappa light chain Cys mutant constructs. SEQ ID NO: 61 is the sequence of the constant region of wild-type human kappa light chain SEQ ID NO: 62 to SEQ ID NO: 90 indicate the sequence ID numbers for 29 Cys mutant constructs in the constant region of human kappa light chain KRTVAAPSVFIFPPSDEQLKSGTASVVCLLNNFYPREAKVQWKVDNALQSG
NSQESVTEQDSKDSTYSLSSTLTLCKADYEKHKVYACEVTHQGLSSPVTKSF
NRGEC

SEQ ID NO: 81

KRTVAAPSVFIFPPSDEQLKSGTASVVCLLNNFYPREAKVQWKVDNALQSG
NSQESVTEQDSKDSTYSLSSTLTLSCADYEKHKVYACEVTHQGLSSPVTKSF
NRGEC

SEQ ID NO: 82

KRTVAAPSVFIFPPSDEQLKSGTASVVCLLNNFYPREAKVQWKVDNALQSG
NSQESVTEQDSKDSTYSLSSTLTLSKADYECHKVYACEVTHQGLSSPVTKSF
NRGEC

SEQ ID NO: 83

KRTVAAPSVFIFPPSDEQLKSGTASVVCLLNNFYPREAKVQWKVDNALQSG
NSQESVTEQDSKDSTYSLSSTLTLSKADYEKHCVYACEVTHQGLSSPVTKSF
NRGEC

SEQ ID NO: 84

KRTVAAPSVFIFPPSDEQLKSGTASVVCLLNNFYPREAKVQWKVDNALQSG
NSQESVTEQDSKDSTYSLSSTLTLSKADYEKHKCYACEVTHQGLSSPVTKSF
NRGEC

SEQ ID NO: 85

KRTVAAPSVFIFPPSDEQLKSGTASVVCLLNNFYPREAKVQWKVDNALQSG
NSQESVTEQDSKDSTYSLSSTLTLSKADYEKHKVYACEVCHQGLSSPVTKSF
NRGEC

SEQ ID NO: 86

KRTVAAPSVFIFPPSDEQLKSGTASVVCLLNNFYPREAKVQWKVDNALQSG
NSQESVTEQDSKDSTYSLSSTLTLSKADYEKHKVYACEVTHCGLSSPVTKSF
NRGEC

SEQ ID NO: 87

KRTVAAPSVFIFPPSDEQLKSGTASVVCLLNNFYPREAKVQWKVDNALQSG
NSQESVTEQDSKDSTYSLSSTLTLSKADYEKHKVYACEVTHQGLSCPVTKSF
NRGEC

SEQ ID NO: 88

KRTVAAPSVFIFPPSDEQLKSGTASVVCLLNNFYPREAKVQWKVDNALQSG
NSQESVTEQDSKDSTYSLSSTLTLSKADYEKHKVYACEVTHQGLSSPVCKSF
NRGEC

SEQ ID NO: 89

DIQMTQSPSSLSASVGDRVTITCRASQDVNTAVAWYQQKPGKAPKLLIYSAS
FLYSGVPSRFSGSRSGTDFTLTISSLQPEDFATYYCQQHYTTPPTFGQGTKVEI
KRTVAAPSVFIFPPSDEQLKSGTASVVCLLNNFYPREAKVQWKVDNALQSG
NSQESVTEQDSKDSTYSLSSTLTLSKADYEKHKVYACEVTHQGLSSPVTKSF
NRGEC

SEQ ID NO: 90

Example 3. Transfer of the Trastuzumab Heavy Chain and Light Chain Cys Mutations to Different Antibodies For trastuzumab, all Cys mutations for the attachment of drug payloads were chosen to be in the constant region of its human IgG1 heavy and human kappa light chain. Because constant regions of antibodies are highly conserved in primary sequence and structure, Cys mutant residues that are identified as good payload attachment sites in the context of trastuzumab will also serve as preferred attachment residues in other antibodies. To demonstrate the transferability of these generic conjugation sites to other antibodies, we cloned a set of Cys mutations into antibody 14090. Antibody 14090 is an antibody with a human IgG1 heavy chain and a human lambda light chain that binds to a different target protein than trastuzumab. The DNA encoding variable region of antibody 14090 was cloned into seven selected pOG trastuzumab HC Cys mutant plasmid constructs (SEQ ID NO listed in Table 11) to replace the variable regions of trastuzumab constructs in the plasmids as described in Example 2. As result, the amino acid sequences of the heavy chain constant regions in corresponding seven Cys constructs of antibody 14090 and trastuzumab are identical (FIG. 3). Subsequent examples show that these sites can be conjugated readily. Conversely, due to a high degree of similarity in primary sequences and in tertiary structures for different human IgG isotypes (FIG. 4), Cys mutations on the kappa light chain of trastuzumab can readily be transferred to equivalent light chains on human antibodies containing different isotype heavy chains. In the same way, the sites identified in the constant region of IgG1 may be transferred to IgG2, IgG3 and IgG4.

Example 4. Cysteine Mutations in Human Lambda Light Chains

Human lambda and kappa light chains have little amino acid sequence similarity (FIG. 5A). Mutations in the lambda light chain of antibody 14090 were selected based on the approximate similarity of the locations of the residues in a protein crystal structure model (Protein Databank structure entry 3G6D.pdb) of a Fab containing the human lambda light chain in reference to the desirable residues in the kappa light chain of trastuzumab (FIGS. 5 A and B). Seven additional Cys mutant constructs were generated in antibody 14090-lambda light chain plasmid using oligonucleotide directed mutagenesis (Higuchi et al. 1988) in combination with PIPE cloning strategy (Klock and Lesley, 2009). The mutation primers used to generate Cys point mutations in the lambda light chain are listed in Table 12. The secretion of antibody 14090 is also directed by the synthetic 24 amino acid signal sequence: MKTFILLLWVLLLWVIFLLPGATA (SEQ ID NO: 99). Sequences of antibody 14090 Cys constructs were confirmed by DNA sequencing. The sequence for the constant region of human wild-type lambda light chain is shown as SEQ ID NO:91. The encoded protein sequences of seven Cys mutant constructs in the light chain (SEQ ID NO:92 to SEQ ID NO:98) are shown in Table 13. Subsequent examples will show that these Cys mutants are efficiently conjugated with an ADC payload. Because all of these mutants are in the constant region of the human lambda light chain, these conjugation sites can readily be transferred to other antibodies with lambda light chains.

TABLE 11

Sequence ID numbers of trastuzumab heavy chain Cys constructs used for cloning of the variable region of antibody 14090.
Sequence ID NO: of trastuzumab HC Cys construct

| |
|---|
| SEQ ID NO: 5 |
| SEQ ID NO: 8 |
| SEQ ID NO: 9 |
| SEQ ID NO: 10 |
| SEQ ID NO: 18 |
| SEQ ID NO: 48 |
| SEQ ID NO: 50 |

TABLE 12

Nucleotide sequences of primers used in mutagenesis of seven Cys mutant constructs in lambda light chain of human IgG1.

| Mutation sites | Primer name | Sequence | SEQ ID NO. |
|---|---|---|---|
| LC-A143C | Seq-0017 | CCGGGATGCGTGACAGTGGCCTGG AAGGCAGATAGC | 276 |
| | Seq-0018 | TGTCACGCATCCCGGGTAGAAGTCA CTTATGAGACA | 277 |
| LC-T145C | Seq-0019 | GCCGTGTGTGTGGCCTGGAAGGCA GATAGCAGCCCC | 278 |
| | Seq-0020 | GGCCACACACACGGCTCCCGGGTA GAAGTCACTTAT | 279 |
| LC-A147C | Seq-0021 | ACAGTGTGTTGGAAGGCAGATAGC AGCCCCGTCAAG | 280 |
| | Seq-0022 | CTTCCAACACACTGTCACGGCTCCC GGGTAGAAGTC | 281 |
| LC-K156C | Seq-0023 | CCCGTCTGTGCGGGAGTGGAGACC ACCACACCCTCC | 282 |
| | Seq-0024 | TCCCGCACAGACGGGGCTGCTATCT GCCTTCCAGGC | 283 |
| LC-V159C | Seq-0025 | GCGGGATGTGAGACCACCACACCC TCCAAACAAAGC | 284 |
| | Seq-0026 | GGTCTCACATCCCGCCTTGACGGGG CTGCTATCTGC | 285 |
| LC-T163C | Seq-0027 | ACCACCTGTCCCTCCAAACAAAGCA ACAACAAGTAC | 286 |
| | Seq-0028 | GGAGGGACAGGTGGTCTCCACTCC CGCCTTGACGGG | 287 |
| LC-5168C | Seq-0029 | AAACAATGCAACAACAAGTACGCG GCCAGCAGCTAT | 288 |
| | Seq-0030 | GTTGTTGCATTGTTTGGAGGGTGTG GTGGTCTCCAC | 289 |

TABLE 13

Amino acid sequence of the constant region of Cys mutant constructs in antibody 14090 lambda light chain. SEQ ID NO: 91 is the sequence for the constant region of wild-type human lambda light chain SEQ ID NO: 91 to SEQ ID NO: 98 indicate the sequences of the 7 Cys mutants in the constant region of human lambda light chain of antibody 14090.

SEQ ID NO: 91
QPKAAPSVTLFPPSSEELQANKATLVCLISDFYPGAVTVAWKADSSPVKAG
VETTTPSKQSNNKYAASSYLSLTPEQWKSHRSYSCQVTHEGSTVEKTVAPT
ECS

SEQ ID NO: 92
QPKAAPSVTLFPPSSEELQANKATLVCLISDFYPGCVTVAWKADSSPVKAG
VETTTPSKQSNNKYAASSYLSLTPEQWKSHRSYSCQVTHEGSTVEKTVAPT
ECS

SEQ ID NO: 93
QPKAAPSVTLFPPSSEELQANKATLVCLISDFYPGAVCVAWKADSSPVKAG
VETTTPSKQSNNKYAASSYLSLTPEQWKSHRSYSCQVTHEGSTVEKTVAPT
ECS

SEQ ID NO: 94
QPKAAPSVTLFPPSSEELQANKATLVCLISDFYPGAVTVCWKADSSPVKAG
VETTTPSKQSNNKYAASSYLSLTPEQWKSHRSYSCQVTHEGSTVEKTVAPT
ECS

SEQ ID NO: 95
QPKAAPSVTLFPPSSEELQANKATLVCLISDFYPGAVTVAWKADSSPVCAG
VETTTPSKQSNNKYAASSYLSLTPEQWKSHRSYSCQVTHEGSTVEKTVAPT
ECS

SEQ ID NO: 96
QPKAAPSVTLFPPSSEELQANKATLVCLISDFYPGAVTVAWKADSSPVKAG
CETTTPSKQSNNKYAASSYLSLTPEQWKSHRSYSCQVTHEGSTVEKTVAPT
ECS

SEQ ID NO: 97
QPKAAPSVTLFPPSSEELQANKATLVCLISDFYPGAVTVAWKADSSPVKAG
VETTCPSKQSNNKYAASSYLSLTPEQWKSHRSYSCQVTHEGSTVEKTVAPT
ECS

SEQ ID NO: 98
QPKAAPSVTLFPPSSEELQANKATLVCLISDFYPGAVTVAWKADSSPVKAG
VETTTPSKQCNNKYAASSYLSLTPEQWKSHRSYSCQVTHEGSTVEKTVAPT
ECS

Example 5. Expression and Purification of Cys Mutant Antibodies in 293 Freestyle™ Cells Cys mutants of the trastuzumab antibody were expressed in 293 Freestyle™ cells by co-transfecting heavy chain and light chain plasmids using transient transfection method as described previously (Meissner, et al., *Biotechnol Bioeng.* 75:197-203 (2001)). The DNA plasmids used in co-transfection were prepared using Qiagen plasmid preparation kit according to manufacturer's protocol. 293 Freestyle™ cells were cultured in suspension in Freestyle™ expression media (Invitrogen) at 37° C. under 5% $CO_2$. On the day before transfection, cells were split to $0.7 \times 10^6$ cells/ml into fresh media. On the day of transfection, the cell density typically reached $1.5 \times 10^6$ cells/ml. The cells were transfected with a mixture of heavy chain and light chain plasmids at the ratio of 1:1 using PEI method (Meissner et al., 2001). The transfected cells were further cultured for five days. The media from the culture was harvested by centrifugation of the culture at 2000×g for 20 min and filtered through 0.2 micrometer filters. The expressed antibodies were purified from the filtered media using Protein A-Sepharose™ (GE Healthcare Life Sciences). Antibody IgGs were eluted from the Protein A-Sepharose™ column by the elution buffer (pH 3.0) and immediately neutralized with 1 M Tris-HCl (pH 8.0) followed by a buffer exchange to PBS.

Figure 6:
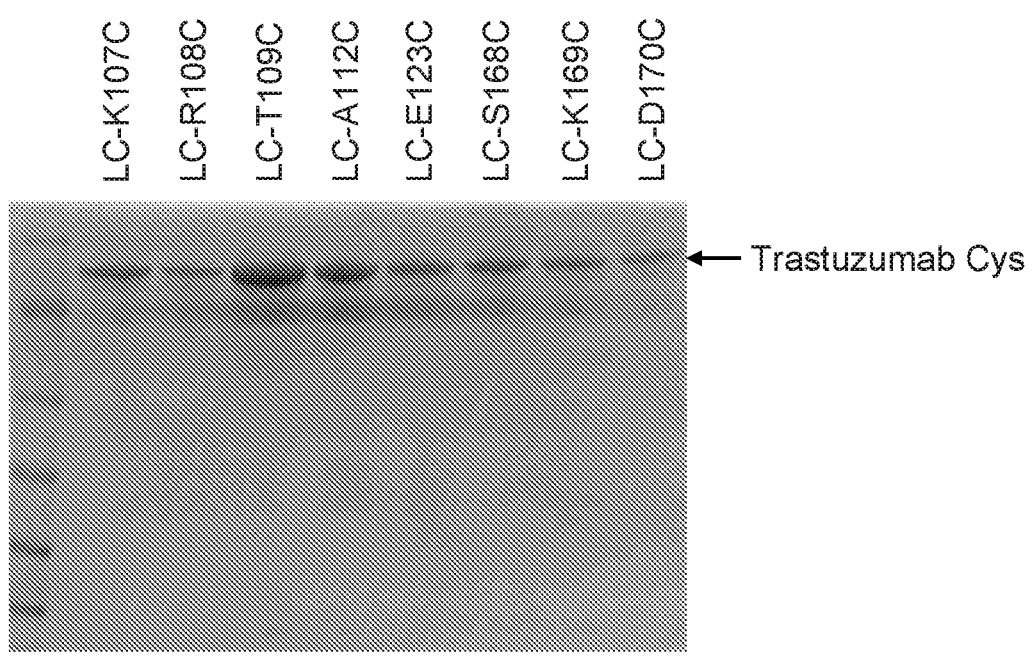
FIG. 6. Analysis of trastuzumab Cys antibodies by non-reducing SDS-PAGE.
Figure 7:
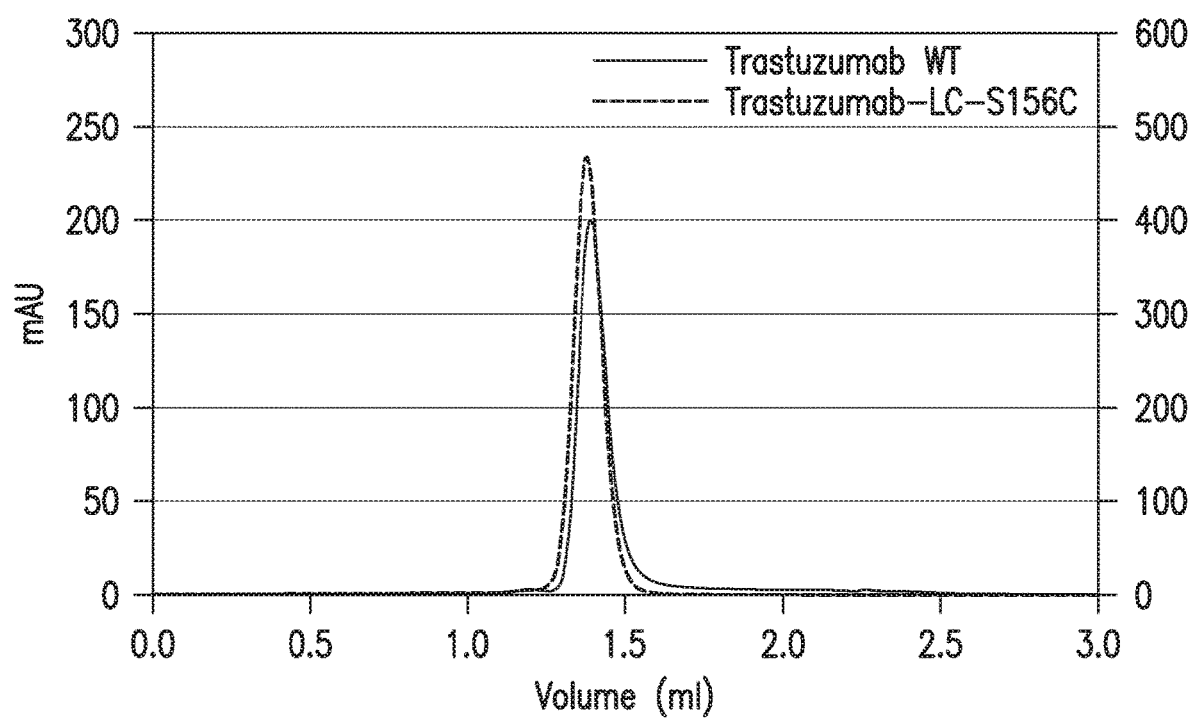
FIG. 7. Size exclusion chromatography of the trastuzumab LC-S156C mutant antibody (dashed line) and wild-type trastuzumab (solid line).
Figure 8A:
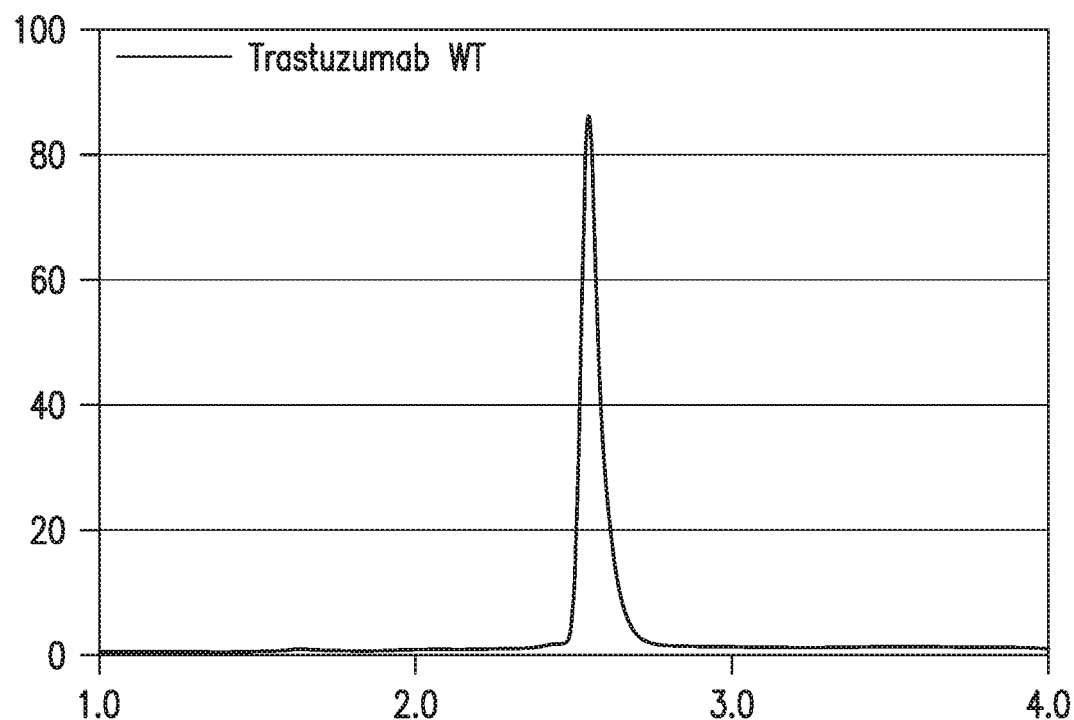
FIG. 8A-FIG. 8B. Analysis of wild-type trastuzumab (A) and the trastuzumab LC-E158C mutant antibody (B) by reverse phase high pressure liquid chromatography (RP-HPLC).
Figure 8B:
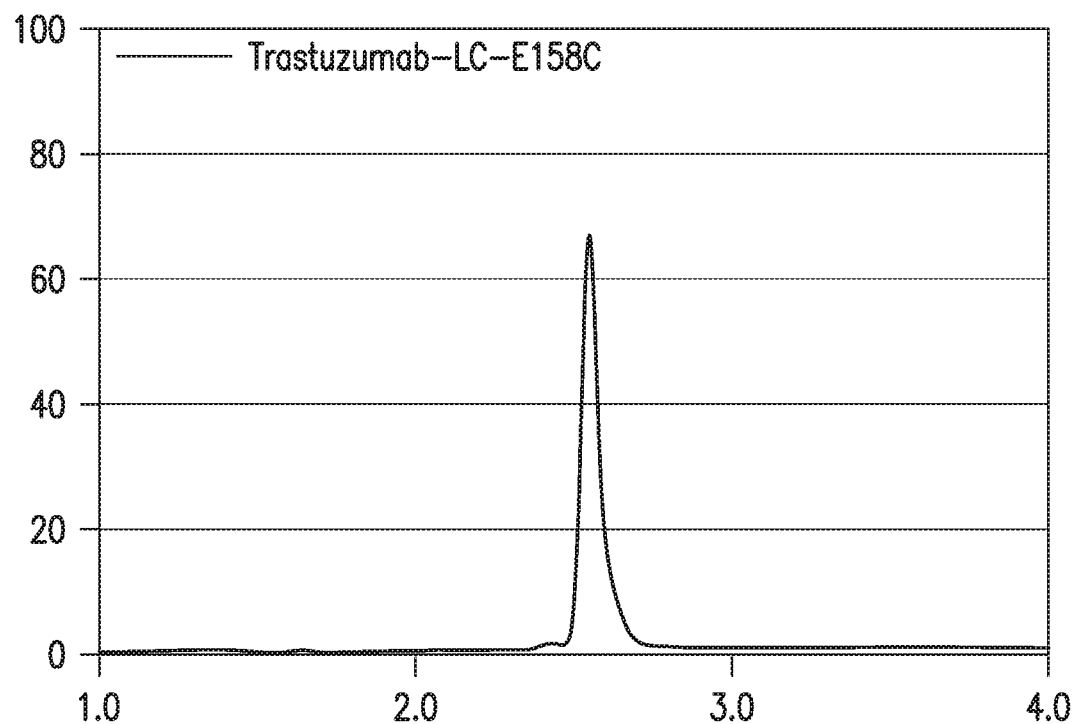
Figure 9:
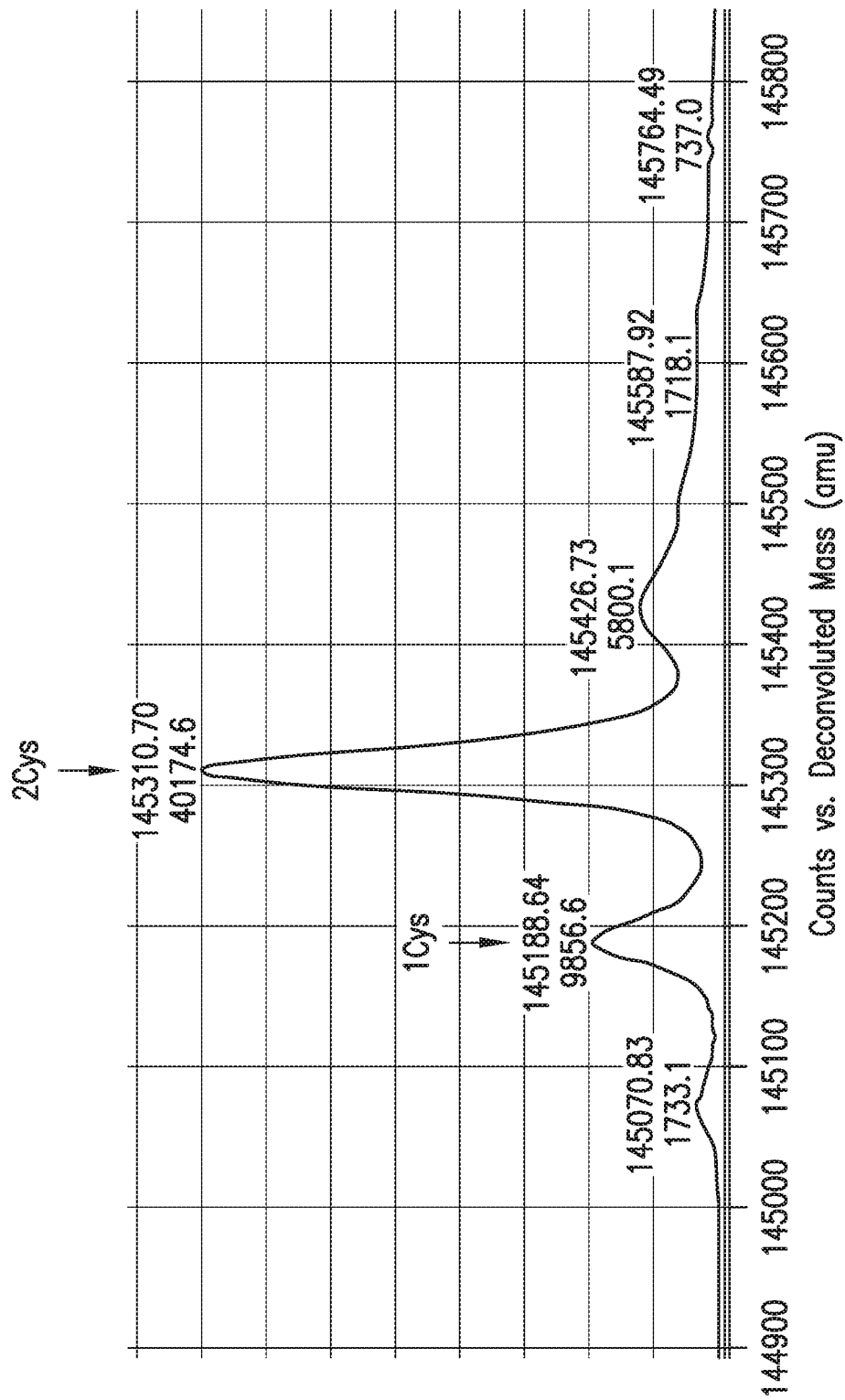
FIG. 9. MS analysis of trastuzumab LC-R108C mutant antibody after Protein A purification (intact MS).

Expression levels of 88 Cys trastuzumab mutant antibodies in transiently transfected 293 Freestyle™ are similar to that of wild-type trastuzumab, with an average yield at 18.6 mg/L+/−9.5 mg/L (Table 14), suggesting that single point mutations in the selected sites did not significantly alter retention of the expressed antibody by the cells' secretion machinery. Analysis of the purified trastuzumab Cys mutant antibodies using non-reducing SDS PAGE indicates that the Cys mutant antibodies did not form oligomers disulfide-linked by the engineered cysteines (FIG. 6). Size exclusion chromatography (FIG. 7) further supported the conclusion that all Cys mutant trastuzumab antibodies are monomeric. HPLC reverse phase analysis of the mutant antibodies also suggests that majority of the Cys mutant antibodies are indistinguishable from wild-type trastuzumab in terms of retention time and homogeneity (FIG. 8). Analysis of non-reduced deglycosylated full length trastuzumab LC-R108C by mass spectrometry (intact LC-MS) revealed that the majority of the antibody was modified by two cysteines (FIG. 9 and Table 15). These observations are consistent with a previous publication indicating that the thiol group of the engineered cysteine in the trastuzumab Cys mutant antibodies is modified by cysteine when expressed in 293 Freestyle™ cells, and that the modification needs to be removed by reducing reagents before conjugation with any thiol reactive reagents (Chen, et al., *mAbs* 1:6, 563-571, 2009).

The Cys mutants of antibody 14090 were also expressed in in 293 Freestyle™ cells by co-transfecting HC and LC plasmids using PEI method as described (Meissner et al., 2001). The expression levels of the Cys mutants of antibody 14090 are similar to that of wild-type antibody 14090 (Table 16).

TABLE 14

Yield of trastuzumab Cys mutant antibodies transiently expressed in 293 Freestyle ™ cells. Yields were measured by UV absorbance at 280 nm after Protein A purification.

| trastuzumab Cys mutant | Purified Ab (mg/L) |
|---|---|
| HC-S117C | 46.9 |
| HC-S119C | 22.5 |
| HC-K121C | 22.1 |
| HC-S124C | 17.8 |
| HC-S132C | 30.9 |
| HC-S134C | 18.6 |
| HC-S136C | 21.2 |
| HC-T139C | 25.9 |
| HC-E152C | 13.0 |
| HC-P153C | 10.8 |
| HC-T155C | 18.4 |
| HC-S157C | 16.9 |
| HC-T164C | 20.2 |
| HC-S165C | 20.6 |
| HC-T169C | 8.2 |
| HC-P171C | 24.6 |
| HC-L174C | 15.2 |
| HC-S176C | 13.4 |
| HC-S177C | 30.0 |
| HC-P189C | 11.7 |
| HC-K205C | 13.3 |
| HC-S207C | 2.5 |
| HC-D212C | 26.5 |
| HC-K246C | 12.0 |
| HC-E258C | 18.7 |
| HC-E269C | 6.3 |
| HC-K273C | 20.7 |
| HC-N286C | 15.0 |
| HC-K288C | 20.9 |
| HC-K290C | 20.0 |
| HC-R292C | 21.0 |
| HC-E293C | 31.2 |
| HC-E294C | 37.5 |
| HC-K320C | 23.6 |
| HC-K322C | 35.1 |
| HC-K326C | 28.0 |
| HC-A330C | 27.1 |
| HC-E333C | 10.3 |
| HC-K334C | 14.0 |
| HC-T335C | 7.0 |
| HC-S337C | 6.9 |
| HC-R344C | 32.6 |
| HC-R355C | 30.1 |
| HC-K360C | 32.0 |
| HC-Q362C | 20.7 |
| HC-S375C | 33.3 |
| HC-E382C | 35.3 |
| HC-N389C | 28.7 |
| HC-N390C | 34.5 |
| HC-K392C | 28.2 |
| HC-T393C | 6.6 |
| HC-L398C | 5.1 |
| HC-S400C | 4.1 |
| HC-D413C | 27.6 |
| HC-S415C | 10.6 |
| HC-V422C | 5.0 |
| LC-K107C | 11.0 |
| LC-R108C | 27.0 |
| LC-T109C | 13.1 |
| LC-A112C | 10.5 |
| LC-S114C | 21.2 |
| LC-D122C | 25.5 |
| LC-E123C | 20.1 |
| LC-T129C | 7.1 |
| LC-R142C | 14.6 |
| LC-E143C | 10.0 |
| LC-K145C | 13.0 |
| LC-N152C | 12.0 |
| LC-L154C | 13.1 |
| LC-S156C | 12.0 |
| LC-S159C | 26.6 |
| LC-E161C | 20.0 |
| LC-E165C | 5.0 |
| LC-S168C | 12.0 |
| LC-K169C | 4.0 |
| LC-D170C | 5.0 |
| LC-S182C | 8.8 |
| LC-K183C | 12.6 |
| LC-K188C | 12.0 |
| LC-K190C | 5.2 |
| LC-V191C | 29.9 |
| LC-T197C | 19.0 |
| LC-Q199C | 16.8 |
| LC-S203C | 26.2 |
| LC-T206C | 27.8 |

TABLE 15

Theoretical and observed mass for trastuzumab LC-R108C antibody after purification from 293 Freestyle ™ cells.

| Antibody species | | Theoretical mass (Da) | Observed mass (Da) |
|---|---|---|---|
| LC-R108C | | 145063 | 145071 |
| LC-R108C-Cys adduct | +1 Cys | 145181 | 145189 |
| LC-R108C-Cys double adduct | +2 Cys | 145299 | 145311 |

TABLE 16

Yield of antibody 14090 Cys mutants transiently expressed in 293 Freestyle ™ cells.

| Antibody 14090 Cys mutant | Ab yield (mg/L) |
|---|---|
| HC-S124C | 4.72 |
| HC-S136C | 3.64 |
| HC-T139C | 4.59 |
| HC-E152C | 2.93 |
| HC-L174C | 5.26 |
| HC-E258C | 5.86 |
| HC-K360C | 4.86 |
| LC-A143C | 4.63 |
| LC-T145C | 6.98 |
| LC-A147C | 8.37 |
| LC-K156C | 5.74 |
| LC-V159C | 9.67 |
| LC-T163C | 9.98 |
| LC-S168C | 5.61 |

Example 6. Reduction, Re-Oxidation and Conjugation of Cys Mutant Antibodies with MC-MMAF Because engineered Cys in antibodies expressed in mammalian cells are modified by adducts (disulfides) such as glutathione (GSH) and/or Cysteine during their biosynthesis (Chen et al. 2009), the modified Cys in the product as initially expressed is unreactive to thiol reactive reagents such as maleimido or bromo- or iodo-acetamide groups. To conjugate the engineered cysteine after expression, the glutathione or cysteine adducts need to be removed by reducing these disulfides, which generally entails reducing all of the disulfides in the expressed protein. This can be accomplished by first exposing the antibody to a reducing agent such as dithiothreitol (DTT) followed by a procedure that allows for the re-oxidation of all native disulfide bonds of the antibody to restore and/or stabilize the functional antibody structure. Accordingly, in order to reduce all native disulfide bonds and the disulfide bound between the cysteine or GSH adducts of the engineered cysteine residue, freshly prepared DTT was added to previously purified Cys mutants of trastuzumab and antibody 14090, to a final concentration of 20 mM. After the antibody incubation with DTT at 37° C. for 1 hour, the mixtures were dialyzed at 4° C. against PBS for three days with daily buffer exchange to remove DTT and re-oxidize the native disulfide bonds. An alternative method is to remove the reducing reagents through a desalting column, Sephadex G-25. Once the protein is fully reduced, 1 mM oxidized ascorbate (dehydro-ascorbic acid) is added to the desalted samples and the re-oxidation incubations are carried out for 20 hours. Both methods have produced similar results. However, attempts to follow the re-oxidation protocols previously described in the literature using $CuSO_4$ resulted in protein precipitation. All examples herein use the dialysis protocol described above. Reoxidation restores intra-chain disulfides, while dialysis allows cysteines and glutathiones connected to the newly-introduced cysteine(s) to dialyze away.

Figure 10:
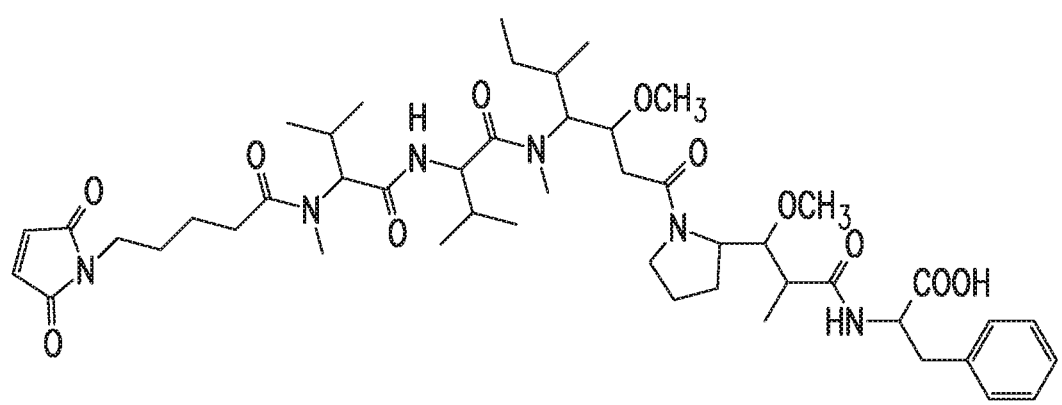
FIG. 10. Structure of MC-MMAF.
Figure 11A:
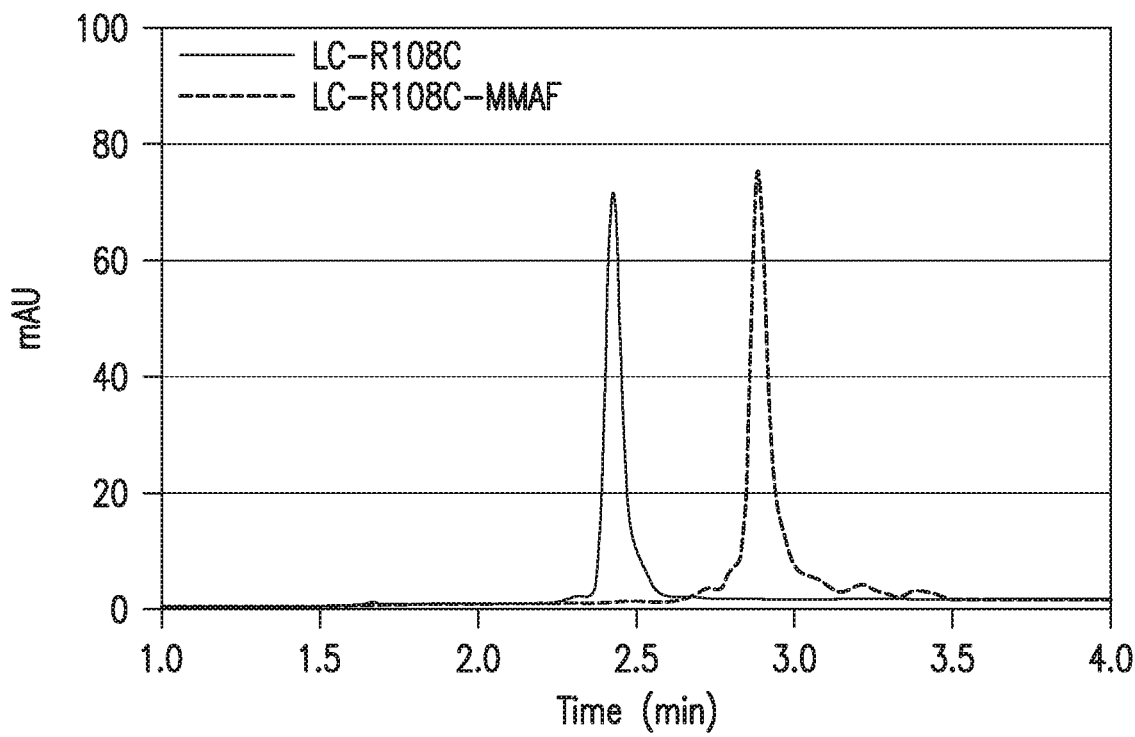
FIG. 11A-FIG. 11D. Analysis of conjugation mixtures of trastuzumab Cys antibodies with MC-MMAF by RP-HPLC. RP-HPLC traces of the conjugation mixtures are shown as dashed lines. RP-HPLC traces of unmodified antibodies are shown as solid lines. A. LC-R108C-MMAF, B. HC-360C-MMAF, C. LC-S156C-MMAF, and D. IC-S275C-MMAF ADC.
Figure 11B:
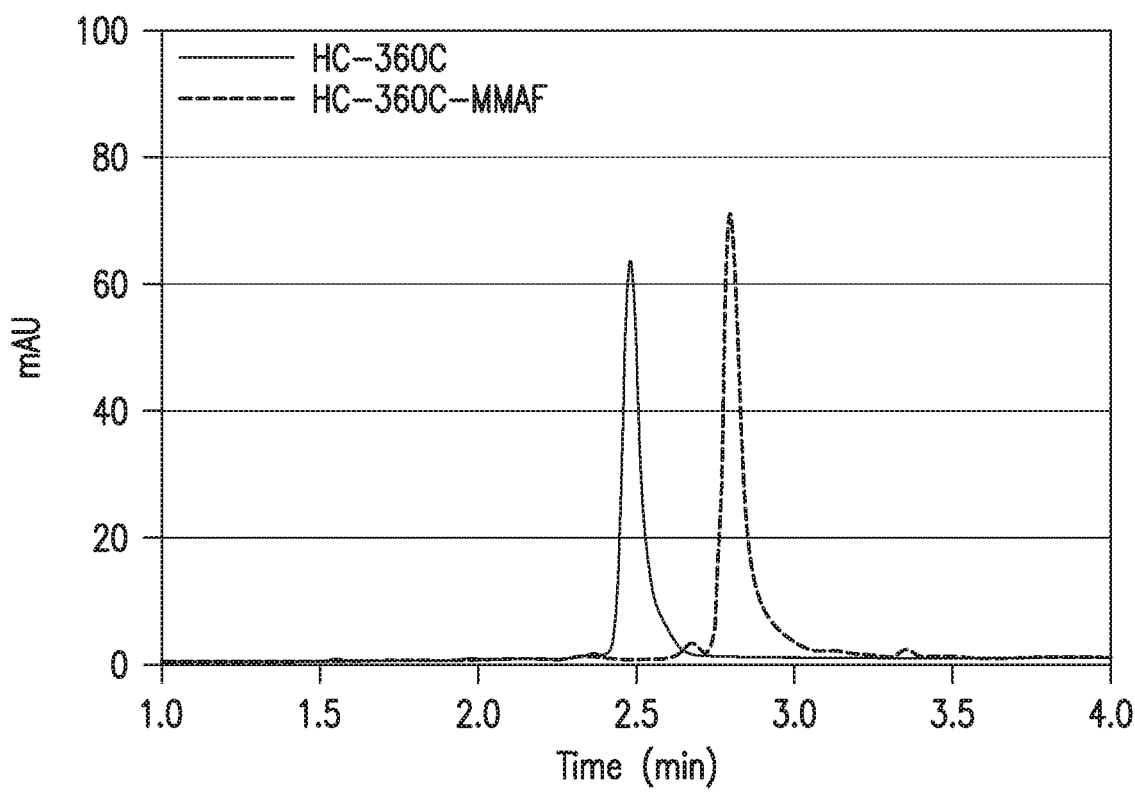
Figure 11C:
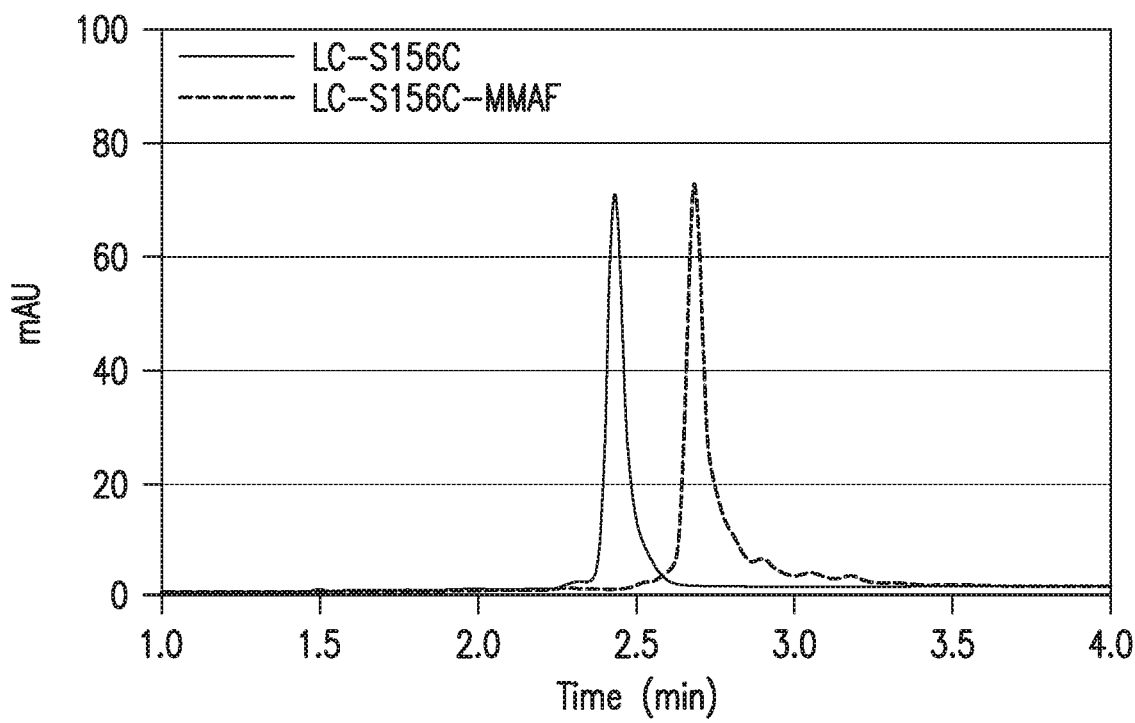
Figure 11D:
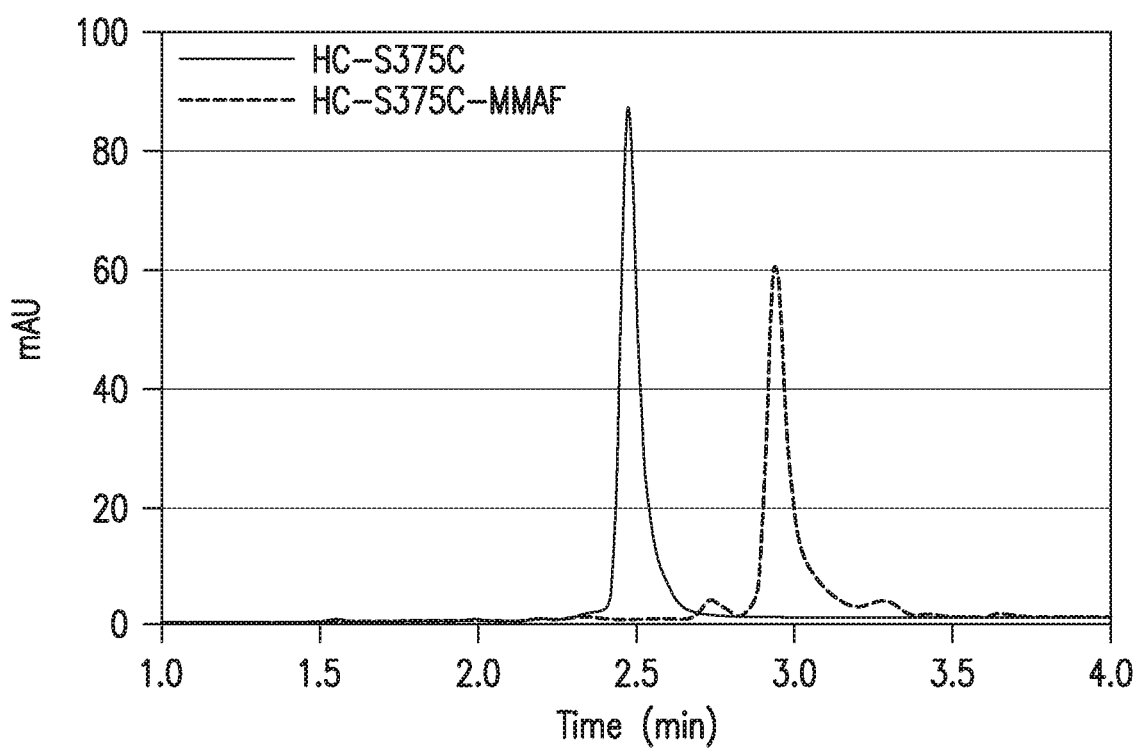

After re-oxidation, the antibodies are ready for conjugation. Maleimide-MMAF (MC-MMAF, 10 equivalents relative to the antibody, FIG. 10) was added to re-oxidized antibodies in PBS buffer (pH7.2). The incubations were carried out from 1 hour to 24 hours. The conjugation process was monitored by reverse-phase HPLC, which is able to separate conjugated antibodies from non-conjugated ones. The conjugation reaction mixtures were analyzed on a PRLP-S 4000A column (50 mm×2.1 mm, Agilent) heated to 80° C. and elution of the column was carried out by a linear gradient of 30-60% acetonitrile in water containing 0.1% TFA at a flow rate of 1.5 ml/min. The elution of proteins from the column was monitored at 280 nm, 254 nm and 215 nm. The reverse-phase HPLC trace of a typical conjugation mixture is shown in FIG. 11.

Figure 12A:
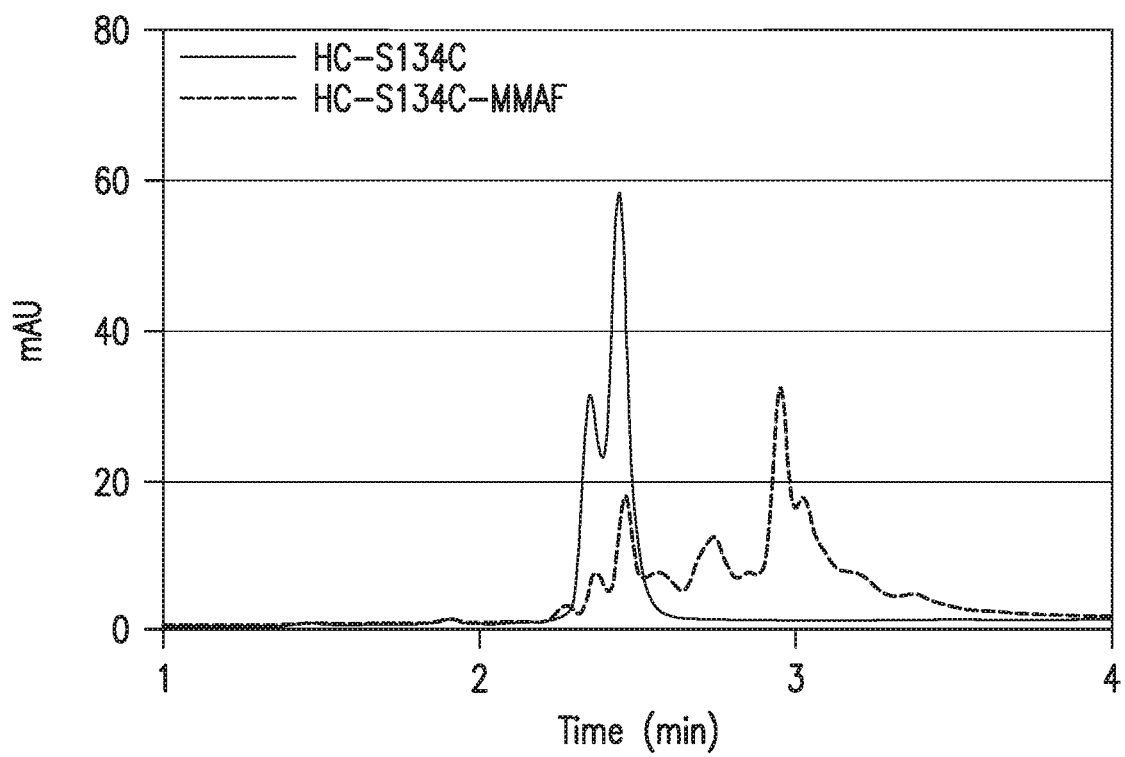
FIG. 12A-FIG. 12B. Analysis of conjugation mixtures of trastuzumab Cys antibodies with MC-MMAF by RP-HPLC. RP-HPLC traces of the conjugation mixtures are shown as dashed lines. RP-HPLC traces of unmodified antibodies are shown as solid lines. A. HC-S134C-MMAF, and B. HC-S136C-MMAF ADC.
Figure 12B:
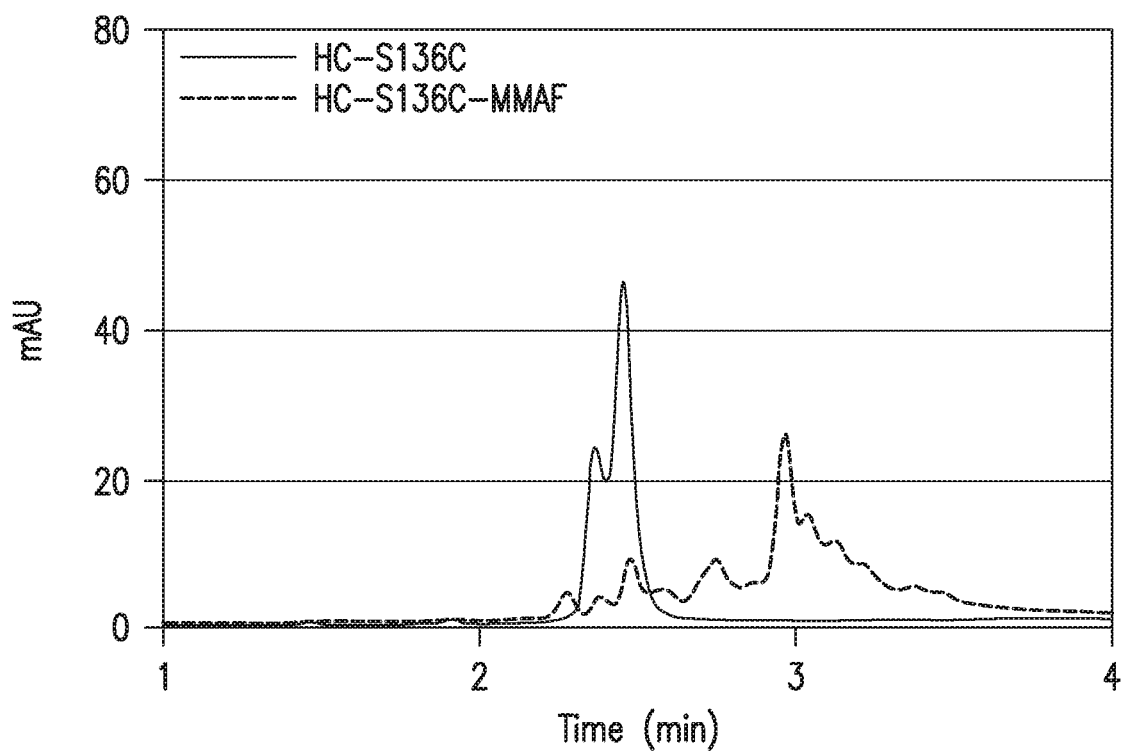

When the conjugation mixtures were analyzed by reverse-phase HPLC, many Cys sites generated homogeneous conjugation products, as suggested by uniform, single peak elution profiles (FIG. 11), while some Cys sites generated heterogeneous conjugation products (FIG. 12). The procedures described above involve reduction and re-oxidation of native disulfide bonds as well as the reduction of bonds between the cysteine and GSH adducts of the engineered cysteine residues. During the re-oxidation process, the engineered cysteine residue may interfere with reforming of the proper native disulfide bonds through a process of disulfide shuffling. This may lead to the formation of mismatched disulfide bonds, either between the engineered cysteine and a native cysteine residue or between incorrectly matched native cysteine residues. Such mismatched disulfide bonds may affect the retention of the antibody on the reverse-phase HPLC column. The mismatch processes may also result in unpaired cysteine residues other than the desired engineered cysteine. Attachment of the maleimide-MMAF to different positions on the antibody affects the retention time differently (see discussion of homogenously conjugated ADCs below). In addition, incomplete re-oxidation will leave the antibody with native cysteine residues that will react with maleimide-MMAF in addition to the desired conjugation with the engineered cysteine residue. Any process that hinders proper and complete formation of the native disulfide bonds will result in a complex HPLC profile (FIG. 11) upon conjugation to Maleimide-MMAF. The yield of the uniform ADC as measured by UV absorption of the unpurified reaction mixtures, varied depending on the Cys mutations (Table 17). Using the reduction/re-oxidation protocol and conjugation procedures described above 65 of the 88 Cys mutant trastuzumab antibodies resulted in homogeneous conjugation products and these sites are advantageous sites for Cys replacements to be made when making cysteine-engineered antibodies for conjugation.

These 65 Cys-MMAF ADCs were analyzed in details in various assays: Differential scanning fluorimetry (DSF) was used to measure thermal stability. Analytical size exclusion chromatograph (AnSEC) was used to measure aggregation. In vitro antigen dependent cell killing potency was measured by cell viability assays and pharmacokinetics behavior was measured in mice. These assays and the respective results are described in more detail below.

Figure 13:
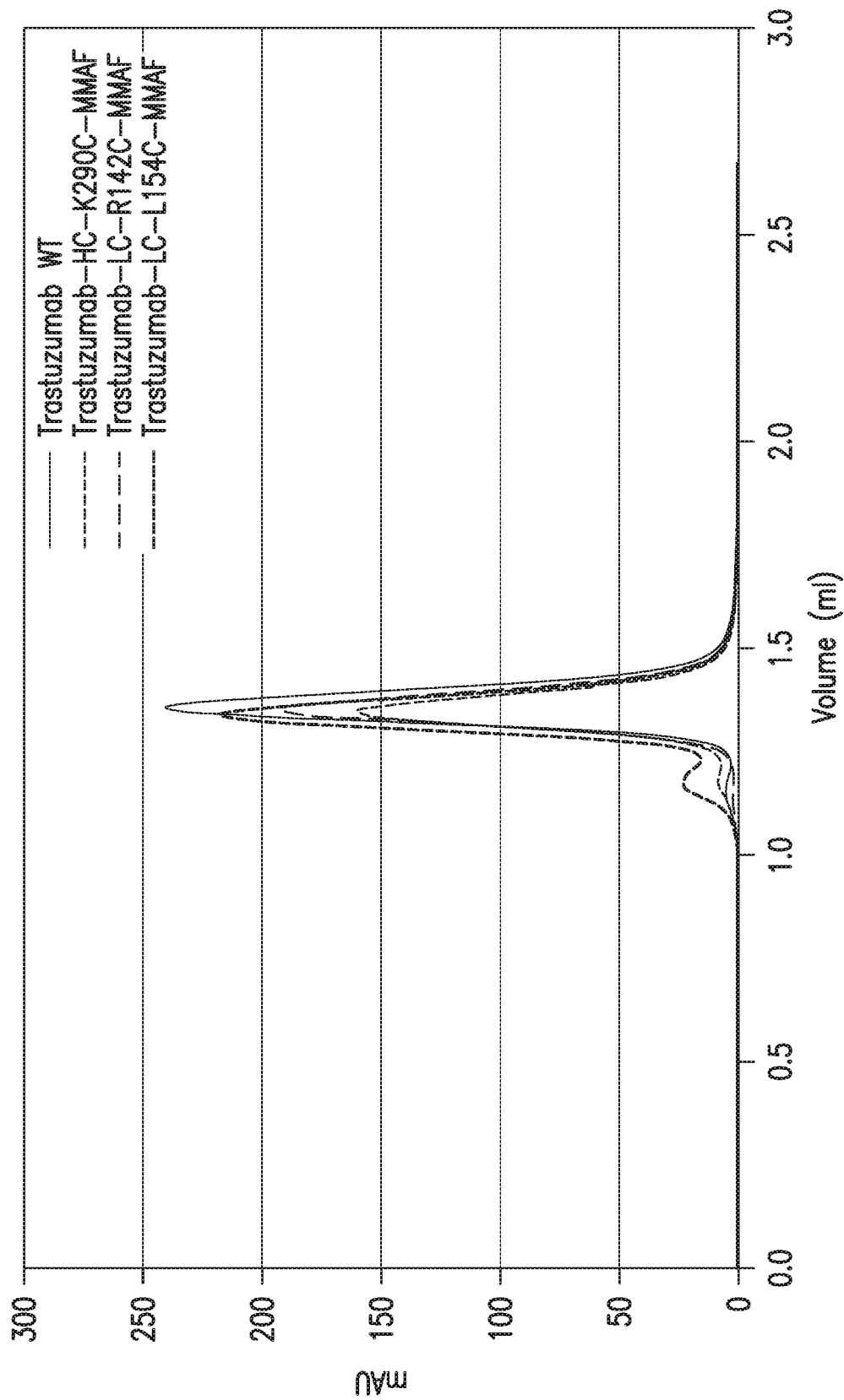
FIG. 13. Analysis of trastuzumab Cys-MMAF ADCs by analytical size-exclusion chromatography (AnSEC). Trastuzumab HC-K290C-MMAF ADC (short dashed line), trastuzumab LC-R142C-MMAF ADC (dashed line), and trastuzumab LC-L154C-MMAF ADC (dotted line) are compared to unmodified wild-type trastuzumab (solid line).

To evaluate the aggregation state of trastuzumab Cys-MMAF ADCs, the ADCs were analyzed in a size exclusion chromatography column (GE, Superdex200, 3.2/30) at a flow rate of 0.1 ml/min in PBS. All 65 Cys-MMAF ADCs were monomeric. The majority of the ADCs contain less than 10% oligomer (FIG. 13, Table 18), indicating that conjugation of MC-MMAF to trastuzumab Cys mutant constructs at the selected sites did not cause aggregation of the antibody.

TABLE 17

Yield of MMAF ADCs generated with trastuzumab Cys mutant constructs. "Hetero" indicates a heterogeneous mixture of species shown in reverse phase HPLC with different retention times.

| trastuzumab Cys-MMAF ADC | Yield (mg/L) | Cys constract | Yield (mg/L) |
|---|---|---|---|
| HC-S117C | 6.9 | HC-R344C | 33.4 |
| HC-S119C | 15.3 | HC-R355C | 24.3 |
| HC-K121C | 4.4 | HC-K360C | 26.5 |
| HC-S124C | 13.2 | HC-Q362C | hetero |
| HC-S132C | Hetero | HC-S375C | 34.3 |
| HC-S134C | Hetero | HC-E382C | 34.9 |
| HC-S136C | Hetero | HC-N389C | hetero |
| HC-T139C | 11.1 | HC-N390C | 33.1 |
| HC-E152C | 7.8 | HC-K392C | 20.8 |
| HC-P153C | 8.2 | HC-T393C | hetero |
| HC-T155C | 12.9 | HC-L398C | 3.4 |
| HC-S157C | 13.5 | HC-S400C | 1.7 |
| HC-T164C | 13.7 | HC-D413C | hetero |
| HC-S165C | Hetero | HC-S415C | hetero |
| HC-T169C | 4.7 | HC-V422C | 3.6 |
| HC-P171C | 14.7 | LC-K107C | 1.6 |
| HC-L174C | 9.1 | LC-R108C | 12.2 |
| HC-S176C | Hetero | LC-T109C | 8.4 |
| HC-S177C | Hetero | LC-A112C | hetero |
| HC-P189C | 7.7 | LC-S114C | 16.9 |
| HC-S191C | Hetero | LC-D122C | Hetero |
| HC-T195C | Hetero | LC-E123C | Hetero |
| HC-T197C | Hetero | LC-T129C | 4.0 |
| HC-K205C | 11.3 | LC-R142C | 11.3 |
| HC-S207C | 1.0 | LC-E143C | 4.0 |
| HC-D212C | Hetero | LC-K145C | 8.7 |
| HC-K246C | 9.0 | LC-N152C | 7.2 |
| HC-E258C | 10.1 | LC-L154C | 1.3 |
| HC-E269C | 5.6 | LC-S156C | 7.2 |
| HC-K274C | 15.3 | LC-S159C | 12.3 |
| HC-N286C | 12.9 | LC-E161C | 12.0 |
| HC-K288C | 14.4 | LC-E165C | 2.0 |
| HC-K290C | 8.0 | LC-S168C | 3.1 |

TABLE 17-continued

Yield of MMAF ADCs generated with trastuzumab Cys mutant constructs. "Hetero" indicates a heterogeneous mixture of species shown in reverse phase HPLC with different retention times.

| trastuzumab Cys-MMAF ADC | Yield (mg/L) | Cys construct | Yield (mg/L) |
|---|---|---|---|
| HC-R292C | 10.3 | LC-K169C | 2.5 |
| HC-E293C | 15.0 | LC-D170C | 2.2 |
| HC-E294C | Hetero | LC-S182C | 7.9 |
| HC-K320C | 18.9 | LC-K183C | 3.8 |
| HC-K322C | 29.1 | LC-K188C | 7.2 |
| HC-K326C | 22.8 | LC-K190C | Hetero |
| HC-A330C | Hetero | LC-V191C | Hetero |
| HC-E333C | 7.4 | LC-T197C | 16.4 |
| HC-K334C | 11.2 | LC-Q199C | 10.3 |
| HC-T335C | 5.2 | LC-S203C | 13.5 |
| HC-S337C | 1.4 | LC-T206C | Hetero |

TABLE 18

Percentage of oligomer in trastuzumab Cys-MMAF ADC preparations as determined by analytical size-exclusion chromatography.

| trastuzumab Cys-MMAF ADC | Oligomer (%) | Conjugation site | Oligomer (%) |
|---|---|---|---|
| HC-S117C | b.d. | HC-R344C | 9.5 |
| HC-S119C | 3.2 | HC-R355C | b.d. |
| HC-K121C | b.d. | HC-K360C | b.d. |
| HC-S124C | b.d. | HC-S375C | b.d. |
| HC-T139C | 4.8 | HC-E382C | b.d. |
| HC-E152C | b.d. | HC-N390C | b.d. |
| HC-P153C | b.d. | HC-K392C | b.d. |
| HC-T155C | b.d. | HC-L398C | b.d. |
| HC-S157C | b.d. | HC-S400C | 9.2 |
| HC-T164C | b.d. | HC-V422C | b.d. |
| HC-T169C | b.d. | LC-K107C | b.d. |
| HC-P171C | b.d. | LC-R108C | b.d. |
| HC-L174C | b.d. | LC-T109C | b.d. |
| HC-P189C | b.d. | LC-S114C | b.d. |
| HC-K205C | b.d. | LC-T129C | b.d. |
| HC-S207C | b.d. | LC-R142C | b.d. |
| HC-K246C | b.d. | LC-E143C | 13.1 |
| HC-E258C | b.d. | LC-K145C | b.d. |
| HC-E269C | b.d. | LC-N152C | b.d. |
| HC-K274C | 11.7 | LC-L154C | 7.3 |
| HC-N286C | 9.2 | LC-S156C | 6.1 |
| HC-K288C | b.d. | LC-S159C | 2.8 |
| HC-K290C | b.d. | LC-E161C | b.d. |
| HC-R292C | b.d. | LC-E165C | b.d. |
| HC-E293C | b.d. | LC-S168C | b.d. |
| HC-K320C | b.d. | LC-K169C | b.d. |
| HC-K322C | b.d. | LC-D170C | b.d. |
| HC-K326C | b.d. | LC-S182C | 6.9 |
| HC-E333C | b.d. | LC-K183C | b.d. |
| HC-K334C | b.d. | LC-K188C | b.d. |
| HC-T335C | b.d. | LC-T197C | b.d. |
| HC-S337C | b.d. | LC-Q199C | 6.3 |
|  |  | LC-S203C | b.d. | b.d.: Below detection limit.

Example 7. In Vitro Thermal Stability Assay of Trastuzumab Cys-MMAF ADCs

Conjugation of MMAF payload to trastuzumab may stabilize or destabilize the antibody, leading to changes in melting temperature of the antibody, which can be determined by differential scanning fluorimetry (DSF) that is based on temperature induced denaturation monitored by an environmentally sensitive dye, such as sypro orange. ADC samples were aliquoted in triplicate to 384-well plates into PBS (6.7 mM sodium phosphate pH7.2; 150 mM NaCl). In each well, 8 μl of 0.25 mg/ml antibody was mixed with 2 μl 25× sypro orange dye (Invitrogen). Plates were sealed and analyzed in a Roche LightCycler 480 system with a temperature ramp from 30 to 85° C. with 20 fluorescence scans recorded per degree C. Melting temperatures were determined from the first derivative of the fluorescence intensity vs. time curves.

Figure 14:
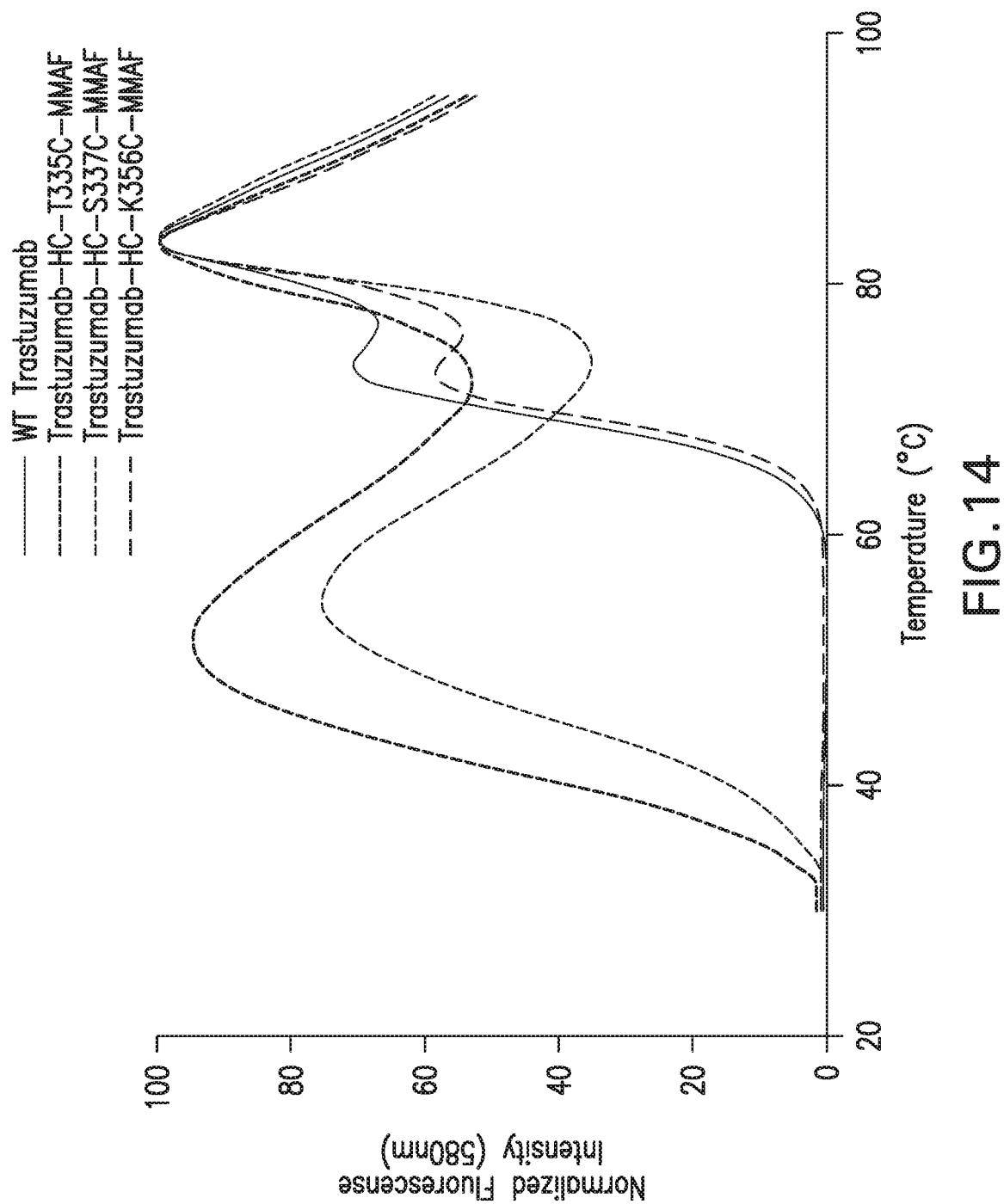
FIG. 14. Thermal melting curve of unmodified wild-type trastuzumab and trastuzumab HC-T335C-MMAF, trastuzumab HC-S337C-MMAF and trastuzumab HC-K360C-MMAF ADCs.

A typical thermal shift assay for wild-type trastuzumab revealed two melting transitions (Tm), Tm1 at 69.7° C. and Tm2 at 81.2° C., respectively (Table 19). When trastuzumab Cys-MMAF ADCs were subjected to protein thermal stability assays, it was evident that conjugation of MC-MMAF to the antibodies induced different Tm changes depending on the sites of conjugation (Table 19). When MC-MMAF was conjugated to majority of the Cys sites in either CH1 or CH3 domains, the resulting ADCs, for example HC-K356C-MMAF, showed a similar pattern as that of wild-type anti-Her with little changes in Tm1 and Tm2. However, when MC-MMAF was conjugated to Cys sites located in the CH2 domain, a decrease in Tm1 was observed for most sites while the Tm2 remained largely unchanged. The Tm1 decrease observed for most CH2 domain Cys-MMAF conjugates ranged from 5° C. to 26° C. The two ADCs with the largest decrease in Tm1 are HC-T335C-MMAF and HC-S337C-MMAF, with Tm1 at 42° C. and 45° C., respectively (FIG. 14). The results indicate that the location of MC-MMAF conjugation can have a significant impact on the stability of the ADCs.

TABLE 19

Melting temperatures Tm1 and Tm2 of trastuzumab Cys-MMAF ADCs observed by differential scanning fluorimetry (DSF).

| trastuzumab Cys-MMAF ADC | HC domain | Tm1 [° C.] | Tm2 [° C.] |
|---|---|---|---|
| wild-type antibody | n.a. | 69.71 | 81.18 |
| HC-S117C | CH1 | 69.09 | 79.85 |
| HC-S119C | CH1 | 69.28 | 78.58 |
| HC-K121C | CH1 | 69.63 | 78.52 |
| HC-S124C | CH1 | 69.27 | 80.56 |
| HC-T139C | CH1 | 69.09 | 80.74 |
| HC-E152C | CH1 | 69.63 | 80.83 |
| HC-P153C | CH1 | 69.71 | 78.52 |
| HC-T155C | CH1 | 69.27 | 80.83 |
| HC-S157C | CH1 | 69.72 | 80.81 |
| HC-T164C | CH1 | 69.17 | 80.7 |
| HC-T169C | CH1 | 68.74 | 80.47 |
| HC-P171C | CH1 | 69.27 | 77.18 |
| HC-L174C | CH1 | 69.89 | 80.03 |
| HC-P189C | CH1 | 69.09 | 81.27 |
| HC-K205C | CH1 | 69.54 | 80.65 |
| HC-S207C | CH1 | 69.00 | 80.65 |
| HC-K246C | CH2 | 64.65 | 80.74 |
| HC-E258C | CH2 | 65.32 | 81.03 |
| HC-E269C | CH2 | 65.36 | 81.01 |
| HC-K274C | CH2 | 67.14 | 81.09 |
| HC-N286C | CH2 | 67.22 | 81.09 |
| HC-K288C | CH2 | 65.54 | 80.83 |
| HC-K290C | CH2 | 69.00 | 80.65 |
| HC-R292C | CH2 | 67.49 | 80.56 |
| HC-E293C | CH2 | 64.34 | 81.03 |
| HC-K320C | CH2 | 60.60 | 80.59 |
| HC-K322C | CH2 | 62.41 | 80.70 |
| HC-K326C | CH2 | 63.05 | 80.74 |
| HC-E333C | CH2 | 63.67 | 80.92 |
| HC-K334C | CH2 | 64.65 | 80.47 |
| HC-T335C | CH2 | 42.93 | 80.04 |
| HC-S337C | CH2 | 45.56 | 80.48 |
| HC-R344C | CH3 | 69.50 | 80.92 |
| HC-R355C | CH3 | 68.18 | 81.25 |
| HC-K360C | CH3 | 69.28 | 80.92 |
| HC-S375C | CH3 | 68.20 | 81.36 |

TABLE 19-continued

Melting temperatures Tm1 and Tm2 of trastuzumab Cys-MMAF ADCs observed by differential scanning fluorimetry (DSF).

| trastuzumab Cys-MMAF ADC | HC domain | Tm1 [° C.] | Tm2 [° C.] |
|---|---|---|---|
| HC-E382C | CH3 | 69.36 | 80.74 |
| HC-N390C | CH3 | 68.73 | 80.92 |
| HC-K392C | CH3 | 67.05 | 80.92 |
| HC-L398C | CH3 | 68.47 | 81.36 |
| HC-S400C | CH3 | 68.65 | 81.27 |
| HC-V422C | CH3 | 69.98 | 81.45 |
| LC-K107C | n.a. | 69.45 | 80.29 |
| LC-R108C | n.a. | 70.10 | n.d.[1] |
| LC-T109C | n.a. | 68.47 | 80.21 |
| LC-T129C | n.a. | 68.47 | 80.12 |
| LC-R142C | n.a. | 69.00 | 78.61 |
| LC-E143C | n.a. | 69.83 | 80.59 |
| LC-K145C | n.a. | 69.00 | 80.65 |
| LC-N152C | n.a. | 67.49 | 81.09 |
| LC-L154C | n.a. | 68.47 | 80.65 |
| LC-S156C | n.a. | 68.83 | 80.47 |
| LC-S159C | n.a. | 69.50 | 79.93 |
| LC-E161C | n.a. | 68.65 | 80.12 |
| LC-E165C | n.a. | 69.27 | 79.76 |
| LC-S168C | n.a. | 69.54 | 79.67 |
| LC-K169C | n.a. | 69.09 | 80.29 |
| LC-D170C | n.a. | 68.83 | 80.12 |
| LC-S182C | n.a | 69.18 | 80.29 |
| LC-K183C | n.a | 69.09 | 80.47 |
| LC-K188C | n.a | 68.74 | 80.65 |
| LC-T197C | n.a | 69.63 | 80.74 |
| LC-Q199C | n.a | 69.54 | 80.21 |
| LC-S203C | n.a | 68.84 | 80.92 | n.d. Not determined because a broad transition in Tm2 prevented accurate Tm determination.,
n.a. Not applicable

Example 8. Cell Proliferation Assays to Measure In Vitro Cell Killing Potency of Cys ADCs Cells that naturally express target antigens or cell lines engineered to express target antigens are frequently used to assay the activity and potency of ADCs. For evaluation of the cell killing potency of trastuzumab ADCs in vitro, two engineered cell lines, MDA-MB231 clone 16 and clone 40, and HCC1954 cells were employed (Clinchy B, Gazdar A, Rabinovsky R, Yefenof E, Gordon B, Vitetta E S. Breast Cancer Res Treat. (2000) 61:217-228). MDA-MB231 clone 16 cells stably express high copy numbers (~5×10$^5$ copies/cell) of recombinant human Her2 while clone 40 expresses low copy numbers (~5×10$^3$ copies/cell) of human Her2. HCC1954 cells endogenously express high level (~5×10$^5$ copies/cell) of human Her2 in the surface. For determination of the cell killing potency of antibody 14090 ADCs, CMK11-5 and Jurkat cells were used. While CMK11-5 cells express a high level of the antigen for antibody 14090 in the cell surface there is no detectable antigen expression in Jurkat cells. An antigen dependent cytotoxic effect should only kill cells that express sufficient antigen in the cell surface and not cells lacking the antigen. The cell proliferation assays were conducted with Cell-Titer-Glo™ (Promega) five days after cells were incubated with various concentrations of ADCs (Riss et al., (2004) Assay Drug Dev Technol. 2:51-62). In some studies, the cell based assays are high throughput and conducted in an automated system (Melnick et al., (2006) Proc Natl Acad Sci USA. 103:3153-3158).

Figure 15A:
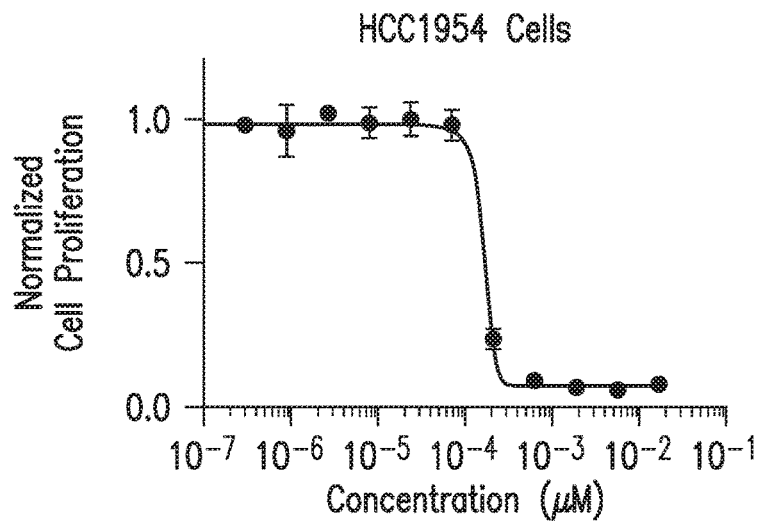
FIG. 15A-FIG. 15C. Cell proliferation assays for trastuzumab LC-S159C-MMAF with A. HCC1954, B. MDA-MB231 clone 16 and C. MDA-MB231 clone 40 cells.
Figure 15B:
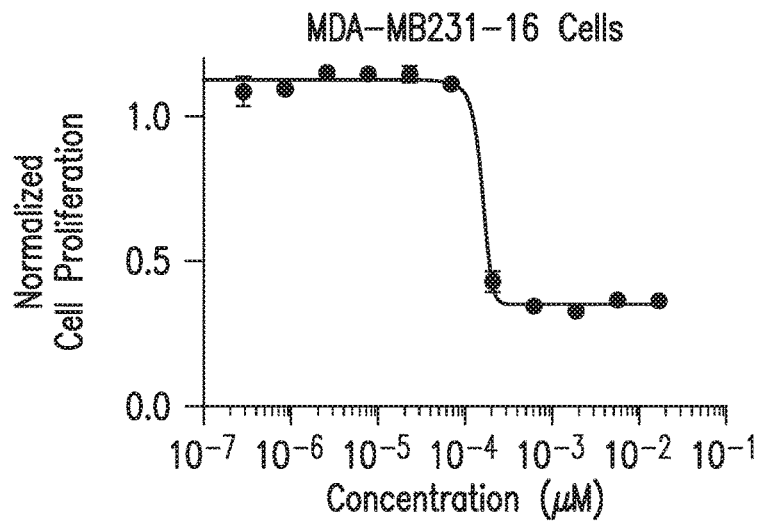
Figure 15C:
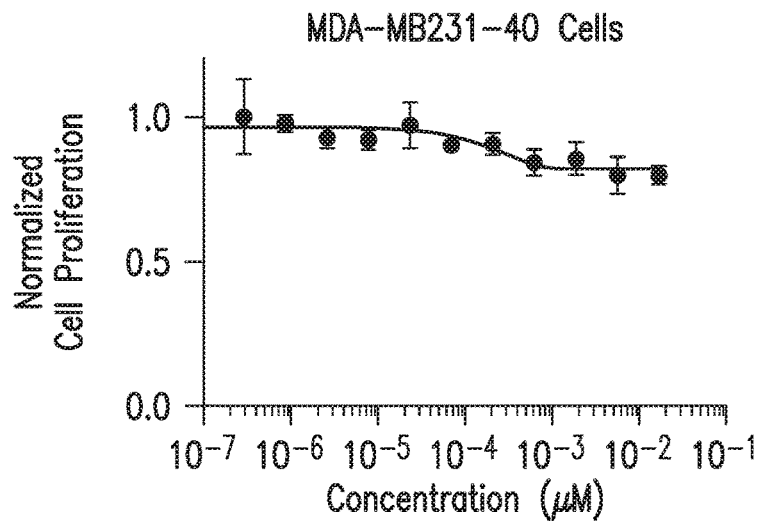
Figure 16:
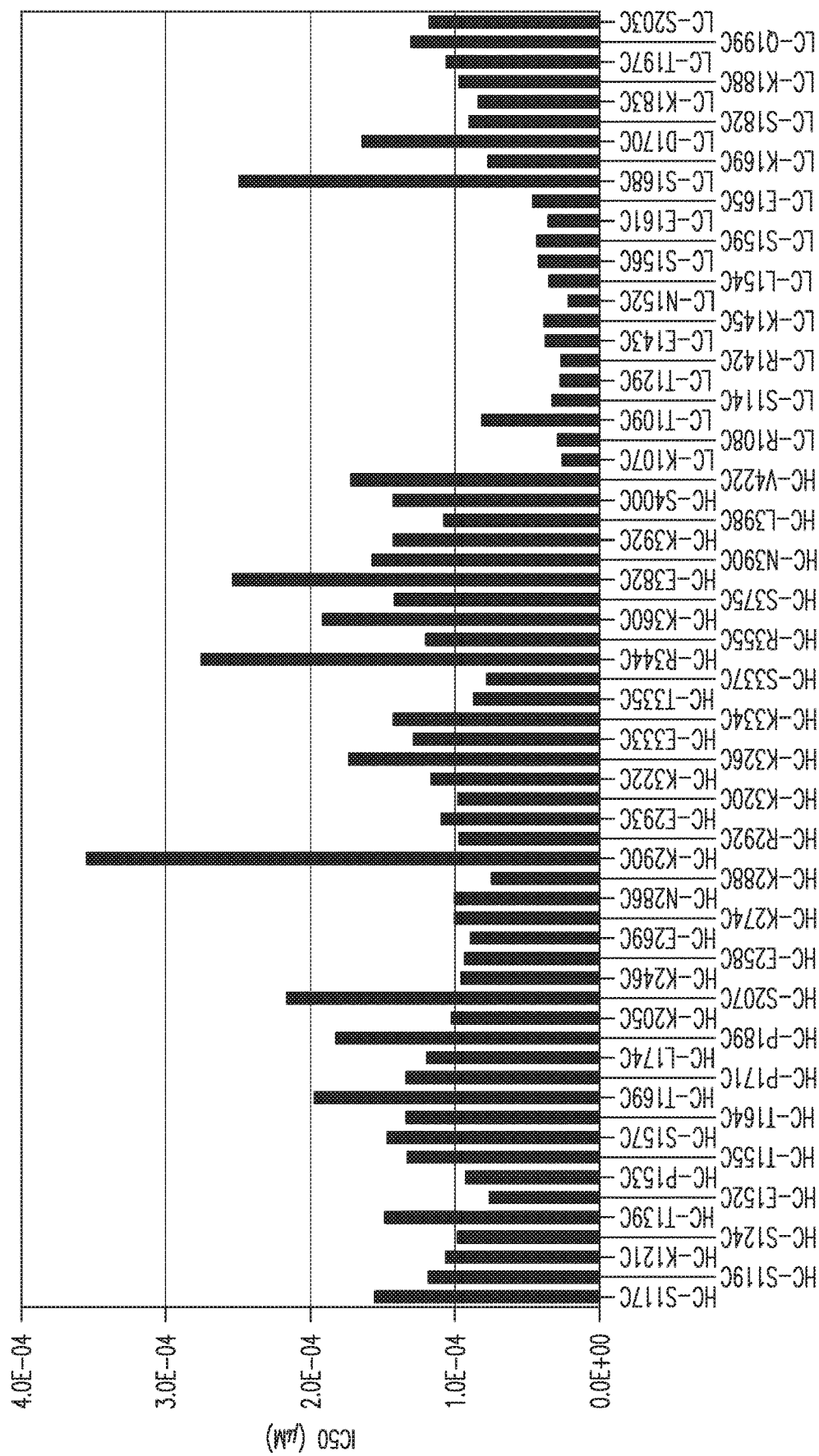
FIG. 16. $IC_{50}$ of trastuzumab Cys-MMAF ADCs in MDA-MB231 clone 16 cell proliferation assay.
Figure 17A:
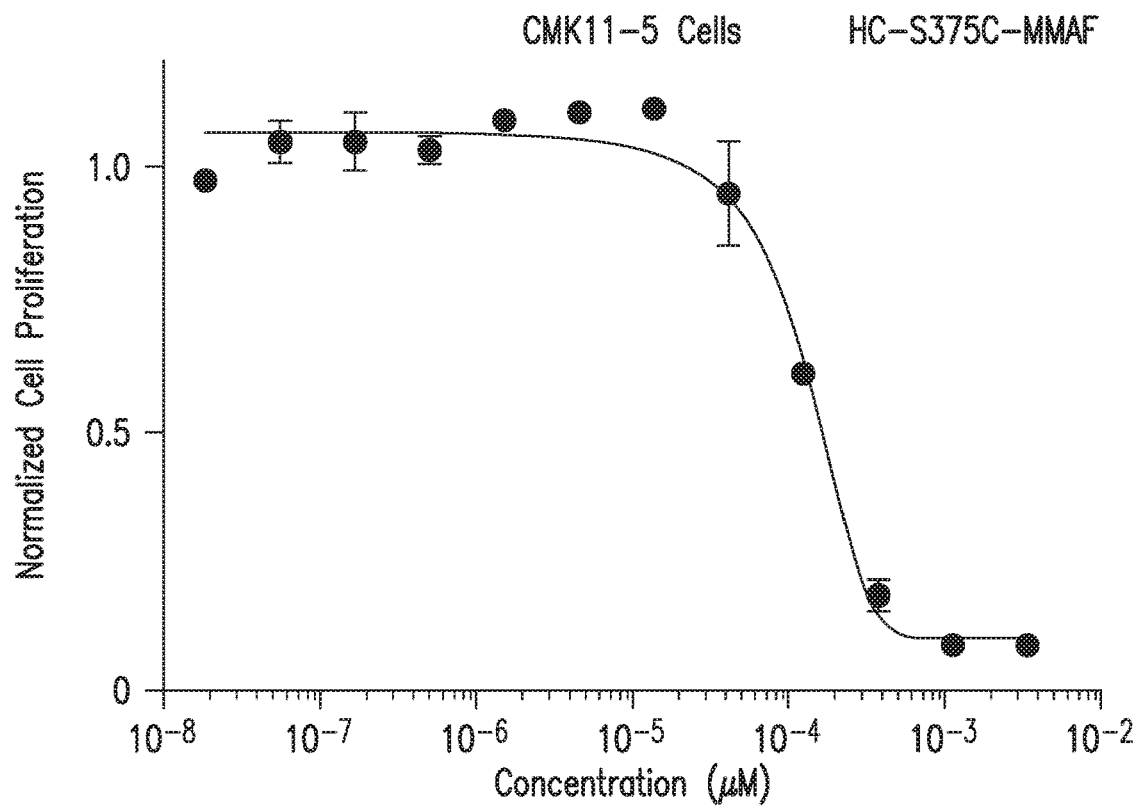
FIG. 17A-FIG. 17B. Cell proliferation assays for Antibody 14090 HC-S375C-MMAF ADC with A. CMK11-5 and B. Jurkat cells.
Figure 17B:
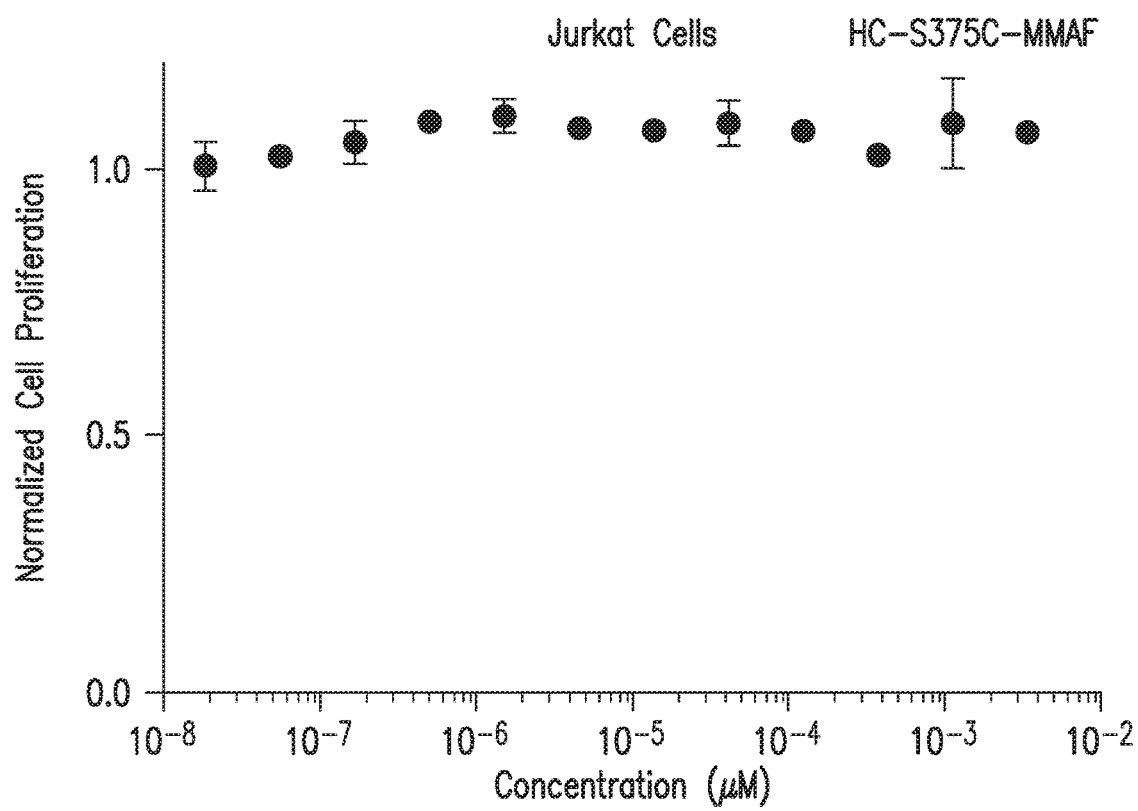
Figure 18A:
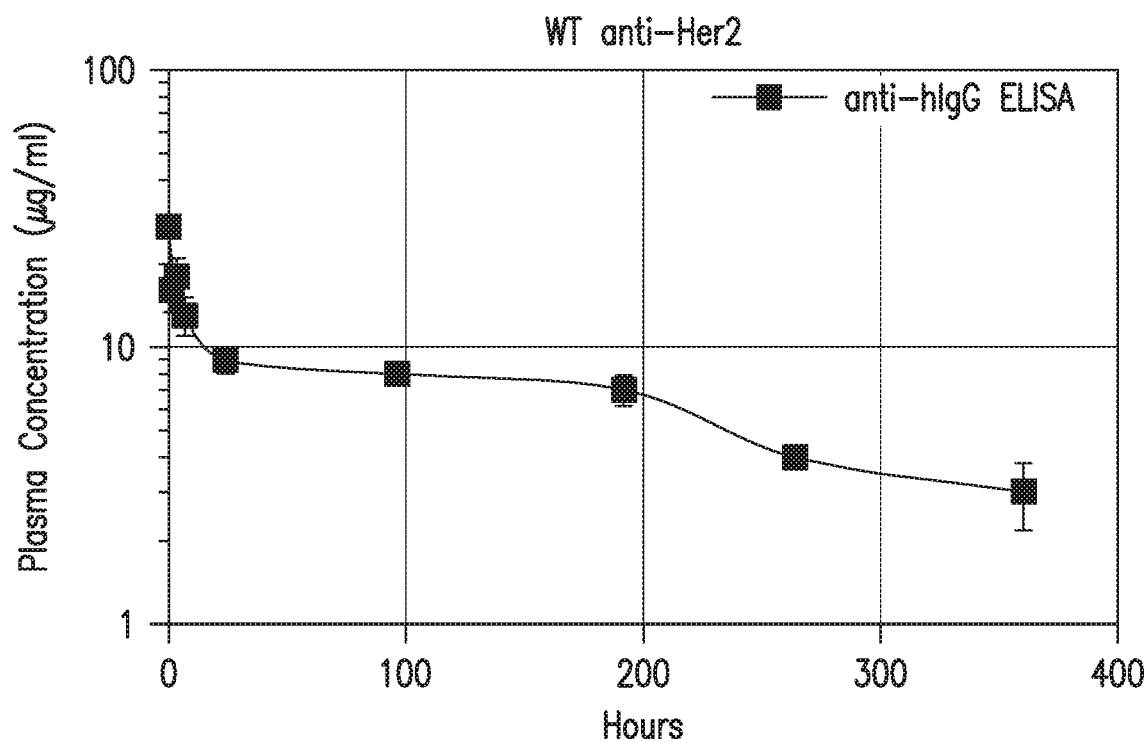
FIG. 18A-FIG. 18E. Pharmacokinetics study of trastuzumab LC-Cys-MMAF ADCs displaying no significant drug lost. A. Wild-type unconjugated trastuzumab, B. LC-K107C-MMAF, C. LC-R108C-MMAF, D. LC-L154C-MMAF, and E. LC-S159C-MMAF ADC.
Figure 18B:
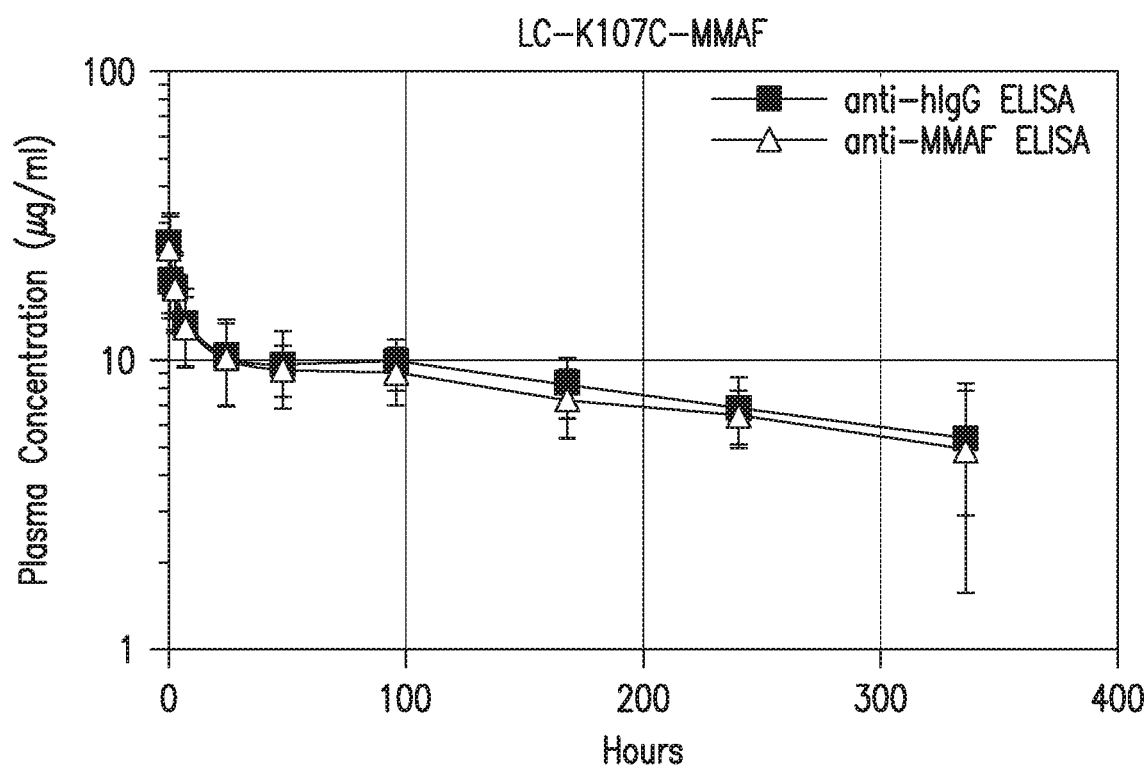
Figure 18C:
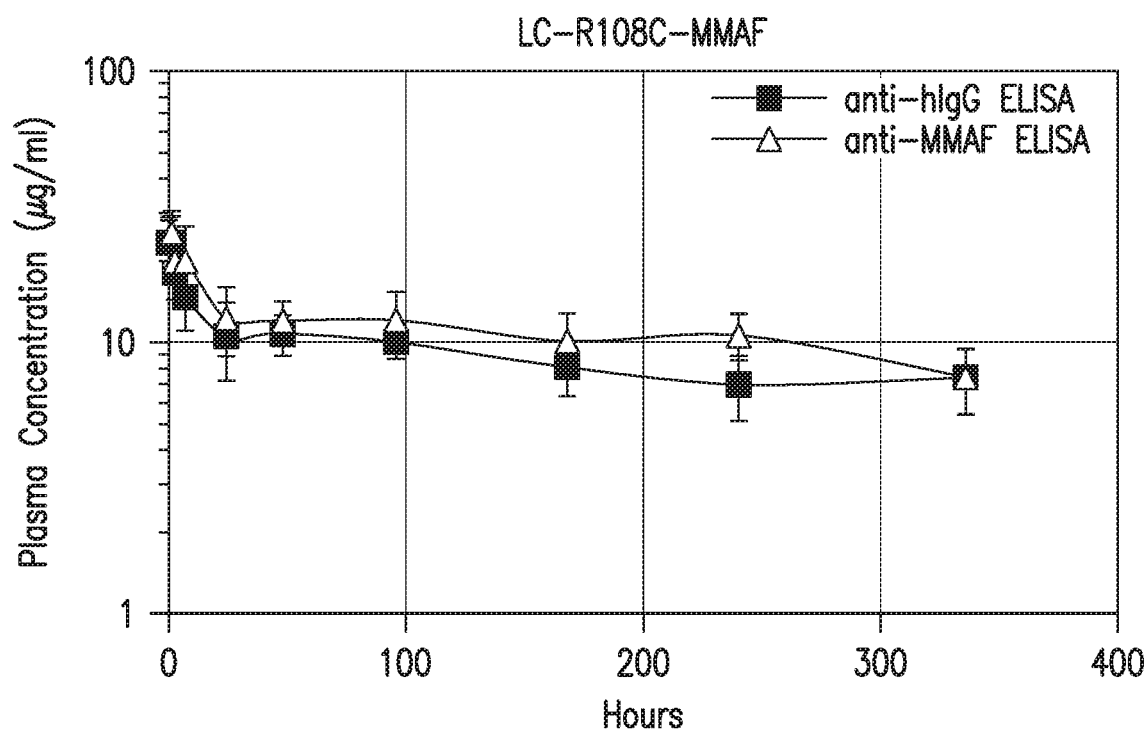
Figure 18D:
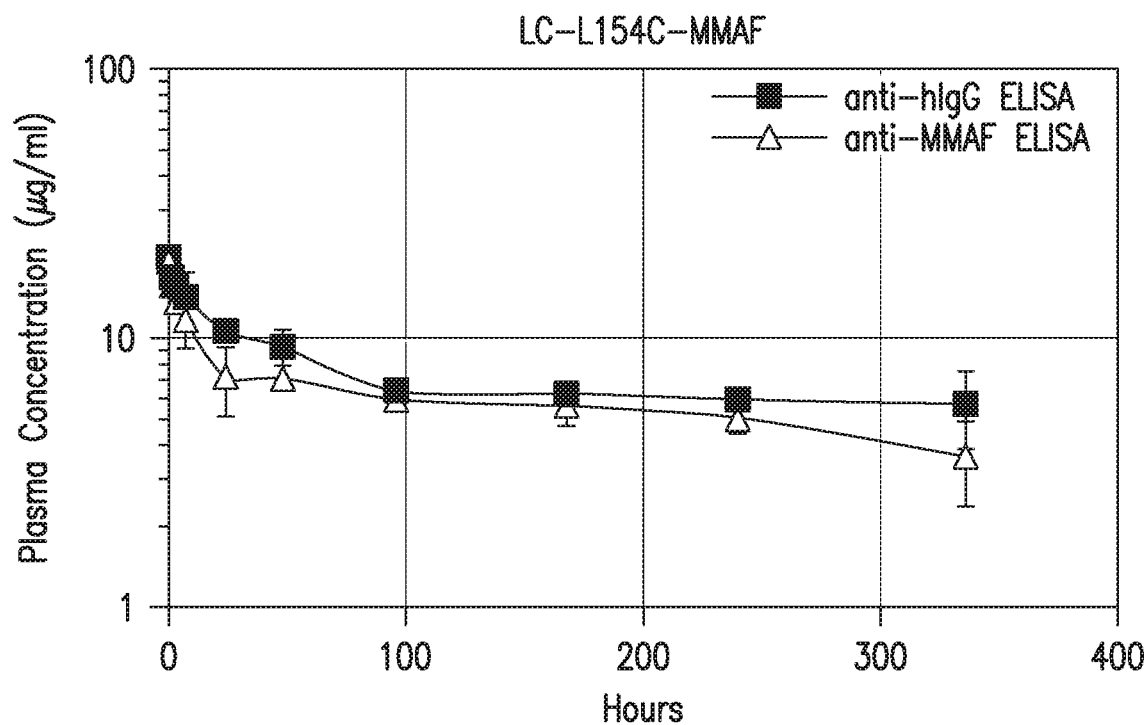
Figure 18E:
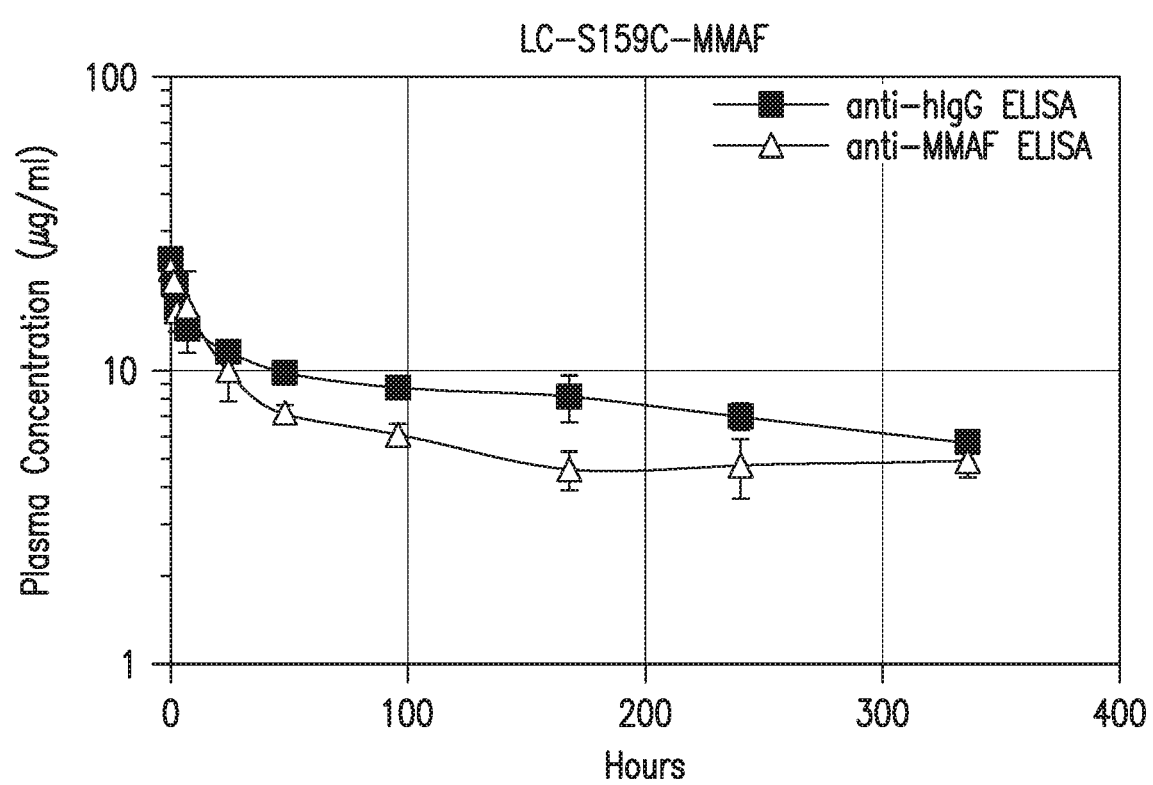
Figure 19A:
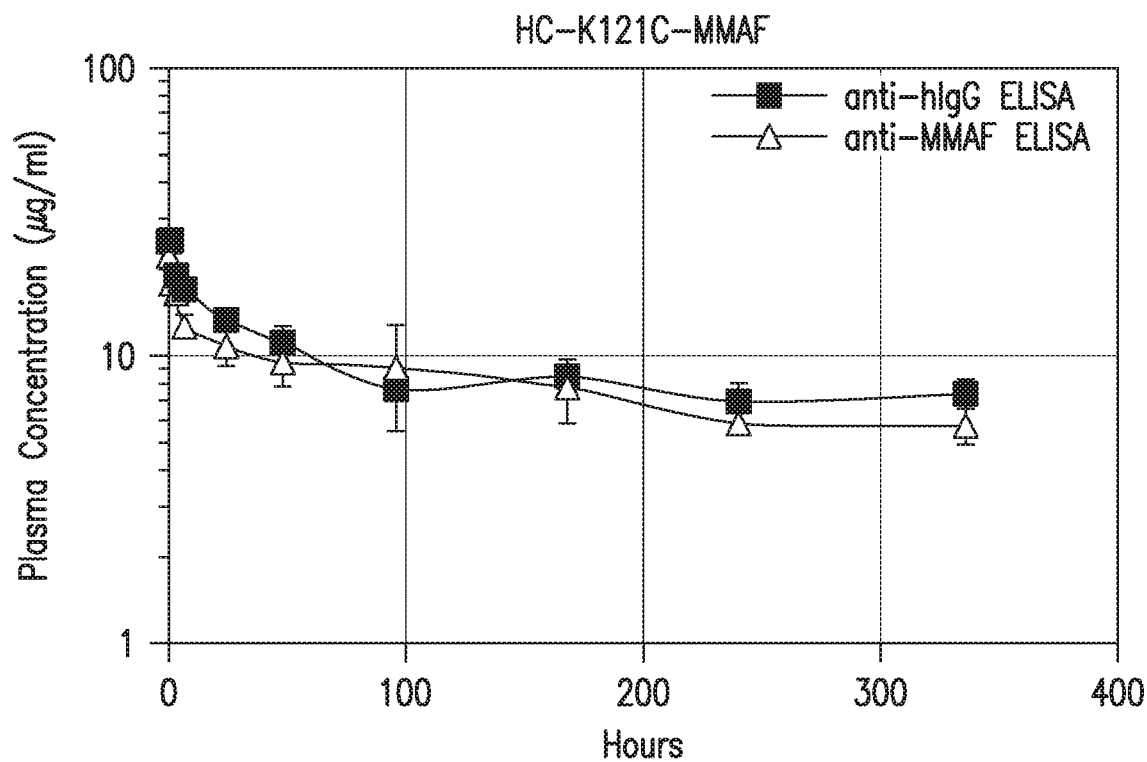
FIG. 19A-FIG. 19D. Pharmacokinetics study of trastuzumab HC-Cys-MMAF ADCs displaying no significant drug lost. A. HC-K121C-MMAD, B. HC-L174C-MMAF, C. HC-E258C-MMAF, and D. HC-R292C-MMAF ADC.
Figure 19B:
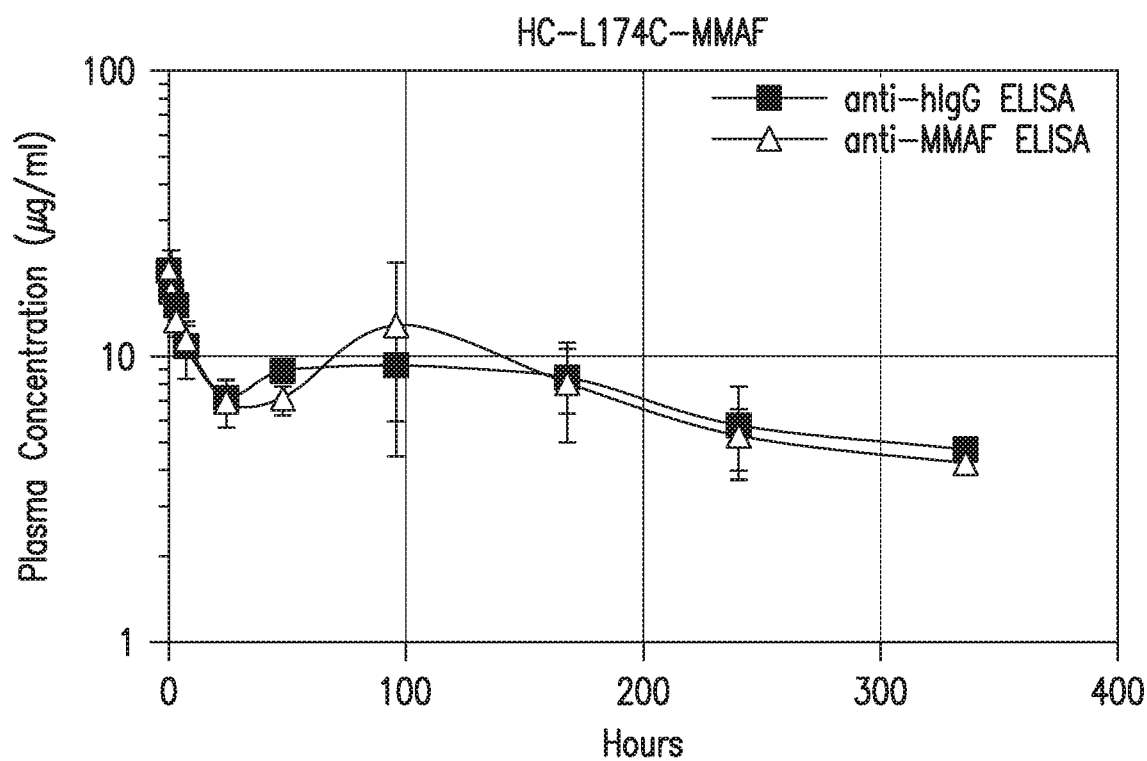
Figure 19C:
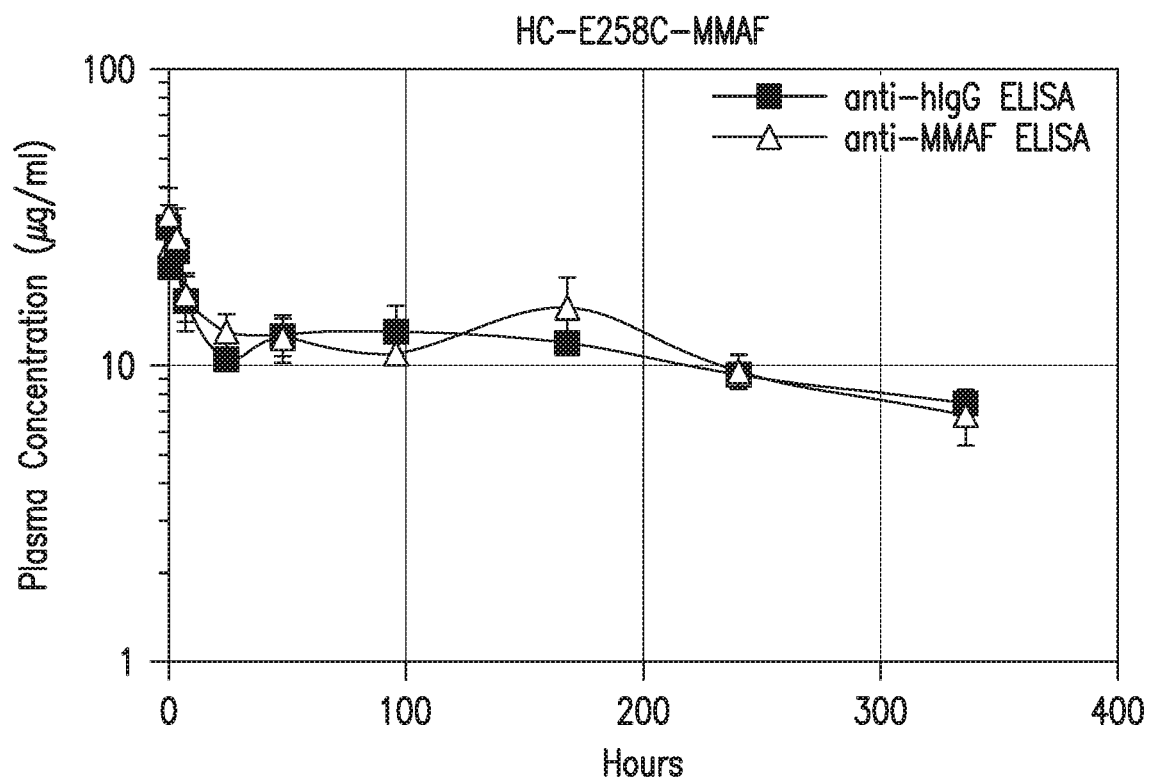
Figure 19D:
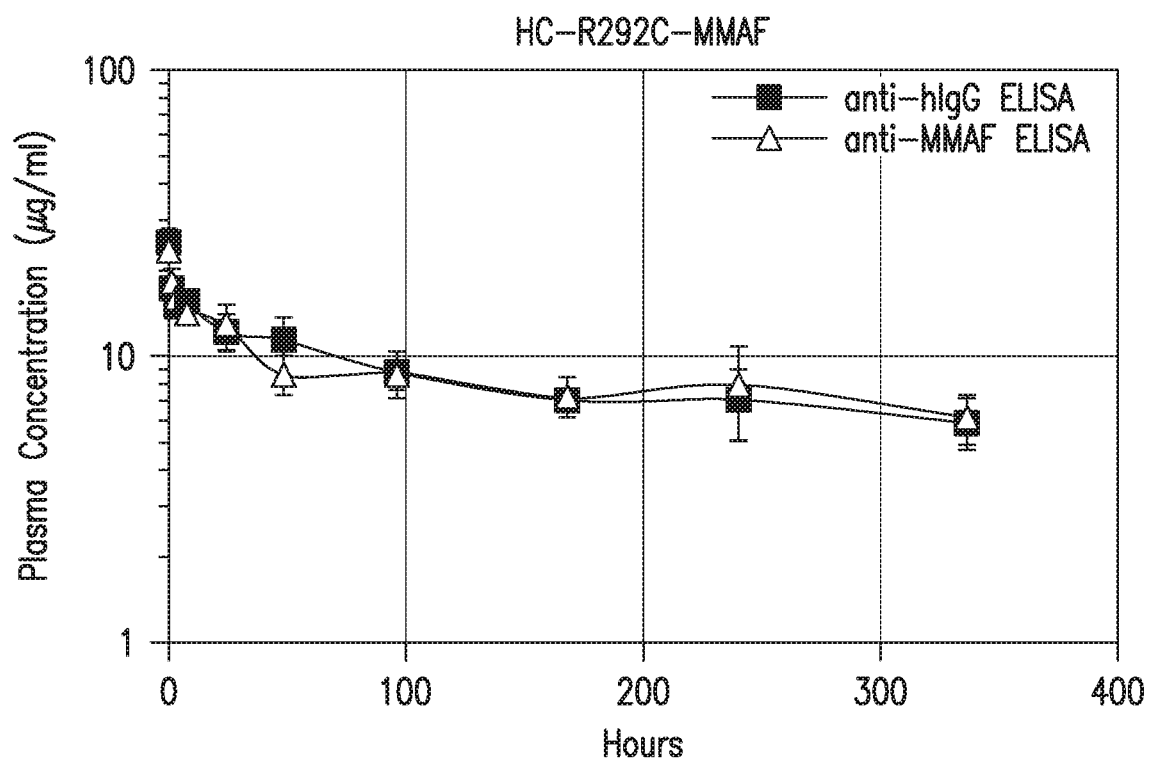
Figure 20A:
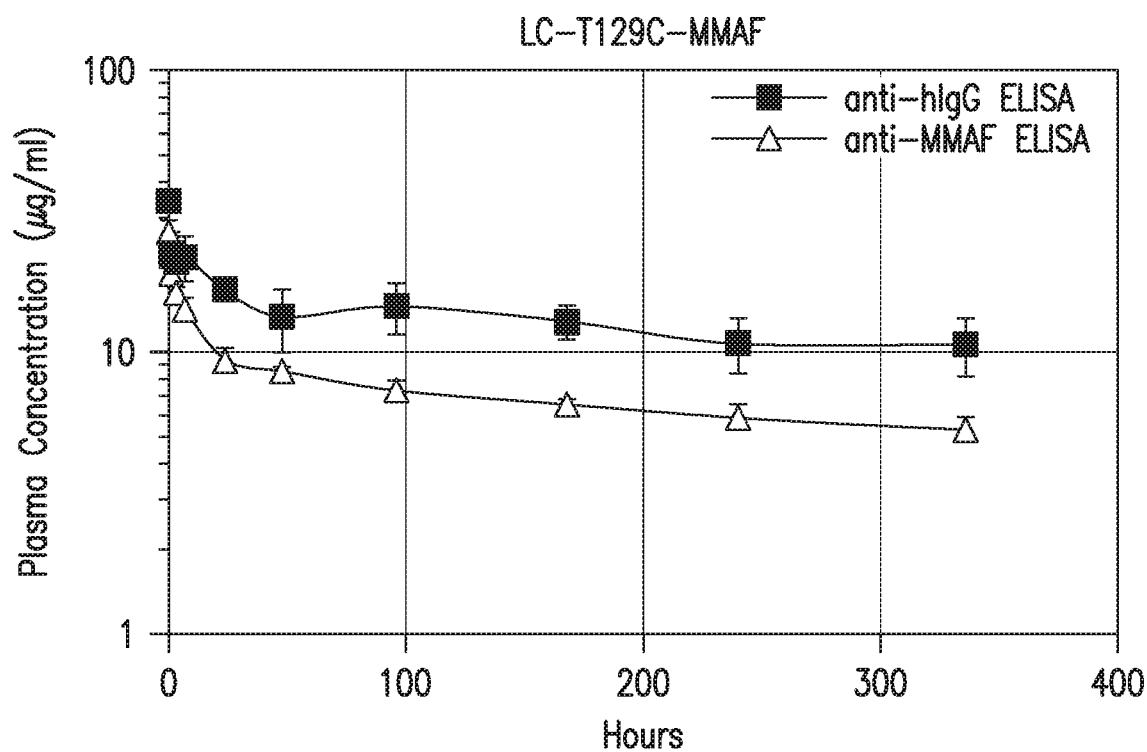
FIG. 20A-FIG. 20D. Pharmacokinetics study of trastuzumab Cys-MMAF ADCs displaying significant drug lost. A. LC-T129C-MMAF, B. LC-E143C-MMAF, C. HC-K246C-MMAF, and D. HC-R344C-MMAF ADC.
Figure 20B:
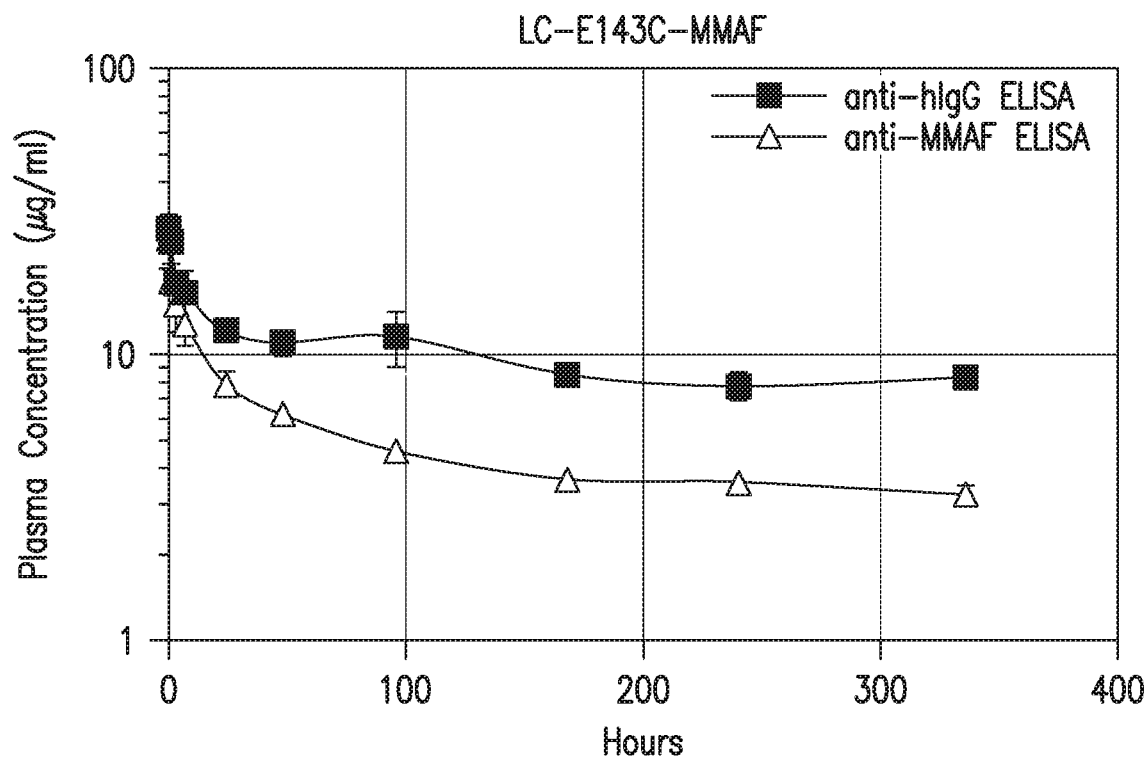
Figure 20C:
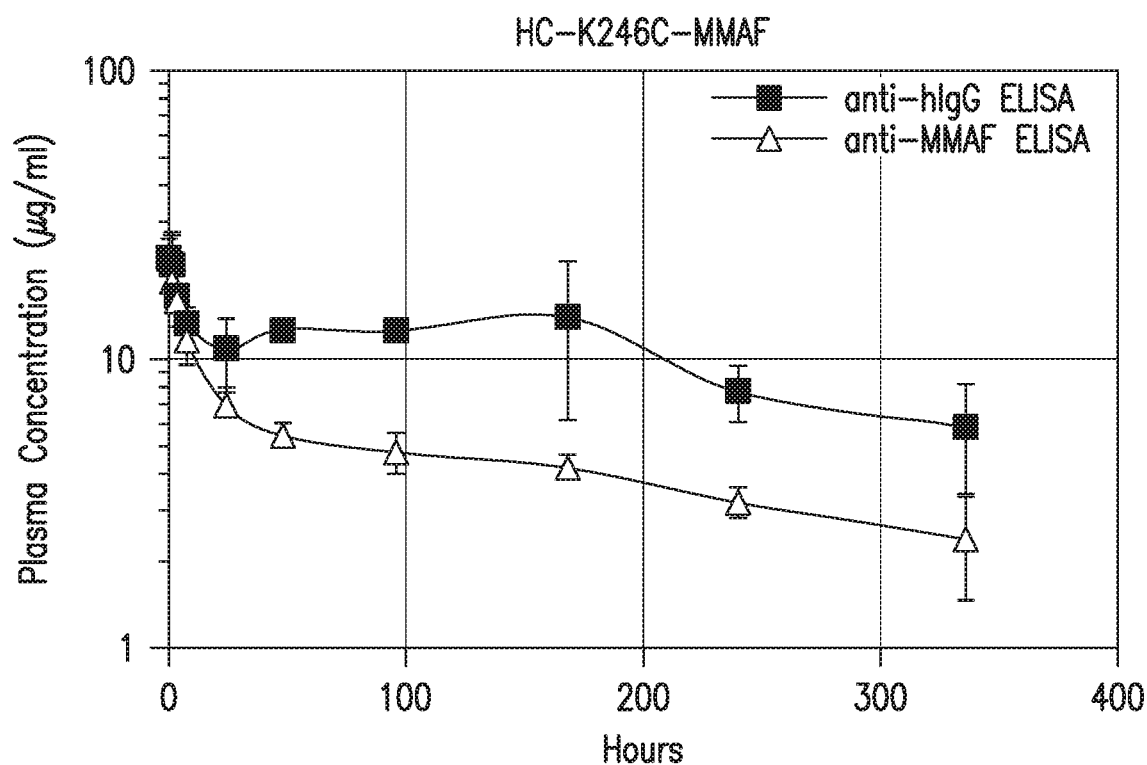
Figure 20D:
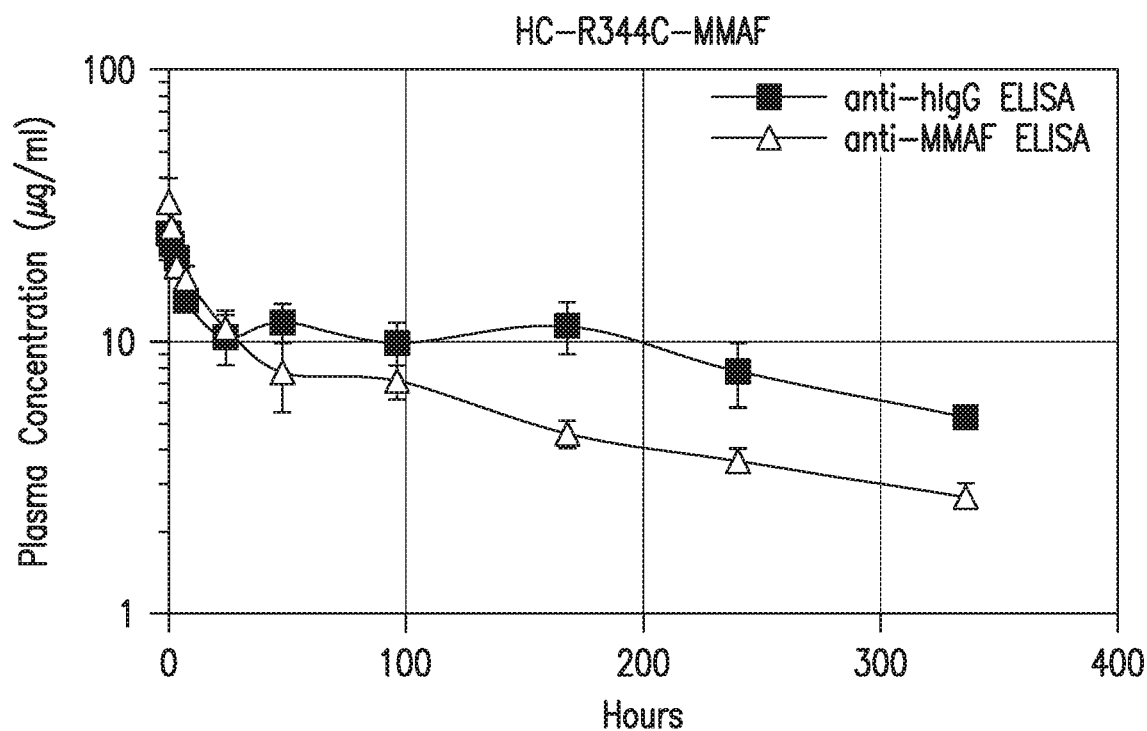

Trastuzumab Cys-MMAF ADCs specifically killed MDA-MB231 clone 16 and HCC1954 but not MDA-MB231 clone 40 cells (FIG. 15). IC$_{50}$ of the trastuzumab Cys-MMAF ADCs in MDA-MB231 clone 16 cell assays ranges from 30 pM to 200 pM (Table 20, FIG. 16). Similarly, antibody 14090 Cys-MMAF ADC displayed antigen dependent cell killing in cell proliferation assays. The antibody 14090 Cys-MMAF ADCs killed antigen expressing CMK11-5 cells but not antigen negative Jurkat cells (FIG. 17). The IC$_{50}$ of the antibody 14090-MMAF ADC in CMK11-5 proliferation assay is in the range of 400 pM to 1 nM (Table 21).

TABLE 20

IC$_{50}$ of trastuzumab Cys-MMAF ADCs in MDA-MB231 clone 16 Her2$^+$ cell proliferation assay.

| trastuzumab Cys-MMAF ADC | IC$_{50}$ (μM) |
|---|---|
| HC-S117C | 1.55E-04 |
| HC-S119C | 1.18E-04 |
| HC-K121C | 1.06E-04 |
| HC-S124C | 9.78E-05 |
| HC-T139C | 1.48E-04 |
| HC-E152C | 7.62E-05 |
| HC-P153C | 9.27E-05 |
| HC-T155C | 1.33E-04 |
| HC-S157C | 1.47E-04 |
| HC-T164C | 1.34E-04 |
| HC-T169C | 1.98E-04 |
| HC-P171C | 1.33E-04 |
| HC-L174C | 1.19E-04 |
| HC-P189C | 1.82E-04 |
| HC-K205C | 1.02E-04 |
| HC-S207C | 2.16E-04 |
| HC-K246C | 9.54E-05 |
| HC-E258C | 9.40E-05 |
| HC-E269C | 8.98E-05 |
| HC-K274C | 9.99E-05 |
| HC-N286C | 9.94E-05 |
| HC-K288C | 7.47E-05 |
| HC-K290C | 3.55E-04 |
| HC-R292C | 9.69E-05 |
| HC-E293C | 1.10E-04 |
| HC-K320C | 9.79E-05 |
| HC-K322C | 1.16E-04 |
| HC-K326C | 1.73E-04 |
| HC-E333C | 1.28E-04 |
| HC-K334C | 1.43E-04 |
| HC-T335C | 8.69E-05 |
| HC-S337C | 7.79E-05 |
| HC-R344C | 2.75E-04 |
| HC-R355C | 1.21E-04 |
| HC-K360C | 1.92E-04 |
| HC-S375C | 1.42E-04 |
| HC-E382C | 2.53E-04 |
| HC-N390C | 1.58E-04 |
| HC-K392C | 1.43E-04 |
| HC-L398C | 1.08E-04 |
| HC-S400C | 1.43E-04 |
| HC-V422C | 1.72E-04 |
| LC-K107C | 2.59E-05 |
| LC-R108C | 2.96E-05 |
| LC-T109C | 8.12E-05 |
| LC-S114C | 3.37E-05 |
| LC-T129C | 2.73E-05 |
| LC-R142C | 2.64E-05 |
| LC-E143C | 3.76E-05 |
| LC-K145C | 3.87E-05 |
| LC-N152C | 2.14E-05 |
| LC-L154C | 3.52E-05 |
| LC-S156C | 4.28E-05 |
| LC-S159C | 4.34E-05 |
| LC-E161C | 3.62E-05 |
| LC-E165C | 4.68E-05 |
| LC-S168C | 2.50E-04 |
| LC-K169C | 7.74E-05 |
| LC-D170C | 1.64E-04 |
| LC-S182C | 9.07E-05 |
| LC-K183C | 8.39E-05 |
| LC-K188C | 9.71E-05 |
| LC-T197C | 1.07E-04 |

TABLE 20-continued

IC$_{50}$ of trastuzumab Cys-MMAF ADCs in MDA-MB231 clone 16 Her2$^+$ cell proliferation assay.

| trastuzumab Cys-MMAF ADC | IC$_{50}$ (μM) |
| --- | --- |
| LC-Q199C | 1.31E−04 |
| LC-S203C | 1.18E−04 |

TABLE 21

IC$_{50}$ of antibody 14090 Cys-MMAF ADCs in CMK11-5 cell proliferation assay

| Antibody 14090 Cys-MMAF ADC | IC$_{50}$ (μM) |
| --- | --- |
| HC-S124C | 9.26E−04 |
| HC-T139C | 1.22E−03 |
| HC-E152C | 4.60E−04 |
| HC-L174C | 6.02E−04 |
| HC-K360C | 8.56E−04 |
| HC-S375C | 4.38E−04 |
| LC-A143C | 7.09E−04 |
| LC-A147C | 1.14E−03 |
| LC-V159C | 5.41E−04 |
| LC-T163C | 6.38E−04 |
| LC-S168C | 1.06E−03 |

Example 9. Pharmacokinetic Study of Trastuzumab Cys-MMAF ADCs

It has been demonstrated that a long serum half-life is critical for high in vivo efficacy of ADCs (Hamblett, et al., "Effects of drug loading on the antitumor activity of a monoclonal antibody drug conjugate," *Clin Cancer Res.*, 10:7063-7070 (2004); Alley et al., *Bioconjug Chem.* 19:759-765 (2008)). Attaching an usually hydrophobic drug payload to an antibody could significantly affect the properties of an antibody, and this may lead to a fast clearance of the ADCs in vivo (Hamblett et al., 2004) and poor in vivo efficacy. To evaluate the effects of different conjugation site on clearance of MMAF ADCs in vivo, pharmacokinetic studies in non-tumor bearing mice were carried out with 65 trastuzumab Cys-MMAF ADCs. To detect MMAF containing ADCs in murine plasma, an anti-MMAF antibody was generated. ELISA assays for the detection of ADCs were developed using the extracellular domain of human HER2 to capture trastuzumab IgG molecules from the plasma and an anti-human IgG (anti-hIgG) antibody and the anti-MMAF antibody for signal generation in two separate assays. The two ELISA assays measure the serum concentration of the trastuzumab antibody and the "intact" ADC respectively as discussed in more detail below.

Three mice per group were administered with a single dose of a trastuzumab Cys-MMAF ADC at 1 mg/kg. Ten plasma samples were collected over the course of two weeks and assayed by ELISA using the extracellular domain of human HER2 to capture all trastuzumab IgG molecules including trastuzumab Cys-MMAF ADCs and trastuzumab lacking MMAF. An anti-MMAF and an anti-hIgG antibody were then used for detection in two separate assays. The anti-MMAF antibody ELISA measures the concentration of trastuzumab MMAF conjugates only and the anti-hIgG ELISA quantitates both trastuzumab Cys-MMAF conjugates and trastuzumab antibodies that lack MMAF. Standard curves were generated for each ADC separately using the same material as injected into the mice. The assays with anti-MMAF and anti-hIgG should therefore yield identical concentration readouts if no changes to the drug loading of the trastuzumab Cys-MMAF ADC occur after injection into mice. For trastuzumab Cys-MMAF ADCs that lost some of the MMAF payload, the ELISA assay with the anti-MMAF antibody will measure a lower concentration than the anti-hIgG ELISA. A comparison of the two concentration readouts therefore allows to measure drug-release from trastuzumab Cys-MMAF ADCs during in vivo incubation in the mouse.

Figure 21A:
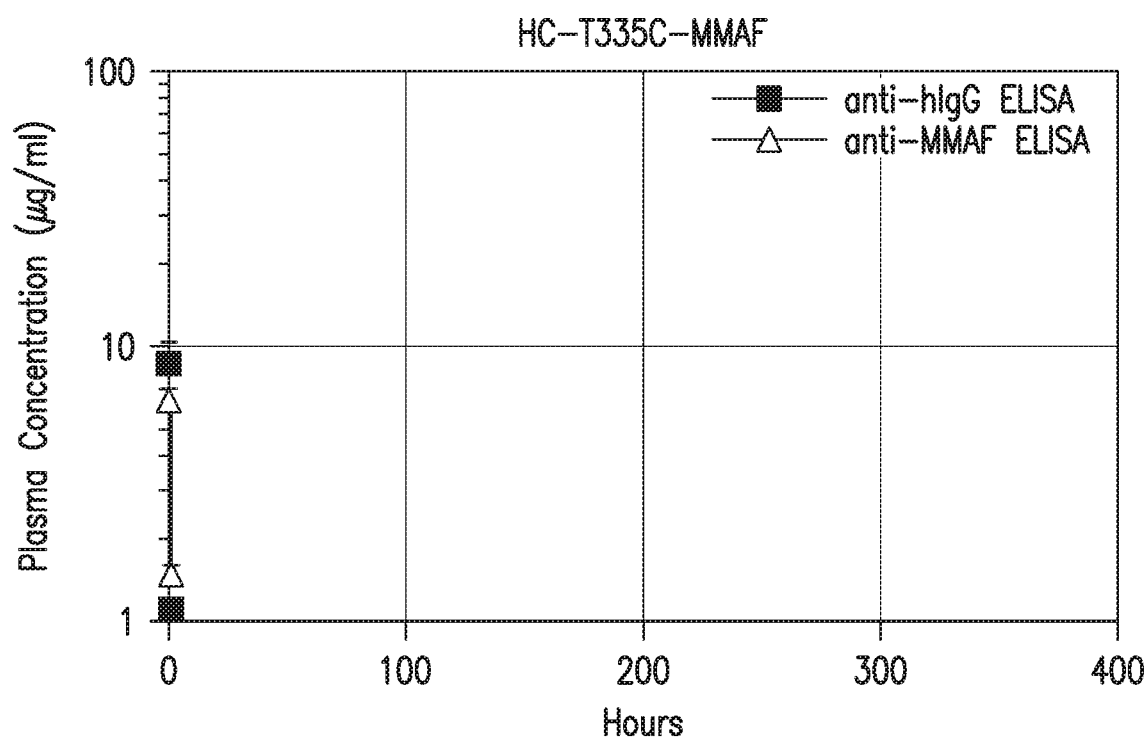
FIG. 21A-FIG. 21B. Pharmacokinetics study of two trastuzumab Cys-MMAF ADCs displaying fast clearance in vivo. A. HC-T335C-MMAF and B. HC-S337C-MMAF ADC.
Figure 21B:
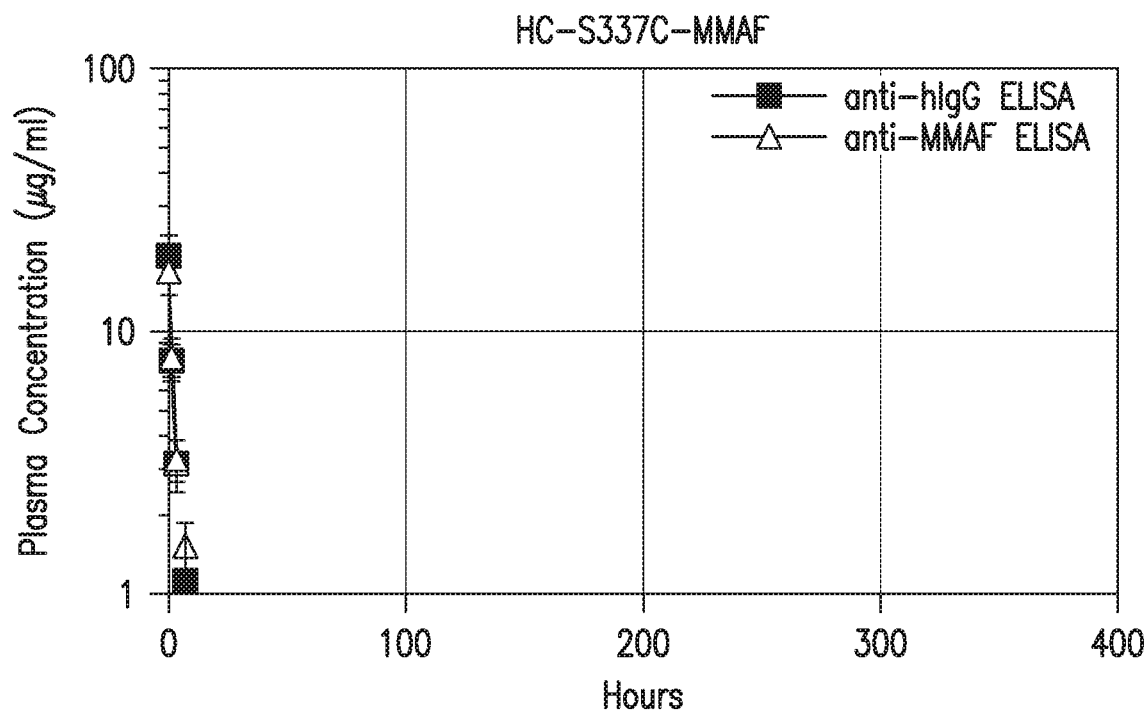

As measured by anti-hIgG ELISA, 63 out of 65 ADCs displayed a pharmacokinetic profile similar to unconjugated wild-type trastuzumab antibody (FIGS. 18, 19, 20), indicating that MC-MMAF payload conjugation to these sites did not significantly affect the antibody's clearance. The two exceptions are HC-T335C and HC-S337C. Conjugation of MC-MMAF to these two sites results in rapid clearance of the ADCs as measured by the anti-MMAF and the anti-hIgG ELISA (FIG. 21). The protein thermal shift assay revealed that the Tm1 for trastuzumab HC-T335C-MMAF and trastuzumab HC-S337C-MMAF decreased from 69° C. in wild-type trastuzumab antibody to 42° C. and 45° C., respectively (FIG. 14). Conjugation of MC-MMAF to the two sites dramatically reduces the thermal stability of the ADC (by 27° C. and 24° C., respectively). For the 63 ADCs that show a pharmacokinetic profile similar to unconjugated antibody, Tm1 changes were smaller than 8° C. suggesting that fast clearance may possibly correlate with low thermal stability of the ADC.

To determine the chemical stability of linkage between the MMAF payload and the antibody at the various Cys sites, the concentrations of trastuzumab Cys-MMAF ADC as measured by the anti-MMAF ELISA and of all trastuzumab molecules as measured by the anti-hIgG ELISA were compared to each other for each sample. Many trastuzumab Cys-MMAF ADCs, within the error of the measurements, displayed a good overlap between the two concentrations over the course of two weeks, suggesting that the bond between MC-MMAF and the cysteine introduced at these sites was stable during circulation in mice over this period (FIGS. 18, 19). In contrast, some trastuzumab Cys-MMAF ADCs displayed a significant drug loss as indicated by the higher anti-hIgG readout than the anti-MMAF readout (FIG. 20). For some trastuzumab Cys-MMAF ADCs, the concentration of ADC was about 50% of that of hIgG. These results suggest that there are significant differences in stability of a thiol-maleimide bond of drug payloads conjugated to different sites as has been suggested previously (Shen et al. Nat. Biotechnol. 2012, 30 (2):184-9). Sites having good stability are preferred sites for use of preparing ADCs as described herein.

In pharmacokinetic studies, the area-under-the-plasma-concentration-versus-time-curve (AUC) is an important parameter in estimating total clearance and bioavailability of an administered drug. In our pharmacokinetic studies, for each trastuzumab Cys-MMAF ADC two AUC values, AUC-MMAF and AUC-hIgG, were calculated separately from measurements with the anti-MMAF and the anti-hIgG ELISA. The ratios of AUC-MMAF to AUC-hIgG for all trastuzumab Cys-MMAF ADCs varied from 0.4 to 1.2 (Table 20). FIGS. 18, 19 and 20 include PK curves for ADCs over the full range of observed AUC-MMAF/AUC-hIgG ratios and illustrate the variability and uncertainty of the measurements. Ratios of AUC-MMAF to AUC-hIgG>1 (Table 20) suggest uncertainties of >25% since the ratio should remain near 1 if no drug loss occurs. As shown in Table 20, out of 63 trastuzumab Cys-MMAF ADCs with measurable AUCs from both ELISAs, 40 ADCs show a ratio of AUC-MMAF/AUC-hIgG>0.7, indicating that within the accuracy of the measurement, little MMAF drug loss was observed at these after administration in mice. However, 23 ADCs displayed a ratio of AUC-MMAF/AUC-hIgG<0.7, suggesting that the amount of MMAF payload conjugate at these 23 sites decreased significant during the in vivo incubation in the mouse.

Differences in stability of the maleimide linkage at different conjugation sites has previously been reported for Cys engineered ADCs (see Shen et al., (2012) Nat Biotechnol. 22; 30(2):184-9 for discussion and references). For the preferred sites that exhibit enhanced serum stability, the antibody environment likely catalyzes the hydrolysis of the succinimide ring formed by the reaction of maleimide with cysteine. The hydrolyzed form cannot revert back and cannot release the maleimide drug. As such, the ability of the antibody environment to catalyze the ring hydrolysis cannot be predicted and is an unexpected property of certain engineered Cys sites. Sites in Table 22 having an AUC (MMAF)/AUC(hIgG) ratio greater than 0.7 are therefore particularly suitable sites for cysteine substitution based on this criterion, and sites having a ratio of about 0.9 or above are especially preferred cysteine substitution sites for purposes of the invention when applying. These include heavy chain sites 322, 334, 121, 288, 171, 139, 360, 117, 392, 375, 292, 333, 174, 258, 337, 422, 320, 390, and 335; and light chain sites 107, 203, 108 and 114.

TABLE 22

AUC-MMAF and AUC-hIgG of trastuzumab Cys-MMAF ADCs in mice

| trastuzumab Cys-MMAF ADC | AUC-MMAF (hrs*µg/ml) | AUC-hIgG (hrs*µg/ml) | AUC(MMAF)/ AUC(hIgG) |
|---|---|---|---|
| HC-K246C-MMAF | 1515 | 3587 | 0.4 |
| HC-K205C-MMAF | 2109 | 4893 | 0.4 |
| LC-S168C-MMAF | 1688 | 3619 | 0.5 |
| LC-E143C-MMAF | 1589 | 3254 | 0.5 |
| HC-E382C-MMAF | 1364 | 2541 | 0.5 |
| HC-T155C-MMAF | 2930 | 5308 | 0.6 |
| HC-S119C-MMAF | 2230 | 4045 | 0.6 |
| LC-T129C-MMAF | 2375 | 4332 | 0.6 |
| LC-T109C-MMAF | 1588 | 2716 | 0.6 |
| LC-K169C-MMAF | 2858 | 4855 | 0.6 |
| HC-S400C-MMAF | 2363 | 3922 | 0.6 |
| HC-R355C-MMAF | 2344 | 3777 | 0.6 |
| HC-R344C-MMAF | 1994 | 3215 | 0.6 |
| LC-Q199C-MMAF | 2042 | 3261 | 0.6 |
| LC-S182C-MMAF | 2434 | 3722 | 0.7 |
| HC-P153C-MMAF | 2201 | 3402 | 0.7 |
| HC-N286C-MMAF | 2286 | 3535 | 0.7 |
| HC-T169C-MMAF | 2113 | 3190 | 0.7 |
| LC-K183C-MMAF | 2014 | 3053 | 0.7 |
| LC-T197C-MMAF | 2126 | 3177 | 0.7 |
| LC-K145C-MMAF | 2339 | 3454 | 0.7 |
| HC-L398C-MMAF | 2063 | 2979 | 0.7 |
| HC-P189C-MMAF | 2042 | 2968 | 0.7 |
| HC-S157C-MMAF | 2625 | 3640 | 0.7 |
| HC-E269C-MMAF | 2373 | 3293 | 0.7 |
| LC-S159C-MMAF | 2063 | 2809 | 0.7 |
| LC-E161C-MMAF | 1974 | 2632 | 0.8 |
| LC-E165C-MMAF | 2481 | 3244 | 0.8 |
| HC-T164C-MMAF | 2514 | 3290 | 0.8 |
| LC-R142C-MMAF | 2903 | 3786 | 0.8 |
| LC-S156C-MMAF | 2217 | 2847 | 0.8 |
| HC-S207C-MMAF | 2378 | 3001 | 0.8 |
| LC-N152C-MMAF | 2303 | 2862 | 0.8 |
| HC-E152C-MMAF | 3403 | 4202 | 0.8 |
| LC-L154C-MMAF | 1959 | 2387 | 0.8 |
| LC-K188C-MMAF | 2230 | 2680 | 0.8 |
| HC-K326C-MMAF | 2621 | 3157 | 0.8 |
| LC-D170C-MMAF | 2048 | 2420 | 0.9 |
| HC-K290C-MMAF | 2668 | 3090 | 0.9 |

TABLE 22-continued

AUC-MMAF and AUC-hIgG of trastuzumab Cys-MMAF ADCs in mice

| trastuzumab Cys-MMAF ADC | AUC-MMAF (hrs*µg/ml) | AUC-hIgG (hrs*µg/ml) | AUC(MMAF)/ AUC(hIgG) |
|---|---|---|---|
| HC-E293C-MMAF | 2167 | 2523 | 0.9 |
| HC-S124C-MMAF | 2107 | 2463 | 0.9 |
| HC-K274C-MMAF | 3080 | 3554 | 0.9 |
| HC-K322C-MMAF | 3108 | 3437 | 0.9 |
| HC-K334C-MMAF | 4527 | 5048 | 0.9 |
| HC-K121C-MMAF | 2647 | 2952 | 0.9 |
| HC-K288C-MMAF | 2681 | 2902 | 0.9 |
| HC-P171C-MMAF | 2312 | 2481 | 0.9 |
| LC-K107C-MMAF | 2621 | 2817 | 0.9 |
| HC-T139C-MMAF | 2951 | 3186 | 0.9 |
| HC-K360C-MMAF | 3791 | 4014 | 0.9 |
| HC-S117C-MMAF | 2661 | 2828 | 0.9 |
| LC-S203C-MMAF | 2730 | 2919 | 0.9 |
| HC-K392C-MMAF | 3148 | 3302 | 1.0 |
| HC-S375C-MMAF | 2593 | 2644 | 1.0 |
| HC-R292C-MMAF | 2816 | 2806 | 1.0 |
| HC-E333C-MMAF | 3850 | 3796 | 1.0 |
| HC-L174C-MMAF | 2604 | 2541 | 1.0 |
| HC-E258C-MMAF | 3941 | 3732 | 1.1 |
| HC-S337C-MMAF | 34.38 | 32.14 | 1.1 |
| HC-V422C-MMAF | 2662 | 2424 | 1.1 |
| HC-K320C-MMAF | 3181 | 2776 | 1.2 |
| HC-N390C-MMAF | 3627 | 3105 | 1.2 |
| LC-R108C-MMAF | 3711 | 2992 | 1.2 |
| LC-S114C-MMAF | n.a. | 2567 | n.a. |
| HC-T335C-MMAF | 6.71 | n.a. | n.a. | n.a: not applicable.

Example 10: Combination of Cys Sites to Produce Antibody Drug Conjugates with Drug-to-Antibody-Ratios Greater than 2

Antibody conjugates produced through conjugation to lysine residues or partially reduced native disulfide bonds often feature drug-to-antibody-ratios (DAR) of between 3 and 4. Cys engineered antibodies more typically feature a DAR of 2. For certain indications, it may be desirable to produce ADCs with higher DAR which can in principle be achieved by introducing multiple Cys mutations in the antibody. As the number of Cys mutation increases, the likelihood that such mutations interfere with the required re-oxidation process during ADC preparation and hence result in heterogeneous products also increases. In this study, a large number of single site heavy and light chain Cys mutants with good re-oxidation behavior were identified.

To demonstrate that several conjugation sites can be combined for the production of ADCs with DAR greater than two, several preferred single site Cys constructs of light and heavy chain of trastuzumab and antibody 14090 (Table 23) were coexpressed in 293 Freestyle™ cells as described in Example 5. Purified antibodies which all contain one Cys mutation on the heavy chain and one Cys mutation on the light chain were reduced, re-oxidized and conjugated with MC-MMAF as described in Example 6. Reverse phase high-pressure liquid chromatography demonstrated a single defined elution peak suggesting efficient re-oxidation of the native disulfide bonds. Reverse phase high-pressure liquid chromatography after MC-MMAF conjugation also showed predominantly a single elution peak for the DAR 4 ADC species. The DAR of all ADCs in Table 23 was confirmed to be 4 by mass spectrometry. Production yields varied from 16 to 24 mg/L transient cell culture. The ADCs were predominantly monomeric as determined by analytical size exclusion chromatography; only for 2 of the 8 antibodies could small amounts of aggregates be detected (Table 23). Trastuzumab and 14090 ADCs exhibited antigen-dependent cell killing in MDA-MB231 clone 16 and CMK1105 cell proliferation assays, respectively (Table 23).

23) which is to be expected when a hydrophobic drug molecule such as ABA-MMAF is attached to an antibody. However, attaching the payload at different sites increases the hydrophobicity of the ADC to various extends.

TABLE 23

Properties of Cys engineered MMAF ADCs with DAR of 4.

| Cys-MMAF ADC (DAR = 4) | LC SEQ ID NO | HC SEQ ID NO | Yield (mg/L) | AnSEC % Monomer | AnSEC % Multimer | $IC_{50}$ MDA-MB231-16 cells (μM) | $IC_{50}$ CMK11-5 cells (μM) |
|---|---|---|---|---|---|---|---|
| trastuzumab LC-S159C-HC-E258C | 75 | 29 | 17.3 | 100 | Not detected | 4.91e−4 | No potency |
| trastuzumab LC-S159C-HC-S375C | 75 | 50 | 17.8 | 100 | Not detected | 2.44e−4 | No potency |
| trastuzumab LC-E165C-HC-E258C | 77 | 29 | 16.5 | 100 | Not detected | 3.24e−4 | No potency |
| trastuzumab LC-E165C-HC-S375C | 77 | 50 | 16.9 | 100 | Not detected | 2.15e−4 | No potency |
| Antibody 14090 LC-A143C-HC-K360C | 92 | 48 | 16.1 | 94.8 | 5.2 | No potency | 4.92e−4 |
| Antibody 14090 LC-A143C-HC-S375C | 92 | 50 | 21.8 | 100 | Not detected | No potency | 4.76e−4 |
| Antibody 14090 LC-V159C-HC-K360C | 96 | 48 | 24.0 | 100 | Not detected | No potency | 4.55e−4 |
| Antibody 14090 LC-V159C-HC-S375C | 96 | 50 | 21.7 | 97.1 | 2.9 | No potency | 3.99e−4 | n.d.: not detectable,
no potency: no sign of cell killing at highest concentration evaluated (66 nM)
SEQ ID NOs only specify constant regions of antibody sequences.

Example 11. Selection of Cys Sites Based on ADC Hydrophobicity

To further optimize the selection Cys mutants and mutant combinations for the preparation of ADCs with DAR 2, 4, 6 and 8, the properties of MMAF ADCs prepared with single site trastuzumab Cys and Pcl mutants (Preparation of Pcl ADCs is described in patent application 55573) were analyzed, and accessibility and solvent exposure of conjugation sites was inspected in the crystal structures of IgG.

Figure 23A:
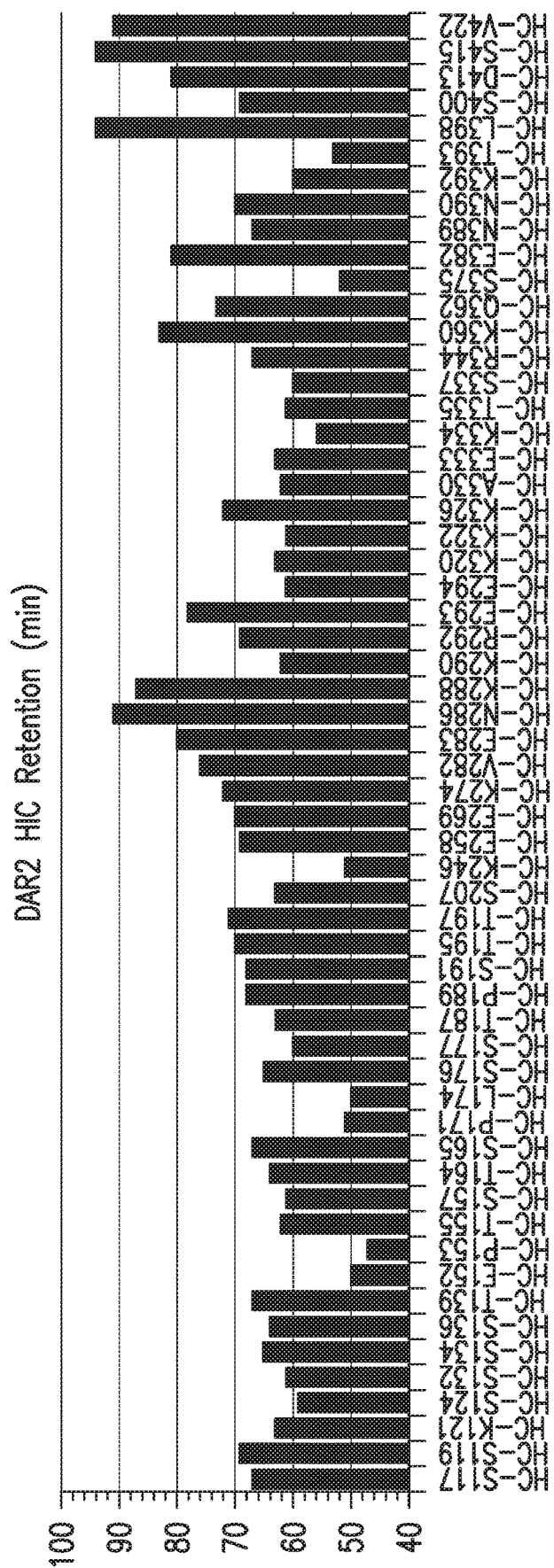
FIG. 23A-FIG. 23B: Retention times of trastuzumab Pcl MMAF DAR 2 ADCs as measured by Hydrophobic Interaction Chromatography. ABA-MMAF is attached at a Pcl residue substituted for the indicated HC or LC residue. A) HC conjugated ADCs. B) LC conjugated ADCs. The retention time of unconjugated wild-type antibody is indicated (WT).
Figure 23B:
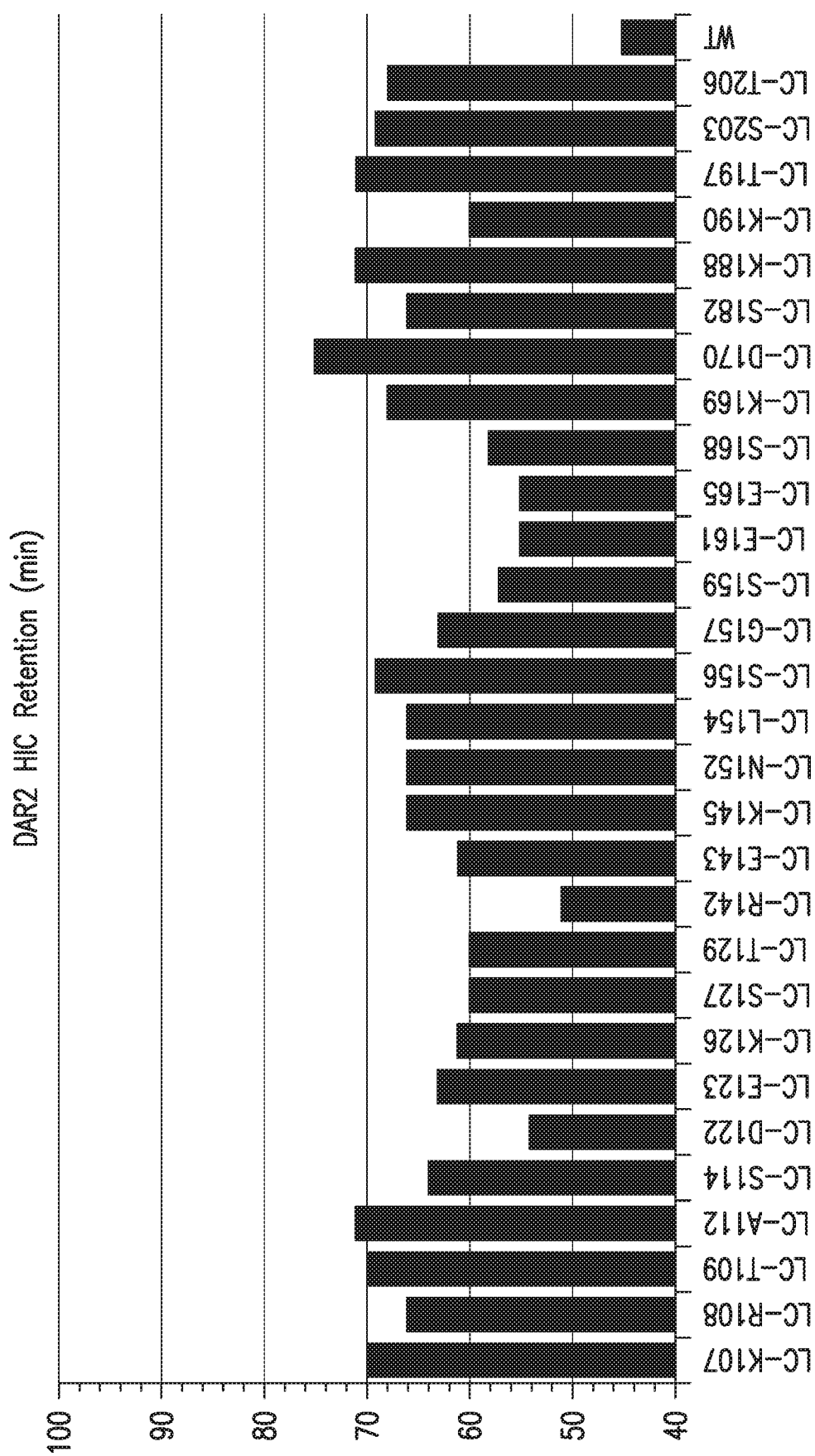

One of the most informative data was the observation that the hydrophobicity of trastuzumab Pcl-MMAF ADCs varied greatly when the payload was attached different sites (FIG. 23). The hydrophobicity of these ADCs was measured by hydrophobic interaction chromatography (HIC) using a TSKgel Phenyl-5PW column (Tosoh Bioscience, TSKgel Phenyl-5PW, 13 □m, 21×150 mm, stainless steel, Cat #07656; running buffer A: 1.5 M ammonium sulfate in 20 mM NaPi (pH7.4); buffer B: 20% isopropanol in 20 mM NaPi (pH7.4); flow rate 5 ml/min; linear gradient from 20% to 80% buffer B over 90 mins; monitored by UV absorbance at 280 nm). Surprisingly, it was observed that retention times of the DAR 2 species varied greatly among ADCs although the only difference is the site of ABA-MMAF attachment (FIG. 23). HIC separates molecules on the basis of the hydrophobicity. All DAR 2 ADCs have a HIC retention time larger than that of unconjugated antibody (WT=45 min, FIG.

Figure 24A:
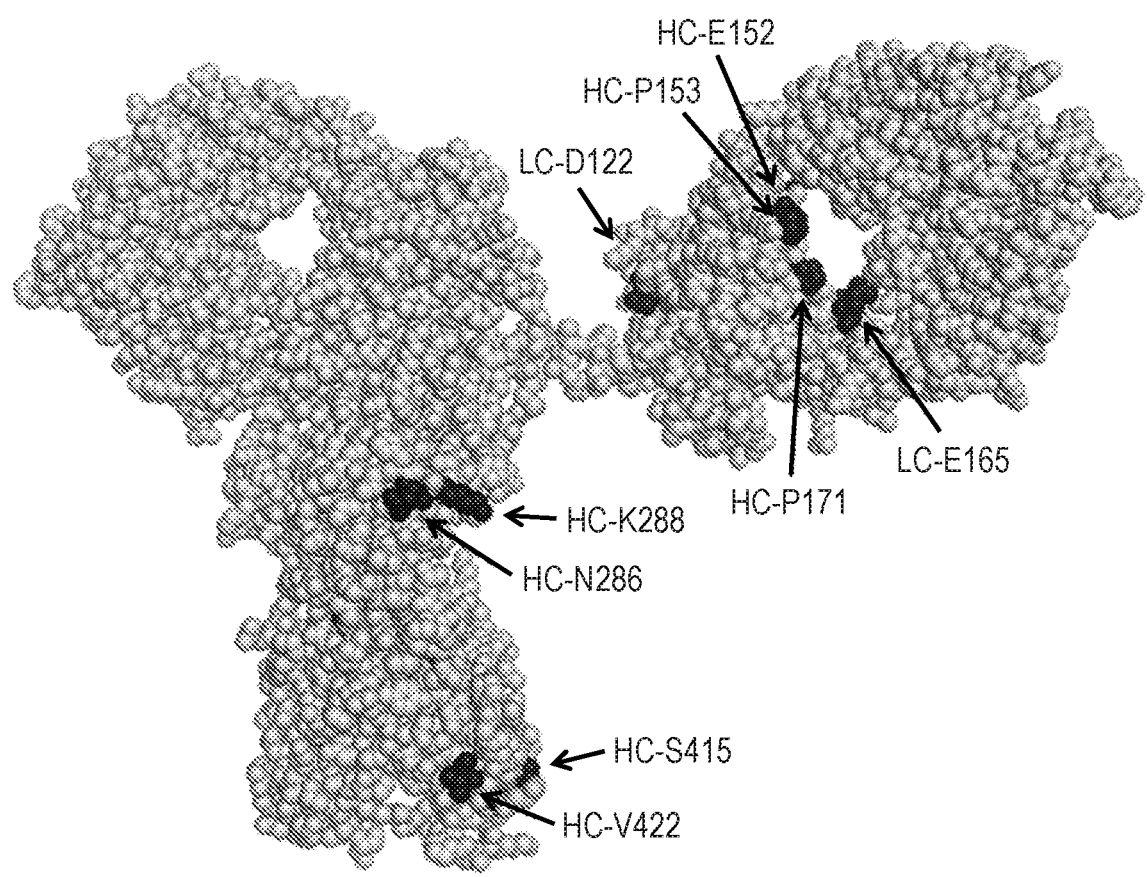
Figure 24B:
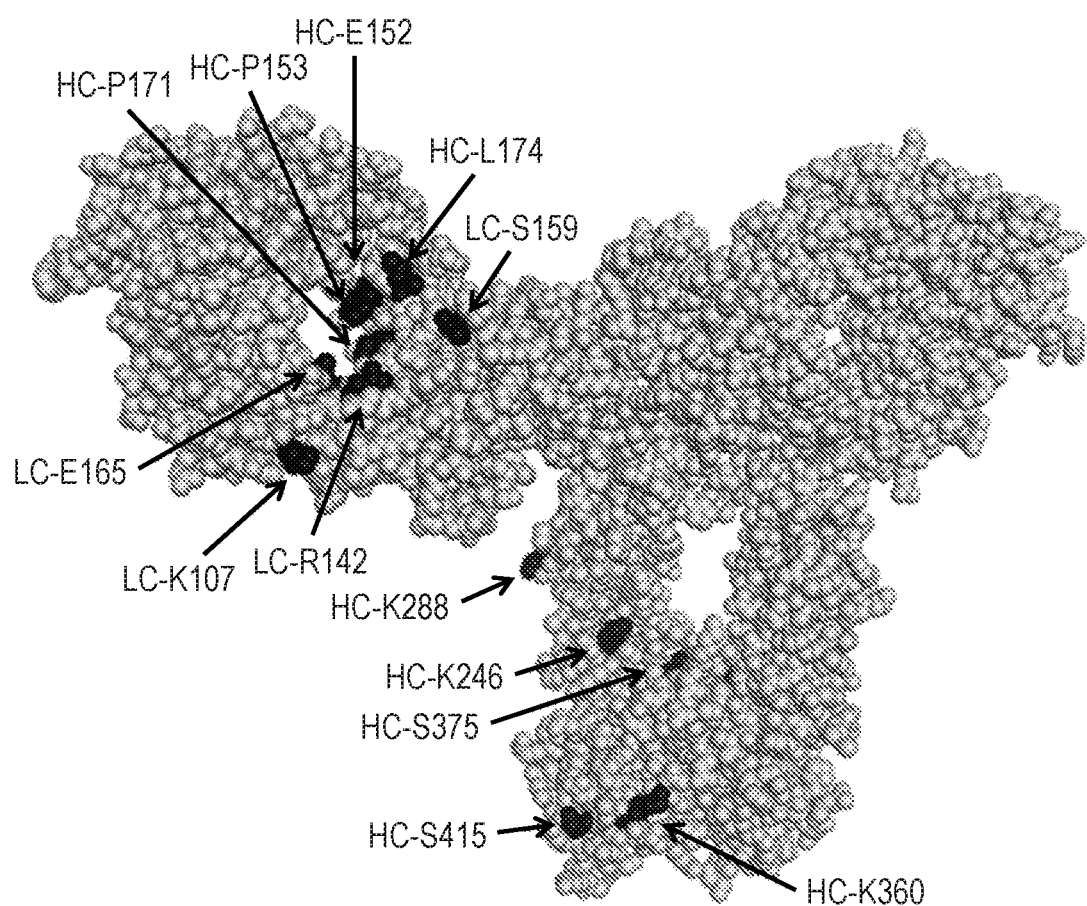
Figure 25A:
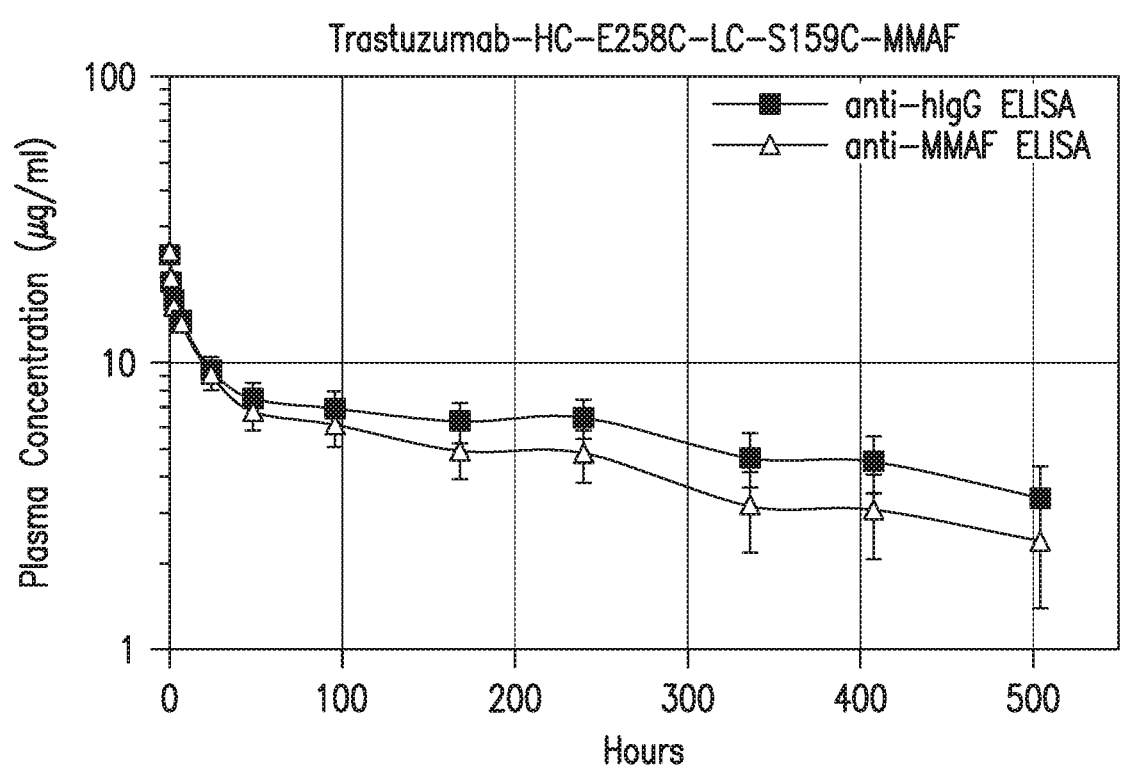
FIG. 25A-FIG. 25L. Pharmacokinetics study of trastuzumab and antibody 14090 Cys-MMAF ADCs with DAR 4, 6 and 8 prepared with antibodies with 2, 3 or 4 Cys mutations. DAR 4 trastuzumab ADCs: HC-E258C-LC-S159C-MMAF (A), HC-S375C-LC-S159C-MMAF (B), HC-E258C-LC-E165C-MMAF (C), HC-S375C-LC-E165C-MMAF (D), HC-E152C-LC-R142C-MMAF (E), HC-P171C-LC-R142C-MMAF, and HC-E152C-LC-S159C-MMAF (G); DAR 4 antibody 14090 ADCs: HC-S375C-LC-A143C-MMAF (H), HC-K360C-LC-V159C-MMAF (I), and HC-S375C-LC-V159C-MMAF (J); K. DAR 6 trastuzumab ADCs HC-K334C-S375C-LC-E165C-MMAF and HC-K334C-K392C-LC-E165C-MMAF; L. DAR 8 trastuzumab ADCs HLC-K334C-K360C-S375C-LC-E165C-MMAF, HC-K334C-K360C-K392C-LC-E165C-MMAF and HC-K334C-S375C-K392C-LC-E165C-MMAF. Antibody 14090 is mouse cross-reactive and therefore is cleared more rapidly that then the trastuzumab ADCs which do not bind to any mouse antigens.
Figure 25B:
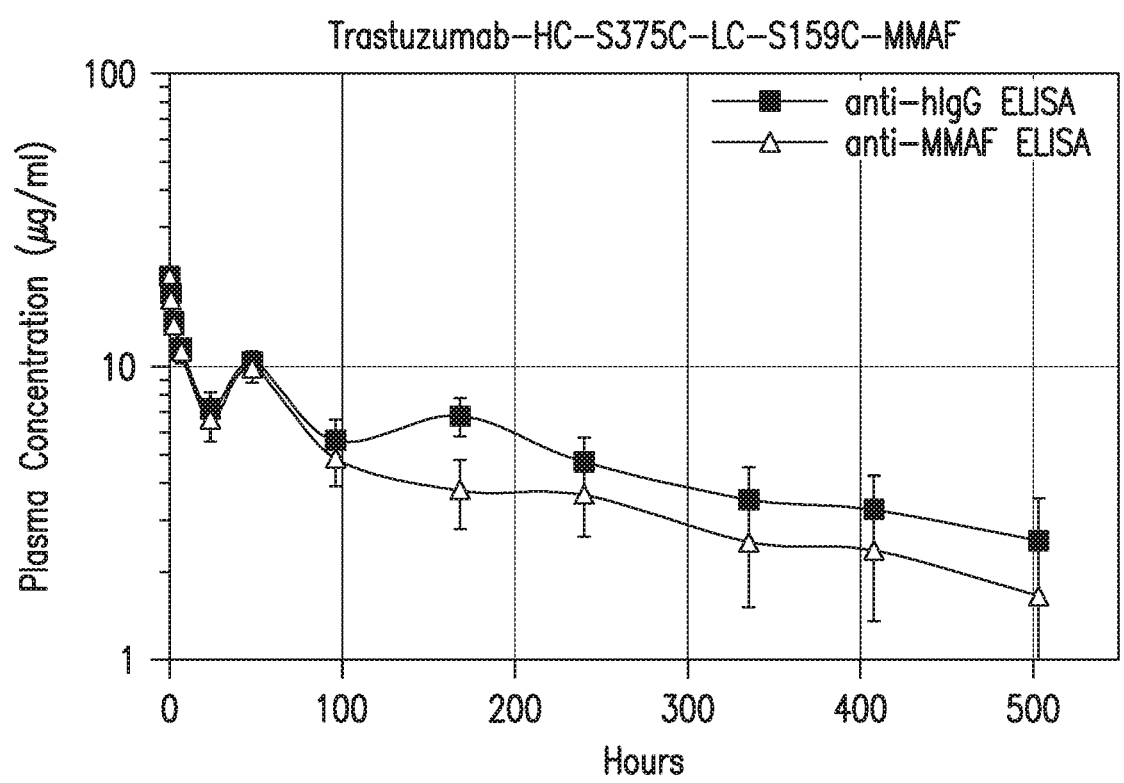
Figure 25C:
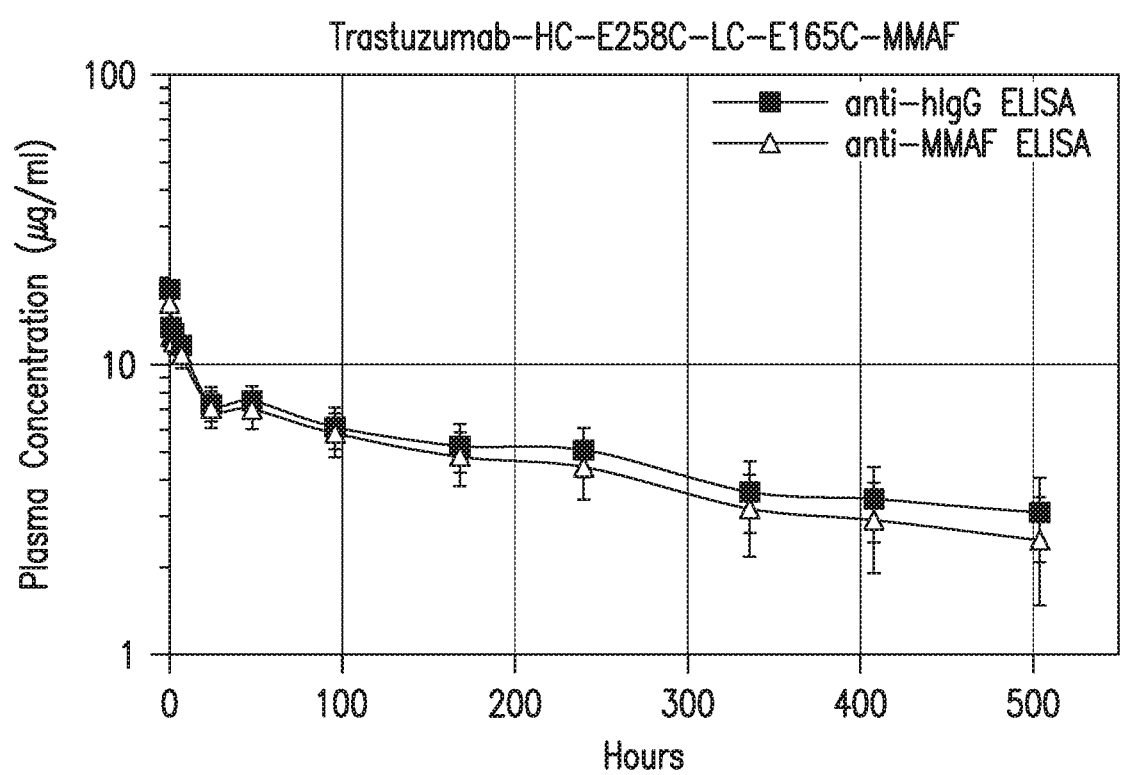
Figure 25D:
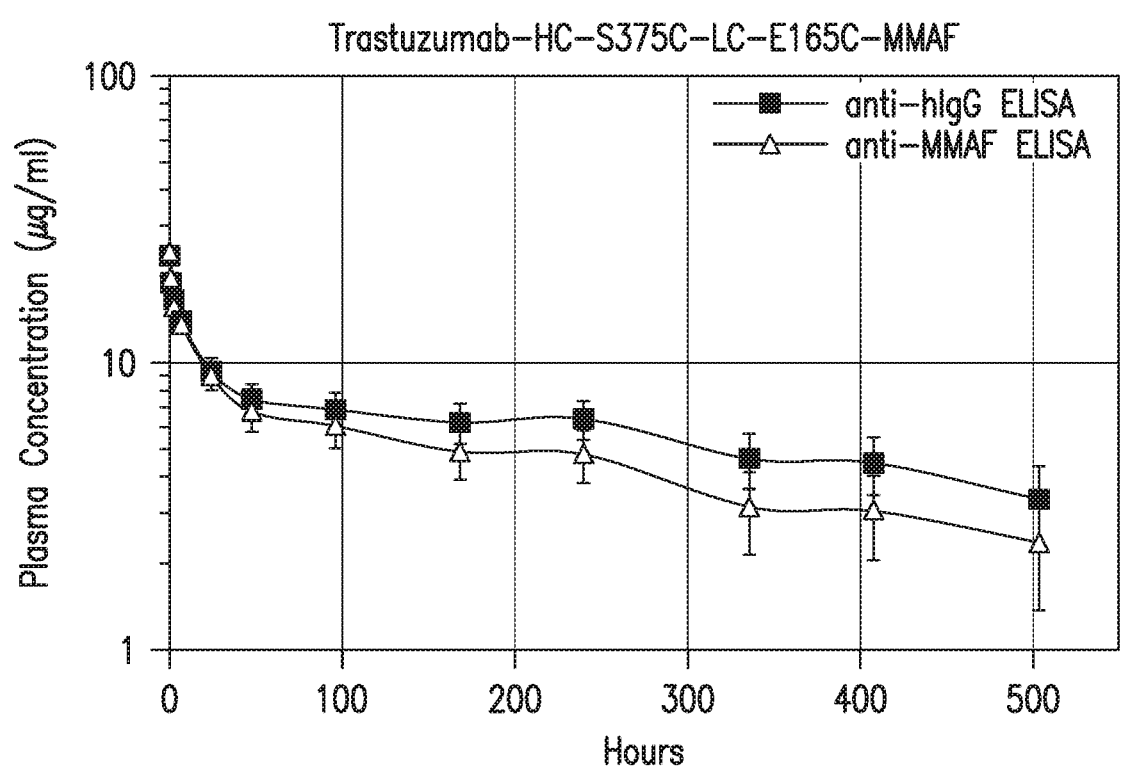
Figure 25E:
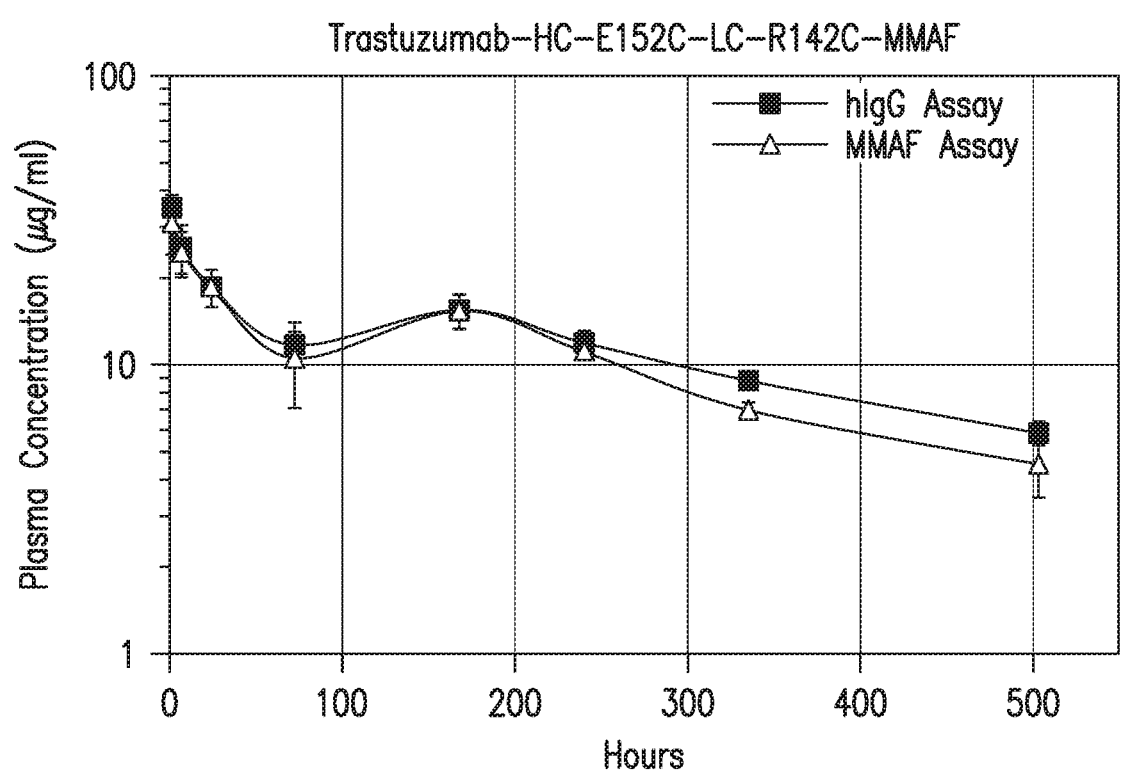
Figure 25F:
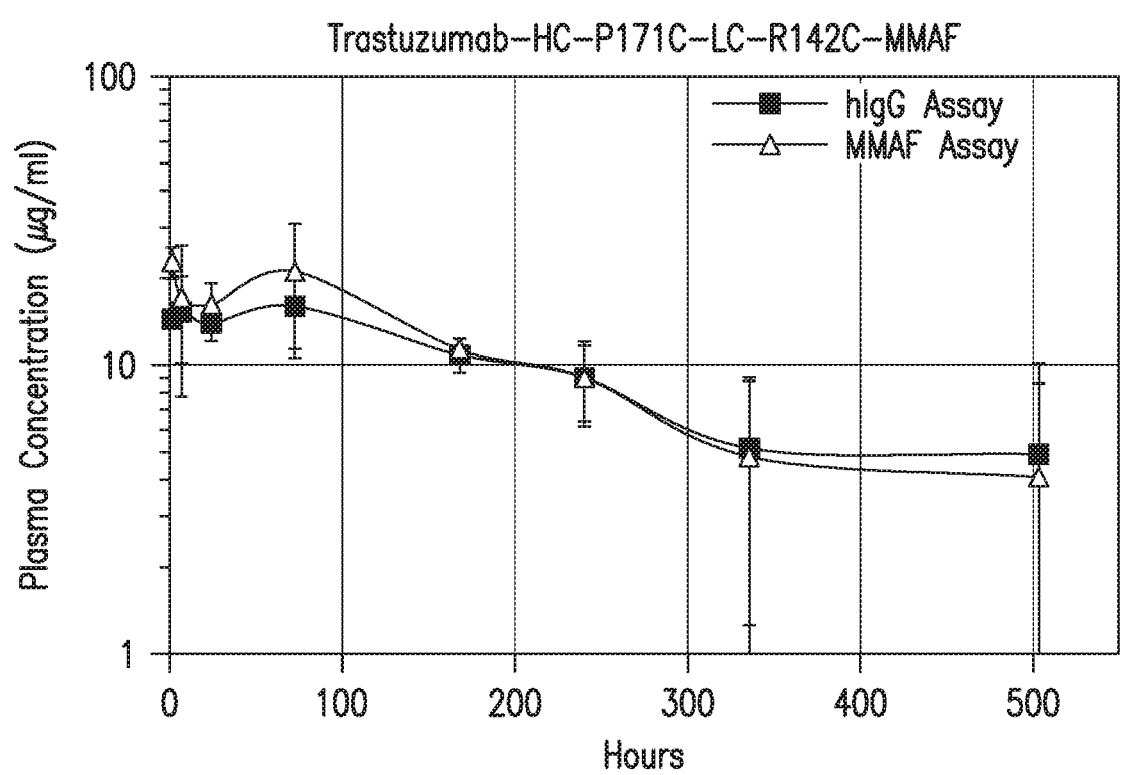
Figure 25G:
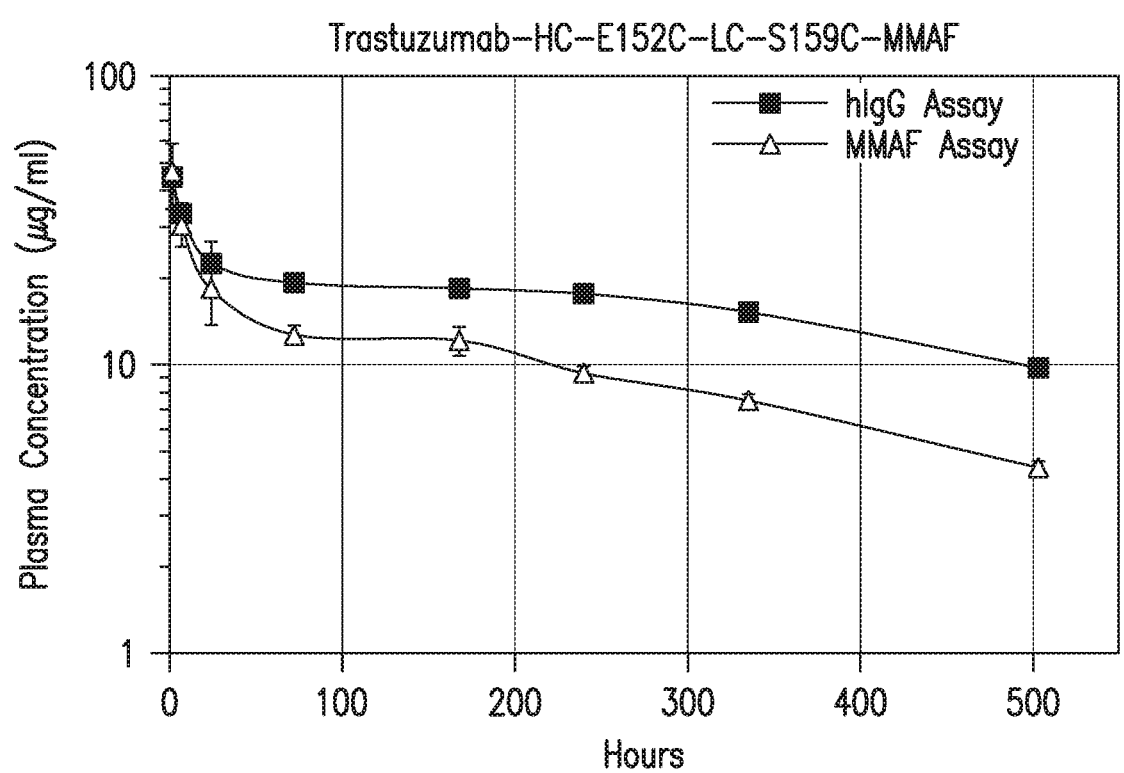
Figure 25H:
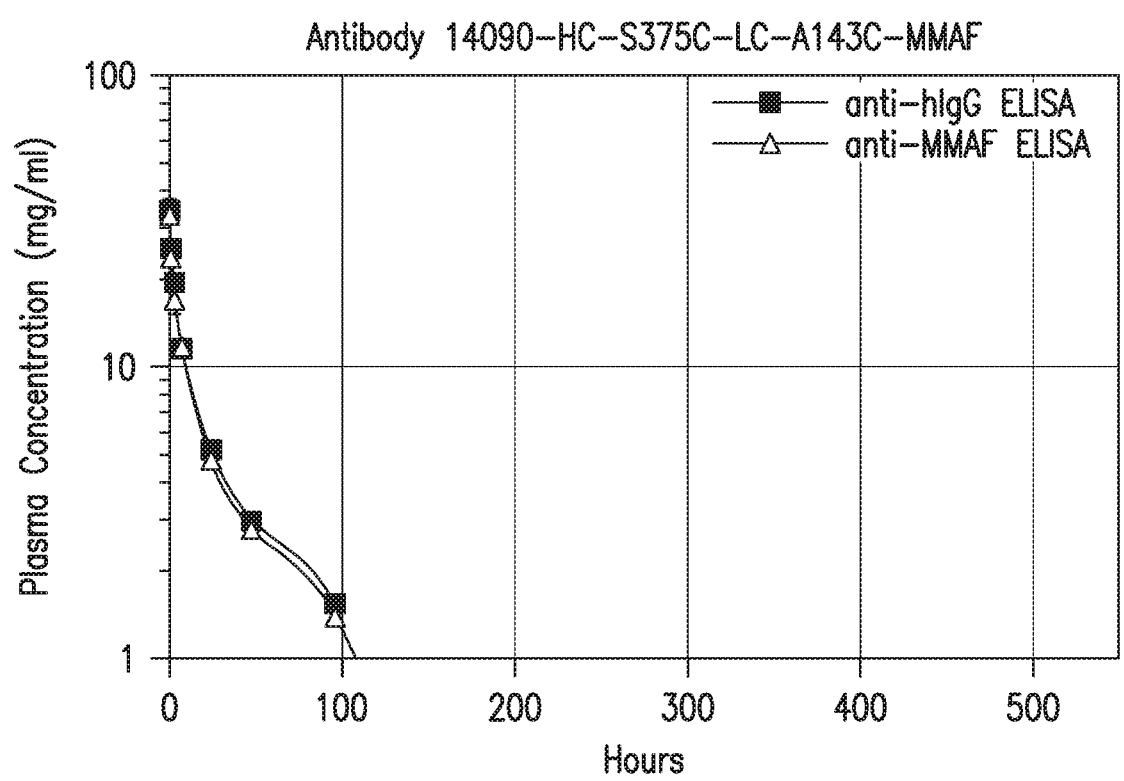
Figure 25I:
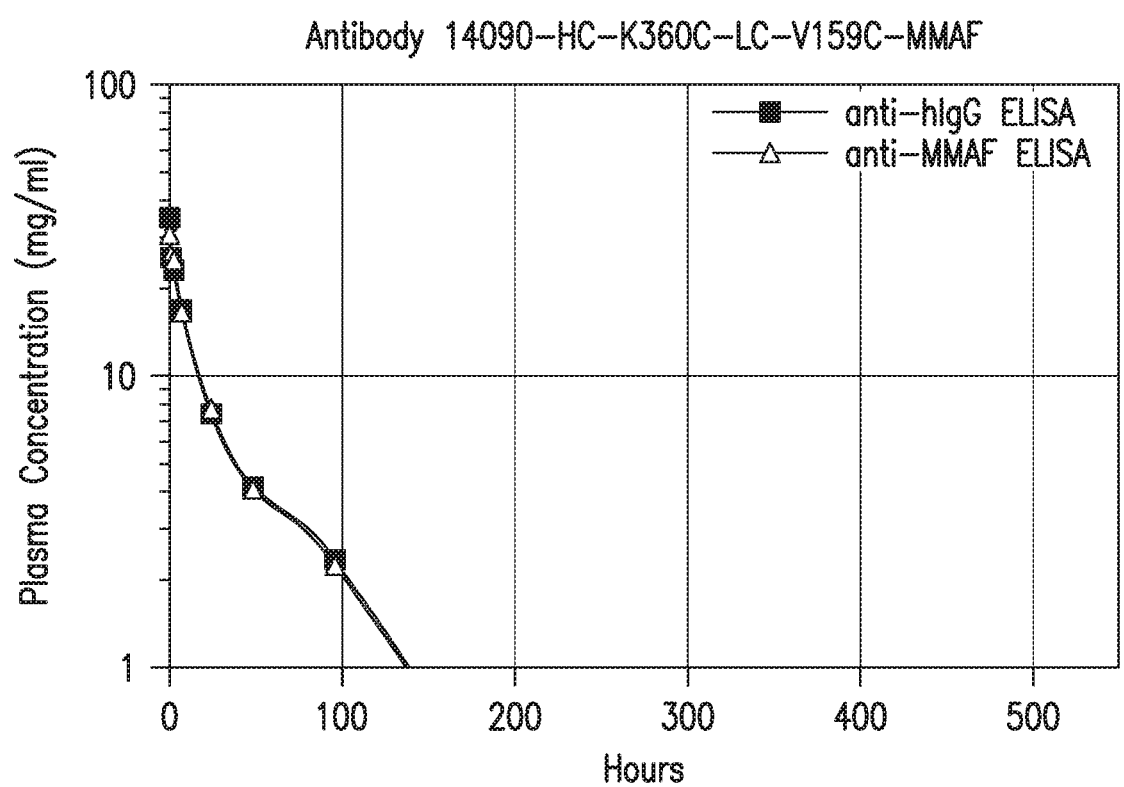
Figure 25J:
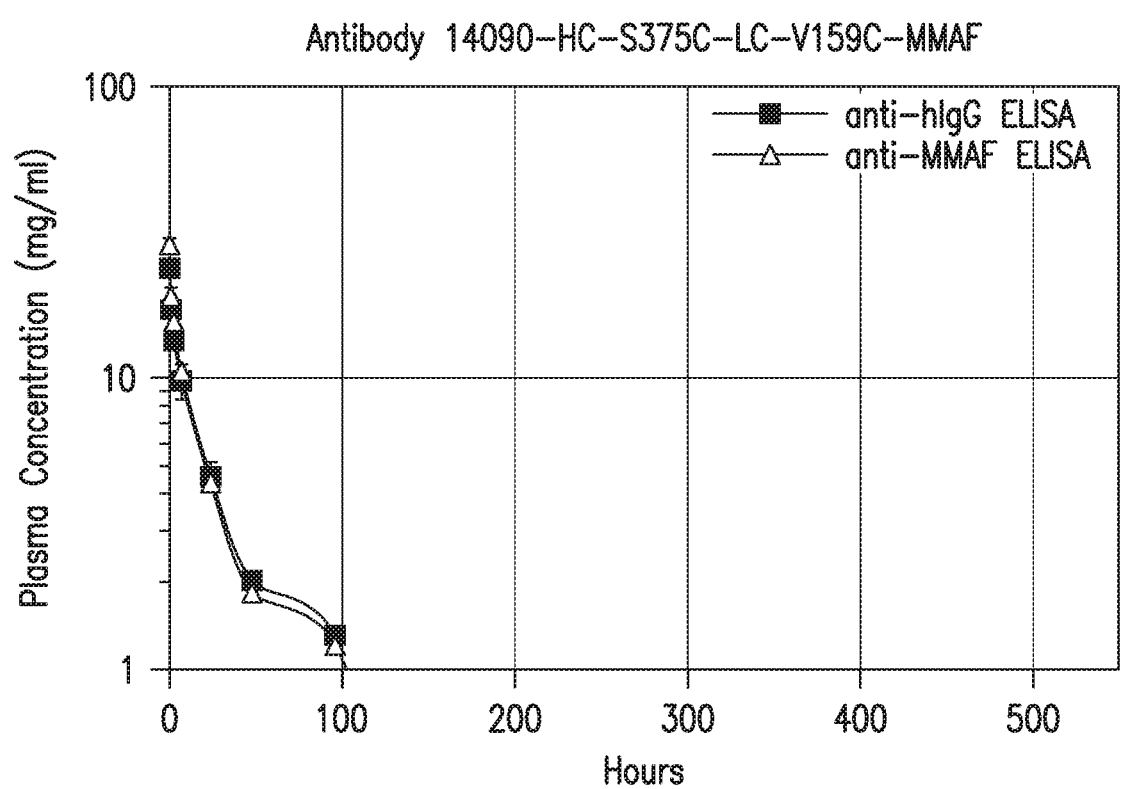
Figure 25K:
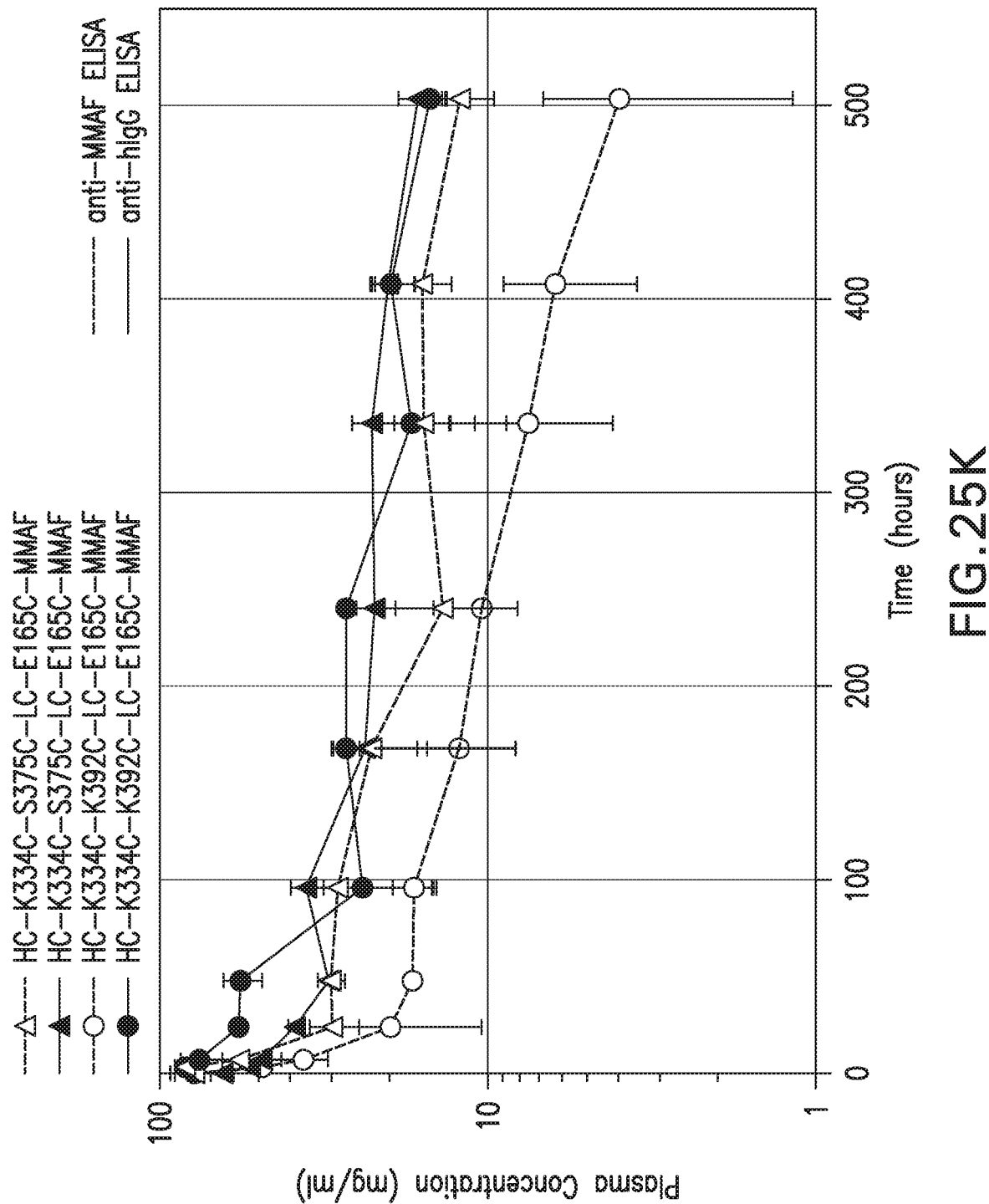
Figure 25L:
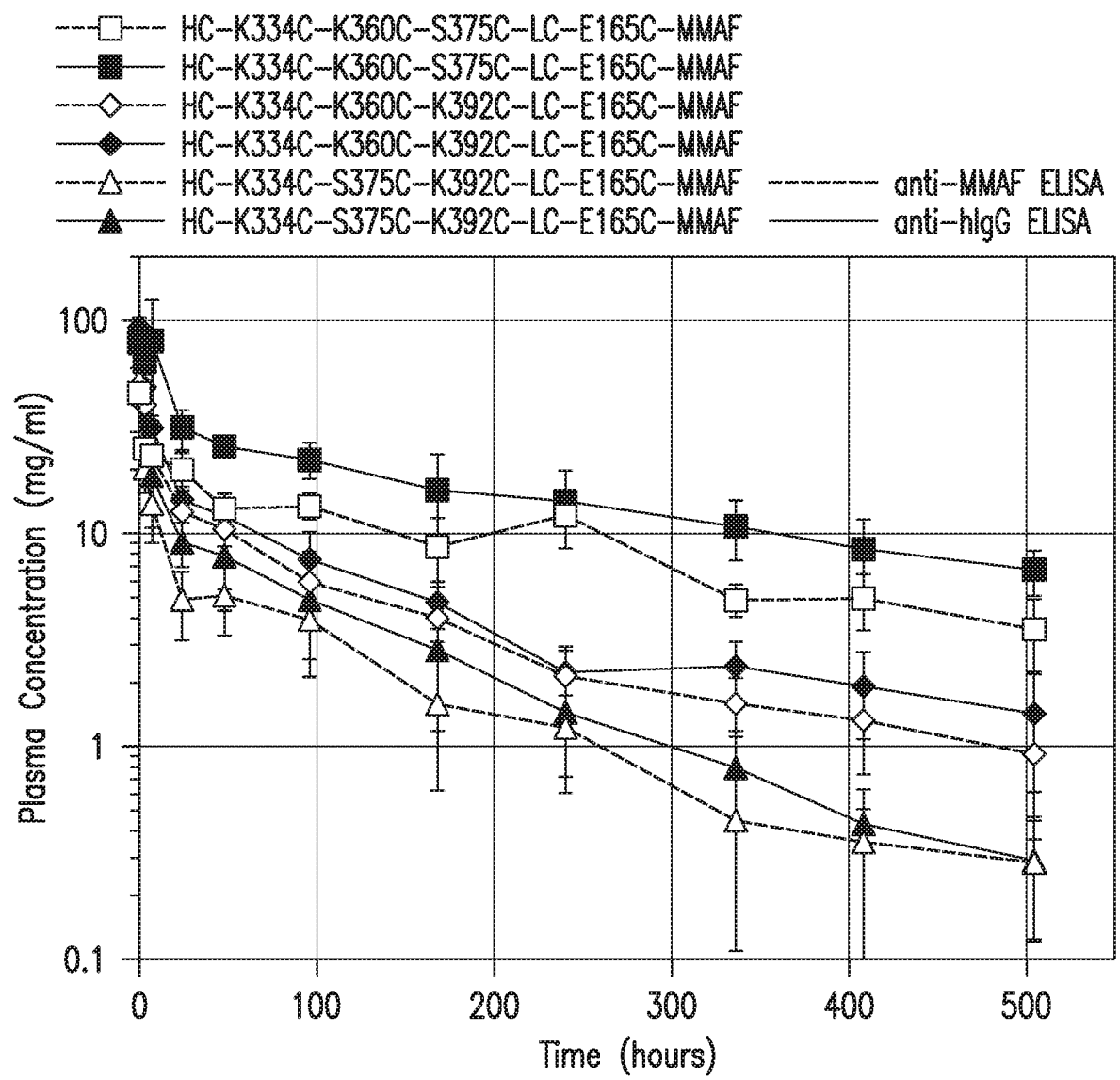

The surprisingly large differences in retention times can be rationalized from the inspection of location of the attachment sites on the structure of an antibody (FIG. 24): The retention times are higher if the drug payload is attached at an exposed site on the outside of an antibody, for example at HC-K288Pcl, HC-N286Pcl, HC-V422Pcl, HC-L398Pcl and HC-S415Pcl where retention time between 87 and 94 min were measured for the respective ADCs (FIG. 23). Conversely, if the payload is attached at an interior site such as the cavity formed between variable and CH1 domains (for examples, HC-P153Pcl, HC-E152Pcl, HC-L174Pcl, HC-P171Pcl, LC-R142Pcl, LC-E161Pcl, LC-E165Pcl, LC-S159Pcl) or the large opening between CH2 and CH3 domains of the antibody (for examples, HC-K246C, HC-S375Pcl, HC-T393Pcl, HC-K334Pcl), the HIC retention time increased to only 47 to 57 mins because the payload is partially sequestered from interacting with solvent and the HIC column. For other sites, for example, the relatively exposed sites, LC-K107Pcl and HC-K360Pcl, intermediate retention time of 70 and 83 min were measured.

Reducing hydrophobicity of a protein drug is generally considered beneficial because it may reduce aggregation and clearance from circulation. We propose that the HIC data presented in FIG. 23 enables selection of preferred payload attachment sites. Conjugating drug payloads at sites where they are sequestered from solvent interactions and attachment minimally increases the hydrophobicity of the antibody upon drug attachment should be beneficial independent of the conjugation chemistry and payload class. Carefully selecting attachment sites that result in minimal changes in hydrophobicity may be particularly beneficial when 4, 6 or 8 drugs are attached per antibody, or when particularly hydrophobic payloads are used.

Cys Sites Selected for ADCs with Low Hydrophobicity:

To minimize hydrophobicity of ADCs, sites were chosen that would point toward the interior of the various protein domains of the antibody. Selection was based on analysis of the antibody structure and behavior of the existing ADCs with DAR=2 where applicable (behavior=retention time on HIC and/or delayed retention time on AnSEC with conjugates that interact with SEC resins). Of the Cys sites identified in Table 1 and Table 2, sites listed in Table 24 fulfill the above criteria.

All ADCs were analyzed by hydrophobic interaction chromatography (HIC). Trastuzumab MMAF ADCs conjugated at the exposed sites HC-K360C, LC-K107C, HC-E258C and HC-R292C were used for comparison purposes. The results are shown in Table 25. The trastuzumab Cys-MMAF ADCs and unconjugated, wild-type antibody were analyzed on a TSKgel Butyl-NPR column as described below. For comparison, HIC data previously obtained for Pcl-MMAF ADCs on a TSKgel Phenyl-5PW (FIG. 23) are also listed. Despite different instrumentation and protocols, and although some variability is expected due to the different geometry and structures of the two linker, the ratio of retention times for the ADC conjugated at the same position but through different conjugation methods remains nearly constant. The HIC data suggests that retention times are indeed a measure of how well a payload is sequestered in the interior of the antibody independent of attachment chemistry and linker structure. As expected the relative ranking of the different attachment sites remains largely identical for Pcl-MMAF and Cys-MMAF ADCs.

Attachment to site selected in Table 24, HC-E333C, HC-K392C, and HC-K326C results in MMAF ADCs that have HIC retention times that are similar to the exposed site ADCs LC-K107C-MMAF, HC-E258C-MMAF, HC-R292C-MMAF and HC-K360C-MMAF (Table 28). Attachment to the HC-E152C, LC-E165C, HC-P171C, LC-R142C, LC-E161C, HC-L174C and HC-S124C sites increases the retention time of the resulting ADC by less than 15% compared to the unconjugated, wild-type antibody. These sites are all located on in the CH1 domain or on the light chain (LC) and HIC retention time data suggests them as preferred attachment sites. Of the CH3 domain sites, HC-K334C and HC-S375C exhibit to lowest increase in hydrophobicity upon conjugation making them preferred attachment sites.

TABLE 24

Cys mutant sites

| Cys mutant site | Site (EU No.) |
|---|---|
| LC-R142C | 142 |
| LC-S159C | 159 |
| LC-E161C | 161 |
| LC-E165C | 165 |
| HC-S124C | 124 |
| HC-E152C | 152 |
| HC-P171C | 171 |
| HC-L174C | 174 |
| HC-K326C | 326 |
| HC-E333C | 333 |
| HC-K334C | 334 |

TABLE 24-continued

Cys mutant sites

| Cys mutant site | Site (EU No.) |
|---|---|
| HC-S375C | 375 |
| HC-K392C | 392 |

TABLE 25

Hydrophobic interaction chromatography (HIC) retention time of the DAR 2 species of trastuzumab MMAF ADCs. Comparing Cys and Pcl conjugation chemistry, the two sets agree well: Sites that hide the drug conjugated by one chemistry also tend to hide the drug when conjugated by the other chemistry. Some variability is expected due to the different geometry of the two linker systems.

| Trastuzumab ADC | DAR2 HIC retention[a] (min) | Trastuzumab ADC | DAR2 HIC retention[b] (min) | Ratio |
|---|---|---|---|---|
| WT | 19.5 | WT | 45 | 0.43 |
| HC-E152C-MMAF | 20.4 | HC-E152Pcl-MMAF | 50 | 0.41 |
| LC-E165C-MMAF | 20.8 | LC-E165Pcl-MMAF | 55 | 0.38 |
| HC-P171C-MMAF | 21.0 | HC-P171Pcl-MMAF | 51 | 0.41 |
| HC-K334C-MMAF | 21.5 | HC-K334Pcl-MMAF | 56 | 0.38 |
| HC-S375C-MMAF | 21.6 | HC-S375Pcl-MMAF | 52 | 0.42 |
| LC-R142C-MMAF | 21.7 | LC-R142Pcl-MMAF | 51 | 0.42 |
| LC-E161C-MMAF | 22.0 | LC-E161Pcl-MMAF | 55 | 0.40 |
| HC-L174C-MMAF | 22.0 | HC-L174Pcl-MMAF | 50 | 0.44 |
| HC-S124C-MMAF | 22.4 | HC-S124Pcl-MMAF | 59 | 0.38 |
| HC-E333C-MMAF | 23.1 | HC-E333Pcl-MMAF | 63 | 0.37 |
| HC-K392C-MMAF | 23.1 | HC-K392Pcl-MMAF | 60 | 0.38 |
| HC-R292C-MMAF | 23.8 | HC-R292Pcl-MMAF | 69 | 0.35 |
| HC-K326C-MMAF | 24.5 | HC-K326Pcl-MMAF | 72 | 0.34 |
| LC-K107C-MMAF | 24.8 | LC-K107Pcl-MMAF | 70 | 0.35 |
| HC-E258C-MMAF | 24.9 | HC-E258Pcl-MMAF | 69 | 0.36 |
| HC-K360C-MMAF | 26.8 | HC-K360Pcl-MMAF | 83 | 0.32 |

[a]Analytical HIC: Tosoh Bioscience (King of Prussia, PA, USA) TSKgel Butyl-NPR column (100 mm x 4.6 mm, 2.5 μm), running buffer A: 50 mM sodium phosphate, 1.5M ammonium sulfate, pH 7.0; buffer B: 50 mM sodium phosphate, pH 7.0; gradient consisted of 5 min holding at 100% A, followed by a linear gradient of 20 to 100% B over 40 min; monitored by UV absorption at 280 nm.
[b]Semi-prep HIC: Tosoh Bioscience (King of Prussia, PA, USA), TSKgel Phenyl-5PW, 13 μm, 21 x 150 mm; running buffer A: 1.5M ammonium sulfate in 20 mM NaPi (pH 7.4); buffer B: 20% isopropanol in 20 mM NaPi (pH 7.4); flow rate 5 ml/min; linear gradient from 20% to 80% buffer B over 90 mins; monitored by UV absorption at 280 nm.

Analytical HIC Protocol in Detail:

Analytical HIC data for trastuzumab Cys-MMAF ADCs were collected using a Tosoh Bioscience (King of Prussia, Pa., USA) TSKgel Butyl-NPR column (100 mm×4.6 mm, 2.5 μm) installed on a Dionex UltiMate 3000 HPLC (Sunnyvale, Calif., USA). The method consisted of a binary gradient of buffer A (50 mM sodium phosphate, 1.5 M ammonium sulfate, pH 7.0) and buffer B (50 mM sodium phosphate, pH 7.0). Samples were prepared by diluting approximately 50 μg of antibody (PBS) with an equal volume of 3 M ammonium sulfate. The gradient consisted of 5 min holding at 100% A, followed a linear gradient of 20 to 100% B over 40 min and finally re-equilibrating at initial conditions for 10 min prior to the next injection. The separation was monitored by UV absorption at 280 nm.

Preparation and Characterization of DAR 4, 6 and 8 Cys ADCs

Cys mutations can be combined for the preparation of DAR 4, 6 and 8 ADCs. In general, the preferred combination is a combination of two Cys mutations resulting in ADCs with DAR 4. Some examples that involve combining a heavy chain (HC) Cys mutant with a light chain (LC) Cys mutant for the preparation of DAR 4 ADCs are shown in Example 10 for trastuzumab and for antibody 14090. Additional data is provided in Table 26. Based on the HIC data and the inspection of attachment sites in the IgG crystal structures, additional Cys combinations were prepared using the protocols described in Examples 2, 5 and 6. Data for selected examples of MMAF ADCs are shown in Table 26. In addition, selected heavy chain sites were combined and double Cys mutations of the heavy chain were cloned following protocols listed in Example 2. Antibodies featuring two HC Cys mutations were prepared and conjugated following protocols described in Example 5 and 6.

For the preparation of DAR 4 ADCs, combinations include single site mutations listed in Table 24. Combinations of single sites resulted in ADCs with low hydrophobicity (Table 25). In thesome combination, one Cys mutation is located in the CH1 domain or on the light chain and the second site is located in the CH3 domain. Examples of such combinations are antibodies featuring Cys mutant combinations of HC-E152C and HC-S375C, and LC-E165C and HC-S375C, and HC-E152C and HC-K334C, and LC-E165C and lC-K334C.

ADCs with DAR 6 and 8 can also be prepared when three or four Cys mutations are combined in one antibody. Selected heavy chain combinations were combined for the preparations of DAR 4, 6 and 8 ADCs. Double and triple Cys mutations of the heavy chain were cloned following protocols listed in Example 2. Antibodies featuring two, three and four Cys mutations were prepared and conjugated following protocols described in Example 5 and 6. The characteristics of some DAR 4, DAR 6 and DAR 8 ADC examples are summarized in Table 26. Some of these ADCs have surprisingly good PK properties as shown in FIG. 25. Antibody 14090 is mouse cross-reactive and therefore, antibody 14090 ADCs, as expected, are cleared more rapidly than trastuzumab ADCs which do not bind to any mouse antigens.

Combinations include those with three and four of the single site mutations listed in Table 24. Combinations include those sites that resulted in ADCs with low hydrophobicity (Table 25). Combinations include one Cys mutation is located in the CH1 domain or on the light chain (LC), and optionally an additional one to three sites are in the CH3 domain. Examples of such combinations include antibodies featuring Cys mutant combinations of HC-E152C or LC-E165C, with HC-S375C, with HC-K334C, and/or HC-K392C. Preferred combinations for the preparation of DAR 6 and DAR 8 ADCs are shown in Table 27 and Table 28 respectively.

With a few of exceptions, attachment of MMAF at all Cys sites studied results in ADCs with high thermal stability (Example 7, Table 19), low propensity to aggregate (Example 6, Table 18) and good pharmacokinetic properties of DAR 2 ADCs (Example 9, Table 22, FIG. 18). Differences in ADC hydrophobicity apparently do not translate into large differences in biophysical and pharmacokinetic properties when a relatively soluble payload such as MMAF is used. In fact, as is shown above, DAR 4, DAR 6 and DAR 8 MMAF ADCs with acceptable pharmacokinetic properties can be prepared even using exposed, "hydrophobic" sites such as HC-K360C in combination with more preferred attachment sites. However, when less well behaved, more hydrophobic payloads are used, carefully selecting attachment sites that result in minimal changes in hydrophobicity may be essential to allow the preparation of non-aggregating ADCs with good pharmacokinetic properties. For such hydrophobic payloads, using combination of sites that reduce hydrophobicity increases might be beneficial when 4, 6 or 8 drugs are attached per antibody.

TABLE 26

Characterization of selected DAR 4, 6 and 8 MMAF ADCs prepared with combinations of Cys mutations.

| Cys-MMAF ADC name | DAR | % Multimer AnSEC | AUC MMAF/ AUC hIgG |
|---|---|---|---|
| trastuzumab-HC-E258C-LC-S159C-MMAF | 4.0 | n.d. | 0.9 |
| trastuzumab-HC-S375C-LC-S159C-MMAF | 4.0 | n.d. | 0.8 |
| trastuzumab-HC-E258C-LC-E165C-MMAF | 4.0 | n.d. | 0.9 |
| trastuzumab-HC-S375C-LC-E165C-MMAF | 4.0 | n.d. | 0.8 |
| trastuzumab-HC-E152C-LC-R142C-MMAF | 3.8 | n.d. | 0.9 |
| trastuzumab-HC-P171C-LC-R142C-MMAF | 3.8 | 0.1 | 1.1 |
| trastuzumab-HC-E152C-LC-S159C-MMAF | 3.8 | n/a | 0.7 |
| Antibody 14090-HC-S375C-LC-A143C-MMAF | 4.0 | n.d. | 0.9 |
| Antibody 14090-HC-K360C-LC-V159C-MMAF | 4.0 | n.d. | 1.0 |
| Antibody 14090-HC-S375C-LC-V159C-MMAF | 4.0 | 2.9 | 1.0 |
| trastuzumab-HC-K334C-S375C-LC-E165C-MMAF | 6.0 | n.d. | 0.8 |
| trastuzumab-HC-K334C-K392C-LC-E165C-MMAF | 5.8 | 11 | 0.4 |
| trastuzumab-HC-K334C-K360C-S375C-LC-E165C-MMAF | 8.0 | 5 | 0.6 |
| trastuzumab-HC-K334C-K360C-K392C-LC-E165C-MMAF | 7.8 | n.d. | 0.8 |
| trastuzumab-HC-K334C-S375C-K392C-LC-E165C-MMAF | 8.0 | n.d. | 0.7 |

*AUC calculations based on mouse PK measurements with anti-MMAF and anti-IgG ELISA assays.
n.d.; not detected, below limited of quantitation.

TABLE 27

Preferred combinations of Cys sites for the preparation of DAR 6 ADCs.

| ADC combination | Site 1 | Site 2 | Site 3 |
|---|---|---|---|
| 1 | HC-E152C | HC-S375C | HC-K392C |
| 2 | HC-E152C | HC-S375C | HC-K334C |
| 3 | HC-E152C | HC-K334C | HC-K392C |
| 4 | LC-E165C | HC-S375C | HC-K392C |
| 5 | LC-E165C | HC-S375C | HC-K334C |
| 6 | LC-E165C | HC-K334C | HC-K392C |

TABLE 28

Preferred combinations of Cys sites for the preparation of DAR 8 ADCs.

| ADC combination | Site 1 | Site 2 | Site 3 | Site 4 |
|---|---|---|---|---|
| 1 | HC-E152C | HC-S375C | HC-K334C | HC-K392C |
| 2 | HC-E152C | HC-S375C | HC-E333C | HC-K392C |
| 3 | LC-E165C | HC-S375C | HC-K334C | HC-K392C |
| 4 | LC-E165C | HC-S375C | HC-E333C | HC-K392C |

Example 12. In Vivo Efficacy Studies of Trastuzumab Cys-MMAF ADCs

Figure 22:
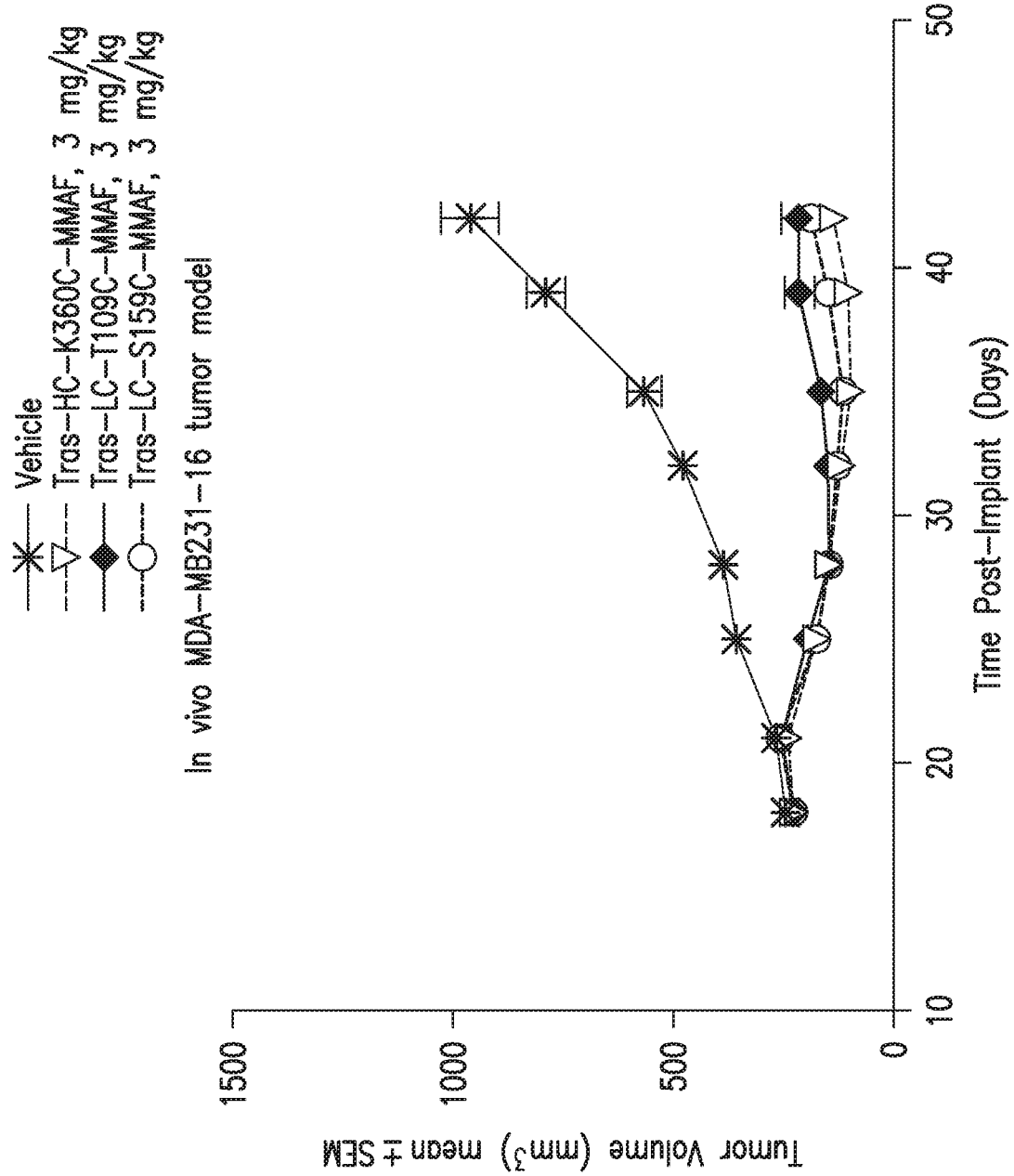
FIG. 22. In vivo efficacy studies of trastuzumab Cys-MMAF ADCs in MDA-MB231 clone 16 xenograft mouse model.

In vivo xenograft tumor models simulate biological activity observed iby grafting relevant and well characterized human primary tumors or tumor cell lines into immune-deficient nude mice. Studies on treatment of tumor xenograft mice with anti-cancer reagents have provided valuable information regarding in vivo efficacy of the tested reagents (Sausville and Burger, 2006). Since MDA-MB231 clone 16 cells were sensitive to trastuzumab Cys-MMAF ADCs in antigen dependent manner (FIG. 15), the cell line was chosen as the in vivo model to evaluate the trastuzumab Cys-MMAF ADCs. All animal studies were conducted in accordance with the Guide for the Care and Use of Laboratory Animals (NIH publication; National Academy Press, 8th edition, 2001). MDA-MB231 clone 16 cells were implanted in nu/nu mice subcutaneously (Morton and Houghton, 2007). After the tumor size reached ~200 mm$^3$, trastuzumab Cys-MMAF ADCs were administered into the mice by IV injection in a single dose at 3 mg/kg. The tumor growth was measured weekly after ADC injection. Each treatment group included 9 mice. An example of the in vivo efficacy study is indicated in FIG. 22 with three trastuzumab Cys-MMAF ADCs. Treatment of mice with 3 mg/kg trastuzumab Cys-MMAF ADCs caused tumor regression for all three tested Cys-MMAF ADCs (FIG. 22). No weight loss was observed associated with the ADC treatment. The results confirmed that with a single dose treatment at 3 mg/kg, trastuzumab Cys-MMAF ADCs effectively caused regression of MDA-MB231 clone 16 tumors.

---

The invention claimed is:

1. An immunoconjugate comprising a modified antibody or antigen binding fragment thereof, wherein said modified antibody or antigen binding fragment comprises a substitution of the amino acid at position 152 of the heavy chain constant region of said antibody or antigen binding fragment thereof with a cysteine, wherein said position is numbered according to the EU system.

2. The immunoconjugate of claim 1, wherein said antibody or antigen binding fragment thereof comprises the amino acid sequence of SEQ ID NO: 10.

3. An immunoconjugate comprising a modified antibody or antigen binding fragment thereof, wherein said modified antibody or antigen binding fragment comprises two amino acid substitutions with a cysteine, wherein the substitutions are selected from:
   a. positions 152 and 375 of the heavy chain constant region of said antibody or antigen binding fragment thereof, wherein said positions are numbered according to the EU system; or
   b. position 107 of the light chain constant region of said antibody or antigen binding fragment thereof, wherein said light chain is a kappa light chain, and position 360 of the heavy chain constant region of said antibody or antigen binding fragment thereof, wherein said positions are numbered according to the EU system.

4. The immunoconjugate of claim 1, wherein the antibody or antigen binding fragment thereof comprises an E152C substitution; wherein the position is numbered according to the EU system.

5. The immunoconjugate of claim 1, wherein the antibody or antigen binding fragment thereof is an IgG1 antibody.

6. The immunoconjugate of claim 3, wherein the antibody or antigen binding fragment thereof comprises substitutions selected from:
   a) E152C and S375C in the heavy chain constant region; or
   b) K107C in the kappa light chain constant region and K360C in the heavy chain constant region; wherein the positions are numbered according to the EU system.

7. The immunoconjugate of claim 3, wherein the antibody or antigen binding fragment thereof is an IgG1 antibody.

8. The immunoconjugate of claim 1 wherein the modified antibody or antigen binding fragment thereof is attached to a drug moiety, directly or indirectly through a linker, by the sulfur atom of said cysteine.

9. The immunoconjugate of claim 1 wherein the modified antibody or antigen binding fragment thereof is attached to a drug moiety, directly or indirectly through a linker, by a thiolmaleimide linkage, a —S—CH2-C(═O)— linkage, or a disulfide linkage.

10. The immunoconjugate of claim 1, wherein said antibody or antigen binding fragment thereof is a monoclonal antibody, a chimeric antibody, a humanized antibody, a fully humanized antibody, a bispecific antibody, or a multi-specific antibody.

11. A composition comprising the immunoconjugate of claim 1 and a pharmaceutically acceptable carrier.

12. A modified antibody or antigen binding fragment thereof comprising a substitution of the amino acid at position 152 of the heavy chain constant region of said antibody or antigen binding fragment with a cysteine, wherein said position is numbered according to the EU system.

13. The modified antibody or antigen binding fragment thereof of claim 12, wherein said antibody or antigen binding fragment thereof comprises the amino acid sequence of SEQ ID NO:10.

14. A modified antibody or antigen binding fragment thereof comprising two amino acid substitutions with cysteine, wherein the substitutions are selected from:
   a. positions 152 and 375 of the heavy chain constant region of said antibody or antigen binding fragment thereof, wherein said positions are numbered according to the EU system; or
   b. position 107 of the light chain constant region of said antibody or antigen binding fragment thereof, wherein said light chain is a kappa light chain, and position 360 of the heavy chain constant region of said antibody or antigen binding fragment thereof, wherein said positions are numbered according to the EU system.

15. The modified antibody or antigen binding fragment thereof of claim 12, wherein the antibody or antigen binding fragment thereof comprises an E152C substitution; wherein the position is numbered according to the EU system.

16. The modified antibody or antigen binding fragment thereof of claim 12, wherein the antibody or antigen binding fragment thereof is an IgG1 antibody.

17. The modified antibody or antigen binding fragment thereof of claim 14, wherein the antibody or antigen binding fragment thereof comprises substitutions selected from:
   a) E152C and S375C in the heavy chain constant region; or
   b) K107C in the kappa light chain constant region and K360C in the heavy chain constant region; wherein the positions are numbered according to the EU system.

18. The modified antibody or antigen binding fragment thereof of claim 14, wherein the antibody or antigen binding fragment thereof is an IgG1 antibody.

* * * * *